(12) United States Patent
Gurney et al.

(10) Patent No.: US 9,181,333 B2
(45) Date of Patent: Nov. 10, 2015

(54) RSPO3 BINDING AGENTS AND USES THEREOF

(71) Applicant: OncoMed Pharmaceuticals, Inc., Redwood City, CA (US)

(72) Inventors: Austin L. Gurney, San Francisco, CA (US); Christopher J. Bond, San Mateo, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 67 days.

(21) Appl. No.: 13/940,834

(22) Filed: Jul. 12, 2013

(65) Prior Publication Data

US 2014/0017253 A1  Jan. 16, 2014

Related U.S. Application Data

(60) Provisional application No. 61/671,421, filed on Jul. 13, 2012, provisional application No. 61/753,184, filed on Jan. 16, 2013, provisional application No. 61/789,156, filed on Mar. 15, 2013, provisional application No. 61/826,747, filed on May 23, 2013.

(51) Int. Cl.
| | |
|---|---|
| *C07K 16/18* | (2006.01) |
| *A61K 39/395* | (2006.01) |
| *A61K 45/06* | (2006.01) |
| *C12Q 1/68* | (2006.01) |
| *C07K 16/30* | (2006.01) |

(52) U.S. Cl.
CPC .......... *C07K 16/18* (2013.01); *A61K 39/39533* (2013.01); *A61K 39/39558* (2013.01); *A61K 45/06* (2013.01); *C07K 16/30* (2013.01); *C12Q 1/6886* (2013.01); *C07K 2317/24* (2013.01); *C07K 2317/92* (2013.01); *C12Q 2600/106* (2013.01); *C12Q 2600/158* (2013.01)

(58) Field of Classification Search
CPC ..... C07K 16/18; C07K 16/30; C07K 2317/24
See application file for complete search history.

(56) References Cited

U.S. PATENT DOCUMENTS

| | | | |
|---|---|---|---|
| 6,004,528 A | 12/1999 | Bergstein | |
| 7,193,069 B2 | 3/2007 | Isogai et al. | |
| 7,319,141 B2 | 1/2008 | Tang et al. | |
| 7,320,880 B2 | 1/2008 | Nishikawa et al. | |
| 7,411,052 B2 | 8/2008 | Tang | |
| 7,439,332 B2 | 10/2008 | Nishikawa | |
| 7,498,416 B2 | 3/2009 | Yayon et al. | |
| 7,541,431 B2 | 6/2009 | Yoon | |
| 7,723,112 B2 | 5/2010 | Clarke et al. | |
| 7,951,381 B2 | 5/2011 | Funk et al. | |
| 8,088,374 B2 | 1/2012 | Niehrs et al. | |
| 8,158,757 B2 | 4/2012 | Gurney et al. | |
| 8,158,758 B2 | 4/2012 | Gurney | |
| 8,540,989 B2 | 9/2013 | Gurney | |
| 8,628,774 B2 | 1/2014 | Gurney et al. | |
| 8,802,097 B2 | 8/2014 | Gurney et al. | |
| 8,883,736 B2 | 11/2014 | Gurney | |
| 2002/0065394 A1 | 5/2002 | Jacobs et al. | |
| 2003/0022217 A1 | 1/2003 | Ceccardi et al. | |
| 2003/0100741 A1 | 5/2003 | Muller et al. | |
| 2004/0197778 A1 | 10/2004 | Morris et al. | |
| 2005/0054829 A1 | 3/2005 | Wiley et al. | |
| 2005/0130145 A1 | 6/2005 | Yue et al. | |
| 2005/0142600 A1 | 6/2005 | Warren et al. | |
| 2005/0232927 A1 | 10/2005 | Clarke et al. | |
| 2005/0256036 A1 | 11/2005 | Boyle et al. | |
| 2005/0256044 A1 | 11/2005 | Boyle et al. | |
| 2006/0019256 A1 | 1/2006 | Clarke et al. | |
| 2006/0263803 A1 | 11/2006 | Tang | |
| 2007/0117751 A1 | 5/2007 | Gurney et al. | |
| 2007/0124581 A1 | 5/2007 | Khare et al. | |
| 2007/0237770 A1 | 10/2007 | Lai et al. | |
| 2007/0244061 A1 | 10/2007 | Niehrs et al. | |
| 2008/0064049 A1 | 3/2008 | Clarke et al. | |
| 2008/0131434 A1 | 6/2008 | Lewicki et al. | |
| 2008/0306004 A1 | 12/2008 | Tang | |
| 2009/0036369 A1 | 2/2009 | Kakitani et al. | |
| 2009/0074782 A1* | 3/2009 | Gurney ..................... 424/139.1 |
| 2009/0118176 A1 | 5/2009 | Emtage et al. | |

(Continued)

FOREIGN PATENT DOCUMENTS

| | | |
|---|---|---|
| AU | 2008270972 A1 | 1/2009 |
| CA | 2 691 378 | 1/2009 |

(Continued)

OTHER PUBLICATIONS

Almagro & Fransson, Frontiers in Bioscience 2008; 13:1619-33.*
De Genst et al., Dev Comp Immunol 2006; 30:187-98.*
PJ Carter, Nat Rev Immunol, 2006; 6:343-357.*
Al-Hajj, M., et al., "Prospective identification of tumorigenic breast cancer cells," *Proc. Natl. Acad. Sci. USA* 100(7):3983-8, National Academy of Sciences, United States (2003).
Aubele, M. and Werner, M., "Heterogeneity in breast cancer and the problem of relevance of findings," *Anal. Cell Pathol.* 19(2):53-8, IOS Press, Netherlands (1999).
Beachy, P.A., et al., "Tissue repair and stem cell renewal in carcinogenesis," *Nature* 432(7015):324-31, Nature Publishing Group, England (2004).

(Continued)

*Primary Examiner* — Sheela J Huff
*Assistant Examiner* — Jessica H Roark
(74) *Attorney, Agent, or Firm* — Sterne, Kessler, Goldstein & Fox PLLC

(57) ABSTRACT

The present invention relates to RSPO-binding agents, particularly RSPO3-binding agents and methods of using the agents for treating diseases such as cancer. The present invention provides antibodies that specifically bind human RSPO3 proteins and modulate β-catenin activity. The present invention further provides methods of using agents that modulate the activity of RSPO3 proteins and inhibit tumor growth. Also described are methods of treating cancer comprising administering a therapeutically effect amount of an agent or antibody of the present invention to a patient having a tumor or cancer.

15 Claims, 20 Drawing Sheets

(56) References Cited

U.S. PATENT DOCUMENTS

| | | | |
|---|---|---|---|
| 2009/0208484 | A1 | 8/2009 | Christiano |
| 2010/0047257 | A1 | 2/2010 | Blanc et al. |
| 2010/0071078 | A1 | 3/2010 | Niehrs |
| 2010/0278800 | A1 | 11/2010 | Boyle et al. |
| 2011/0123532 | A1 | 5/2011 | Gurney et al. |
| 2011/0287444 | A1* | 11/2011 | Kanamori et al. ............ 435/7.1 |
| 2012/0039912 | A1 | 2/2012 | Rawadi et al. |
| 2012/0082659 | A1 | 4/2012 | Land et al. |
| 2012/0088727 | A1 | 4/2012 | Niehrs et al. |
| 2012/0171226 | A1 | 7/2012 | Horwitz |
| 2012/0184616 | A9 | 7/2012 | Rabbani et al. |
| 2012/0263730 | A1 | 10/2012 | Niehrs et al. |
| 2013/0095116 | A1 | 4/2013 | Gurney et al. |
| 2013/0115206 | A1 | 5/2013 | Gurney et al. |
| 2013/0121993 | A1 | 5/2013 | Gurney |
| 2014/0127223 | A1* | 5/2014 | Yamazaki et al. ......... 424/143.1 |
| 2014/0134177 | A1 | 5/2014 | Gurney et al. |
| 2015/0010565 | A1 | 1/2015 | Gurney et al. |
| 2015/0010571 | A1 | 1/2015 | Gurney et al. |

FOREIGN PATENT DOCUMENTS

| | | |
|---|---|---|
| DE | 10339820 A1 | 3/2005 |
| EP | 2 081 586 | 7/2009 |
| EP | 2 157 192 A1 | 2/2010 |
| EP | 1 673 475 | 4/2010 |
| EP | 2 173 379 | 4/2010 |
| EP | 2 419 133 | 2/2012 |
| EP | 1 427 747 B1 | 4/2012 |
| EP | 2 515 933 | 10/2012 |
| JP | 2010-532169 A | 10/2010 |
| WO | WO 98/49302 | 11/1998 |
| WO | WO 99/15660 | 4/1999 |
| WO | WO-0107611 A2 | 2/2001 |
| WO | WO-0177169 A2 | 10/2001 |
| WO | WO 01/87338 A1 | 11/2001 |
| WO | WO 02/12447 A2 | 2/2002 |
| WO | WO 02/102972 A2 | 12/2002 |
| WO | WO 03/029405 A2 | 4/2003 |
| WO | WO 03/050502 A2 | 6/2003 |
| WO | WO 03/054152 A2 | 7/2003 |
| WO | WO 2004/074436 A2 | 9/2004 |
| WO | WO 2005/040418 A2 | 5/2005 |
| WO | WO 2006/110581 A2 | 10/2006 |
| WO | WO 2007/096149 A1 | 8/2007 |
| WO | WO 2008/020942 A2 | 2/2008 |
| WO | WO 2008/042236 A2 | 4/2008 |
| WO | WO 2008/046649 A1 | 4/2008 |
| WO | WO 2008/075796 A1 | 6/2008 |
| WO | WO 2008/088524 A2 | 7/2008 |
| WO | WO 2009/005809 A2 | 1/2009 |
| WO | WO 2009/045443 A2 | 4/2009 |
| WO | WO 2010/121923 A1 | 10/2010 |
| WO | WO 2011/076932 A1 | 6/2011 |
| WO | WO-2012092336 A2 | 7/2012 |
| WO | WO 2012/140274 A2 | 10/2012 |
| WO | WO 2013/012747 A1 | 1/2013 |
| WO | WO-2014012007 A2 | 1/2014 |

OTHER PUBLICATIONS

Beerman, H., et al., "Flow cytometric analysis of DNA stemline heterogeneity in primary and metastatic breast cancer," *Cytometry* 12(2):147-54, Wiley-Liss, United States (1991).

Bonsing, B.A., et al., "High levels of DNA index heterogeneity in advanced breats carcinomas. Evidence for DNA ploidy differences between lymphatic and hematogenous metastases," *Cancer* 71(2):382-391, Wiley, United States (1993).

Bonsing, B.A., et al., "Allelotype analysis of flow-sorted breast cancer cells demonstrates genetically related diploid and aneuploid subpopulations in primary tumors and lymph node metastases," *Genes Chromosomes Cancer* 28(2):173-183, Wiley-Liss, United States, (2000).

Brennan, K.R. and Brown, A.M., "Wnt proteins in mammary development and cancer," *J. Mammary Gland Biol. Neoplasia* 9(2):119-131, Kluwer Academic/Plenum Publishers, United States (2004).

Cabrera, C.V., et al., "Phenocopies induced with antisense RNA identify the wingless gene," *Cell* 50(4):659-663, Cell Press, United States (1987).

Campbell, A.M., *Monoclonal Antibody Technology Eds.*, pp. 1-29, Elsevier Science Publishers B.V., Netherlands (1984).

Casset, F., et al., "A peptide mimetic of an anti-CD4 monoclonal antibody by rational design," *Biochem. Biophys. Res. Commun.* 307(1):198-205, Academic Press, United States (2003).

Chien, A.J., et al., "Activated Wnt/beta-catenin signaling in melanoma is associated with decreased proliferation in patient tumors and a murine melanoma model," *Proc. Natl. Acad. Sci, USA* 106(4):1193-1198, National Academy of Sciences, United States (2009).

Dermer, G.B., "Another Anniversary for the War on Cancer," *Bio/Technology* 12:320, Nature Publishing Co., United States (1994).

Freshney, R.I., *Culture of Animal Cells, A Manual of Basic Technique*, pp. 4, Alan R. Liss, Inc., United States (1983).

Gazit, A., et al., "Human frizzled 1 interacts with transforming Wnts to transduce a TCF dependent transcriptional response," *Oncogene* 18(44):5959-5966, Nature Publishing Group, England (1999).

Gradl, D., et al., "The Wnt/Wg signal transducer beta-catenin controls fibronectin expression," *Mol. Cell Biol.* 19(8):5576-5587, American Society for Microbiology, United States (1999).

Gura, T., "Systems for identifying new drugs are often faulty," *Science* 278(5340):1041-1042, American Association for the Advancement of Science, United States (1997).

Harada, N., et al., "Intestinal polyposis in mice with a dominant stable mutation of the beta-catenin gene," *EMBO J.* 18(21):5931-5942, IRL Press, England (1999).

Hatsell, S., et al., "Beta-catenin and Tcfs in mammary development and cancer," *J. Mammary Gland Biol. Neoplasia* 8(2):145-158, Kluwer Academic/Plenum Publishers, United States (2003).

He, T.C., et al., "Identification of c-MYC as a target of the APC pathway," *Science* 281(5382):1509-1512, American Association for the Advancement of Science, United States (1998).

Hsu, S.Y., et al, "Activation of Orphan Receptors by the Hormone Relaxin," *Science*, 295:671-674, American Association for the Advancement of Science, United States (2002).

Imbert, A., et al., "Delta N89 beta-catenin induces precocious development, differentiation, and neoplasia in mammary gland," *J. Cell. Biol.* 153(3):555-568, Rockefeller University Press, United States (2001).

Jain, R.K., "Barriers to drug delivery in solid tumors," *Sci. Am.* 271(1):58-65, Scientific American, United States (1994).

Jemal, A., et al., "Cancer Statistics, 2003," *CA Cancer J. Clin.* 53(1):5-26, American Cancer Society, United States, (2003).

Kamata, T., et al., "R-spondin, a novel gene with thrombospondin type 1 domain, was expressed in the dorsal neural tube and affected in Wnts mutants," *Biochim. Biophys. Acta* 1676(1):51-62, Elsevier Pub. Co., Netherlands (2004).

Kazanskaya, O., et al., "R-Spondin2 is a secreted activator of Wnt/beta-catenin signaling and is required for *Xenopus* myogenesis," *Dev. Cell* 7(4):525-534, Cell Press, United States (2004).

Kim, K.A., et al., "Mitogenic influence of human R-spondin1 on the intestinal epithelium," *Science* 309(5738):1256-1259, American Association for the Advancement of Science, United States (2005).

Kim, K.A., et al., "R-Spondin proteins: a novel link to beta-catenin activation," *Cell Cycle* 5(1):23-26, Landes Bioscience, United States (2006).

Kuukasjrvi, P., et al., "Overview of systematic reviews on invasive treatment of stable coronary artery disease," *Int. J. Technol. Assess Health Care* 22(2):219-34, Cambridge University Press, England (2006).

LaRue, L. and Delmas, V., "The WNT/Beta-catenin pathway in melanoma," *Front Biosci.* 11:733-742, Frontiers in Bioscience Publications, United States (2006).

Mazerbourg, S., et al., "Leucine-Rich Repeat-Containing, G Protein-Coupled Receptor 4 Null Mice Exhibit Intrauterine Growth Retardation Associated with Embryonic and Perinatal Lethality," *Molecular Endocrinology*, 18(9):2241-2254, The Endocrine Society, United States (2004).

(56) References Cited

OTHER PUBLICATIONS

McClanahan, T., et al, "Identification of Overexpression of Orphan G Protein-Coupled Receptor GPR49 in Human Colon and Ovarian Primary Tumors," *Cancer Biology and Therapy*, 5(4):419-426, Landes Bioscience, United States (2006).

Milovanovic, T., et al., "Expression of Wnt genes and frizzled 1 and 2 receptors in normal breats epithelium and infiltrating breast carcinoma," *Int. J. Oncol.* 25:1337-1342, D.A. Spandidos, Greece (2004).

Michaelson, J.S. and Leder, P., "Beta-catenin is a downstream effector of Wnt-mediated tumorigenesis in the mammary gland," *Oncogene* 20(37):5093-5099, Nature Publishing Group, England (2001).

Miller, J.R., et al., "Mechanism and function of signal transduction by the Wnt/beta-catenin and Wnt/Ca2+ pathways," *Oncogene* 18(55):7860-7872, Nature Publishing Group, England (1999).

Morita, H., et al., "Neonatal Lethality of LGR5 Null Mice is Associated with Ankyloglossia and Gastrointestinal Distension," *Mol. Cell. Biol.*, 24(22):9736-9743, American Society for Microbiology, United States (2004).

Morrison, S.J., et al., "The biology of hematopoietic stem cells," *Annu. Rev. Cell Dev. Biol.* 11:35-71, Annual Reviews, United States (1995).

Morrison, S.J., et al., "Regulatory mechanisms in stem cell biology," *Cell* 88(3):287-98, Cell Press, United States (1997).

Morrison, S.J., et al., "Hematopoietic stem cells: challenges to expectations," *Curr. Opin. Immunol.* 9(2):216-221, Elsevier, England (1997).

Nam, J.S., et al., "Mouse cristin/R-spondin family proteins are novel ligands for the Fizzled 8 and LRP6 receptors and activate beta-catenin-dependent gene expression," *J. Biol. Chem.* 281(19):13247-13257, American Society for Biochemistry and Molecular Biology, United States (2006).

Nusse, R. and Varmus, H.E., "Many tumors induced by the mouse mammary tumor virus contain a provirus integrated in the same region of the host genome," *Cell* 31(1):99-109, Cell Press, United States (1982).

Oshima, H., et al., "Morphological and molecular processes of polyp formation in Apc(delta716) knockout mice," *Cancer Res.* 57(9):1644-1649, American Association for Cancer Research, United States (1997).

Pandis, N., et al., "Cytogenic Comparison of Primary Tumors and Lymph Node Metastases in Breast Cancer Patients," *Genes, Chromosomes & Cancer* 22:122-129, Wiley-Liss, Inc. United States, (1998).

De Pascalis, R., et al., "Grafting of "abbreviated" complimentarity-determining regions containing specificit-determining residues essential for ligand contact to engineer a less immunogenic humanized monclonal antibody," *J. Immunol.* 169(6):3076-3084, American Association of Immunologists, United States (2002).

Paul, W.D., *Fundamental Immunology*, 3rd Edition, pp. 292-295, Raven Press, Ltd., United States (1993).

Reya, T. and Clevers, H., "Wnt signlaing in stem cells and cancer," *Nature* 434(7035):843-50, Nature Publishing Group, England (2005).

Rijsewijk, F., et al., "The *Drosophila* homolog of the mouse mammary oncogene int-1 is identical to the segment polarity gene wingless," *Cell* 50(4):649-657, Cell Press, United States (1987).

Rudikoff, S., et al., "Single amino acid substitution altering antigen-binding specificity," *Proc. Natl. Acad. Sci. USA* 79(6):1979-1983, National Academy of Sciences, United States (1982).

Shen, C.Y., et al., "Genome-wide search for loss of heterozygosity using laser capture microdissected tissue of breast carcinoma: an implication for mutator phenotype and breats cancer pathogenesis," *Cancer Res.* 60(14):3884-92, American Association for Cancer Research, United States (2000).

Tepera, S.B., et al., "A beta-catenin survival signal is required for normal lobular development in the mammary gland," *J. Cell. Sci.* 116(Pt 6):1137-1149, Company of Biologists, England (2003).

Tetsu, O. and McCormick, F., "Beta-catenin regulates expression of cyclin D1 in colon carcinoma cells," *Nature* 398(6726):422-426, Nature Publishing Group, England (1999).

Van Ooyen, A. and Nusse, R., "Structure and nucleotide sequence of the putative mammary oncogene int-1; proviral insertions leave the protein-encoding domain intact," *Cell* 39(1):233-240, Cell Press, United States (1984).

Wu, C.H. and Nusse, R., "Ligand receptor interactions in the Wnt signlaing pathway in *Drosophila*," *J. Biol. Chem.* 277(44):41762-41769, American Society for Biochemistry and Molecular Biology, United States (2002).

Zhao, J., et al., "R-spondin1, A Novel Intestinotrophic Mitogen, Ameliorates Experimental Colitis in Mice," *Gastroenterology*, 132(4):1331-1334, Elsevier, United States (2007).

International Search Report for International Application No. PCT/US2008/008210, European Patent Office, Netherlands, mailed on Mar. 2, 2009.

The Written Opinion of the International Searching Authority for International Application No. PCT/US2008/008210, European Patent Office, Netherlands, mailed on Jan. 5, 2010.

International Preliminary Report on Patentability for International Application No. PCT/US2008/008210, dated Jan. 5, 2010 from the International Bureau of WIPO, Geneva, Switzerland.

International Search Report for International Application No. PCT/US2012/046746, dated Oct. 23, 2012 from the International Searching Authority, Alexandria.

The Written Opinion of the International Searching Authority for International Application No. PCT/US2012/046746, dated Oct. 4, 2012.

Notice of Allowance dated Feb. 23, 2012 in U.S. Appl. No. 12/167,176, filed Jul. 2, 2008.

Notice of Allowance dated Jan. 18, 2012 in U.S. Appl. No. 12/167,176, filed Jul. 2, 2008.

Non-Final Office Action dated Jun. 24, 2011 in U.S. Appl. No. 12/167,176, filed Jul. 2, 2008.

Final Office Action dated Apr. 27, 2010 in U.S. Appl. No. 12/167,176, filed Jul. 2, 2008.

Non-Final Office Action dated Oct. 30, 2009 in U.S. Appl. No. 12/167,176, filed Jul. 2, 2008.

Notice of Allowance dated Jan. 23, 2012 in U.S. Appl. No. 12/167,172, filed Jul. 2, 2008.

Non-Final Office Action dated Jun. 24, 2011 in U.S. Appl. No. 12/167,172, filed Jul. 2, 2008.

Final Office Action dated May 13, 2010 in U.S. Appl. No. 12/167,172, filed Jul. 2, 2008.

Non-Final Office Action dated Oct. 7, 2009 in U.S. Appl. No. 12/167,172, filed Jul. 2, 2008.

English language abstract of DE 10339820 A1, espacenet database, Worldwide, published Mar. 17, 2005.

English language abstract of JP 2010-532169 A, espacenet database, Worldwide, published Jan. 8, 2009.

Luu, H.H., et al., "Wnt/β-Catenin Signaling Pathway as Novel Cancer Drug Targets," *Current Cancer Drug Targets* 4:653-671, Bentham Science Publishers Ltd., Netherlands (2004).

Carmon, K.S., et al., "R-spondins function as ligands of the orphan receptors LGR4 and LGR5 to regulate Wnt/β-catenin signaling," *Proc. Natl. Acad. Sci. USA* 108(28):11452-11457, National Academy of Sciences, United States (2011).

Takahashi-Yanaga, F. and Sasaguri, T., "The Wnt/β-Catenin Signaling Pathway as a Target in Drug Discovery," *J. Pharmacol. Sci.* 104:293-302, The Japanese Pharmacological Society, Japan (2007).

Co-pending U.S. Appl. No. 13/801,198, filed Mar. 13, 2013, inventor Gurney, A.

Co-pending U.S. Appl. No. 13/323,534, filed Dec. 12, 2011, inventor Boyle et al.

Chen, J-Z., et al., "Cloning and indentification of a cDNA that encodes a novel human protein with thrombospondin type I repeat domain, hPWTSR," *Mol. Biol. Rep.* 29:287-292, Kluwer Academic Publishers, Netherlands (2002).

Kazanskaya, O., et al., "R-Spondin2 is a Secreted Activator of Wnt/β-Catenin Signaling and is Required for *Xenopus* Myogenesis," *Devel. Cell* 7:525-534, Cell Press, United States (2004).

(56) References Cited

OTHER PUBLICATIONS

Kim, K-A., et al., "R-Spondin Family Members Regulate the Wnt Pathway by a Common Mechanism," Mol. Biol. of the Cell 19:2588-2596, The American Society for Cell Biology, United States (2008).
Anonymous, Human R-Spondin 2 Antibody. Antigen Affinity-purified Polyclonal Goat IgG, Catalog No. AF3266, RnDsystems.com, accessed at //www.rndsystems.comjpdf/AF3266.pdf, accessed on Jun. 23, 2010, 1 page.
Bienz, M. and Clevers, H., "Linking Colorectal Cancer to Wnt Signaling," Cell 103(2):311-320, Cell Press, United States (2000).
Boyden, L.M., et al., "High Bone Density Due to a Mutation in LDL-Receptor-Related Protein 5," The New England Journal of Medicine 346(20):1513-1521, Massachusetts Medical Society, United States (2002).
Campbell, A.M., "General properties and application of monoclonal antibodies," in Monoclonal Antibody Technology the Production and Characterization of Rodent and Human Hybridomas, Chapter 1, pp. 1-32, Elsevier Science Publishers B.V., Amsterdam (1984).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Co-pending U.S. Appl. No. 14/504,680 inventor Gurney, A.L., filed Oct. 2, 2014 (Not Published).
Easwaran, V., et al., "Beta-Catenin Regulates Vascular Endothelial Growth Factor Expression in Colon Cancer," Cancer Research 63(12):3145-3153, American Association for Cancer Research, United States (2003).
European Opposition Brief for European Patent No. 2157192 filed May 8, 2014, 46 pages.
Extended European Search Report for EP Application No. 12814264, European Patent Office, Germany, mailed on Jan. 28, 2015, 7 pages.
Fischer, L., et al., "Wnt-3A Enhances Bone Morphogenetic Protein-2-Mediated Chondrogenesis of Murine C3H10T1/2 Mesenchymal Cells," The Journal of Biological Chemistry 277(34):30870-30878, JBC Papers in Press, American Society for Biochemistry and Molecular Biology, United States (2002).
Fujino, T., et al., "Low-Density Lipoprotein Receptor-Related Protein 5 (LRP5) is Essential for Normal Cholesterol Metabolism and Glucose-Induced Insulin Secretion," Proceedings of the National Academy of Sciences 100(1):229-234, National Academy of Sciences, United States (2003).
Goldblum, S.E., et al., "Thrombospondin-1 Induces Tyrosine Phosphorylation of Adherens Junction Proteins and Regulates an Endothelial Paracellular Pathway," Molecular Biology of the Cell 10(5):1537-1551, The American Society for Cell Biology, United States (1999).
Gong, Y., et al., "LDL Receptor-Related Protein 5 (LRP5) Affects Bone Accrual and Eye Development," Cell 107(4):513-523, Cell Press, United States (2001).
Gurney, A., et al., "Inhibition of R-spondin (RSPO) signaling reduces the growth of multiple human tumors," AACR Annual Meeting 2014, Abstract 1764, Apr. 5-9, 2014 1 page.
Hartmann, C., "Wnt-Signaling and Skeletogenesis," Journal of Musculoskelet & Neuronal Interactions 2(3):274-276, International Society of Musculoskeletal and Neuronal Interactions, Greece (2002).
Horesh, Y., et al., "A Rapid Method for Detection of Putative RNAi Target Genes in Genomic Data," Bioinformatics 19(Suppl 2):ii73-ii80, Oxford University Press, England (2003).
International Search Report for International Application No. PCT/US2013/050300, from the International Bureau of WO, Geneva Switzerland, mailed Feb. 7, 2014, 7 pages.
Jackson, A.L. and Linsley, P.S., "Noise Amidst The Silence: Off-Target Effects of siRNAs?," Trends in Genetics 20(11):521-524, Elsevier Science Publishers B.V., Netherlands (2004).

Korinek, V., et al., "Constitutive Transcriptional Activation by a Beta-Catenin-Tcf Complex in APC -/- Colon Carcinoma," Science 275(5307):1784-1787, American Association for the Advancement of Science, United States (1997).
Li, S.J., et al., "Loss-of-Function Point Mutations and Two-Furin Domain Derivatives Provide Insights about R-Spondin2 Structure and Function," Cellular Signalling 21(6): 916-925, Elsevier Science Ltd, England (2009).
Lonberg, N., "Human Antibodies from Transgenic Animals," Nature Biotechnology 23(9):1117-1125, Nature Publishing Group, United Kingdom (2005). (D4 as submitted in OPPO_EP2157192).
MacCallum, R.M., et al., "Antibody-Antigen Interactions: Contact Analysis and Binding Site Topography," Journal of Molecular Biology 262(5):732-745, Academic Press, England (1996).
Meniel, V. and Clarke, A.R., "Wnt-Cadherin Connections in Normal and Neoplastic Mammary Epithelium," Journal of Mammary Gland Biology and Neoplasia 8(4):435-447, Kluwer Academic/Plenum Publishers, United States (2003).
OncoMed Pharmaceuticals, Press Release, "OncoMed Presents Data on Multiple Anti-Cancer Stem Cell Programs at American Association for Cancer Research Annual Meeeting," Apr. 8, 2014, 4 pages.
Perantoni, A.O., "Renal Development: Perspectives on a Wnt-Dependent Process," Seminars in Cells and Development Biology Abstract, 1 page, Academic Press, United Kingdom (2003).
Polakis, P., "Wnt signaling and cancer," Genes & Development 14:1837-1851, Cold Spring Harbor Laboratory Press, United States (2000).
Polesskaya, A., et al., "Wnt Signaling Induces the Myogenic Specification of Resident CD45+ Adult Stem Cells during Muscle Regeneration," Cell Abstract, 1 page, MIT Press, United States (2003).
Reply to European Opposition Brief for European Patent No. 2157192 filed Jan. 8, 2015, 42 pages.
Response to European Opposition Brief Reply for European Patent No. 2157192, filed May 14, 2015, 14 pages.
Saadi-Kheddouci, S., et al., "Early Development of Polycystic Kidney Disease in Transgenic Mice Expressing an Activated Mutant of the Beta-Catenin Gene," Oncogene 20(42):5972-5981, Nature Publishing Group, England (2001).
Smalley, M.J. and Dale, T.C., "Wnt Signalling in Mammalian Development and Cancer," Cancer and Metastasis Reviews 18(2):215-230, Kluwer Academic Publishers, Netherlands (1999).
Stump, R.J., et al., "A Role for Wnt/Beta-Catenin Signaling in Lens Epithelial Differentiation," Developmental Biology Abstract, 1 page, Elsevier Inc., United States (2003).
Surendran, K., et al, "A Role for Wnt-4 in Renal Fibrosis," American Journal of Physiology. Renal Physiology 282(3):F431-F441, American Physiological Society, United Sates (2002).
Tan, B.T., et al., "The Cancer Stem Cell Hypothesis: A Work in Progress," Laboratory Investigation 86(12):1203-1207, USCAP, United States (2006).
Transmittal of third party observations sent on Dec. 17, 2014 in European Application No. 08779934.2, 6 pages.
UniProt "Thrombospondin-1," identifying No. P07996-TSP1_HUMAN, accessed at //www.uniprot.org/uniprot/P07996, accessed on Sep. 25, 2014, 14 pages.
Written Opinion of the International Searching Authority for International Application No. PCT/US2013/050300, mailed Feb. 7, 2014, 11 pages.
Wu, H., et al., "Humanization of a Murine Monoclonal Antibody by Simultaneous Optimization of Framework and CDR Residues," Journal of Molecular Biology 294(1):151-162, Elsevier, England (1999).
Wu, W., et al., "Mutual Antagonism between Dickkopf1 and Dickkopf2 Regulates Wnt/Beta-Catenin Signalling," Current Biology 10(24):1611-1614, Elsevier Science Ltd., England (2000).

* cited by examiner

Fig. 1A

RSPO1

| ID | Original Source | Purity | Treatment | Tissue Type | Avg Sig | STDev | PA Cells P | PA Cells A | PA Cells M |
|---|---|---|---|---|---|---|---|---|---|
| Colon Diseased | Colon | Diseased | Colon:DISE... | | 4.86 | 0.14 | 0 | 21 | 0 |
| Colon Benign | Colon | Benign | Colon:BEN... | | 4.92 | 0.09 | 0 | 24 | 0 |
| Breast Normal | Breast | Normal | Breast:NORM... | | 11.25 | 13.18 | 5 | 17 | 0 |
| Breast Malignant | Breast | Malignant | Breast:MAL... | | 4.96 | 0.87 | 1 | 160 | 0 |
| Breast Benign | Breast | Benign | Breast:BEN... | | 42.26 | 72.70 | 2 | 7 | 0 |
| Brain Benign | Brain | Benign | Brain:BEN... | | 4.82 | 0.05 | 0 | 16 | 0 |
| Brain Malignant | Brain | Malignant | Brain:MAL... | | 4.82 | 0.16 | 0 | 23 | 0 |
| Liver Benign | Liver | Benign | Liver:BEN... | | 4.91 | 0.14 | 0 | 4 | 0 |
| Kidney Normal | Kidney | Normal | Cortex of K... | | 4.69 | 0.12 | 0 | 61 | 0 |
| Kidney Malignant | Kidney | Malignant | Kidney:MAL... | | 5.7 | 5.24 | 3 | 88 | 0 |
| Kidney Benign | Kidney | Benign | Kidney:BEN... | | 4.94 | 0.12 | 0 | 15 | 0 |
| Endometrium Malignant | Endometrium | Malignant | Endometrium... | | 11.76 | 22.09 | 5 | 52 | 0 |
| Endometrium Benign | Endometrium | Benign | Endometrium... | | 16.09 | 23.46 | 3 | 7 | 0 |
| Colon Normal | Colon | Normal | Ascending c... | | 4.92 | 0.36 | 0 | 74 | 0 |
| Colon Malignant | Colon | Malignant | Colon:MAL... | | 4.93 | 0.85 | 1 | 140 | 0 |
| Ovary Malignant | Ovary | Malignant | Ovary:MAL... | | 33.80 | 85.09 | 32 | 105 | 1 |
| Ovary Normal | Ovary | Normal | Ovary:NORM... | | 5.61 | 1.28 | 0 | 7 | 0 |
| Lung Normal | Lung | Normal | Lung:NORM... | | 5.33 | 0.95 | 1 | 63 | 0 |
| Ovary Benign | Ovary | Benign | Ovary:BEN... | | 20.32 | 36.55 | 5 | 30 | 0 |
| Lung Malignant | Lung | Malignant | Lung:MAL... | | 4.94 | 0.73 | 0 | 124 | 0 |
| Lung Benign | Lung | Benign | Lung:BEN... | | 4.80 | 0.08 | 0 | 5 | 0 |
| Liver Diseased | Liver | Diseased | Liver:DIS... | | 4.89 | 0.22 | 0 | 22 | 0 |
| Liver Malignant | Liver | Malignant | Liver:MAL... | | 4.92 | 0.15 | 0 | 25 | 0 |
| Liver Normal | Liver | Normal | Liver:NORM... | | 4.95 | 0.13 | 0 | 6 | 0 |
| Prostate Malignant | Prostate | Malignant | Prostate:MAL | | 5.00 | 0.69 | 0 | 73 | 0 |
| Prostate Normal | Prostate | Normal | Prostate:NOR... | | 6.03 | 6.23 | 0 | 32 | 0 |
| Pancreas Normal | Pancreas | Normal | Pancreas:NOR... | | 4.99 | 0.11 | 0 | 13 | 0 |
| Prostate Diseased | Prostate | Diseased | Prostate:DIS... | | 5.97 | 2.20 | 0 | 18 | 0 |
| Pancreas Benign | Pancreas | Benign | Pancreas:BEN... | | 4.93 | 0.13 | 0 | 5 | 0 |
| Pancreas Malignant | Pancreas | Malignant | Pancrease:MAL... | | 4.79 | 0.11 | 0 | 66 | 0 |

Fig. 1C

RSPO2

| ID | Original Source | Purity | Treatment | Tissue Type | Avg Sig | STDev | P | A | M |
|---|---|---|---|---|---|---|---|---|---|
| Colon Diseased | Colon | Diseased | Colon:DISE... | | 28.82 | 51.62 | 16 | 5 | 0 |
| Colon Benign | Colon | Benign | Colon:BEN. | | 7.40 | 6.58 | 3 | 21 | 0 |
| Breast Normal | Breast | Normal | Breast:NORM... | | 7.04 | 7.00 | 1 | 21 | 0 |
| Breast Malignant | Breast | Malignant | Breast:MAL... | | 5.82 | 2.16 | 5 | 156 | 0 |
| Breast Benign | Breast | Benign | Breast:BEN... | | 5.59 | 0.12 | 1 | 8 | 0 |
| Brain Benign | Brain | Benign | Brain:BEN... | | 5.66 | 0.15 | 0 | 16 | 0 |
| Brain Malignant | Brain | Malignant | Brain:MAL... | | 16.70 | 30.11 | 11 | 12 | 0 |
| Liver Benign | Liver | Benign | Liver:BEN. | | 6.00 | 0.43 | 0 | 4 | 0 |
| Kidney Normal | Kidney | Normal | Cortex of k... | | 5.76 | 0.22 | 0 | 61 | 0 |
| Kidney Malignant | Kidney | Malignant | Kidney:MAL... | | 5.61 | 0.20 | 1 | 90 | 0 |
| Kidney Benign | Kidney | Benign | Kidney:BEN | | 18.30 | 34.71 | 5 | 10 | 1 |
| Endometrium Malignant | Endometrium | Malignant | Endometrium... | | 6.31 | 3.17 | 7 | 49 | 0 |
| Endometrium Benign | Endometrium | Benign | Endometrium... | | 5.54 | 0.10 | 0 | 10 | 0 |
| Colon Normal | Colon | Normal | Ascending c... | | 14.65 | 25.57 | 43 | 28 | 3 |
| Colon Malignant | Colon | Malignant | Colon:MAL... | | 6.67 | 11.61 | 10 | 130 | 1 |
| Ovary Malignant | Ovary | Malignant | Ovary:MAL... | | 10.33 | 50.15 | 7 | 131 | 0 |
| Ovary Normal | Ovary | Normal | Ovary:NORM... | | 5.64 | 0.10 | 53 | 10 | 0 |
| Lung Normal | Lung | Normal | Lung:NORM... | | 16.18 | 14.17 | 4 | 11 | 0 |
| Ovary Benign | Ovary | Benign | Ovary:BEN... | | 5.66 | 0.41 | 4 | 31 | 0 |
| Lung Malignant | Lung | Malignant | Lung:MAL... | | 7.00 | 5.27 | 26 | 96 | 2 |
| Lung Benign | Lung | Benign | Lung:BEN... | | 5.61 | 0.15 | 0 | 5 | 0 |
| Liver Diseased | Liver | Diseased | Liver:DIS... | | 6.30 | 2.71 | 1 | 21 | 0 |
| Liver Malignant | Liver | Malignant | Liver:MAL... | | 5.91 | 0.42 | 0 | 24 | 0 |
| Liver Normal | Liver | Normal | Liver:NORM... | | 5.96 | 0.27 | 0 | 6 | 0 |
| Prostate Malignant | Prostate | Malignant | Prostate:MAL | | 18.11 | 61.02 | 40 | 31 | 2 |
| Prostate Normal | Prostate | Normal | Prostate:NOR... | | 18.65 | 23.89 | 22 | 9 | 1 |
| Pancreas Normal | Pancreas | Normal | Pancreas:NOR... | | 5.98 | 0.23 | 0 | 13 | 0 |
| Prostate Diseased | Prostate | Diseased | Prostate:DIS... | | 23.87 | 18.90 | 17 | 3 | 0 |
| Pancreas Benign | Pancreas | Benign | Pancrease:BEN... | | 156.95 | 337.57 | 1 | 4 | 0 |
| Pancreas Malignant | Pancreas | Malignant | Pancrease:MAL... | | 5.57 | 0.17 | 1 | 65 | 0 |

Fig. 1D

RSPO2

| ID | | 152 | 304 | 456 | 609 |
|---|---|---|---|---|---|
| Colon Diseased | ▮▮ ▮ | ▮ | | | |
| Colon Benign | ▮ ▮ | | | | |
| Breast Normal | ▮ ▮ | | | | |
| Breast Malignant | ▮▮▮ | | | | |
| Breast Benign | ▮ | | | | |
| Brain Benign | ▮ | | | | |
| Brain Malignant | ▮▮▮ | ▮ | | | |
| Liver Benign | ▮ | | | | |
| Kidney Normal | ▮ | | | | |
| Kidney Malignant | ▮▮ ▮ | ▮ | | | |
| Kidney Benign | ▮▮ | ▮ | | | |
| Endometrium Malignant | ▮▮ | | | | |
| Endometrium Benign | ▮ | | | | |
| Colon Normal | ▮▮▮▮ | ▮ | ▮ | | |
| Colon Malignant | ▮ | ▮ | | | |
| Ovary Malignant | ▮▮ | | | | |
| Ovary Normal | ▮ | | | | |
| Lung Normal | ▮▮▮▮ | | | | |
| Ovary Benign | ▮ | | | | |
| Lung Malignant | ▮▮▮ | | | | |
| Lung Benign | ▮ | | | | |
| Liver Diseased | ▮▮ | | | | |
| Liver Malignant | ▮ | | | | |
| Liver Normal | ▮ | | | | |
| Prostate Malignant | ▮▮▮ | | | | |
| Prostate Normal | ▮▮▮ | ▮ | | | |
| Pancreas Normal | ▮ | | | | |
| Prostate Diseased | ▮▮▮▮ | | | ▮ | |
| Pancreas Benign | ▮ | | ▮ | | |
| Pancreas Malignant | ▮ | | | | |

Fig. 1E

RSPO3

| ID | Original Source | Purity | Treatment | Tissue Type | Avg Sig | STDev | PA Cells | | |
|---|---|---|---|---|---|---|---|---|---|
| | | | | | | | P | A | M |
| Colon Diseased | Colon | Diseased | Colon:DISE... | | 424.06 | 396.34 | 21 | 0 | 0 |
| Colon Benign | Colon | Benign | Colon:BEN... | | 20.73 | 33.58 | 9 | 15 | 0 |
| Breast Normal | Breast | Normal | Breast:NORM... | | 176.15 | 140.69 | 21 | 1 | 0 |
| Breast Malignant | Breast | Malignant | Breast:MAL... | | 75.62 | 435.84 | 133 | 26 | 2 |
| Breast Benign | Breast | Benign | Breast:BEN... | | 237.01 | 342.37 | 9 | 0 | 0 |
| Brain Benign | Brain | Benign | Brain:BEN... | | 803.26 | 1306.74 | 13 | 2 | 1 |
| Brain Malignant | Brain | Malignant | Brain:MAL... | | 10.15 | 8.10 | 5 | 17 | 1 |
| Liver Benign | Liver | Benign | Liver:BEN... | | 87.84 | 68.68 | 4 | 0 | 0 |
| Kidney Normal | Kidney | Normal | Cortex of k... | | 24.72 | 27.21 | 39 | 22 | 0 |
| Kidney Malignant | Kidney | Malignant | Kidney:MAL... | | 99.48 | 283.90 | 54 | 33 | 4 |
| Kidney Benign | Kidney | Benign | Kidney:BEN... | | 1032.08 | 1889.99 | 7 | 8 | 0 |
| Endometrium Malignant | Endometrium | Malignant | Endometrium... | | 176.43 | 285.60 | 43 | 14 | 0 |
| Endometrium Benign | Endometrium | Benign | Endometrium... | | 3288.94 | 1998.11 | 10 | 0 | 0 |
| Colon Normal | Colon | Normal | Ascending c... | | 118.87 | 137.80 | 73 | 1 | 0 |
| Colon Malignant | Colon | Malignant | Colon:MAL... | | 108.15 | 360.84 | 119 | 20 | 2 |
| Ovary Malignant | Ovary | Malignant | Ovary:MAL... | | 154.28 | 556.65 | 76 | 61 | 1 |
| Ovary Normal | Ovary | Normal | Ovary:NORM... | | 23.20 | 31.46 | 2 | 5 | 0 |
| Lung Normal | Lung | Normal | Lung:NORM... | | 60.79 | 43.83 | 62 | 2 | 0 |
| Ovary Benign | Ovary | Benign | Ovary:BEN... | | 226.13 | 736.49 | 8 | 26 | 1 |
| Lung Malignant | Lung | Malignant | Lung:MAL... | | 111.01 | 340.16 | 103 | 20 | 1 |
| Lung Benign | Lung | Benign | Lung:BEN... | | 189.94 | 406.63 | 1 | 4 | 0 |
| Liver Diseased | Liver | Diseased | Liver:DIS... | | 67.81 | 46.12 | 22 | 0 | 0 |
| Liver Malignant | Liver | Malignant | Liver:MAL... | | 48.36 | 128.64 | 14 | 11 | 0 |
| Liver Normal | Liver | Normal | Liver:NORM... | | 58.22 | 18.95 | 6 | 0 | 0 |
| Prostate Malignant | Prostate | Malignant | Prostate:MAL | | 53.33 | 76.76 | 64 | 8 | 1 |
| Prostate Normal | Prostate | Normal | Prostate:NOR... | | 101.58 | 188.93 | 30 | 2 | 0 |
| Pancreas Normal | Pancreas | Normal | Pancreas:NOR... | | 50.23 | 47.53 | 12 | 1 | 0 |
| Prostate Diseased | Prostate | Diseased | Prostate:DIS... | | 43.30 | 45.82 | 17 | 2 | 1 |
| Pancreas Benign | Pancreas | Benign | Pancreas:BEN... | | 31.14 | 27.97 | 3 | 2 | 0 |
| Pancreas Malignant | Pancreas | Malignant | Pancrease:MAL... | | 66.48 | 83.74 | 54 | 10 | 2 |

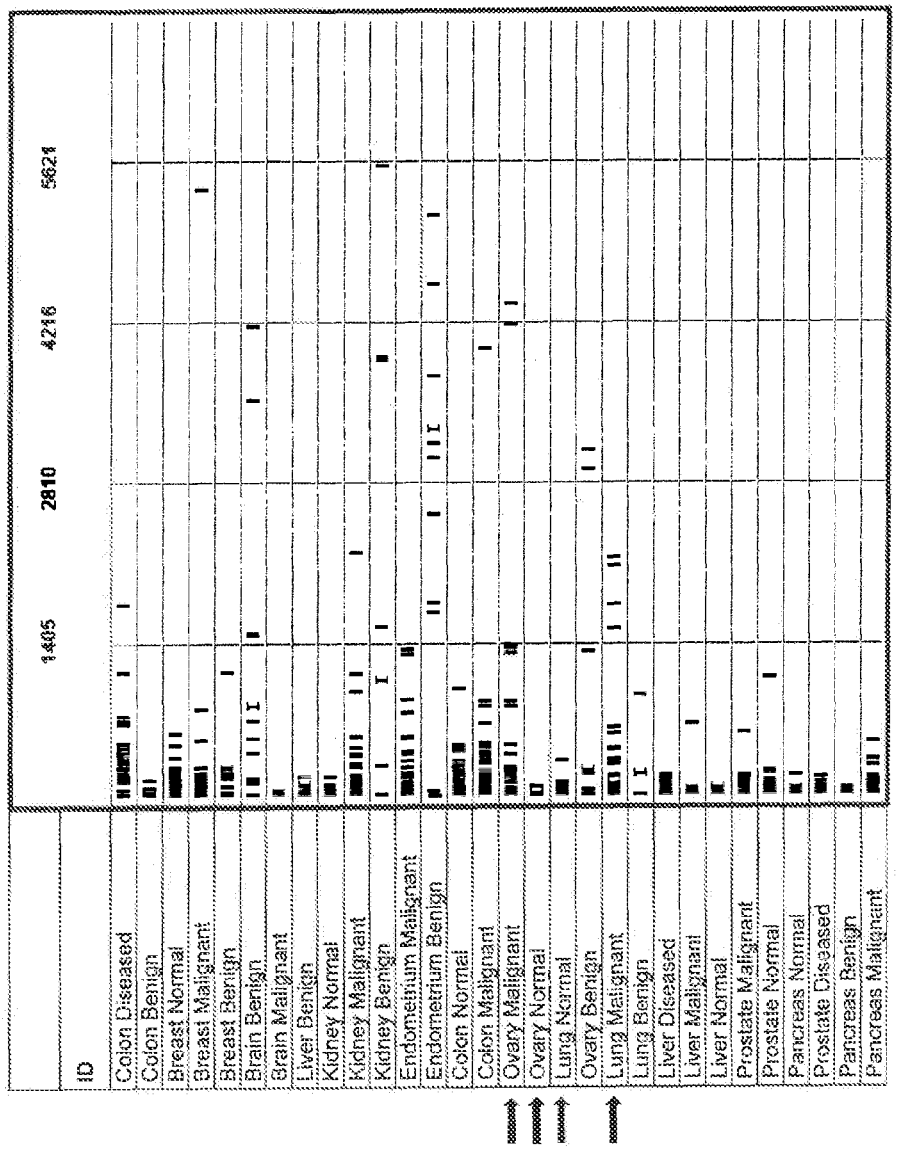

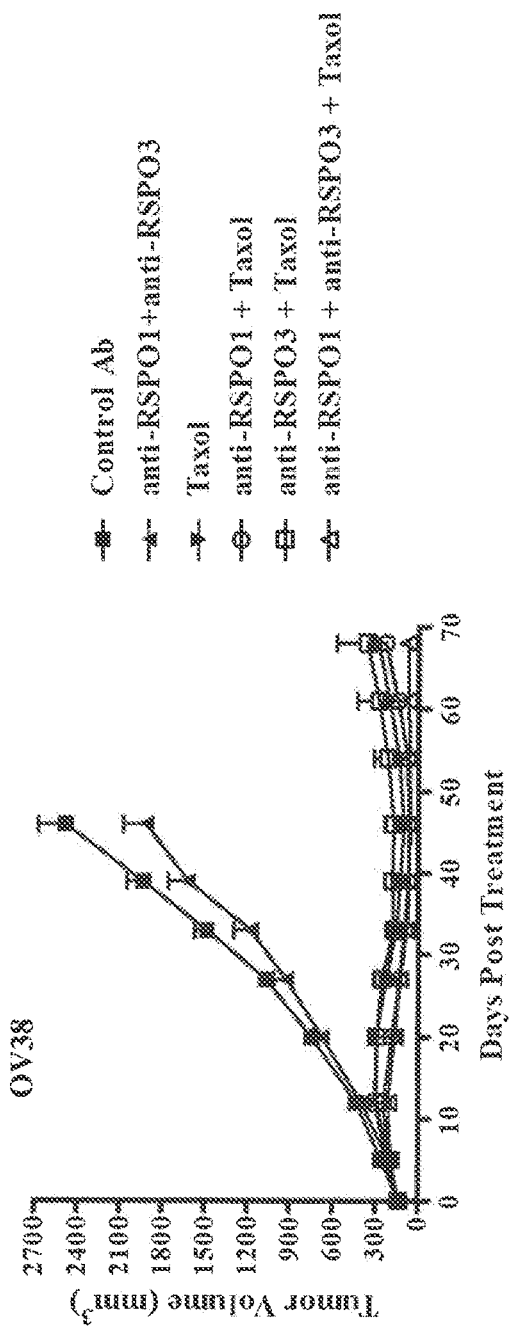

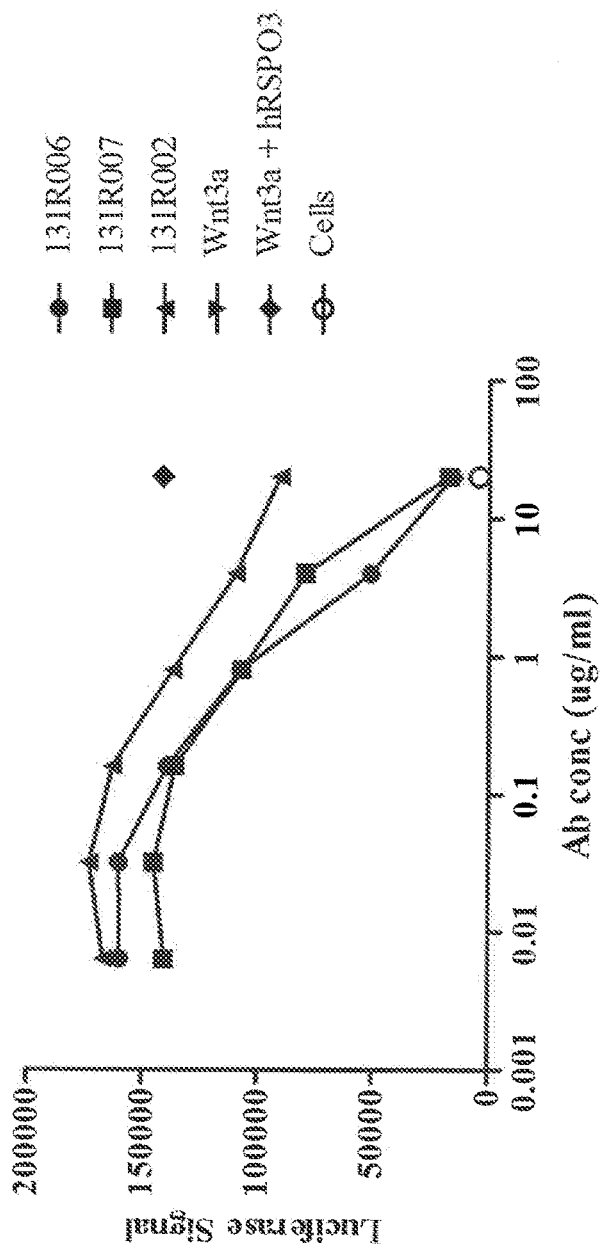

Fig. 11B

Anti-RSPO3 antibody + Carboplatin

| Geneset | SIZE | p-val |
|---|---|---|
| BATLLE_HU_PROLIFERATION | 184 | 0.00E+00 |
| TIAN_GBM_CD133_UP | 83 | 0.00E+00 |
| NEVINS_CSR | 85 | 0.00E+00 |
| OMP_CD201+_HIGH | 240 | 0.00E+00 |
| WONG_EMBRYONIC_STEM_CELL_CORE | 329 | 0.00E+00 |
| WEINBERG_PROLIFERATION | 147 | 0.00E+00 |
| WEINBERG_ES_1 | 371 | 0.00E+00 |
| RICKMAN_TUMOR_DIFFERENTIATED_W | 106 | 0.00E+00 |
| WEINBERG_OCT4_TARGETS | 286 | 1.33E-02 |
| MILANO_GSI_RAT_DN | 57 | 1.66E-02 |
| WEINBERG_ES_2 | 35 | 2.34E-02 |
| PN_CD201_LOGIT18 | 18 | 4.71E-02 |

Anti-RSPO3 antibody as single agent

| Geneset | SIZE | p-val |
|---|---|---|
| OMP_DLL4_UP | 88 | 0.00E+00 |
| WEINBERG_ES_1 | 371 | 7.30E-03 |
| OMP_NEWCSC_UP | 66 | 8.32E-03 |
| CURATED_TGFB | 200 | 2.23E-02 |
| CURATED_STEMCELL | 280 | 2.48E-02 |

Carboplatin as single agent

| Geneset | SIZE | p-val |
|---|---|---|
| ASSOU_ESC_DN | 69 | 1.43E-03 |

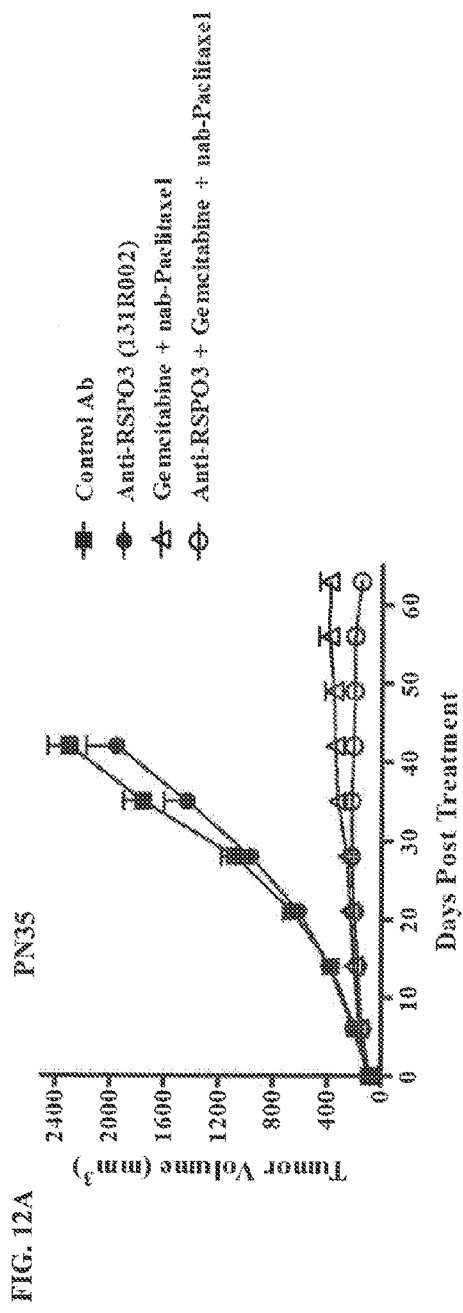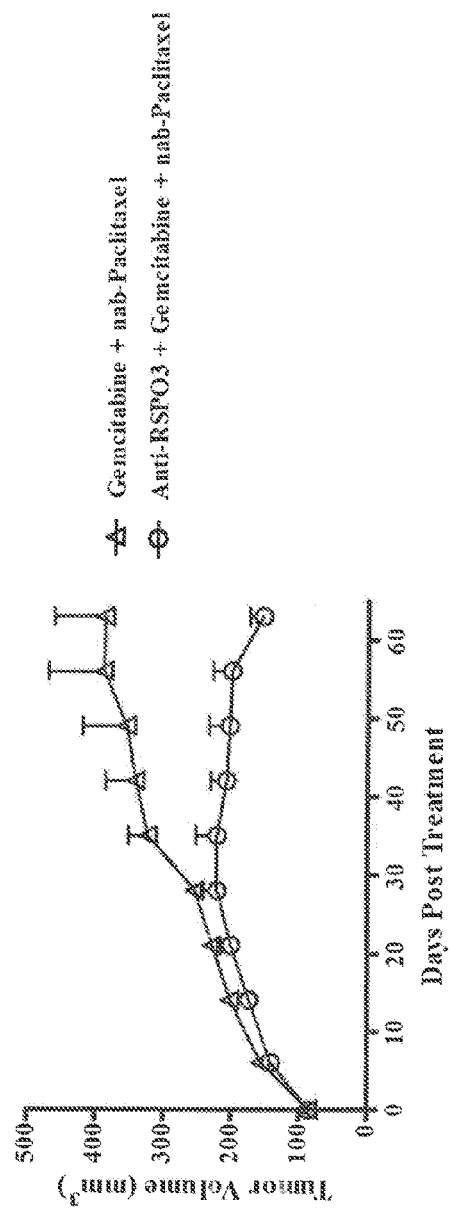
Figs. 12A and 12B
FIG. 12A
FIG. 12B

RSPO3 BINDING AGENTS AND USES THEREOF

CROSS-REFERENCE TO RELATED APPLICATIONS

This application claims priority benefit of U.S. Provisional Application No. 61/671,421, filed Jul. 13, 2012, U.S. Provisional Application No. 61/753,184, filed Jan. 16, 2013, U.S. Provisional Application No. 61/789,156, filed Mar. 15, 2013, and U.S. Provisional Application No. 61/826,747, filed May 23, 2013, each of which is hereby incorporated by reference herein in its entirety.

FIELD OF THE INVENTION

The field of this invention generally relates to antibodies and other agents that bind R-Spondin proteins (RSPO), particularly human R-Spondin protein RSPO3, as well as to methods of using the antibodies or other agents for the treatment of diseases such as cancer.

BACKGROUND OF THE INVENTION

The R-Spondin (RSPO) family of proteins is conserved among vertebrates and comprises four members, RSPO1, RSPO2, RSPO3, and RSPO4. These proteins have been referred to by a variety of names, including roof plate-specific spondins, hPWTSR (hRSPO3), THS2D (RSPO3), Cristin 1-4, and Futrin 1-4. The RSPOs are small secreted proteins that overall share approximately 40-60% sequence homology and domain organization. All RSPO proteins contain two furin-like cysteine-rich domains at the N-terminus followed by a thrombospondin domain and a basic charged C-terminal tail (Kim et al., 2006, Cell Cycle, 5:23-26).

Studies have shown that RSPO proteins have a role during vertebrate development (Kamata et al., 2004, Biochim. Biophys Acta, 1676:51-62) and in Xenopus myogenesis (Kazanskaya et al., 2004, Dev. Cell, 7:525-534). RSPO1 has also been shown to function as a potent mitogen for gastrointestinal epithelial cells (Kim et al., 2005, Science, 309:1256-1259). It has been reported that RSPO3 is prominently expressed in or close by endothelial cells and their cellular precursors in Xenopus and mouse. Furthermore, it has been suggested that RSPO3 may act as an angiogenic factor in embryogenesis (Kazanskaya et al., 2008, Development, 135: 3655-3664). RSPO proteins are known to activate β-catenin signaling similar to Wnt signaling, however the relationship between RSPO proteins and Wnt signaling is still being investigated. It has been reported that RSPO proteins possess a positive modulatory activity on Wnt ligands (Nam et al., 2006, JBC 281:13247-57). This study also reported that RSPO proteins could function as Frizzled8 and LRP6 receptor ligands and induce β-catenin signaling (Nam et al., 2006, JBC 281:13247-57). Recent studies have identified an interaction between RSPO proteins and LGR (leucine-rich repeat containing, G protein-coupler receptor) proteins, such as LGR5 (U.S. Patent Publication Nos. 2009/0074782 and 2009/0191205), and these data present an alternative pathway for the activation of β-catenin signaling.

The Wnt signaling pathway has been identified as a potential target for cancer therapy. The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it is believed the activation can alter the developmental fate of cells. The activation of the Wnt pathway may maintain tumor cells in an undifferentiated state and/or lead to uncontrolled proliferation. Thus carcinogenesis can proceed by overtaking homeostatic mechanisms which control normal development and tissue repair (reviewed in Reya & Clevers, 2005, Nature, 434:843-50; Beachy et al., 2004, Nature, 432:324-31).

The Wnt signaling pathway was first elucidated in the Drosophila developmental mutant wingless (wg) and from the murine proto-oncogene int-1, now Wnt1 (Nusse & Varmus, 1982, Cell, 31:99-109; Van Ooyen & Nusse, 1984, Cell, 39:233-40; Cabrera et al., 1987, Cell, 50:659-63; Rijsewijk et al., 1987, Cell, 50:649-57). Wnt genes encode secreted lipid-modified glycoproteins of which 19 have been identified in mammals. These secreted ligands activate a receptor complex consisting of a Frizzled (FZD) receptor family member and low-density lipoprotein (LDL) receptor-related protein 5 or 6 (LRP5/6). The FZD receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fri domain. There are ten human FZD receptors, FZD1, FZD2, FZD3, FZD4, FZD5, FZD6, FZD7, FZD8, FZD9, and FZD10. Different FZD CRDs have different binding affinities for specific Wnt proteins (Wu & Nusse, 2002, J. Biol. Chem., 277:41762-9), and FZD receptors have been grouped into those that activate the canonical β-catenin pathway and those that activate non-canonical pathways (Miller et al., 1999, Oncogene, 18:7860-72).

A role for Wnt signaling in cancer was first uncovered with the identification of Wnt1 (originally int1) as an oncogene in mammary tumors transformed by the nearby insertion of a murine virus (Nusse & Varmus, 1982, Cell, 31:99-109). Additional evidence for the role of Wnt signaling in breast cancer has since accumulated. For instance, transgenic over-expression of β-catenin in the mammary glands results in hyperplasias and adenocarcinomas (Imbert et al., 2001, J. Cell Biol., 153:555-68; Michaelson & Leder, 2001, Oncogene, 20:5093-9) whereas loss of Wnt signaling disrupts normal mammary gland development (Tepera et al., 2003, J. Cell Sci., 116: 1137-49; Hatsell et al., 2003, J. Mammary Gland Biol. Neoplasia, 8:145-58). In human breast cancer, β-catenin accumulation implicates activated Wnt signaling in over 50% of carcinomas, and though specific mutations have not been identified, up-regulation of Frizzled receptor expression has been observed (Brennan & Brown, 2004, J. Mammary Gland Biol. Neoplasia, 9:119-31; Malovanovic et al., 2004, Int. J. Oncol., 25:1337-42).

Activation of the Wnt pathway is also associated with colorectal cancer. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including Axin and β-catenin. Individual adenomas are clonal outgrowths of epithelial cells containing a second inactivated allele, and the large number of FAP adenomas inevitably results in the development of adenocarcinomas through additional mutations in oncogenes and/or tumor suppressor genes. Furthermore, activation of the Wnt signaling pathway, including loss-of-function mutations in APC and stabilizing mutations in β-catenin, can induce hyperplastic development and tumor growth in mouse models (Oshima et al., 1997, Cancer Res., 57:1644-9; Harada et al., 1999, EMBO J., 18:5931-42).

Similar to breast cancer and colon cancer, melanoma often has constitutive activation of the Wnt pathway, as indicated by the nuclear accumulation of β-catenin. Activation of the Wnt/β-catenin pathway in some melanoma tumors and cell lines is due to modifications in pathway components, such as APC, ICAT, LEF1 and β-catenin (see e.g., Larue et al. 2006, Frontiers Biosci., 11:733-742). However, there are conflicting reports in the literature as to the exact role of Wnt/β-catenin signaling in melanoma. For example, one study found that elevated levels of nuclear β-catenin correlated with improved survival from melanoma, and that activated Wnt/β-catenin signaling was associated with decreased cell proliferation (Chien et al., 2009, PNAS, 106:1193-1198).

The focus of cancer drug research is shifting toward targeted therapies aimed at genes, proteins, and pathways involved in human cancer. There is a need for new agents targeting signaling pathways and new combinations of agents that target multiple pathways that could provide therapeutic benefit for cancer patients. Thus, biomolecules (e.g., anti-RSPO3 antibodies) that disrupt β-catenin signaling are a potential source of new therapeutic agents for cancer, as well as other β-catenin-associated diseases.

BRIEF SUMMARY OF THE INVENTION

The present invention provides binding agents, such as antibodies, that bind RSPO3 proteins, as well as compositions, such as pharmaceutical compositions, comprising the binding agents. Binding agents that bind RSPO3 as well as at least one additional antigen or target, and pharmaceutical compositions of such binding agents, are also provided. In certain embodiments, the RSPO3-binding agents are novel polypeptides, such as antibodies, antibody fragments, and other polypeptides related to such antibodies. The invention further provides methods of inhibiting the growth of a tumor by administering the RSPO3-binding agents to a subject with a tumor. The invention further provides methods of treating cancer by administering the RSPO3-binding agents to a subject in need thereof. In some embodiments, the methods of treating cancer or inhibiting tumor growth comprise targeting cancer stem cells with the RSPO3-binding agents. In some embodiments, the methods comprise disrupting β-catenin signaling. In some embodiments, the methods comprise modulating (e.g., inhibiting) angiogenesis. In certain embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor.

In one aspect, the invention provides a binding agent, such as an antibody, that specifically binds human RSPO3. The sequence of human RSPO3 is known in the art and is included herein as SEQ ID NO:3. In certain embodiments, the RSPO3-binding agent binds within amino acids 22-272 of human RSPO3. In certain embodiments, the RSPO3-binding agent binds within amino acids 22-207 of human RSPO3. In certain embodiments, the RSPO3-binding agent binds within amino acids 35-135 of human RSPO3. In certain embodiments, the RSPO3-binding agent binds within amino acids 35-86 of human RSPO3. In certain embodiments, the RSPO3-binding agent binds within amino acids 92-135 of human RSPO3. In some embodiments, the RSPO3-binding agent (e.g., an antibody) specifically binds at least one other human RSPO selected from the group consisting of RSPO1, RSPO2, and RSPO4. In some embodiments, the RSPO3-binding agent or antibody modulates β-catenin activity, is an antagonist of β-catenin signaling, inhibits β-catenin signaling, and/or inhibits activation of β-catenin. In some embodiments, the RSPO3-binding agent inhibits RSPO3 signaling. In some embodiments, the RSPO3-binding agent inhibits, interferes with, and/or disrupts binding of RSPO3 to one or more LGR proteins (e.g., LGR4, LGR5, and/or LGR6). In some embodiments, the RSPO3-binding agent inhibits binding of RSPO3 to LGR5.

In certain embodiments, the RSPO3-binding agent is an antibody which binds human RSPO3. In some embodiments, the antibody binds human RSPO3 and mouse RSPO3. In certain embodiments, the antibody comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35), or TYFANNFD (SEQ ID NO:80). In some embodiments, the antibody further comprises a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83). In some embodiments, the antibody comprises a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANNFDY (SEQ ID NO:35), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In some embodiments, the antibody comprises a heavy chain CDR1 comprising DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and/or a light chain CDR1 comprising KASQSVDYDGDSYMN (SEQ ID NO:81), a light chain CDR2 comprising AASNLES (SEQ ID NO:82), and a light chain CDR3 comprising QQSNEDPLTF (SEQ ID NO:83). In some embodiments, the antibody comprises a heavy chain CDR1 comprising DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and/or a light chain CDR1 comprising KASQSVDYDGDSYMN (SEQ ID NO:81), a light chain CDR2 comprising AASNLES (SEQ ID NO:82), and a light chain CDR3 comprising QQSNEDPLT (SEQ ID NO:14). In some embodiments, the antibody comprises a heavy chain CDR1 comprising KASGYTFTDYS (SEQ ID NO:9) or DYSIH (SEQ ID NO:78), a heavy chain CDR2 comprising IYPSNGDS (SEQ ID NO:10), and a heavy chain CDR3 comprising TYFANNFD (SEQ ID NO:80), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14).

In certain embodiments, the RSPO3-binding agent is an antibody which comprises: (a) a heavy chain CDR1 comprising KASGYTFTDYS (SEQ ID NO:9), KASGYTFTSYTF (SEQ ID NO:34), DYSIH (SEQ ID NO:78), or a variant thereof comprising 1, 2, 3, or 4 amino acid substitutions; (b) a heavy chain CDR2 comprising IYPSNGDS (SEQ ID NO:10), YIYPSNGDSGYNQKFK (SEQ ID NO:79), or a variant thereof comprising 1, 2, 3, or 4 amino acid substitutions; (c) a heavy chain CDR3 comprising ATYFANYFDY (SEQ ID NO:11), ATYFANNFDY (SEQ ID NO:35), TYFANNFD (SEQ ID NO:80), or a variant thereof comprising 1, 2, 3, or 4 amino acid substitutions; (d) a light chain CDR1 comprising QSVDYDGDSYM (SEQ ID NO:12), KASQSVDYDGDSYMN (SEQ ID NO:81), or a variant thereof comprising 1, 2, 3, or 4 amino acid substitutions; (e) a light chain CDR2 comprising AAS (SEQ ID NO:13), AASNLES (SEQ ID NO:82), or a variant thereof comprising 1, 2, 3, or 4 amino acid substitutions; and (f) a light chain CDR3 comprising QQSNEDPLT (SEQ ID NO:14), QQSNEDPLTF (SEQ ID NO:83), or a variant thereof comprising 1, 2, 3, or 4 amino acid substitutions. In some embodiments, the amino acid substitutions are conservative amino acid substitutions. In some embodiments, the substitutions are made as part of a germline humanization process.

In certain embodiments, the RSPO3-binding agent is an antibody which comprises: (a) a heavy chain variable region having at least 80% sequence identity to SEQ ID NO:15, SEQ ID NO:16, SEQ ID NO:36, SEQ ID NO:37, SEQ ID NO:44, SEQ ID NO:45, or SEQ ID NO:62; and/or (b) a light chain variable region having at least 80% sequence identity to SEQ ID NO:17, SEQ ID NO:72, or SEQ ID NO:86. In certain embodiments, the RSPO3-binding agent is an antibody that comprises: (a) a heavy chain variable region having at least 90% sequence identity to SEQ ID NO:15, SEQ ID NO:16, SEQ ID NO:36, SEQ ID NO:37, SEQ ID NO:44, SEQ ID NO:45, or SEQ ID NO:62; and/or (b) a light chain variable region having at least 90% sequence identity to SEQ ID NO:17, SEQ ID NO:72, or SEQ ID NO:86.

In some embodiments, the RSPO3-binding agent is a monoclonal antibody. In some embodiments, the monoclonal antibody is an IgG1 antibody. In some embodiments, the monoclonal antibody is an IgG2 antibody. In some embodiments, the RSPO3-binding agent is monoclonal antibody 131R002 or monoclonal antibody 131R003. In some embodiments, the RSPO3-binding agent is an affinity-matured variant of monoclonal antibody 131R002 or monoclonal antibody 131R003. In some embodiments, the RSPO3-binding agent is a chimeric antibody comprising the antigen-binding sites from antibody 131R002 or antibody 131R003. In some embodiments, the RSPO3-binding agent is a humanized form of antibody 131R002 or antibody 131R003. In some embodiments, the RSPO3-binding agent is antibody h131R006A, h131R006B, h131R005/131R007, h131R008, h131R010, or h131R011.

In another aspect, the invention provides a binding agent (e.g., an antibody) that competes for specific binding to human RSPO3 with an antibody of the invention. In some embodiments, the binding agent (e.g., an antibody) competes for specific binding to human RSPO3 with an antibody that comprises a heavy chain variable region comprising SEQ ID NO:15, SEQ ID NO:16, SEQ ID NO:36, SEQ ID NO:37, SEQ ID NO:44, SEQ ID NO:45, or SEQ ID NO:62, and a light chain variable region comprising SEQ ID NO:17, SEQ ID NO:72, or SEQ ID NO:86. In some embodiments, the antibody with which the RSPO3-binding agent competes is antibody 131R002 or antibody 131R003. In some embodiments, the antibody with which the RSPO3-binding agent competes is a humanized form of antibody 131R002 or antibody 131R003. In some embodiments, the antibody with which the RSPO3-binding agent competes is antibody 131R006A, 131R006B, h131R005/131R007, h131R008, h131R010, or h131R011. In some embodiments, the binding agent competes for specific binding to RSPO3 with an antibody of the invention in an in vitro competitive binding assay.

In certain embodiments, the binding agent is an antibody that binds the same epitope, or essentially the same epitope, on RSPO3 as an antibody of the invention (e.g., 131R002, 131R003, or humanized forms/variants thereof). In certain embodiments, the binding agent is an antibody that antibody binds the same epitope, or essentially the same epitope, on RSPO3 as antibody h131R005/131R007, h131R008, h131R010, or h131R011.

In still another aspect, the binding agent is an antibody that binds an epitope on RSPO3 that overlaps with the epitope on RSPO3 bound by an antibody of the invention (e.g., 131R002, 131R003, or humanized forms/variants thereof). In some embodiments, the binding agent is an antibody that binds an epitope on RSPO3 that overlaps with the epitope on RSPO3 bound by antibody h131R005/131R007, h131R008, h131R010, or h131R011.

In certain embodiments of each of the aforementioned aspects or embodiments, as well as other aspects and/or embodiments described elsewhere herein, the binding agent is a bispecific antibody. In some embodiments, the bispecific antibody specifically binds human RSPO3 and a second target. In some embodiments, the bispecific antibody specifically binds human RSPO3 and human RSPO1. In some embodiments, the bispecific antibody specifically binds human RSPO3 and human RSPO2. In some embodiments, the bispecific antibody specifically binds human RSPO3 and human RSPO4. In some embodiments, the bispecific antibody modulates β-catenin activity. In certain embodiments, the bispecific antibody inhibits β-catenin activity. In certain embodiments, the bispecific antibody inhibits β-catenin signaling. In certain embodiments, the bispecific antibody inhibits activation of β-catenin. In some embodiments, the bispecific antibody reduces the number of frequency of cancer stem cells. In certain embodiments, the bispecific antibody comprises two identical light chains. In certain embodiments, the bispecific antibody is an IgG antibody. In certain embodiments, the bispecific antibody is an IgG1 antibody. In certain embodiments, the bispecific antibody is an IgG2 antibody.

In some embodiments, the bispecific antibody comprises: a first antigen-binding site that specifically binds human RSPO3, wherein the first antigen-binding site comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35), or TYFANNFD (SEQ ID NO:80). In some embodiments, the first antigen-binding site comprises a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83). In some embodiments, the bispecific antibody further comprises a second antigen-binding site that specifically binds human RSPO1. In some embodiments, the bispecific antibody further comprises a second antigen-binding site that specifically binds human RSPO2. Non-limiting examples of antibodies to RSPO1 or antibodies to RSPO2 have been described in, for example, International Patent Application Pub. No. WO 2013/012747. In some embodiments, the first and second binding sites comprise a common (e.g., identical) light chain.

In some embodiments, the bispecific antibody comprises: a) a first antigen-binding site that specifically binds human RSPO3, and b) a second antigen-binding site that specifically binds human RSPO1, wherein the first antigen-binding site comprises a heavy chain CDR1 comprising KASGYTFT-DYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATY-FANYFDY (SEQ ID NO:11), ATYFANNFDY (SEQ ID NO:35), or TYFANNFD (SEQ ID NO:80). In some embodiments, the bispecific antibody comprises: a) a first antigen-binding site that specifically binds human RSPO3, and b) a second antigen-binding site that specifically binds human RSPO2, wherein the first antigen-binding site comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATY-FANYFDY (SEQ ID NO:11), ATYFANNFDY (SEQ ID NO:35), or TYFANNFD (SEQ ID NO:80). In some embodiments, the first antigen-binding site comprises a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83).

In some embodiments, the bispecific antibody specifically binds human RSPO3 and comprises: a heavy chain variable region having at least 90% sequence identity to SEQ ID NO:15, SEQ ID NO:16, SEQ ID NO:36, SEQ ID NO:37, SEQ ID NO:44, SEQ ID NO:45, or SEQ ID NO:62. In some embodiments, the bispecific antibody specifically binds human RSPO3 and comprises: a heavy chain variable region having at least 95% sequence identity to SEQ ID NO:15, SEQ ID NO:16, SEQ ID NO:36, SEQ ID NO:37, SEQ ID NO:44, SEQ ID NO:45, or SEQ ID NO:62. In some embodiments, the bispecific antibody comprises a first and second binding site, wherein the first and second binding sites comprise a common (e.g., identical) light chain. In some embodiments, the bispecific antibody comprises a light chain variable region having at least 95% sequence identity to SEQ ID NO:17, SEQ ID NO:72, or SEQ ID NO:86.

In certain embodiments of each of the aforementioned aspects, as well as other aspects and/or embodiments described elsewhere herein, the RSPO3-binding agent or antibody is isolated. In some embodiments, the RSPO3-binding agent or antibody is substantially pure.

In another aspect, the invention provides polypeptides. In some embodiments, the polypeptide comprises a sequence selected from the group consisting of: SEQ ID NO:15, SEQ ID NO:16, SEQ ID NO:17, SEQ ID NO:21, SEQ ID NO:22. SEQ ID NO:23, SEQ ID NO:27, SEQ ID NO:28, SEQ ID NO:29, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, SEQ ID NO:48, SEQ ID NO:49, SEQ ID NO:62, SEQ ID NO:63, SEQ ID NO:64, SEQ ID NO:68, SEQ ID NO:69, SEQ ID NO:72, SEQ ID NO:73, SEQ ID NO:74, SEQ ID NO:86, SEQ ID NO:87, and SEQ ID NO:88. In some embodiments, the polypeptide comprises SEQ ID NO:15 and/or SEQ ID NO:17. In some embodiments, the polypeptide comprises SEQ ID NO:16 and/or SEQ ID NO:17. In some embodiments, the polypeptide comprises SEQ ID NO:36 and/or SEQ ID NO:17. In some embodiments, the polypeptide comprises SEQ ID NO:37 and/or SEQ ID NO:17. In some embodiments, the polypeptide comprises SEQ ID NO:44 and/or SEQ ID NO:17. In some embodiments, the polypeptide comprises SEQ ID NO:45 and/or SEQ ID NO:17. In some embodiments, the polypeptide comprises SEQ ID NO:62 and/or SEQ ID NO:17. In some embodiments, the polypeptide comprises SEQ ID NO:44 and/or SEQ ID NO:72. In some embodiments, the polypeptide comprises SEQ ID NO:45 and/or SEQ ID NO:72. In some embodiments, the polypeptide comprises SEQ ID NO:62 and/or SEQ ID NO:72. In some embodiments, the polypeptide comprises SEQ ID NO:44 and/or SEQ ID NO:86. In some embodiments, the polypeptide comprises SEQ ID NO:45 and/or SEQ ID NO:86. In some embodiments, the polypeptide comprises SEQ ID NO:62 and/or SEQ ID NO:86.

In some embodiments, the polypeptide comprises SEQ ID NO:21 and/or SEQ ID NO:23. In some embodiments, the polypeptide comprises SEQ ID NO:22 and/or SEQ ID NO:23. In some embodiments, the polypeptide comprises SEQ ID NO:38 and/or SEQ ID NO:23. In some embodiments, the polypeptide comprises SEQ ID NO:41 and/or SEQ ID NO:23. In some embodiments, the polypeptide comprises SEQ ID NO:46 and/or SEQ ID NO:23. In some embodiments, the polypeptide comprises SEQ ID NO:47 and/or SEQ ID NO:23. In some embodiments, the polypeptide comprises SEQ ID NO:63 and/or SEQ ID NO:23. In some embodiments, the polypeptide comprises SEQ ID NO:68 and/or SEQ ID NO:23. In some embodiments, the polypeptide comprises SEQ ID NO:46 and/or SEQ ID NO:73. In some embodiments, the polypeptide comprises SEQ ID NO:47 and/or SEQ ID NO:73. In some embodiments, the polypeptide comprises SEQ ID NO:63 and/or SEQ ID NO:73. In some embodiments, the polypeptide comprises SEQ ID NO:68 and/or SEQ ID NO:73. In some embodiments, the polypeptide comprises SEQ ID NO:46 and/or SEQ ID NO:87. In some embodiments, the polypeptide comprises SEQ ID NO:47 and/or SEQ ID NO:87. In some embodiments, the polypeptide comprises SEQ ID NO:63 and/or SEQ ID NO:87. In some embodiments, the polypeptide comprises SEQ ID NO:68 and/or SEQ ID NO:87.

In some embodiments, the polypeptide comprises SEQ ID NO:27 and/or SEQ ID NO:29. In some embodiments, the polypeptide comprises SEQ ID NO:28 and/or SEQ ID NO:29. In some embodiments, the polypeptide comprises SEQ ID NO:39 and/or SEQ ID NO:29. In some embodiments, the polypeptide comprises SEQ ID NO:42 and/or SEQ ID NO:29. In some embodiments, the polypeptide comprises SEQ ID NO:48 and/or SEQ ID NO:29. In some embodiments, the polypeptide comprises SEQ ID NO:49 and/or SEQ ID NO:29. In some embodiments, the polypeptide comprises SEQ ID NO:64 and/or SEQ ID NO:29. In some embodiments, the polypeptide comprises SEQ ID NO:69 and/or SEQ ID NO:29. In some embodiments, the polypeptide comprises SEQ ID NO:48 and/or SEQ ID NO:74. In some embodiments, the polypeptide comprises SEQ ID NO:49 and/or SEQ ID NO:74. In some embodiments, the polypeptide comprises SEQ ID NO:64 and/or SEQ ID NO:74. In some embodiments, the polypeptide comprises SEQ ID NO:69 and/or SEQ ID NO:74. In some embodiments, the polypeptide comprises SEQ ID NO:48 and/or SEQ ID NO:88. In some embodiments, the polypeptide comprises SEQ ID NO:49 and/or SEQ ID NO:88. In some embodiments, the polypeptide comprises SEQ ID NO:64 and/or SEQ ID NO:88. In some embodiments, the polypeptide comprises SEQ ID NO:69 and/or SEQ ID NO:88.

In some embodiments, the polypeptide is isolated. In certain embodiments, the polypeptide is substantially pure. In certain embodiments, the polypeptide is an antibody or part of any antibody, such as an antibody fragment.

In another aspect, the invention provides isolated polynucleotide molecules comprising a polynucleotide that encodes the antibodies and/or polypeptides of each of the aforementioned aspects, as well as other aspects and/or embodiments described herein. In some embodiments, the polynucleotide comprises a sequence selected from the group consisting of SEQ ID NO:18, SEQ ID NO:19, SEQ ID NO:20, SEQ ID NO:24, SEQ ID NO:25, SEQ ID NO:26, SEQ ID NO:30, SEQ ID NO:31, SEQ ID NO:32, SEQ ID NO:40, SEQ ID NO:43, SEQ ID NO:50, SEQ ID NO:51, SEQ ID NO:52, SEQ ID NO:53, SEQ ID NO:54, SEQ ID NO:55, SEQ ID NO:65, SEQ ID NO:66, SEQ ID NO:67, SEQ ID NO:70, SEQ ID NO:71, SEQ ID NO:75, SEQ ID NO:76, SEQ ID NO:77, SEQ ID NO:84, SEQ ID NO:85, SEQ ID NO:89, SEQ ID NO:90, SEQ ID NO:91, SEQ ID NO:92, SEQ ID NO:93, SEQ ID NO:94, and SEQ ID NO:95. In some embodiments, the polynucleotide comprises a polynucleotide that encodes a polypeptide selected from the group consisting of: SEQ ID NO:15, SEQ ID NO:16, SEQ ID NO:17, SEQ ID NO:21, SEQ ID NO:22, SEQ ID NO:23, SEQ ID NO:27, SEQ ID NO:28, SEQ ID NO:29, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, SEQ ID NO:48, SEQ ID NO:49, SEQ ID NO:62, SEQ ID NO:63, SEQ ID NO:64, SEQ ID NO:68, SEQ ID NO:69, SEQ ID NO:72, SEQ ID NO:73, SEQ ID NO:74, SEQ ID NO:86, SEQ ID NO:87, and SEQ ID NO:88.

The invention further provides expression vectors that comprise the polynucleotides, as well as cells that comprise the expression vectors and/or the polynucleotides. In some embodiments, the cell is a hybridoma cell line. In some embodiments, the cell is a monoclonal cell line. In some embodiments, the cell is a prokaryotic cell. In some embodiments, the cell is an eukaryotic cell.

In other aspects, the invention provides methods of inhibiting growth of a tumor, comprising contacting the tumor with an effective amount of a RSPO3-binding agent or antibody, including each of those described herein.

In another aspect, the invention provides a method of inhibiting the growth of a tumor in a subject, comprising administering to the subject a therapeutically effective amount of a RSPO3-binding agent or antibody, including each of those described herein.

In another aspect, the invention provides a method of inhibiting β-catenin signaling in a cell, comprising contacting the cell with an effective amount of a RSPO3-binding agent or antibody, including each of those described herein. In some embodiments, the cell is a tumor cell. In some embodiments, the tumor is a colorectal tumor. In some embodiments, the tumor is an ovarian tumor. In some embodiments, the tumor is a pancreatic tumor. In some embodiments, the tumor is a hung tumor. In some embodiments, the tumor is a breast tumor. In some embodiments, the tumor expresses elevated levels of at least one RSPO protein. In some embodiments, the tumor expresses elevated levels of RSPO1. In some embodiments, the tumor expresses elevated levels of RSPO2. In some embodiments, the tumor expresses elevated levels of RSPO3. In some embodiments, the tumor expresses a high level of at least one RSPO protein. In some embodiments, the tumor expresses a high level of RSPO1. In some embodiments, the tumor expresses a high level of RSPO2. In some embodiments, the tumor expresses a high level of RSPO3. In certain embodiments, the RSPO3-binding agent inhibits growth of the tumor, for example, by reducing the number and/or frequency of cancer stem cells in the tumor. In some embodiments, the tumor contains a RSPO gene fusion. In some embodiments, the tumor contains a RSPO2 gene fusion. In some embodiments, the tumor contains a RSPO3 gene fusion.

In another aspect, the invention provides methods of treating cancer in a subject. In some embodiments, the method comprises administering to a subject a therapeutically effective amount of any of the RSPO3-binding agents or antibodies described above, as well as those described elsewhere herein. In some embodiments, the cancer is pancreatic cancer. In some embodiments, the cancer is colorectal cancer. In some embodiments, the colorectal cancer comprises an inactivating mutation in the adenomatous polyposis coli (APC) gene. In some embodiments, the colorectal cancer does not comprise an inactivating mutation in the APC gene. In some embodiments, the colorectal cancer comprises a wild-type APC gene. In some embodiments, the colorectal cancer comprises a RSPO gene fusion. In some embodiments, the colorectal cancer comprises a RSPO2 gene fusion. In some embodiments, the colorectal cancer comprises a RSPO3 gene fusion. In some embodiments, the cancer is ovarian cancer. In some embodiments, the cancer is lung cancer. In some embodiments, the cancer is breast cancer. In some embodiments, the cancer expresses elevated levels of at least one RSPO protein. In some embodiments, the cancer is an ovarian cancer that expresses elevated levels of RSPO3. In some embodiments, the cancer is lung cancer that expresses elevated levels of RSPO3. In some embodiments, the cancer is breast cancer that expresses elevated levels of RSPO3. In some embodiments, the cancer is pancreatic cancer that expresses elevated levels of RSPO3.

In another aspect, the invention provides methods of treating a disease in a subject wherein the disease is associated with activation of β-catenin, increased β-catenin signaling, and/or aberrant β-catenin signaling, wherein the method comprises administering to the subject a therapeutically effective amount of a RSPO3-binding agent or antibody, including each of those described herein.

In certain embodiments of each of the aforementioned aspects, as well as other aspects and/or embodiments described elsewhere herein, the treatment methods further comprise a step of determining the expression level of at least one RSPO protein in the tumor or cancer.

In another aspect, the invention provides a method of identifying a human subject or selecting a human subject for treatment with a RSPO3-binding agent or antibody, including but not limited to, each of those described herein. In some embodiments, the method comprises determining if the subject has a tumor that has an elevated expression level of a specific RSPO (e.g., RSPO3) as compared to the expression of the same RSPO protein in normal tissue or to a pre-determined level of the same RPSO protein. In some embodiments, the method comprises identifying a subject for treatment or selecting a subject for treatment if the tumor has an elevated level of RSPO expression. In some embodiments, the method comprises determining if the subject has a tumor that comprises an inactivating mutation in the APC gene. In some embodiments, the method comprises identifying a subject for treatment or selecting a subject for treatment if the tumor comprises an inactivating mutation in the APC gene. In some embodiments, the method comprises determining if the subject has a tumor that comprises a RSPO gene fusion (e.g., a RSPO3 gene fusion). In some embodiments, the method comprises identifying a subject for treatment or selecting a subject for treatment if the tumor comprises a RSPO gene fusion (e.g., a RSPO3 gene fusion).

In certain embodiments of each of the aforementioned aspects, as well as other aspects and/or embodiments described elsewhere herein, the treatment methods comprise administering to the subject the RSPO3-binding agent and at least one additional therapeutic agent.

Pharmaceutical compositions comprising a RSPO3-binding agent or antibody described herein and a pharmaceutically acceptable carrier are further provided, as are cell lines that produce the RSPO3-binding agents. Methods of treating cancer and/or inhibiting tumor growth in a subject (e.g., a human) comprising administering to the subject an effective amount of a pharmaceutical composition comprising the RSPO3-binding agents are also provided.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE FIGURES

FIG. 1A. RSPO1 expression in tumors and normal tissues. Shown is a summary of microarray data from normal, benign, and malignant tissue human samples.

FIG. 1C. RSPO2 expression in tumors and normal tissues. Shown is a summary of microarray data from normal, benign, and malignant tissue human samples.

FIG. 1D. RSPO2 expression in tumors and normal tissues. Shown is a summary of microarray data from normal, benign, and malignant tissue human samples. Individual tick marks indicate the expression level of RSPO2 mRNA.

FIG. 1E. RSPO3 expression in tumors and normal tissues. Shown is a summary of microarray data from normal, benign, and malignant tissue human samples.

FIG. 1F. RSPO3 expression in tumors and normal tissues. Shown is a summary of microarray data from normal, benign, and malignant tissue human samples. Individual tick marks indicate the expression level of RSPO3 mRNA.

FIG. 6. Inhibition of tumor growth with anti-RSPO antibodies. OV38 ovarian tumor cells were injected subcutaneously into NOD/SCID mice. Mice were treated with a combination of anti-RSPO1 antibody 89M5 and anti-RSPO3 antibody 131R002 (-▲-), a combination of anti-RSPO1 antibody 89M5 and taxol (-○-), a combination of anti-RSPO3 antibody 131R002 and taxol (-□-), a combination of anti-RSPO1 antibody 89M5, anti-RSPO3 antibody 131R002, and taxol (-Δ-), taxol alone (-▼-), or a control antibody (-■-). Data is shown as tumor volume ($mm^3$) over days post-treatment.

FIG. 8. Affinity-matured antibody variants inhibit β-catenin signaling induced by RSPO3 and WNT3A. A TOPflash luciferase reporter assay was used to measure β-catenin signaling in HEK-293T cells after exposure to a combination of WNT3a and human RSPO3 and in the presence of increasing concentrations of anti-RSPO3 antibody 131R002 (-▲-), 131R006 (-●-), or 131R007 (-■-). Antibodies were used as 5-fold serial dilutions from 20 µg/ml to 0.0064 µg/ml. Controls included exposure to control medium (no WNT3a and no RSPO/cells (-○-)), WNT3a alone (-▼-), or a combination of WNT3a and human RSPO3 in the absence of antibody (-♦-).

FIG. 11B. Gene set enrichment analysis results.

FIG. 12A. Inhibition of tumor growth with anti-RSPO antibodies. PN35 pancreatic tumor cells were injected subcutaneously into NOD/SCID mice. Mice were treated with anti-RSPO3 antibody 131R002 (-●-), a combination of gemcitabine and nab-paclitaxel (ABRAXANE) (-Δ-), a combination of anti-RSPO3 antibody 131R002 and gemcitabine and nab-paclitaxel (ABRAXANE) (-○-), or a control antibody (-■-). Data is shown as tumor volume (mm³) over days post-treatment. All four treatment groups are shown.

FIG. 12B. Inhibition of tumor growth with anti-RSPO antibodies. PN35 pancreatic tumor cells were injected subcutaneously into NOD/SCID mice. Mice were treated with anti-RSPO3 antibody 131R002 (-●-), a combination of gemcitabine and nab-paclitaxel (ABRAXANE) (-Δ-), a combination of anti-RSPO3 antibody 131R002 and gemcitabine and nab-paclitaxel (ABRAXANE) (-○-), or a control antibody (-■-). Data is shown as tumor volume (mm³) over days post-treatment. The gemcitabine and nab-paclitaxel treatment group and the anti-RSPO3 antibody gemcitabine and nab-paclitaxel treatment are shown on an expanded scale.

DETAILED DESCRIPTION OF THE INVENTION

Figure 1B:
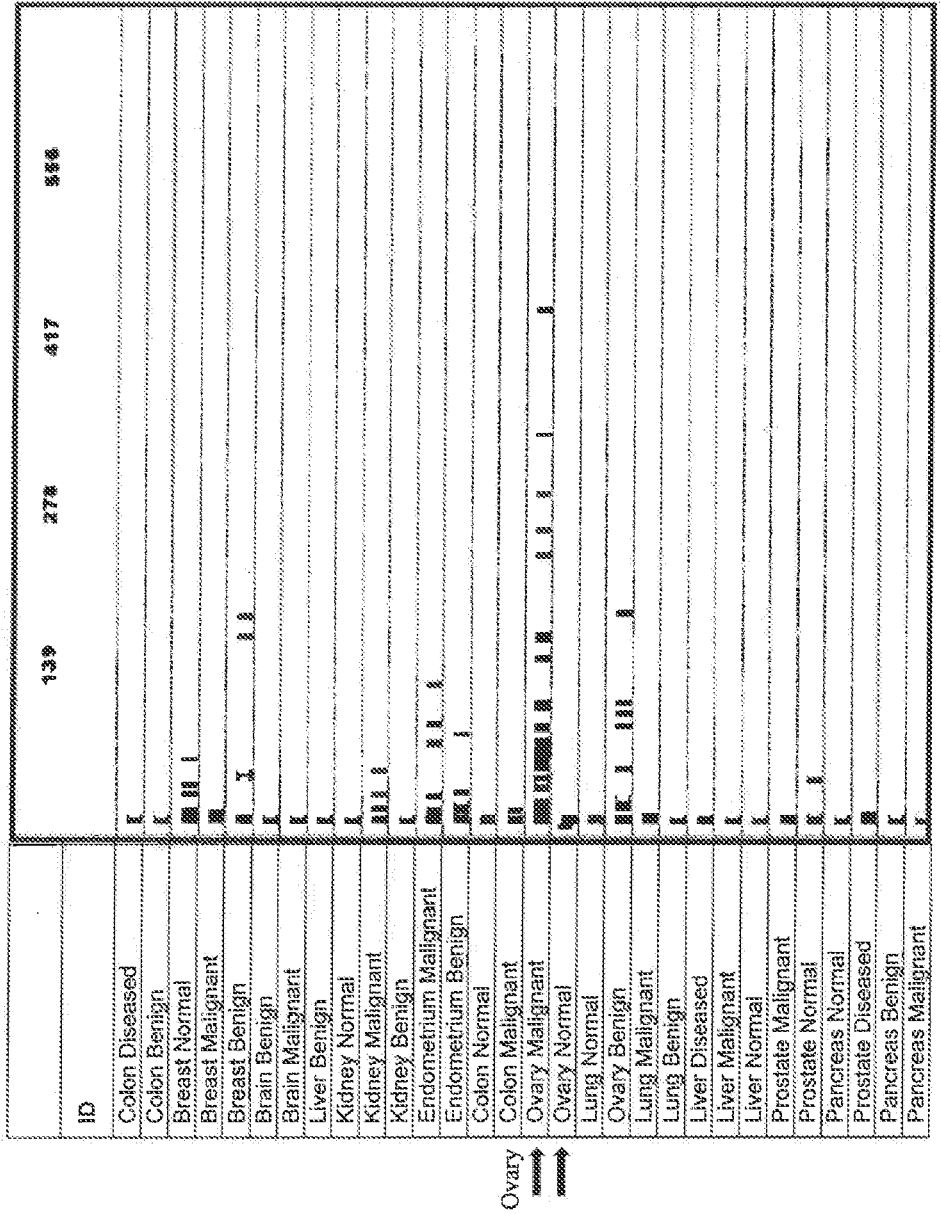
FIG. 1B. RSPO1 expression in tumors and normal tissues. Shown is a summary of microarray data from normal, benign, and malignant tissue human samples. Individual tick marks indicate the expression level of RSPO1 mRNA.

The present invention provides novel agents, including, but not limited to polypeptides such as antibodies, that bind RSPO proteins, particularly human RSPO3. The RSPO3-binding agents include, but are not limited to, antagonists of β-catenin signaling. The RSPO3-binding agents include, but are not limited to, inhibitors of RSPO3 and LGR protein interactions. Related polypeptides and polynucleotides, compositions comprising the RSPO3-binding agents, and methods of making the RSPO3-binding agents are also provided. Methods of using the novel RSPO3-binding agents, such as methods of inhibiting tumor growth, methods of treating cancer, methods of modulating angiogenesis, methods of reducing the frequency of cancer stem cells in a tumor, methods of inhibiting β-catenin signaling, and/or methods of identifying and/or selecting subjects for treatment, are further provided.

Monoclonal antibodies that specifically bind human RSPO3 have been identified—monoclonal antibodies 131R002 and 131R003 (Example 3). Anti-RSPO3 antibodies 131R002 and 131R003 have binding affinities for human RSPO3 of less than 10 nM (Example 3). Anti-RSPO3 antibodies 131R002 and 131R003 inhibit RSPO3-induced β-catenin signaling (Example 4, FIG. 3). Affinity-matured variants of 131R003 inhibit RSPO3-induced β-catenin signaling and have greater activity than parental 131R003 (Example 5, FIG. 4). Anti-RSPO3 antibodies inhibit tumor growth as single agents, in combination with anti-RSPO1 antibodies, and in combination with one or more chemotherapeutic agents (Examples 6, 7, 11, 12 and 14; FIGS. 5-7, 10-12 and 14). Humanized anti-RSPO3 antibodies h131R006 and h131R007 are stronger inhibitors of β-catenin activity than antibody 131R002 (Example 8, FIG. 8). Anti-RSPO3 antibodies h131R006 and h131R007 block binding of RSPO3 to LGR5 (Example 9, FIG. 9). Humanized anti-RSPO3 antibody h131R010 isotype IgG1 inhibits β-catenin activity similar to the IgG2 isotype antibody h131R007 (Example 13, FIG. 13).

I. Definitions

To facilitate an understanding of the present invention, a number of terms and phrases are defined below.

The terms "antagonist" and "antagonistic" as used herein refer to any molecule that partially or fully blocks, inhibits, reduces, or neutralizes a biological activity of a target and/or signaling pathway (e.g., the β-catenin signaling). The term "antagonist" is used herein to include any molecule that partially or fully blocks, inhibits, reduces, or neutralizes the activity of a protein (e.g., a RSPO protein). Suitable antagonist molecules specifically include, but are not limited to, antagonist antibodies or antibody fragments.

The terms "modulation" and "modulate" as used herein refer to a change or an alteration in a biological activity. Modulation includes, but is not limited to, stimulating or inhibiting an activity. Modulation may be an increase or a decrease in activity (e.g., a decrease in RSPO signaling; a decrease in β-catenin signaling), a change in binding characteristics, or any other change in the biological, functional, or immunological properties associated with the activity of a protein, pathway, or other biological point of interest.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen-binding site within the variable region(s) of the immunoglobulin molecule. As used herein, the term encompasses intact polyclonal antibodies, intact monoclonal antibodies, single chain antibodies, antibody fragments (such as Fab, Fab', F(ab')2, and Fv fragments), single chain Fv (scFv) antibodies, multispecific antibodies such as bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen recognition site (i.e., antigen-binding site) as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain, or the variable region of an antibody heavy chain, either alone or in combination. The variable regions of the heavy and light chains each consist of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding site of the antibody. There are at least two techniques for determining CDRs: (1) an approach based on cross-species sequence variability (i.e., Kabat et al., 1991, Sequences of Proteins of Immunological Interest, 5th Edition, National Institutes of Health, Bethesda, Md.), and (2) an approach based on crystallographic studies of antigen-antibody complexes (Al-Lazikani et al., 1997, J. Mol. Biol., 273:927-948). In addition, combinations of these two approaches are sometimes used in the art to determine CDRs.

The term "monoclonal antibody" as used herein refers to a homogeneous antibody population involved in the highly specific recognition and binding of a single antigenic determinant or epitope. This is in contrast to polyclonal antibodies that typically include a mixture of different antibodies directed against a variety of different antigenic determinants. The term "monoclonal antibody" encompasses both intact and full-length monoclonal antibodies as well as antibody fragments (e.g., Fab, Fab', F(ab')2, Fv), single chain (scFv) antibodies, bispecific antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, Nature, 321: 522-525; Riechmann et al., 1988, Nature, 332:323-327; Verhoeyen et al., 1988, Science, 239:1534-1536). In some instances, the Fv framework region residues of a human immunoglobulin are replaced with the corresponding residues in an antibody from a non-human species that has the desired specificity, affinity, structural, and/or binding capability. The humanized antibody can be further modified by the substitution of additional residues either in the Fv framework region and/or within the replaced non-human residues to refine and optimize antibody specificity, affinity, structural, and/or binding capability. In general, the humanized antibody will comprise substantially all of at least one, and typically two or three of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in, for example, U.S. Pat. No. 5,225,539.

The term "human antibody" as used herein refers to an antibody produced by a human or an antibody having an amino acid sequence corresponding to an antibody produced by a human. A human antibody may be made using any of the techniques known in the art. This definition of a human antibody specifically excludes a humanized antibody comprising non-human CDRs.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammal (e.g., mouse, rat, rabbit, etc.) with the desired specificity, affinity, and/or binding capability, while the constant regions correspond to sequences in antibodies derived from another species (usually human).

The phrase "affinity-matured antibody" as used herein refers to an antibody with one or more alterations in one or more CDRs thereof that result in an improvement in the affinity of the antibody for an antigen, compared to a parent antibody that does not possess those alterations(s). The definition also includes alterations in non-CDR residues made in conjunction with alterations to CDR residues. Preferred affinity-matured antibodies will have nanomolar or even picomolar affinities for the target antigen. Affinity-matured antibodies are produced by procedures known in the art. For example, Marks et al., 1992, Bio/Technology 10:779-783, describes affinity maturation by VH and VL domain shuffling. Random mutagenesis of CDR and/or framework residues is described by Barbas et al., 1994, PNAS, 91:3809-3813; Schier et al., 1995, Gene, 169:147-155; Yelton et al., 1995, J. Immunol. 155:1994-2004; Jackson et al., 1995, J. Immunol., 154:3310-9; and Hawkins et al., 1992, J. Mol. Biol., 226:889-896. Site-directed mutagenesis may also be used to obtain affinity-matured antibodies.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "heteromultimeric molecule" or "heteromultimer" or "heteromultimeric complex" or "heteromultimeric polypeptide" are used interchangeably herein to refer to a molecule comprising at least a first polypeptide and a second polypeptide, wherein the second polypeptide differs in amino acid sequence from the first polypeptide by at least one amino acid residue. The heteromultimeric molecule can comprise a "heterodimer" formed by the first and second polypeptide or can form higher order tertiary structures where additional polypeptides are present.

The terms "selectively binds" or "specifically binds" mean that a binding agent or an antibody reacts or associates more frequently, more rapidly, with greater duration, with greater affinity, or with some combination of the above to the epitope, protein or target molecule than with alternative substances, including unrelated proteins. In certain embodiments "specifically binds" means, for instance, that an antibody binds a protein with a $K_D$ of about 0.1 mM or less, but more usually less than about 1 µM. In certain embodiments, "specifically binds" means that an antibody binds a target at times with a $K_D$ of at least about 0.1 µM or less, at other times at least about 0.01 µM or less, and at other times at least about 1 nM or less. Because of the sequence identity between homologous proteins in different species, specific binding can include an antibody that recognizes a protein in more than one species (e.g., human RSPO3 and mouse RSPO3). Likewise, because of homology within certain regions of polypeptide sequences of different proteins, specific binding can include an antibody (or other polypeptide or binding agent) that recognizes more than one protein (e.g., human RSPO3 and human RSPO1). It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins (e.g., RSPO3 and RSPO1). In certain alternative embodiments, an antibody may be multispecific and comprise at least two antigen-binding sites with differing specificities. By way of non-limiting example, a bispecific antibody may comprise one antigen-binding site that recognizes an epitope on one protein (e.g., human RSPO3) and further comprise a second, different antigen-binding site that recognizes a different epitope on a second protein (e.g., human RSPO2). Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains.

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

"Conditions of high stringency" may be identified by those that: (1) employ low ionic strength and high temperature for washing, for example 15 mM NaCl/1.5 mM sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ during hybridization 50% formamide in 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 50% formamide, followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value therebetween. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more RSPO protein(s) to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions.

The term "metastasis" as used herein refers to the process by which a cancer spreads or transfers from the site of origin to other regions of the body with the development of a similar cancerous lesion at a new location. A "metastatic" or "metastasizing" cell is one that loses adhesive contacts with neighboring cells and migrates via the bloodstream or lymph from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form rumors with abnormal cell types that can change over time as mutations occur.

The terms "cancer cell" and "tumor cell" refer to the total population of cells derived from a cancer or tumor or precancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into immunocompromised hosts (e.g., mice). This definition also includes enriched and/or isolated populations of cancer stem cells that form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a product or compound approved (or approvable) by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the activity of the binding agent. The excipient, carrier, or adjuvant should be non-toxic when administered with a binding agent in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., an antibody) has a therapeutic effect and as such can reduce the number of cancer cells; decrease tumorigenicity, tumorigenic frequency or tumorigenic capacity; reduce the number or frequency of cancer stem cells; reduce the tumor size; reduce the cancer cell population; inhibit and/or stop cancer cell infiltration into peripheral organs including, for example, the spread of cancer into soft tissue and bone; inhibit and/or stop tumor or cancer cell metastasis; inhibit and/or stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. In some embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. RSPO-binding agents

The present invention provides agents that specifically bind human RSPO proteins. These agents are referred to herein as "RSPO-binding agents". In some embodiments, the RSPO-binding agent is an antibody. In some embodiments, the RSPO-binding agent is a polypeptide. In certain embodiments, the RSPO-binding agent binds RSPO3 ("RSPO3-binding agents"). In certain embodiments, the RSPO3-binding agent specifically binds at least one other human RSPO. In some embodiments, the at least one other human RSPO bound by a RSPO3-binding agent is selected from the group consisting of RSPO1, RSPO2, and RSPO4. In some embodiments, the RSPO3-binding agent is an antibody that binds a common epitope on RSPO1, RSPO2, and/or RSPO4. In some embodiments, the RSPO3-binding agent is a bispecific antibody that binds a first epitope on RSPO3 and binds a second, different epitope on RSPO1, RSPO2, and/or RSPO4. The full-length amino acid (aa) sequences for human RSPO1, RSPO2, RSPO3, and RSPO4 are known in the art and are provided herein as SEQ ID NO:1 (RSPO1), SEQ ID NO:2 (RSPO2), SEQ ID NO:3 (RSPO3), and SEQ ID NO:4 (RSPO4).

In certain embodiments, the antigen-binding site of a RSPO-binding agent (e.g., an antibody or a bispecific antibody) described herein is capable of binding (or binds) one, two, three, or four RSPOs. In certain embodiments, the antigen-binding site of a RSPO-binding agent (e.g., an antibody or a bispecific antibody) described herein is capable of binding (or binds) RSPO3 as well as one, two, or three other RSPOs. For example, in certain embodiments, the antigen-binding site of a RSPO3-binding agent is capable of specifically binding RSPO3 as well as at least one other RSPO selected from the group consisting of RSPO1, RSPO2, and RSPO4. In certain embodiments, the RSPO3-binding agent specifically binds RSPO3 and RSPO1. In certain embodiments, the RSPO3-binding agent specifically binds RSPO3 and RSPO2. In certain embodiments, the RSPO3-binding agent specifically binds RSPO3 and RSPO4. In certain embodiments, the RSPO3-binding agent specifically binds RSPO3, RSPO1, and RSPO2. In certain embodiments, the RSPO3-binding agent specifically binds RSPO3, RSPO1, and RSPO4. In certain embodiments, the RSPO3-binding agent specifically binds RSPO3, RSPO2, and RSPO4. In some embodiments, the RSPO3-binding agent specifically binds human RSPO3. In some embodiments, the RSPO3-binding agent (e.g., antibody) specifically binds both human RSPO3 and mouse RSPO3.

In certain embodiments, the agent-binding agent is an antibody that specifically binds within amino acids 22-272 of human RSPO3. In certain embodiments, the agent-binding agent is an antibody that specifically binds within amino acids 22-207 of human RSPO3. In certain embodiments, the antigen-binding agent is an antibody that specifically binds within amino acids 35-135 of human RSPO3. In certain embodiments, the antigen-binding agent is an antibody that specifically binds within amino acids 35-86 of human RSPO3. In certain embodiments, the antigen-binding agent is an antibody that specifically binds within amino acids 92-135 of human RSPO3. In certain embodiments, the RSPO3-binding agent binds within SEQ ID NO:5. In certain embodiments, the RSPO3-binding agent or antibody binds a furin-like cysteine-rich domain of RSPO3. In some embodiments, the agent or antibody binds at least one amino acid within a furin-like cysteine-rich domain of RSPO3. In certain embodiments, the RSPO3-binding agent or antibody binds within sequence SEQ ID NO:6 or SEQ ID NO:7. In certain embodiments, the RSPO3-binding agent or antibody binds within sequence SEQ ID NO:6 and SEQ ID NO:7. In some embodiments, the RSPO3-binding agent binds the thrombospondin domain of RSPO3. In some embodiments, the RSPO3-binding agent or antibody binds at least one amino acid within the thrombospondin domain of RSPO3. In some embodiments, the RSPO3-binding agent or antibody binds within SEQ ID NO:8.

In certain embodiments, the RSPO-binding agent or antibody binds at least one RSPO protein with a dissociation constant ($K_D$) of about 1 μM or less, about 100 nM or less, about 40 nM or less, about 20 nM or less, about 10 nM or less, about 1 nM or less, or about 0.1 nM or less. In certain embodiments, a RSPO3-binding agent or antibody binds RSPO3 with a dissociation constant ($K_D$) of about 1 μM or less, about 100 nM or less, about 40 nM or less, about 20 nM or less, about 10 μM or less, about 1 nM or less, or about 0.1 nM or less. In some embodiments, a RSPO3-binding agent or antibody binds RSPO3 with a $K_D$ of about 20 nM or less. In some embodiments, a RSPO3-binding agent or antibody binds RSPO3 with a $K_D$ of about 10 nM or less. In some embodiments, a RSPO3-binding agent or antibody binds RSPO3 with a $K_D$ of about 1 nM or less. In some embodiments, a RSPO3-binding agent or antibody binds RSPO3 with a $K_D$ of about 0.5 nM or less. In some embodiments, a RSPO3-binding agent or antibody binds RSPO3 with a $K_L$ of about 0.1 nM or less. In certain embodiments, a RSPO3-binding agent or antibody described herein binds at least one other RSPO. In certain embodiments, a RSPO3-binding agent or antibody described herein that binds at least one other RSPO, binds at least one other RSPO with a $K_D$ of about 100 nM or less, about 20 nM or less, about 10 nM or less, about 1 nM or less or about 0.1 nM or less. For example, in some embodiments, a RSPO3-binding agent or antibody also binds RSPO1, RSPO2, and/or RSPO4 with a $K_L$ of about 10 nM or less. In some embodiments, the RSPO-binding agent binds both human RSPO and mouse RSPO with a $K_D$ of about 10 nM or less. In some embodiments, a RSPO3-binding agent binds both human RSPO3 and mouse RSPO3 with a $K_D$ of about 1 nM or less. In some embodiments, a RSPO3-binding agent binds both human RSPO3 and mouse RSPO3 with a $K_D$ of about 0.1 nM or less. In some embodiments, the dissociation constant of the binding agent (e.g., an antibody) to a RSPO3 protein is the dissociation constant determined using a RSPO3 fusion protein comprising at least a portion of the RSPO3 protein immobilized on a Biacore chip. In some embodiments, the dissociation constant of the binding agent (e.g., an antibody) to a RSPO3 protein is the dissociation constant determined using the binding agent captured by an anti-human IgG antibody on a Biacore chip and a RSPO3 protein.

In some embodiments, the RSPO3-binding agent is a bispecific antibody which comprises a first antigen-binding site that specifically binds RSPO3 and a second antigen-binding site that specifically binds a second target. In some embodiments, a RSPO3-binding agent or antibody binds both RSPO3 and the second target with a $K_D$ of about 100 nM or less. In some embodiments, a RSPO3-binding agent or antibody binds both RSPO3 and the second target with a $K_D$ of about 50 nM or less. In some embodiments, a RSPO3-binding agent or antibody binds both RSPO3 and the second target with a $K_D$ of about 20 nM or less. In some embodiments, a RSPO3-binding agent or antibody binds both RSPO3 and the second target with a $K_D$ of about 10 nM or less. In some embodiments, a RSPO3-binding agent or antibody binds both RSPO3 and the second target with a $K_D$ of about 1 nM or less. In some embodiments, the affinity of one of the antigen-binding sites may be weaker than the affinity of the other antigen-binding site. For example, the $K_D$ of one antigen binding site may be about 1 nM and the $K_D$ of the second antigen-binding site may be about 10 nM. In some embodiments, the difference in affinity between the two antigen-binding sites may be about 2-fold or more, about 3-fold or more, about 5-fold or more, about 8-fold or more, about 10-fold or more, about 5-fold or more, about 20-fold or more, about 30-fold or more, about 50-fold or more, or about 100-fold or more. Modulation of the affinities of the two antigen-binding sites may affect the biological activity of the bispecific antibody. For example, decreasing the affinity of the antigen-binding site for RSPO3 or the second target, may have a desirable effect, for example decreased toxicity of the binding agent and/or increased therapeutic index.

By way of non-limiting example, the bispecific antibody may comprise (a) a first antigen-binding site that binds human RSPO3 with a $K_D$ between about 0.1 nM and about 10 nM, and (b) a second antigen-binding site that specifically binds a second target (e.g., human RSPO2) with a $K_D$ between about 0.1 nM and about 20 nM, between about 0.5 nM and about 20 nM, or between about 1.0 nM and 10 nM.

In certain embodiments, the RSPO-binding agent (e.g., an antibody) binds to at least one human RSPO protein with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a RSPO3-binding agent (e.g., an antibody) binds to human RSPO3 with a half maximal effective concentration ($EC_{50}$) of about IgM or less, about 100 nM or less, about 40 nM or less, about 20 nM or less, about 10 nM or less, about 1 nM or less, or about 0.1 nM or less. In certain embodiments, a RSPO3-binding agent (e.g., an antibody) also binds to human RSPO1, RSPO2, and/or RSPO4 with an $EC_{50}$ of about 40 nM or less, about 20 nM or less, about 10 nM or less, about 1 nM or less or about 0.1 nM or less.

In certain embodiments, the RSPO3-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody. In some embodiments, the antibody is conjugated to a cytotoxic moiety. In some embodiments, the antibody is isolated. In some embodiments, the antibody is substantially pure.

The RSPO3-binding agents (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well-known in the art (see, e.g., Ausubel et al., Editors, 1994-present, *Current Protocols in Molecular Biology*, John Wiley & Sons, Inc., New York, N.Y.).

For example, the specific binding of an antibody to human RSPO3 may be determined using ELISA. An ELISA assay comprises preparing antigen, coating wells of a 96 well microtiter plate with antigen, adding the RSPO3-binding antibody or other RSPO3-binding agent conjugated to a detectable compound such as an enzymatic substrate (e.g. horseradish peroxidase or alkaline phosphatase) to the well, incubating for a period of time and detecting the presence of the antibody bound to the antigen. In some embodiments, the RSPO3-binding antibody or agent is not conjugated to a detectable compound, but instead a second conjugated antibody that recognizes the RSPO3-binding agent or antibody (e.g., an anti-Fc antibody) and is conjugated to a detectable compound is added to the well. In some embodiments, instead of coating the well with the antigen, the RSPO3-binding agent or antibody can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art.

In another example, the specific binding of an antibody to human RSPO3 may be determined using FACS. A FACS screening assay may comprise generating a cDNA construct that expresses an antigen as a fusion protein (e.g., RSPO3-Fc or RSPO3-CD4TM), transfecting the construct into cells, expressing the antigen on the surface of the cells, mixing the RSPO3-binding agent with the transfected cells, and incubating for a period of time. The cells bound by the RSPO3-binding agent may be identified using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antibody or other binding-agent to an antigen (e.g., RSPO3) and the off-rate of an antibody-antigen interaction can be determined by competitive binding assays. One example of a competitive binding assay is a radioimmunoassay comprising the incubation of labeled antigen (e.g., $^3H$ or $^{125}I$), or fragment or variant thereof, with the antibody of interest in the presence of increasing amounts of unlabeled antigen followed by the detection of the antibody bound to the labeled antigen. The affinity of the antibody for the antigen and the binding off-rates can be determined from the data by Scatchard plot analysis. In some embodiments, Biacore kinetic analysis is used to determine the binding on and off rates of antibodies or agents that bind an antigen (e.g., RSPO3). In some embodiments, Biacore kinetic analysis comprises analyzing the binding and dissociation of antibodies from chips with immobilized antigen (e.g., RSPO3) on their surface. In some embodiments, Biacore kinetic analysis comprises analyzing the binding and dissociation of antigen (e.g., RSPO3) from chips with immobilized antibody (e.g., anti-RSPO3 antibody) on their surface.

In certain embodiments, the invention provides a RSPO3-binding agent (e.g., an antibody) that specifically binds human RSPO3, wherein the RSPO3-binding agent (e.g., an antibody) comprises one, two, three, four, five, and/or six of the CDRs of antibody 131R002, antibody 131R003, or the humanized variants thereof, including h131R005/131R007, h131R006A, h131R006B, h131R008, h131R010, or h131R011 (see Table 1). In some embodiments, the RSPO3-binding agent comprises one or more of the CDRs of 131R002, 131R003, or the humanized variants thereof, including h131R005/131R007, h131R006A, h131R006B, h131R008, h131R010, or h131R011; two or more of the CDRs of 131R002, 131R003, or the humanized variants thereof, including h131R005/131R007, h131R006A, h131R006B, h131R008, h131R010, or h131R011; three or more of the CDRs of 131R002, 131R003, or the humanized variants thereof, including h131R005/131R007, h131R006A, h131R006B, h131R008, h131R010, or h131R011; four or more of the CDRs of 131R002, 131R003, or the humanized variants thereof, including h131R005/131R007, h131R006A, h131R006B, h131R008, h131R010, or h131R011; five or more of the CDRs of 131R002, 131R003, or the humanized variants thereof, including 131R005/131R007, h131R006A, h131R006B, or h131R008, h131R010, or h131R011; or all six of the CDRs of 131R002, 131R003, or the humanized variants thereof, including h131R005/131R007, h131R006A, h131R006B, h131R008, h131R010, or h131R011.

TABLE 1

| | 131R002/131R003 and Humanized Variants |
|---|---|
| HC CDR1 | KASGYTFTDYS (SEQ ID NO: 9) or KASGYTFTSYTF (SEQ ID NO: 34) or DYSIH (SEQ ID NO: 78) |
| HC CDR2 | IYPSNGDS (SEQ ID NO: 10) or YIYPSNGDSGYNQKFK (SEQ ID NO: 79) |
| HC CDR3 | ATYFANYFDY (SEQ ID NO: 11) or ATYFANNFDY (SEQ ID NO: 35) or TYFANNFD (SEQ ID NO: 80 |
| LC CDR1 | QSVDYDGDSYM (SEQ ID NO: 12) or KASQSVDYDGDSYMN (SEQ ID NO: 81) |
| LC CDR2 | AAS (SEQ ID NO: 13) or AASNLES (SEQ ID NO: 82) |
| LC CDR3 | QQSNEDPLT (SEQ ID NO: 14) or QQSNEDPLTF (SEQ ID NO: 83) |

In certain embodiments, the invention provides a RSPO3-binding agent (e.g., an antibody) that specifically binds human RSPO3, wherein the RSPO3-binding agent comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35), or TYFANNFD (SEQ ID NO:80). In some embodiments, the RSPO3-binding agent further comprises a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83). In some embodiments, the RSPO3-binding agent comprises a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83). In certain embodiments, the RSPO3-binding agent comprises: (a) a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANYFDY (SEQ ID NO:11), and (b) a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In certain embodiments, the RSPO3-binding agent comprises: (a) a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANNFDY (SEQ ID NO:35), and (b) a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In certain embodiments, the RSPO3-binding agent comprises: (a) a heavy chain CDR1 comprising KASGYTFTSYTF (SEQ ID NO:34), a heavy chain CDR2 comprising IYPSNGDS (SEQ ID NO:10), and a heavy chain CDR3 comprising ATYFANYFDY (SEQ ID NO:11), and (b) a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In certain embodiments, the RSPO3-binding agent comprises: (a) a heavy chain CDR1 comprising KASGYTFTSYTF (SEQ ID NO:34), a heavy chain CDR2 comprising IYPSNGDS (SEQ ID NO:10), and a heavy chain CDR3 comprising ATYFANNFDY (SEQ ID NO:35), and (b) a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In certain embodiments, the RSPO3-binding agent comprises: (a) a heavy chain CDR1 comprising DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and (b) a light chain CDR1 comprising KASQSVDYDGDSYMN (SEQ ID NO:81), a light chain CDR2 comprising AASNLES (SEQ ID NO:82), and a light chain CDR3 comprising QQSNEDPLTF (SEQ ID NO:83). In certain embodiments, the RSPO3-binding agent comprises: (a) a heavy chain CDR1 comprising DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and (b) a light chain CDR1 comprising KASQSVDYDGDSYMN (SEQ ID NO:81), a light chain CDR2 comprising AASNLES (SEQ ID NO:82), and a light chain CDR3 comprising QQSNEDPLT (SEQ ID NO:14). In certain embodiments, the RSPO3-binding agent comprises: (a) a heavy chain CDR1 comprising KASGYTFTDYS (SEQ ID NO:9) or DYSIH (SEQ ID NO:78), a heavy chain CDR2 comprising IYPSNGDS (SEQ ID NO:10), and a heavy chain CDR3 comprising TYFANNFD (SEQ ID NO:80), and (b) a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14).

In certain embodiments, the invention provides a RSPO3-binding agent (e.g., an antibody or bispecific antibody) that specifically binds human RSPO3, wherein the RSPO3-binding agent comprises: (a) a heavy chain CDR1 comprising KASGYTFTDYS (SEQ ID NO:9), KASGYTFTSYTF (SEQ ID NO:34), DYSIH (SEQ ID NO:78), or a variant thereof comprising 1, 2, 3, or 4 amino acid substitutions; (b) a heavy chain CDR2 comprising IYPSNGDS (SEQ ID NO:10), YIYPSNGDSGYNQKFK (SEQ ID NO:79), or a variant thereof comprising 1, 2, 3, or 4 amino acid substitutions; (c) a heavy chain CDR3 comprising ATYFANYFDY (SEQ ID NO:11), ATYFANNFDY (SEQ ID NO:35), TYFANNFD (SEQ ID NO:80), or a variant thereof comprising 1, 2, 3, or 4 amino acid substitutions; (d) a light chain CDR1 comprising QSVDYDGDSYM (SEQ ID NO:12), KASQSVDYDGDSYMN (SEQ ID NO:81), or a variant thereof comprising 1, 2, 3, or 4 amino acid substitutions; (e) a light chain CDR2 comprising AAS (SEQ ID NO:13), AASNLES (SEQ ID NO:82), or a variant thereof comprising 1, 2, 3, or 4 amino acid substitutions; and (f) a light chain CDR3 comprising QQSNEDPLT (SEQ ID NO:14), QQSNEDPLTF (SEQ ID NO:83), or a variant thereof comprising 1, 2, 3, or 4 amino acid substitutions. In certain embodiments, the amino acid substitutions are conservative substitutions. In some embodiments, the substitutions are made as part of a germline humanization process.

In certain embodiments, the invention provides a RSPO3-binding agent (e.g., an antibody) that specifically binds RSPO3, wherein the RSPO3-binding agent comprises a heavy chain variable region having at least about 80% sequence identity to SEQ ID NO:15, SEQ ID NO:16, SEQ ID NO:36, SEQ ID NO:37, SEQ ID NO:44, SEQ ID NO:45, or SEQ ID NO:62 and/or a light chain variable region having at least 80% sequence identity to SEQ ID NO:17, SEQ ID NO:72, or SEQ ID NO:86. In certain embodiments, the RSPO3-binding agent comprises a heavy chain variable region having at least about 85%, at least about 90%, at least about 95%, at least about 97%, or at least about 99% sequence identity to SEQ ID NO:15. In certain embodiments, the RSPO3-binding agent comprises a heavy chain variable region having at least about 85%, at least about 90%, at least about 95%, at least about 97%, or at least about 99% sequence identity to SEQ ID NO:16. In certain embodiments, the RSPO3-binding agent comprises a heavy chain variable region having at least about 85%, at least about 90%, at least about 95%, at least about 97%, or at least about 99% sequence identity to SEQ ID NO:36. In certain embodiments, the RSPO3-binding agent comprises a heavy chain variable region having at least about 85%, at least about 90%, at least about 95%, at least about 97%, or at least about 99% sequence identity to SEQ ID NO:37. In certain embodiments, the RSPO3-binding agent comprises a heavy chain variable region having at least about 85%, at least about 90%, at least about 95%, at least about 97%, or at least about 99% sequence identity to SEQ ID NO:44. In certain embodiments, the RSPO3-binding agent comprises a heavy chain variable region having at least about 85%, at least about 90%, at least about 95%, at least about 97%, or at least about 99% sequence identity to SEQ ID NO:45. In certain embodiments, the RSPO3-binding agent comprises a heavy chain variable region having at least about 85%, at least about 90%, at least about 95%, at least about 97%, or at least about 99% sequence identity to SEQ ID NO:62. In certain embodiments, the RSPO3-binding agent comprises a light chain variable region having at least about 85%, at least about 90%, at least about 95%, at least about 97%, or at least about 99% sequence identity to SEQ ID NO:17. In certain embodiments, the RSPO3-binding agent comprises a light chain variable region having at least about 85%, at least about 90%, at least about 95%, at least about 97%, or at least about 99% sequence identity to SEQ ID NO:72. In certain embodiments, the RSPO3-binding agent comprises a light chain variable region having at least about 85%, at least about 90%, at least about 95%, at least about 97%, or at least about 99% sequence identity to SEQ ID NO:86. In certain embodiments, the RSPO3-binding agent comprises a heavy chain variable region having at least about 95% sequence identity to SEQ ID NO:15, SEQ ID NO:16, SEQ ID NO:36, SEQ ID NO:37, SEQ ID NO:44, SEQ ID NO:45, or SEQ ID NO:62 and/or a light chain variable region having at least about 95% sequence identity to SEQ ID NO:17, SEQ ID NO:72, or SEQ ID NO:86. In certain embodiments, the RSPO3-binding agent comprises a heavy chain variable region comprising SEQ ID NO:15, SEQ ID NO:16, SEQ ID NO:36, SEQ ID NO:37, SEQ ID NO:44, SEQ ID NO:45, or SEQ ID NO:62, and/or a light chain variable region comprising SEQ ID NO:17, SEQ ID NO:72, or SEQ ID NO:86. In certain embodiments, the RSPO3-binding agent comprises a heavy chain variable region comprising SEQ ID NO:15, SEQ ID NO:16, SEQ ID NO:36, SEQ ID NO:37, SEQ ID NO:44, SEQ ID NO:45, or SEQ ID NO:62 and a light chain variable region comprising SEQ ID NO:17, SEQ ID NO:72, or SEQ ID NO:86. In certain embodiments, the RSPO3-binding agent comprises a heavy chain variable region consisting essentially of SEQ ID NO:15, SEQ ID NO:16, SEQ ID NO:36, SEQ ID NO:37, SEQ ID NO:44, SEQ ID NO:45, or SEQ ID NO:62, and a light chain variable region consisting essentially of SEQ ID NO:17, SEQ ID NO:72, or SEQ ID NO:86. In certain embodiments, the RSPO3-binding agent comprises a heavy chain variable region consisting of SEQ ID NO:15, SEQ ID NO:16, SEQ ID NO:36, SEQ ID NO:37, SEQ ID NO:44, SEQ ID NO:45, or SEQ ID NO:62, and a light chain variable region consisting of SEQ ID NO:17, SEQ ID NO:72, or SEQ ID NO:86.

In certain embodiments, the RSPO3-binding agent comprises a heavy chain variable region comprising SEQ ID NO:44 and a light chain variable region comprising SEQ ID NO:17. In certain embodiments, the RSPO3-binding agent comprises a heavy chain variable region comprising SEQ ID NO:45 and a light chain variable region comprising SEQ ID NO:17. In certain embodiments, the RSPO3-binding agent comprises a heavy chain variable region comprising SEQ ID NO:62 and a light chain variable region comprising SEQ ID NO:17. In certain embodiments, the RSPO3-binding agent comprises a heavy chain variable region consisting essentially of SEQ ID NO:44 and a light chain variable region consisting essentially of SEQ ID NO:17. In certain embodiments, the RSPO3-binding agent comprises a heavy chain variable region consisting essentially of SEQ ID NO:45 and a light chain variable region consisting essentially of SEQ ID NO:17. In certain embodiments, the RSPO3-binding agent comprises a heavy chain variable region consisting essentially of SEQ ID NO:62 and a light chain variable region consisting essentially of SEQ ID NO:17. In certain embodiments, the RSPO3-binding agent comprises a heavy chain variable region consisting of SEQ ID NO:44 and a light chain variable region consisting of SEQ ID NO:17. In certain embodiments, the RSPO3-binding agent comprises a heavy chain variable region consisting of SEQ ID NO:45 and a light chain variable region consisting of SEQ ID NO:17. In certain embodiments, the RSPO3-binding agent comprises a heavy chain variable region consisting of SEQ ID NO:62 and a light chain variable region consisting of SEQ ID NO:17.

In certain embodiments, the RSPO3-binding agent comprises a heavy chain variable region comprising SEQ ID NO:44 and a light chain variable region comprising SEQ ID NO:72. In certain embodiments, the RSPO3-binding agent comprises a heavy chain variable region comprising SEQ ID NO:45 and a light chain variable region comprising SEQ ID NO:72. In certain embodiments, the RSPO3-binding agent comprises a heavy chain variable region comprising SEQ ID NO:62 and a light chain variable region comprising SEQ ID NO:72. In certain embodiments, the RSPO3-binding agent comprises a heavy chain variable region consisting essentially of SEQ ID NO:44 and a light chain variable region consisting essentially of SEQ ID NO:72. In certain embodiments, the RSPO3-binding agent comprises a heavy chain variable region consisting essentially of SEQ ID NO:45 and a light chain variable region consisting essentially of SEQ ID NO:72. In certain embodiments, the RSPO3-binding agent comprises a heavy chain variable region consisting essentially of SEQ ID NO:62 and a light chain variable region consisting essentially of SEQ ID NO:72. In certain embodiments, the RSPO3-binding agent comprises a heavy chain variable region consisting of SEQ ID NO:44 and a light chain variable region consisting of SEQ ID NO:72. In certain embodiments, the RSPO3-binding agent comprises a heavy chain variable region consisting of SEQ ID NO:45 and a light chain variable region consisting of SEQ ID NO:72. In certain embodiments, the RSPO3-binding agent comprises a heavy chain variable region consisting of SEQ ID NO:62 and a light chain variable region consisting of SEQ ID NO:72.

In certain embodiments, the RSPO3-binding agent comprises a heavy chain variable region comprising SEQ ID NO:44 and a light chain variable region comprising SEQ ID NO:86. In certain embodiments, the RSPO3-binding agent comprises a heavy chain variable region comprising SEQ ID NO:45 and a light chain variable region comprising SEQ ID NO:86. In certain embodiments, the RSPO3-binding agent comprises a heavy chain variable region comprising SEQ ID NO:62 and a light chain variable region comprising SEQ ID NO:86. In certain embodiments, the RSPO3-binding agent comprises a heavy chain variable region consisting essentially of SEQ ID NO:44 and a light chain variable region consisting essentially of SEQ ID NO:86. In certain embodiments, the RSPO3-binding agent comprises a heavy chain variable region consisting essentially of SEQ ID NO:45 and a light chain variable region consisting essentially of SEQ ID NO:86. In certain embodiments, the RSPO3-binding agent comprises a heavy chain variable region consisting essentially of SEQ ID NO:62 and a light chain variable region consisting essentially of SEQ ID NO:86. In certain embodiments, the RSPO3-binding agent comprises a heavy chain variable region consisting of SEQ ID NO:44 and a light chain variable region consisting of SEQ ID NO:86. In certain embodiments, the RSPO3-binding agent comprises a heavy chain variable region consisting of SEQ ID NO:45 and a light chain variable region consisting of SEQ ID NO:86. In certain embodiments, the RSPO3-binding agent comprises a heavy chain variable region consisting of SEQ ID NO:62 and a light chain variable region consisting of SEQ ID NO:86.

In certain embodiments, the invention provides a RSPO3-binding agent (e.g., an antibody) that specifically binds RSPO3, wherein the RSPO3-binding agent comprises: (a) a heavy chain having at least 90% sequence identity to SEQ ID NO:27, SEQ ID NO:28, SEQ ID NO:39, SEQ ID NO:42, SEQ ID NO:48, SEQ ID NO:49, SEQ ID NO:64, or SEQ ID NO:69; and/or (b) a light chain having at least 90% sequence identity to SEQ ID NO:29, SEQ ID NO:74, or SEQ ID NO:88. In some embodiments, the RSPO3-binding agent comprises: (a) a heavy chain having at least 95% sequence identity to SEQ ID NO:27, SEQ ID NO:28, SEQ ID NO:39, SEQ ID NO:42, SEQ ID NO:48, SEQ ID NO:49, SEQ ID NO:64, or SEQ ID NO:69; and/or (b) a light chain having at least 95% sequence identity to SEQ ID NO:29, SEQ ID NO:74, or SEQ ID NO:88. In some embodiments, the RSPO3-binding agent comprises a heavy chain comprising SEQ ID NO:27 and/or a light chain comprising SEQ ID NO:29. In some embodiments, the RSPO3-binding agent comprises a heavy chain comprising SEQ ID NO:28 and/or a light chain comprising SEQ ID NO:29. In some embodiments, the RSPO3-binding agent comprises a heavy chain comprising SEQ ID NO:39 and/or a light chain comprising SEQ ID NO:29. In some embodiments, the RSPO3-binding agent comprises a heavy chain comprising SEQ ID NO:42 and/or a light chain comprising SEQ ID NO:29. In some embodiments, the RSPO3-binding agent comprises a heavy chain comprising SEQ ID NO:48 and/or a light chain comprising SEQ ID NO:29. In some embodiments, the RSPO3-binding agent comprises a heavy chain comprising SEQ ID NO:49 and/or a light chain comprising SEQ ID NO:29. In some embodiments, the RSPO3-binding agent comprises a heavy chain comprising SEQ ID NO:64 and/or a light chain comprising SEQ ID NO:29. In some embodiments, the RSPO3-binding agent comprises a heavy chain comprising SEQ ID NO:69 and/or a light chain comprising SEQ ID NO:29. In some embodiments, the RSPO3-binding agent comprises a heavy chain comprising SEQ ID NO:48 and/or a light chain comprising SEQ ID NO:88. In some embodiments, the RSPO3-binding agent comprises a heavy chain comprising SEQ ID NO:49 and/or a light chain comprising SEQ ID NO:88. In some embodiments, the RSPO3-binding agent comprises a heavy chain comprising SEQ ID NO:64 and/or a light chain comprising SEQ ID NO:88. In some embodiments, the RSPO3-binding agent comprises a heavy chain comprising SEQ ID NO:69 and/or a light chain comprising SEQ ID NO:88. In some embodiments, the RSPO3-binding agent comprises a heavy chain consisting essentially of SEQ ID NO:27, SEQ ID NO:28, SEQ ID NO:39, SEQ ID NO:42, SEQ ID NO:48, SEQ ID NO:49, SEQ ID NO:64, or SEQ ID NO:69; and a light chain consisting essentially of SEQ ID NO:29. In some embodiments, the RSPO3-binding agent comprises a heavy chain consisting of SEQ ID NO:28, SEQ ID NO:28, SEQ ID NO:39, SEQ ID NO:42, SEQ ID NO:48, SEQ ID NO:49, SEQ ID NO:64, or SEQ ID NO:69 and a light chain consisting of SEQ ID NO:29. In some embodiments, the RSPO3-binding agent comprises a heavy chain consisting of SEQ ID NO:28, SEQ ID NO:28, SEQ ID NO:39, SEQ ID NO:42, SEQ ID NO:48, SEQ ID NO:49, SEQ ID NO:64, or SEQ ID NO:69 and a light chain consisting of SEQ ID NO:88. In some embodiments, the RSPO3-binding agent comprises a heavy chain comprising SEQ ID NO:27 and/or a light chain comprising SEQ ID NO:74. In some embodiments, the RSPO3-binding agent comprises a heavy chain comprising SEQ ID NO:28 and/or a light chain comprising SEQ ID NO:74. In some embodiments, the RSPO3-binding agent comprises a heavy chain comprising SEQ ID NO:39 and/or a light chain comprising SEQ ID NO:74. In some embodiments, the RSPO3-binding agent comprises a heavy chain comprising SEQ ID NO:42 and/or a light chain comprising SEQ ID NO:74. In some embodiments, the RSPO3-binding agent comprises a heavy chain comprising SEQ ID NO:48 and/or a light chain comprising SEQ ID NO:74. In some embodiments, the RSPO3-binding agent comprises a heavy chain comprising SEQ ID NO:49 and/or a light chain comprising SEQ ID NO:74. In some embodiments, the RSPO3-binding agent comprises a heavy chain comprising SEQ ID NO:64 and/or a light chain comprising SEQ ID NO:74. In some embodiments, the RSPO3-binding agent comprises a heavy chain comprising SEQ ID NO:69 and/or a light chain comprising SEQ ID NO:74. In some embodiments, the RSPO3-binding agent comprises a heavy chain comprising SEQ ID NO:48 and/or a light chain comprising SEQ ID NO:88. In some embodiments, the RSPO3-binding agent comprises a heavy chain comprising SEQ ID NO:49 and/or a light chain comprising SEQ ID NO:88. In some embodiments, the RSPO3-binding agent comprises a heavy chain comprising SEQ ID NO:64 and/or a light chain comprising SEQ ID NO:88. In some embodiments, the RSPO3-binding agent comprises a heavy chain comprising SEQ ID NO:69 and/or a light chain comprising SEQ ID NO:88. In some embodiments, the RSPO3-binding agent comprises a heavy chain consisting essentially of SEQ ID NO:27, SEQ ID NO:28, SEQ ID NO:39, SEQ ID NO:42, SEQ ID NO:48, SEQ ID NO:49, SEQ ID NO:64, or SEQ ID NO:69; and a light chain consisting essentially of SEQ ID NO:74. In some embodiments, the RSPO3-binding agent comprises a heavy chain consisting of SEQ ID NO:27, SEQ ID NO:28, SEQ ID NO:39, SEQ ID NO:42, SEQ ID NO:48, SEQ ID NO:49, SEQ ID NO:64, or SEQ ID NO:69 and a light chain consisting of SEQ ID NO:74. In some embodiments, the RSPO3-binding agent comprises a heavy chain consisting essentially of SEQ ID NO:48, SEQ ID NO:49, SEQ ID NO:64, or SEQ ID NO:69; and a light chain consisting essentially of SEQ ID NO:88. In some embodiments, the RSPO3-binding agent comprises a heavy chain consisting of SEQ ID NO:48, SEQ ID NO:49, SEQ ID NO:64, or SEQ ID NO:69 and a light chain consisting of SEQ ID NO:88.

In certain embodiments, the RSPO3-binding agent comprises a heavy chain comprising SEQ ID NO:48 and a light chain comprising SEQ ID NO:29. In certain embodiments, the RSPO3-binding agent comprises a heavy chain comprising SEQ ID NO:49 and a light chain variable region comprising SEQ ID NO:29. In certain embodiments, the RSPO3-binding agent comprises a heavy chain comprising SEQ ID NO:64 and a light chain variable region comprising SEQ ID NO:29. In certain embodiments, the RSPO3-binding agent comprises a heavy chain comprising SEQ ID NO:69 and a light chain variable region comprising SEQ ID NO:29. In certain embodiments, the RSPO3-binding agent comprises a heavy chain consisting essentially of SEQ ID NO:48 and a light chain consisting essentially of SEQ ID NO:29. In certain embodiments, the RSPO3-binding agent comprises a heavy chain consisting essentially of SEQ ID NO:49 and a light chain consisting essentially of SEQ ID NO:29. In certain embodiments, the RSPO3-binding agent comprises a heavy chain consisting essentially of SEQ ID NO:64 and a light chain consisting essentially of SEQ ID NO:29. In certain embodiments, the RSPO3-binding agent comprises a heavy chain consisting essentially of SEQ ID NO:69 and a light chain consisting essentially of SEQ ID NO:29. In certain embodiments, the RSPO3-binding agent comprises a heavy chain consisting of SEQ ID NO:48 and a light chain consisting of SEQ ID NO:29. In certain embodiments, the RSPO3-binding agent comprises a heavy chain consisting of SEQ ID NO:49 and a light chain consisting of SEQ ID NO:29. In certain embodiments, the RSPO3-binding agent comprises a heavy chain consisting of SEQ ID NO:64 and a light chain consisting of SEQ ID NO:29. In certain embodiments, the RSPO3-binding agent comprises a heavy chain consisting of SEQ ID NO:69 and a light chain consisting of SEQ ID NO:29.

In certain embodiments, the RSPO3-binding agent comprises a heavy chain comprising SEQ ID NO:48 and a light chain comprising SEQ ID NO:74. In certain embodiments, the RSPO3-binding agent comprises a heavy chain comprising SEQ ID NO:49 and a light chain variable region comprising SEQ ID NO:74. In certain embodiments, the RSPO3-binding agent comprises a heavy chain comprising SEQ ID NO:64 and a light chain variable region comprising SEQ ID NO:74. In certain embodiments, the RSPO3-binding agent comprises a heavy chain comprising SEQ ID NO:69 and a light chain variable region comprising SEQ ID NO:74. In certain embodiments, the RSPO3-binding agent comprises a heavy chain consisting essentially of SEQ ID NO:48 and a light chain consisting essentially of SEQ ID NO:74. In certain embodiments, the RSPO3-binding agent comprises a heavy chain consisting essentially of SEQ ID NO:49 and a light chain consisting essentially of SEQ ID NO:74. In certain embodiments, the RSPO3-binding agent comprises a heavy chain consisting essentially of SEQ ID NO:64 and a light chain consisting essentially of SEQ ID NO:74. In certain embodiments, the RSPO3-binding agent comprises a heavy chain consisting essentially of SEQ ID NO:69 and a light chain consisting essentially of SEQ ID NO:74. In certain embodiments, the RSPO3-binding agent comprises a heavy chain consisting of SEQ ID NO:48 and a light chain consisting of SEQ ID NO:74. In certain embodiments, the RSPO3-binding agent comprises a heavy chain consisting of SEQ ID NO:49 and a light chain consisting of SEQ ID NO:74. In certain embodiments, the RSPO3-binding agent comprises a heavy chain consisting of SEQ ID NO:64 and a light chain consisting of SEQ ID NO:74. In certain embodiments, the RSPO3-binding agent comprises a heavy chain consisting of SEQ ID NO:69 and a light chain consisting of SEQ ID NO:74.

In certain embodiments, the RSPO3-binding agent comprises a heavy chain comprising SEQ ID NO:48 and a light chain comprising SEQ ID NO:88. In certain embodiments, the RSPO3-binding agent comprises a heavy chain comprising SEQ ID NO:49 and a light chain variable region comprising SEQ ID NO:88. In certain embodiments, the RSPO3-binding agent comprises a heavy chain comprising SEQ ID NO:64 and a light chain variable region comprising SEQ ID NO:88. In certain embodiments, the RSPO3-binding agent comprises a heavy chain comprising SEQ ID NO:69 and a light chain variable region comprising SEQ ID NO:88. In certain embodiments, the RSPO3-binding agent comprises a heavy chain consisting essentially of SEQ ID NO:48 and a light chain consisting essentially of SEQ ID NO:88. In certain embodiments, the RSPO3-binding agent comprises a heavy chain consisting essentially of SEQ ID NO:49 and a light chain consisting essentially of SEQ ID NO:88. In certain embodiments, the RSPO3-binding agent comprises a heavy chain consisting essentially of SEQ ID NO:64 and a light chain consisting essentially of SEQ ID NO:88. In certain embodiments, the RSPO3-binding agent comprises a heavy chain consisting essentially of SEQ ID NO:69 and a light chain consisting essentially of SEQ ID NO:88. In certain embodiments, the RSPO3-binding agent comprises a heavy chain consisting of SEQ ID NO:48 and a light chain consisting of SEQ ID NO:88. In certain embodiments, the RSPO3- binding agent comprises a heavy chain consisting of SEQ ID NO:49 and a light chain consisting of SEQ ID NO:88. In certain embodiments, the RSPO3-binding agent comprises a heavy chain consisting of SEQ ID NO:64 and a light chain consisting of SEQ ID NO:88. In certain embodiments, the RSPO3-binding agent comprises a heavy chain consisting of SEQ ID NO:69 and a light chain consisting of SEQ ID NO:88.

In certain embodiments, a RSPO3-binding agent comprises the heavy chain variable region and light chain variable region of the 131R002 antibody. In certain embodiments, a RSPO3-binding agent comprises the heavy chain and light chain of the 131R002 antibody (with or without the leader sequence). In certain embodiments, a RSPO3-binding agent is the 131R002 antibody. In certain embodiments, a RSPO3-binding agent comprises the heavy chain variable region and/or light chain variable region of the 131R002 antibody in a chimeric form of the antibody. In certain embodiments, a RSPO3-binding agent comprises the heavy chain variable region and/or light chain variable region of the 131R002 antibody in a humanized form of the antibody. In certain embodiments, a RSPO3-binding agent comprises the heavy chain CDRs and/or light chain CDRs of the 131R002 antibody in a humanized form of the antibody. In some embodiments, the humanized version of 131R002 is an IgG1 antibody. In some embodiments, the humanized version of 131R002 is an IgG2 antibody.

In certain embodiments, a RSPO3-binding agent comprises, consists essentially of, or consists of, the antibody 131R002.

In certain embodiments, a RSPO3-binding agent comprises the heavy chain variable region and light chain variable region of the 131R003 antibody. In some embodiments, the RSPO3-binding agent comprises the heavy chain variable region of the 131R003 antibody wherein the heavy chain variable region from 131R003 has been affinity-matured. In some embodiments, the RSPO3-binding agent comprises the heavy chain variable region of the 131R003 antibody wherein the heavy chain variable region comprises at least one modified or altered CDR as compared to the parent 131R003 antibody. In some embodiments, the RSPO-binding agent comprises the heavy chain variable region of the 131R003 antibody wherein the heavy chain variable region comprises a modified CDR1 as compared to the parent 131R003 antibody. In some embodiments, the RSPO-binding agent comprises the heavy chain variable region of the 131R003 antibody wherein the heavy chain variable region comprises a modified CDR2 as compared to the parent 131R003 antibody. In some embodiments, the RSPO-binding agent comprises the heavy chain variable region of the 131R003 antibody wherein the heavy chain variable region comprises a modified CDR3 as compared to the parent 131R003 antibody. In some embodiments, the RSPO-binding agent comprises the heavy chain variable region of the 131R003 antibody wherein the heavy chain variable region comprises a modified CDR1 and CDR3 as compared to the parent 131R003 antibody. In certain embodiments, a RSPO3-binding agent comprises the heavy chain and light chain of the 131R003 antibody (with or without the leader sequence). In certain embodiments, a RSPO3-binding agent is the 131R003 antibody. In certain embodiments, a RSPO3-binding agent is a variant of the 131R003 antibody that comprises a different heavy chain CDR1 as compared to the parent 131R003 antibody. In certain embodiments, a RSPO3-binding agent is a variant of the 131R003 antibody that comprises a different heavy chain CDR3 as compared to the parent 131R003 antibody. In certain embodiments, a RSPO3-binding agent is a variant of the 131R003 antibody that comprises a different heavy chain CDR1 and a different heavy chain CDR3 as compared to the parent 131R003 antibody. In certain embodiments, a RSPO3-binding agent comprises the heavy chain variable region and/or light chain variable region of the 131R003 antibody or of any of the variants of 131R003 in a chimeric form of the antibody. In certain embodiments, a RSPO3-binding agent comprises the heavy chain variable region and/or light chain variable region of the 131R003 antibody or of any of the variants of 131R003 in a humanized form of the antibody. In certain embodiments, a RSPO3-binding agent comprises the heavy chain CDRs and/or light chain CDRs of the 131R003 antibody or of any of the variants of 131R003 in a humanized form of the antibody. In some embodiments, the humanized version of 131R003 or of 131R003 variants is an IgG1 antibody. In some embodiments, the humanized version of 131R003 or of 131R003 variants is an IgG2 antibody.

In certain embodiments, a RSPO3-binding agent comprises, consists essentially of, or consists of, the antibody 131R003. In certain embodiments, a RSPO3-binding agent comprises, consists essentially of, or consists of, a variant of the antibody 131R003.

In certain embodiments, a RSPO3-binding agent comprises the heavy chain variable region and light chain variable region of the 131R006B antibody. In certain embodiments, a RSPO3-binding agent comprises the heavy chain and light chain of the 131R006B antibody (with or without the leader sequence). In certain embodiments, a RSPO3-binding agent is the 131R006B antibody. In certain embodiments, a RSPO3-binding agent comprises the heavy chain variable region and/or light chain variable region of the 131R006B antibody in a chimeric form of the antibody. In certain embodiments, a RSPO3-binding agent comprises the heavy chain variable region and/or light chain variable region of the 131R006B antibody in a humanized form of the antibody. In certain embodiments, a RSPO3-binding agent comprises the heavy chain CDRs and/or light chain CDRs of the 131R006B antibody in a humanized form of the antibody. In some embodiments, the humanized version of 131R006B is an IgG1 antibody. In some embodiments, the humanized version of 131R006B is an IgG2 antibody.

In certain embodiments, a RSPO3-binding agent comprises, consists essentially of, or consists of, the antibody 131R006B. In certain embodiments, a RSPO3-binding agent comprises, consists essentially of, or consists of, a variant of the antibody 131R006B.

In certain embodiments, a RSPO3-binding agent comprises the heavy chain variable region and light chain variable region of the 131R005/131R007 antibody. In certain embodiments, a RSPO3-binding agent comprises the heavy chain and light chain of the 131R005/131R007 antibody (with or without the leader sequence). In certain embodiments, a RSPO3-binding agent is the 131R005/131R007 antibody. In certain embodiments, a RSPO3-binding agent comprises the heavy chain variable region and/or light chain variable region of the 131R005/131R007 antibody in a chimeric form of the antibody. In certain embodiments, a RSPO3-binding agent comprises the heavy chain variable region and/or light chain variable region of the 131R005/131R007 antibody in a humanized form of the antibody. In certain embodiments, a RSPO3-binding agent comprises the heavy chain CDRs and/or light chain CDRs of the 131R005/131R007 antibody in a humanized form of the antibody. In some embodiments, the humanized version of 131R005/131R007 is an IgG1 antibody. In some embodiments, the humanized version of 131R005/131R007 is an IgG2 antibody. In some embodiments, the anti-RSPO3 antibody is 131R008.

In certain embodiments, a RSPO3-binding agent comprises, consists essentially of, or consists of, the antibody 131R005/131R007. In certain embodiments, a RSPO3-binding agent comprises, consists essentially of, or consists of, a variant of the antibody 131R005/131R007.

In certain embodiments, a RSPO3-binding agent comprises, consists essentially of, or consists of, the antibody 131R008. In certain embodiments, a RSPO3-binding agent comprises, consists essentially of, or consists of, a variant of the antibody 131R008.

In certain embodiments, a RSPO3-binding agent comprises the heavy chain variable region and light chain variable region of the h131R010 or h131R0011 antibody. In certain embodiments, a RSPO3-binding agent comprises the heavy chain and light chain of the h131R010 or 131R011 antibody (with or without the leader sequence). In certain embodiments, a RSPO3-binding agent is the h131R010 antibody. In certain embodiments, a RSPO3-binding agent is the h131R011 antibody. In certain embodiments, a RSPO3-binding agent comprises the heavy chain variable region and/or light chain variable region of the h131R010 or h131R011 antibody in a chimeric form of the antibody. In certain embodiments, a RSPO3-binding agent comprises the heavy chain CDRs and/or light chain CDRs of the h131R010 or h131R011 antibody. In some embodiments, the anti-RSPO3 antibody is h131R010. In some embodiments, the anti-RSPO3 antibody is h131R011.

In some embodiments, the RSPO3-binding agent comprises a heavy chain variable region encoded by the plasmid deposited with American Type Culture Collection (ATCC), and designated PTA-120420. In some embodiments, the RSPO3-binding agent comprises a light chain variable region encoded by the plasmid deposited with ATCC and designated PTA-120421. In some embodiments, the RSPO3-binding agent comprises a heavy chain variable region encoded by the plasmid deposited with ATCC and designated PTA-120420, and a light chain variable region encoded by the plasmid deposited with ATCC and designated PTA-120421. In some embodiments, the RSPO3-binding agent comprises a heavy chain encoded by the plasmid deposited with ATCC and designated PTA-120420. In some embodiments, the RSPO3-binding agent comprises a light chain encoded by the plasmid deposited with ATCC and designated PTA-120421. In some embodiments, the RSPO3-binding agent comprises a heavy chain encoded by the plasmid deposited with ATCC and designated PTA-120420, and a light chain encoded by the plasmid deposited with ATCC and designated PTA-120421.

In certain embodiments, a RSPO3-binding agent comprises, consists essentially of or consists of, the antibody h131R010. In certain embodiments, a RSPO3-binding agent comprises, consists essentially of, or consists of, a variant of the antibody h131R010.

In certain embodiments, a RSPO3-binding agent comprises, consists essentially of, or consists of, the antibody h131R011. In certain embodiments, a RSPO3-binding agent comprises, consists essentially of, or consists of, a variant of the antibody h131R011.

In certain embodiments, the invention provides a RSPO3-binding agent that is a bispecific antibody. In some embodiments, the RSPO3-binding agent is a bispecific antibody comprising a first antigen-binding site that specifically binds human RSPO3. In some embodiments, the RSPO3-binding agent is a bispecific antibody comprising a first antigen-binding site that specifically binds human RSPO3 and a second antigen-binding site that binds a second target. In some embodiments, the RSPO3-binding agent is a bispecific antibody comprising: a first antigen-binding site that specifically binds human RSPO3, wherein the first antigen-binding site comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35), OR TYFANNFD (SEQ ID NO:80). In some embodiments, the RSPO3-binding agent is a bispecific antibody comprising: a first antigen-binding site that specifically binds human RSPO3, wherein the first antigen-binding site comprises a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANNFDY (SEQ ID NO:35). In some embodiments, the RSPO3-binding agent is a bispecific antibody comprising: a first antigen-binding site that specifically binds human RSPO3, wherein the first antigen-binding site comprises a heavy chain CDR1 comprising KASGYTFTSYTF (SEQ ID NO:34), a heavy chain CDR2 comprising IYPSNGDS (SEQ ID NO:10), and a heavy chain CDR3 comprising ATYFANNFDY (SEQ ID NO:35). In some embodiments, the RSPO3-binding agent is a bispecific antibody comprising: a first antigen-binding site that specifically binds human RSPO3, wherein the first antigen-binding site comprises a heavy chain CDR1 comprising KASGYTFTSYTF (SEQ ID NO:34), a heavy chain CDR2 comprising IYPSNGDS (SEQ ID NO:10), and a heavy chain CDR3 comprising ATYFANYFDY (SEQ ID NO:11). In some embodiments, the RSPO3-binding agent is a bispecific antibody comprising: a first antigen-binding site that specifically binds human RSPO3, wherein the first antigen-binding site comprises a heavy chain CDR1 comprising DYSIH (SEQ ID NO:80), a heavy chain CDR2 comprising YIYPSNGDSGYNQKFK (SEQ ID NO:79), and a heavy chain CDR3 comprising TYFANNFD (SEQ ID NO:80). In some embodiments, the RSPO3-binding agent is a bispecific antibody comprising: a first antigen-binding site that specifically binds human RSPO3, wherein the first antigen-binding site comprises a heavy chain CDR1 comprising DYSIH (SEQ ID NO:80) or KASGYTFTDYS (SEQ ID NO:9), a heavy chain CDR2 comprising IYPSNGDS (SEQ ID NO:10), and a heavy chain CDR3 comprising TYFANNFD (SEQ ID NO:80). In some embodiments, the RSPO3-binding agent is a bispecific antibody comprising: a first antigen-binding site that specifically binds human RSPO3, wherein the first antigen-binding site comprises (a) a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35) or TYFANNFD (SEQ ID NO:80), and a second antigen-binding site, wherein the first antigen-binding site and the second antigen-binding site comprise a common (i.e., identical) light chain. In some embodiments, the bispecific antibody comprises a first antigen-binding site comprising a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83).

In some embodiments, the RSPO3-binding agent is a bispecific antibody comprising a first heavy, chain variable region having at least about 80% sequence identity to SEQ ID NO:15, SEQ ID NO:16, SEQ ID NO:36, SEQ ID NO:37, SEQ ID NO:44, SEQ ID NO:45, or SEQ ID NO:62. In certain embodiments, the RSPO3-binding agent is a bispecific antibody comprising a first heavy chain variable region having at least about 85%, at least about 90%, at least about 95%, at least about 97%, or at least about 99% sequence identity to SEQ ID NO:15, SEQ ID NO:16, SEQ ID NO:36, SEQ ID NO:37, SEQ ID NO:44, SEQ ID NO:45, or SEQ ID NO:62. In some embodiments, the bispecific antibody comprises a light chain variable region at least about 85%, at least about 90%, at least about 95%, at least about 97%, or at least about 99% sequence identity to SEQ ID NO:17, SEQ ID NO:72, or SEQ ID NO:86. In some embodiments, the RSPO3-binding agent is a bispecific antibody comprising a first heavy, chain variable region comprising SEQ ID NO:44. In some embodiments, the RSPO3-binding agent is a bispecific antibody comprising a first heavy chain variable region comprising SEQ ID NO:45. In some embodiments, the RSPO3-binding agent is a bispecific antibody comprising a first heavy chain variable region comprising SEQ ID NO:62. In some embodiments, the RSPO3-binding agent is a bispecific antibody comprising a first light chain variable region comprising SEQ ID NO:17. In some embodiments, the RSPO3-binding agent is a bispecific antibody comprising a first light chain variable region comprising SEQ ID NO:72. In some embodiments, the RSPO3-binding agent is a bispecific antibody comprising a first light chain variable region comprising SEQ ID NO:86.

In some embodiments, the RSPO3-binding agent is a bispecific antibody comprising a first heavy chain variable region comprising SEQ ID NO:15, SEQ ID NO:16, SEQ ID NO:36, SEQ ID NO:37, SEQ ID NO:44, SEQ ID NO:45, or SEQ ID NO:62 and a first heavy chain constant region comprising SEQ ID NO:60 or SEQ ID NO:61. In some embodiments, the RSPO3-binding agent is a bispecific antibody comprising a first heavy chain variable region comprising SEQ ID NO:44 and a first heavy chain constant region comprising SEQ ID NO:60 or SEQ ID NO:61. In some embodiments, the RSPO3-binding agent is a bispecific antibody comprising a first heavy chain variable region comprising SEQ ID NO:45 and a first heavy chain constant region comprising SEQ ID NO:60 or SEQ ID NO:61. In some embodiments, the RSPO3-binding agent is a bispecific antibody comprising a first heavy chain variable region comprising SEQ ID NO:62 and a first heavy chain constant region comprising SEQ ID NO:60 or SEQ ID NO:61.

In certain embodiments, the RSPO3-binding agent is a bispecific antibody that specifically binds human RSPO3 and a second target. In some embodiments, the RSPO3-binding agent is a bispecific antibody that specifically binds human RSPO3 and a second human RSPO. In some embodiments, the RSPO3-binding agent is a bispecific antibody that specifically binds human RSPO3 and a second human RSPO selected from the group consisting of RSPO1, RSPO2, and RSPO4. Non-limiting examples of antibodies to human RSPO have been described in, for example, International Patent Pub. No. WO 2013/012747.

In some embodiments, the RSPO3-binding agent is a bispecific antibody that specifically binds human RSPO3 and human RSPO1. In some embodiments, the bispecific antibody comprises: a) a first antigen-binding site that specifically binds human RSPO3, and b) a second antigen-binding site that specifically binds human RSPO1, wherein the first antigen-binding site comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35) or TYFANNFD (SEQ ID NO:80); and wherein both the first and second antigen-binding sites comprise a common light chain.

In some embodiments, the RSPO3-binding agent is a bispecific antibody that specifically binds human RSPO3 and human RSPO2. In some embodiments, the bispecific antibody comprises: a) a first antigen-binding site that specifically binds human RSPO3, and b) a second antigen-binding site that specifically binds human RSPO2, wherein the first antigen-binding site comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35) or TYFANNFD (SEQ ID NO:80); and wherein both the first and second antigen-binding sites comprise a common light chain.

In some embodiments, the RSPO3-binding agent is a bispecific antibody that comprises a heavy chain variable region from the anti-RSPO3 antibody 131R003. In some embodiments, the RSPO3-binding agent is a bispecific antibody which comprises a heavy chain variable region from a variant of the anti-RSPO3 antibody 131R003. In some embodiments, the RSPO3-binding agent is a bispecific antibody that comprises a heavy chain variable region from the anti-RSPO3 antibody 131R006B. In some embodiments, the RSPO3-binding agent is a bispecific antibody that comprises a heavy chain variable region from the anti-RSPO3 antibody h131R005/131R007. In some embodiments, the RSPO3-binding agent is a bispecific antibody that comprises a heavy chain variable region from the anti-RSPO3 antibody h131R010 or h131R011.

In some embodiments, the RSPO3-binding agent is a bispecific antibody that comprises a first CH3 domain and a second CH3 domain, each of which is modified to promote formation of heteromultimers. In some embodiments, the first and second CH3 domains are modified using a knobs-into-holes technique. In some embodiments, the first and second CH3 domains comprise changes in amino acids that result in altered electrostatic interactions. In some embodiments, the first and second CH3 domains comprise changes in amino acids that result in altered hydrophobic/hydrophilic interactions.

In some embodiments, the RSPO3-binding agent is a bispecific antibody that comprises heavy chain constant regions selected from the group consisting of: (a) a first human IgG1 constant region, wherein the amino acids corresponding to positions 253 and 292 of IgG1 (SEQ ID NO:56) are replaced with glutamate or aspartate, and a second human IgG1 constant region, wherein the amino acids corresponding to positions 240 and 282 of IgG1 (SEQ ID NO:56) are replaced with lysine; (b) a first human IgG2 constant region, wherein the amino acids corresponding to positions 249 and 288 of IgG2 (SEQ ID NO:57) are replaced with glutamate or aspartate, and a second human IgG2 constant region wherein the amino acids corresponding to positions 236 and 278 of IgG2 (SEQ ID NO:57) are replaced with lysine; (c) a first human IgG3 constant region, wherein the amino acids corresponding to positions 300 and 339 of IgG3 (SEQ ID NO:58) are replaced with glutamate or aspartate, and a second human IgG3 constant region wherein the amino acids corresponding to positions 287 and 329 of IgG3 (SEQ ID NO:58) are replaced with lysine; and (d) a first human IgG4 constant region, wherein the amino acids corresponding to positions 250 and 289 of IgG4 (SEQ ID NO:59) are replaced with glutamate or aspartate, and a second IgG4 constant region wherein the amino acids corresponding to positions 237 and 279 of IgG4 (SEQ ID NO:59) are replaced with lysine.

In some embodiments, the RSPO3-binding agent is a bispecific antibody which comprises a first human IgG1 constant region with amino acid substitutions at positions corresponding to positions 253 and 292 of IgG1 (SEQ ID NO:56), wherein the amino acids at positions corresponding to positions 253 and 292 of IgG1 (SEQ ID NO:56) are replaced with glutamate or aspartate, and a second human IgG1 constant region with amino acid substitutions at positions corresponding to positions 240 and 282 of IgG1 (SEQ ID NO:56), wherein the amino acids at positions corresponding to positions 240 and 282 of IgG1 (SEQ ID NO:56) are replaced with lysine. In some embodiments, the RSPO3-binding agent is a bispecific antibody which comprises a first human IgG2 constant region with amino acid substitutions at positions corresponding to positions 249 and 288 of IgG2 (SEQ ID NO:57), wherein the amino acids at positions corresponding to positions 249 and 288 of IgG2 (SEQ ID NO:57) are replaced with glutamate or aspartate, and a second human IgG2 constant region with amino acid substitutions at positions corresponding to positions 236 and 278 of IgG2 (SEQ ID NO:57), wherein the amino acids at positions corresponding to positions 236 and 278 of IgG2 (SEQ ID NO:57) are replaced with lysine. In some embodiments, the RSPO-binding agent is a bispecific antibody which comprises a first human IgG3 constant region with amino acid substitutions at positions corresponding to positions 300 and 339 of IgG3 (SEQ ID NO:58), wherein the amino acids at positions corresponding to positions 300 and 339 of IgG3 (SEQ ID NO:58) are replaced with glutamate or aspartate, and a second human IgG3 constant region with amino acid substitutions at positions corresponding to positions 287 and 329 of IgG3 (SEQ ID NO:58), wherein the amino acids at positions corresponding to positions 287 and 329 of IgG3 (SEQ ID NO:58) are replaced with lysine. In some embodiments, the RSPO-binding agent is a bispecific antibody which comprises a first human IgG4 constant region with amino acid substitutions at positions corresponding to positions 250 and 289 of IgG4 (SEQ ID NO:59), wherein the amino acids at positions corresponding to positions 250 and 289 of IgG4 (SEQ ID NO:59) are replaced with glutamate or aspartate, and a second human IgG4 constant region with amino acid substitutions at positions corresponding to positions 237 and 279 of IgG4 (SEQ ID NO:59), wherein the amino acids at positions corresponding to positions 237 and 279 of IgG4 (SEQ ID NO:59) are replaced with lysine.

In some embodiments, the RSPO3-binding agent is a bispecific antibody which comprises a first human IgG1 constant region with amino acid substitutions at positions corresponding to positions 253 and 292 of IgG1 (SEQ ID NO:56), wherein the amino acids are replaced with glutamate, and a second human IgG1 constant region with amino acid substitutions at positions corresponding to positions 240 and 282 of IgG1 (SEQ ID NO:56), wherein the amino acids are replaced with lysine. In some embodiments, the RSPO3-binding agent is a bispecific antibody which comprises a first human IgG1 constant region with amino acid substitutions at positions corresponding to positions 253 and 292 of IgG1 (SEQ ID NO:56), wherein the amino acids are replaced with aspartate, and a second human IgG1 constant region with amino acid substitutions at positions corresponding to positions 240 and 282 of IgG1 (SEQ ID NO:56), wherein the amino acids are replaced with lysine.

In some embodiments, the RSPO3-binding agent is a bispecific antibody which comprises a first human IgG2 constant region with amino acid substitutions at positions corresponding to positions 249 and 288 of IgG2 (SEQ ID NO:57), wherein the amino acids are replaced with glutamate, and a second human IgG2 constant region with amino acid substitutions at positions corresponding to positions 236 and 278 of IgG2 (SEQ ID NO:57), wherein the amino acids are replaced with lysine. In some embodiments, the RSPO3-binding agent is a bispecific antibody which comprises a first human IgG2 constant region with amino acid substitutions at positions corresponding to positions 249 and 288 of IgG2 (SEQ ID NO:57), wherein the amino acids are replaced with aspartate, and a second human IgG2 constant region with amino acid substitutions at positions corresponding to positions 236 and 278 of IgG2 (SEQ ID NO:57), wherein the amino acids are replaced with lysine.

In some embodiments, the RSPO3-binding agent is a bispecific antibody which comprises a heavy chain constant region of SEQ ID NO:60. In some embodiments, the RSPO-binding agent is a bispecific antibody which comprises a heavy chain constant region of SEQ ID NO:61. In some embodiments, the RSPO3-binding agent is a bispecific antibody which comprises a first heavy chain constant region of SEQ ID NO:60 and a second heavy chain constant region of SEQ ID NO:61.

In some embodiments, the RSPO3-binding agent is a bispecific antibody which binds RSPO3 with a $K_D$ of about 50 nM or less, about 25 nM or less, about 10 nM or less, about 1 nM or less, or about 0.1 nM or less. In some embodiments, the RSPO3-binding agent is a bispecific antibody which binds a second target (e.g., RSPO2) with a $K_D$ of about 50 nM or less, about 25 nM or less, about 10 nM or less, about 1 nM or less, or about 0.1 nM or less. In some embodiments, the RSPO3-binding agent is a bispecific antibody which binds RSPO3 with a $K_D$ of about 50 nM or less and binds a second target (e.g., RSPO2) with a $K_D$ of about 50 nM or less. In some embodiments, the RSPO3-binding agent is a bispecific antibody which binds RSPO3 with a $K_D$ of about 25 nM or less and binds a second target (e.g., RSPO2) with a $K_D$ of about 25 nM or less. In some embodiments, the RSPO3-binding agent is a bispecific antibody which binds RSPO3 with a $K_D$ of about 10 nM or less and binds a second target (e.g., RSPO2) with a $K_D$ of about 10 nM or less. In some embodiments, the RSPO3-binding agent is a bispecific antibody which binds RSPO3 with a $K_D$ of about 1 nM or less and binds a second target (e.g., RSPO2) with a $K_D$ of about 1 nM or less.

In some embodiments, the RSPO3-binding agent is a bispecific antibody which comprises one antigen-binding site with a binding affinity that is weaker than the binding affinity of the second antigen-binding site. For example, in some embodiments, the bispecific antibody may bind RSPO3 with a $K_D$ ranging from about 0.1 nM to 1 nM and may bind a second target (e.g., RSPO2) with a $K_D$ ranging from about 1 nM to 10 nM. Or the bispecific antibody may bind RSPO3 with a $K_D$ ranging from about 1 nM to 10 nM and may bind a second target (e.g., RSPO2) with a $K_D$ ranging from about 0.1 nM to 1 nM. In some embodiments, the bispecific antibody may bind RSPO3 with a $K_D$ ranging from about 0.1 nM to 1 nM and may bind a second target (e.g., RSPO2) with a $K_D$ ranging from about 1 nM to 10 nM. Or the bispecific antibody may bind RSPO3 with a $K_D$ ranging from about 1 nM to 10 nM and may bind a second target (e.g., RSPO2) with a $K_D$ ranging from about 0.1 nM to 1 nM. In some embodiments, the difference in affinity between the two antigen-binding sites may be about 2-fold or more, about 3-fold or more, about 5-fold or more, about 8-fold or more, about 10-fold or more, about 15-fold or more, about 30-fold or more, about 50-fold or more, or about 100-fold or more. In some embodiments, at least one amino acid residue in at least one CDR of the antigen-binding site for RSPO3 is substituted with a different amino acid so that the affinity of the RSPO3-binding site is altered. In some embodiments, the affinity of the RSPO3-binding site is increased. In some embodiments, the affinity of the RSPO3-binding site is decreased. In some embodiments, at least one amino acid residue in at least one CDR of the antigen-binding site for the second target (e.g., RSPO2) is substituted with a different amino acid so that the affinity of the second antigen-binding site is altered. In some embodiments, the affinity of the second antigen-binding site is increased. In some embodiments, the affinity of the second antigen-binding site is decreased. In some embodiments, the affinities of both the RSPO3 and the second antigen-binding sites are altered.

The invention provides polypeptides, including, but not limited to, antibodies that specifically bind human RSPO proteins. In some embodiments, the polypeptides bind human RSPO3. In some embodiments, the polypeptides bind human RSPO3 and at least one additional human RSPO selected from the group consisting of RSPO1, RSPO2, and RSPO4.

In certain embodiments, the polypeptide comprises one, two, three, four, five, and/or six of the CDRs of antibody 131R002, 131R003, or variants of 131R003 including h131R005/131R007, h131R006A, h131R006B, h131R010, and h131R011 (see Table 1 herein). In some embodiments, the polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, the invention provides a polypeptide that specifically binds human RSPO3, wherein the polypeptide comprises an amino acid sequence having at least about 80% sequence identity to SEQ ID NO:15, SEQ ID NO:16, SEQ ID NO:36, SEQ ID NO:37, SEQ ID NO:44, SEQ ID NO:45, or SEQ ID NO:62, and/or an amino acid sequence having at least about 80% sequence identity to SEQ ID NO:17, SEQ ID NO:72, or SEQ ID NO:86. In certain embodiments, the polypeptide comprises an amino acid sequence having at least about 85%, at least about 90%, at least about 95%, at least about 97%, or at least about 99% sequence identity to SEQ ID NO:15, SEQ ID NO:16, SEQ ID NO:36, SEQ ID NO:37, SEQ ID NO:44, SEQ ID NO:45, or SEQ ID NO:62. In certain embodiments, the polypeptide comprises an amino acid sequence having at least about 85%, at least about 90%, at least about 95%, at least about 97%, or at least about 99% sequence identity to SEQ ID NO:17, SEQ ID NO:72, or SEQ ID NO:86. In certain embodiments, the polypeptide comprises an amino acid sequence having at least about 95% sequence identity to SEQ ID NO:15, SEQ ID NO:16, SEQ ID NO:36, SEQ ID NO:37, SEQ ID NO:44, SEQ ID NO:45, or SEQ ID NO:62, and/or an amino acid sequence having at least about 95% sequence identity to SEQ ID NO:17, SEQ ID NO:72, or SEQ ID NO:86. In certain embodiments, the polypeptide comprises an amino acid sequence comprising SEQ ID NO:15 and/or an amino acid sequence comprising SEQ ID NO:17. In certain embodiments, the polypeptide comprises an amino acid sequence comprising SEQ ID NO:16 and/or an amino acid sequence comprising SEQ ID NO:17. In certain embodiments, the polypeptide comprises an amino acid sequence comprising SEQ ID NO:36 and/or an amino acid sequence comprising SEQ ID NO:17. In certain embodiments, the polypeptide comprises an amino acid sequence comprising SEQ ID NO:37 and/or an amino acid sequence comprising SEQ ID NO:17. In certain embodiments, the polypeptide comprises an amino acid sequence comprising SEQ ID NO:44 and/or an amino acid sequence comprising SEQ ID NO:17. In certain embodiments, the polypeptide comprises an amino acid sequence comprising SEQ ID NO:45 and/or an amino acid sequence comprising SEQ ID NO:17. In certain embodiments, the polypeptide comprises an amino acid sequence comprising SEQ ID NO:62 and/or an amino acid sequence comprising SEQ ID NO:17. In certain embodiments, the polypeptide comprises an amino acid sequence comprising SEQ ID NO:15 and/or an amino acid sequence comprising SEQ ID NO:72. In certain embodiments, the polypeptide comprises an amino acid sequence comprising SEQ ID NO:16 and/or an amino acid sequence comprising SEQ ID NO:72. In certain embodiments, the polypeptide comprises an amino acid sequence comprising SEQ ID NO:36 and/or an amino acid sequence comprising SEQ ID NO:72. In certain embodiments, the polypeptide comprises an amino acid sequence comprising SEQ ID NO:37 and/or an amino acid sequence comprising SEQ ID NO:72. In certain embodiments, the polypeptide comprises an amino acid sequence comprising SEQ ID NO:44 and/or an amino acid sequence comprising SEQ ID NO:72. In certain embodiments, the polypeptide comprises an amino acid sequence comprising SEQ ID NO:45 and/or an amino acid sequence comprising SEQ ID NO:72. In certain embodiments, the polypeptide comprises an amino acid sequence comprising SEQ ID NO:62 and/or an amino acid sequence comprising SEQ ID NO:72. In certain embodiments, the polypeptide comprises an amino acid sequence comprising SEQ ID NO:44 and/or an amino acid sequence comprising SEQ ID NO:86. In certain embodiments, the polypeptide comprises an amino acid sequence comprising SEQ ID NO:45 and/or an amino acid sequence comprising SEQ ID NO:86. In certain embodiments, the polypeptide comprises an amino acid sequence comprising SEQ ID NO:62 and/or an amino acid sequence comprising SEQ ID NO:86.

In some embodiments, the invention provides a polypeptide that specifically binds human RSPO3, wherein the polypeptide comprises an amino acid sequence having at least about 80% sequence identity to SEQ ID NO:21, SEQ ID NO:22, SEQ ID NO:38, SEQ ID NO:41, SEQ ID NO:46, SEQ ID NO:47, SEQ ID NO:63, or SEQ ID NO:68, and/or an amino acid sequence having at least about 80% sequence identity to SEQ ID NO:23, SEQ ID NO:73, or SEQ ID NO:87. In certain embodiments, the polypeptide comprises an amino acid sequence having at least 85%, at least about 90%, at least about 95%, at least about 97%, or at least about 99% sequence identity to SEQ ID NO:21, SEQ ID NO:22, SEQ ID NO:38, SEQ ID NO:41, SEQ ID NO:46, SEQ ID NO:47, SEQ ID NO:63, or SEQ ID NO:68. In certain embodiments, the polypeptide comprises an amino acid sequence having at least about 85%, at least about 90%, at least about 95%, at least about 97%, or at least about 99% sequence identity to SEQ ID NO:23, SEQ ID NO:73, or SEQ ID NO:87. In certain embodiments, the polypeptide comprises an amino acid sequence having at least about 95% sequence identity to SEQ ID NO:21, SEQ ID NO:22, SEQ ID NO:38, SEQ ID NO:41, SEQ ID NO:46, SEQ ID NO:47, SEQ ID NO:63, or SEQ ID NO:68, and/or an amino acid sequence having at least about 95% sequence identity to SEQ ID NO:23, SEQ ID NO:73, or SEQ ID NO:87. In certain embodiments, the polypeptide comprises an amino acid sequence comprising SEQ ID NO:21, SEQ ID NO:22, SEQ ID NO:38, SEQ ID NO:41, SEQ ID NO:46, SEQ ID NO:47, SEQ ID NO:63, or SEQ ID NO:68, and/or an amino acid sequence comprising SEQ ID NO:23, SEQ ID NO:73, or SEQ ID NO:87. In certain embodiments, the polypeptide consists essentially of SEQ ID NO:21, SEQ ID NO:22, SEQ ID NO:38, SEQ ID NO:41, SEQ ID NO:46, SEQ ID NO:47, SEQ ID NO:63, or SEQ ID NO:68, and/or SEQ ID NO:23, SEQ ID NO:73, or SEQ ID NO:87.

In certain embodiments, the polypeptide comprises an amino acid sequence comprising SEQ ID NO:27, SEQ ID NO:28, SEQ ID NO:39, SEQ ID NO:42, SEQ ID NO:48, SEQ ID NO:49, SEQ ID NO:64, or SEQ ID NO:69, and/or an amino acid sequence comprising SEQ ID NO:29, SEQ ID NO:74, or SEQ ID NO:88. In certain embodiments, the polypeptide comprises an amino acid sequence comprising SEQ ID NO:48 and/or an amino acid sequence comprising SEQ ID NO:29. In certain embodiments, the polypeptide comprises an amino acid sequence comprising SEQ ID NO:49 and/or an amino acid sequence comprising SEQ ID NO:29. In certain embodiments, the polypeptide comprises an amino acid sequence comprising SEQ ID NO:64 and/or an amino acid sequence comprising SEQ ID NO:29. In certain embodiments, the polypeptide comprises an amino acid sequence comprising SEQ ID NO:69 and/or an amino acid sequence comprising SEQ ID NO:29. In certain embodiments, the polypeptide comprises an amino acid sequence comprising SEQ ID NO:48 and/or an amino acid sequence comprising SEQ ID NO:74. In certain embodiments, the polypeptide comprises an amino acid sequence comprising SEQ ID NO:49 and/or an amino acid sequence comprising SEQ ID NO:74. In certain embodiments, the polypeptide comprises an amino acid sequence comprising SEQ ID NO:64 and/or an amino acid sequence comprising SEQ ID NO:74. In certain embodiments, the polypeptide comprises an amino acid sequence comprising SEQ ID NO:69 and/or an amino acid sequence comprising SEQ ID NO:74. In certain embodiments, the polypeptide comprises an amino acid sequence comprising SEQ ID NO:48 and/or an amino acid sequence comprising SEQ ID NO:88. In certain embodiments, the polypeptide comprises an amino acid sequence comprising SEQ ID NO:49 and/or an amino acid sequence comprising SEQ ID NO:88. In certain embodiments, the polypeptide comprises an amino acid sequence comprising SEQ ID NO:64 and/or an amino acid sequence comprising SEQ ID NO:88. In certain embodiments, the polypeptide comprises an amino acid sequence comprising SEQ ID NO:69 and/or an amino acid sequence comprising SEQ ID NO:88. In certain embodiments, the polypeptide comprises an amino acid sequence consisting essentially of SEQ ID NO:27, SEQ ID NO:28, SEQ ID NO:39, SEQ ID NO:42, SEQ ID NO:48, SEQ ID NO:49, SEQ ID NO:64, or SEQ ID NO:69 and/or an amino acid sequence consisting essentially of SEQ ID NO:29, SEQ ID NO:74, SEQ ID NO:88. In certain embodiments, the polypeptide comprises an amino acid sequence consisting essentially of SEQ ID NO:48 and/or an amino acid sequence consisting essentially of SEQ ID NO:29. In certain embodiments, the polypeptide comprises an amino acid sequence consisting essentially of SEQ ID NO:49 and/or an amino acid sequence consisting essentially of SEQ ID NO:29. In certain embodiments, the polypeptide comprises an amino acid sequence consisting essentially of SEQ ID NO:64 and/or an amino acid sequence consisting essentially of SEQ ID NO:29. In certain embodiments, the polypeptide comprises an amino acid sequence consisting essentially of SEQ ID NO:69 and/or an amino acid sequence consisting essentially of SEQ ID NO:29. In certain embodiments, the polypeptide comprises an amino acid sequence consisting essentially of SEQ ID NO:48 and/or an amino acid sequence consisting essentially of SEQ ID NO:74. In certain embodiments, the polypeptide comprises an amino acid sequence consisting essentially of SEQ ID NO:49 and/or an amino acid sequence consisting essentially of SEQ ID NO:74. In certain embodiments, the polypeptide comprises an amino acid sequence consisting essentially of SEQ ID NO:64 and/or an amino acid sequence consisting essentially of SEQ ID NO:74. In certain embodiments, the polypeptide comprises an amino acid sequence consisting essentially of SEQ ID NO:69 and/or an amino acid sequence consisting essentially of SEQ ID NO:74. In certain embodiments, the polypeptide comprises an amino acid sequence consisting essentially of SEQ ID NO:48 and/or an amino acid sequence consisting essentially of SEQ ID NO:88. In certain embodiments, the polypeptide comprises an amino acid sequence consisting essentially of SEQ ID NO:49 and/or an amino acid sequence consisting essentially of SEQ ID NO:88. In certain embodiments, the polypeptide comprises an amino acid sequence consisting essentially of SEQ ID NO:64 and/or an amino acid sequence consisting essentially of SEQ ID NO:88. In certain embodiments, the polypeptide comprises an amino acid sequence consisting essentially of SEQ ID NO:69 and/or an amino acid sequence consisting essentially of SEQ ID NO:88.

In some embodiments, the invention provides a polypeptide that specifically binds human RSPO3, wherein the polypeptide comprises an amino acid sequence having at least about 80% sequence identity to SEQ ID NO:27, SEQ ID NO:28, SEQ ID NO:39, SEQ ID NO:42, SEQ ID NO:48, SEQ ID NO:49, SEQ ID NO:64, or SEQ ID NO:69, and/or an amino acid sequence having at least about 80% sequence identity to SEQ ID NO:29, SEQ ID NO:74, or SEQ ID NO:88. In certain embodiments, the polypeptide comprises an amino acid sequence having at least about 85%, at least about 90%, at least about 95%, at least about 97%, or at least about 99% sequence identity to SEQ ID NO:27, SEQ ID NO:28, SEQ ID NO:39, SEQ ID NO:42, SEQ ID NO:48, SEQ ID NO:49, SEQ ID NO:64, or SEQ ID NO:69. In certain embodiments, the polypeptide comprises an amino acid sequence having at least about 85%, at least about 90%, at least about 95%, at least about 97%, or at least about 99% sequence identity to SEQ ID NO:29, SEQ ID NO:74, or SEQ ID NO:88. In certain embodiments, the polypeptide comprises an amino acid sequence having at least about 95% sequence identity to SEQ ID NO:27, SEQ ID NO:28, SEQ ID NO:39, SEQ ID NO:42, SEQ ID NO:48, SEQ ID NO:49, SEQ ID NO:64, or SEQ ID NO:69, and/or an amino acid sequence having at least about 95% sequence identity to SEQ ID NO:29, SEQ ID NO:74, SEQ ID NO:88. In certain embodiments, the polypeptide comprises an amino acid sequence comprising SEQ ID NO:27, SEQ ID NO:28, SEQ ID NO:39, SEQ ID NO:42, SEQ ID NO:48, SEQ ID NO:49, SEQ ID NO:64, or SEQ ID NO:69, and/or an amino acid sequence comprising SEQ ID NO:29, SEQ ID NO:74, or SEQ ID NO:88. In certain embodiments, the polypeptide comprises an amino acid sequence comprising SEQ ID NO:48 and/or an amino acid sequence comprising SEQ ID NO:29. In certain embodiments, the polypeptide comprises an amino acid sequence comprising SEQ ID NO:49 and/or an amino acid sequence comprising SEQ ID NO:29. In certain embodiments, the polypeptide comprises an amino acid sequence comprising SEQ ID NO:64 and/or an amino acid sequence comprising SEQ ID NO:29. In certain embodiments, the polypeptide comprises an amino acid sequence comprising SEQ ID NO:69 and/or an amino acid sequence comprising SEQ ID NO:29. In certain embodiments, the polypeptide consists essentially of SEQ ID NO:27 and/or SEQ ID NO:29. In certain embodiments, the polypeptide consists essentially of SEQ ID NO:28 and/or SEQ ID NO:29. In certain embodiments, the polypeptide consists essentially of SEQ ID NO:48 and/or SEQ ID NO:29. In certain embodiments, the polypeptide consists essentially of SEQ ID NO:49 and/or SEQ ID NO:29. In certain embodiments, the polypeptide consists essentially of SEQ ID NO:64 and/or SEQ ID NO:29. In certain embodiments, the polypeptide consists essentially of SEQ ID NO:69 and/or SEQ ID NO:29. In certain embodiments, the polypeptide comprises an amino acid sequence comprising SEQ ID NO:48 and/or an amino acid sequence comprising SEQ ID NO:74. In certain embodiments, the polypeptide comprises an amino acid sequence comprising SEQ ID NO:49 and/or an amino acid sequence comprising SEQ ID NO:74. In certain embodiments, the polypeptide comprises an amino acid sequence comprising SEQ ID NO:64 and/or an amino acid sequence comprising SEQ ID NO:74. In certain embodiments, the polypeptide comprises an amino acid sequence comprising SEQ ID NO:69 and/or an amino acid sequence comprising SEQ ID NO:74. In certain embodiments, the polypeptide consists essentially of SEQ ID NO:27 and/or SEQ ID NO:74. In certain embodiments, the polypeptide consists essentially of SEQ ID NO:28 and/or SEQ ID NO:74. In certain embodiments, the polypeptide consists essentially of SEQ ID NO:48 and/or SEQ ID NO:74. In certain embodiments, the polypeptide consists essentially of SEQ ID NO:49 and/or SEQ ID NO:74. In certain embodiments, the polypeptide consists essentially of SEQ ID NO:64 and/or SEQ ID NO:74. In certain embodiments, the polypeptide consists essentially of SEQ ID NO:69 and/or SEQ ID NO:74. In certain embodiments, the polypeptide comprises an amino acid sequence comprising SEQ ID NO:48 and/or an amino acid sequence comprising SEQ ID NO:88. In certain embodiments, the polypeptide comprises an amino acid sequence comprising SEQ ID NO:49 and/or an amino acid sequence comprising SEQ ID NO:88. In certain embodiments, the polypeptide comprises an amino acid sequence comprising SEQ ID NO:64 and/or an amino acid sequence comprising SEQ ID NO:88. In certain embodiments, the polypeptide comprises an amino acid sequence comprising SEQ ID NO:69 and/or an amino acid sequence comprising SEQ ID NO:88. In certain embodiments, the polypeptide consists essentially of SEQ ID NO:48 and/or SEQ ID NO:88. In certain embodiments, the polypeptide consists essentially of SEQ ID NO:49 and/or SEQ ID NO:88. In certain embodiments, the polypeptide consists essentially of SEQ ID NO:64 and/or SEQ ID NO:88. In certain embodiments, the polypeptide consists essentially of SEQ ID NO:69 and/or SEQ ID NO:88.

In some embodiments, a RSPO3-binding agent comprises a polypeptide comprising a sequence selected from the group consisting of: SEQ ID NO:15, SEQ ID NO:16, SEQ ID NO:17, SEQ ID NO:21, SEQ ID NO:22, SEQ ID NO:23, SEQ ID NO:27, SEQ ID NO:28, SEQ ID NO:29, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, SEQ ID NO:48, SEQ ID NO:49, SEQ ID NO:62, SEQ ID NO:63, SEQ ID NO:64, SEQ ID NO:68, SEQ ID NO:69, SEQ ID NO:72, SEQ ID NO:73, SEQ ID NO:74, SEQ ID NO:86, SEQ ID NO:87, and SEQ ID NO:88.

Many proteins, including antibodies, contain a signal sequence that directs the transport of the proteins to various locations. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or may be used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions as compared to a "native" or "parental" signal sequence. In some embodiments, the signal sequence of the polypeptide comprises amino acid substitutions and/or deletions that allow one cleavage site to be dominant, thereby resulting in a substantially homogeneous polypeptide with one N-terminus. In some embodiments, a signal sequence of the polypeptide affects the expression level of the polypeptide, e.g., increased expression or decreased expression.

In certain embodiments, a RSPO3-binding agent (e.g., antibody) competes for specific binding to RSPO3 with an antibody that comprises a heavy chain variable region comprising SEQ ID NO:15, SEQ ID NO:16, SEQ ID NO:36, SEQ ID NO:37, SEQ ID NO:44, SEQ ID NO:45, or SEQ ID NO:62, and a light chain variable region comprising SEQ ID NO:17, SEQ ID NO:72, or SEQ ID NO:86. In certain embodiments, a RSPO3-binding agent (e.g., antibody) competes for specific binding to RSPO3 with an antibody that comprises a heavy chain variable region comprising SEQ ID NO:44 and a light chain variable region comprising SEQ ID NO:17. In certain embodiments, a RSPO3-binding agent (e.g., antibody) competes for specific binding to RSPO3 with an antibody that comprises a heavy chain variable region comprising SEQ ID NO:45 and a light chain variable region comprising SEQ ID NO:17. In certain embodiments, a RSPO3-binding agent (e.g., antibody) competes for specific binding to RSPO3 with an antibody that comprises a heavy chain variable region comprising SEQ ID NO:62 and a light chain variable region comprising SEQ ID NO:17. In certain embodiments, a RSPO3-binding agent (e.g., antibody) competes for specific binding to RSPO3 with an antibody that comprises a heavy chain variable region comprising SEQ ID NO:44 and a light chain variable region comprising SEQ ID NO:72. In certain embodiments, a RSPO3-binding agent (e.g., antibody) competes for specific binding to RSPO3 with an antibody that comprises a heavy chain variable region comprising SEQ ID NO:45 and a light chain variable region comprising SEQ ID NO:72. In certain embodiments, a RSPO3-binding agent (e.g., antibody) competes for specific binding to RSPO3 with an antibody that comprises a heavy chain variable region comprising SEQ ID NO:62 and a light chain variable region comprising SEQ ID NO:72. In certain embodiments, a RSPO3-binding agent (e.g., antibody) competes for specific binding to RSPO3 with an antibody that comprises a heavy chain variable region comprising SEQ ID NO:44 and a light chain variable region comprising SEQ ID NO:86. In certain embodiments, a RSPO3-binding agent (e.g., antibody) competes for specific binding to RSPO3 with an antibody that comprises a heavy chain variable region comprising SEQ ID NO:45 and a light chain variable region comprising SEQ ID NO:86. In certain embodiments, a RSPO3-binding agent (e.g., antibody) competes for specific binding to RSPO3 with an antibody that comprises a heavy chain variable region comprising SEQ ID NO:62 and a light chain variable region comprising SEQ ID NO:86.

In certain embodiments, a RSPO3-binding agent (e.g., antibody) competes for specific binding to RSPO3 with an antibody that comprises a heavy chain comprising SEQ ID NO:27, SEQ ID NO:28, SEQ ID NO:39, SEQ ID NO:42, SEQ ID NO:48, SEQ ID NO:49, SEQ ID NO:64, or SEQ ID NO:69 and a light chain comprising SEQ ID NO:29, SEQ ID NO:74, or SEQ ID NO:88. In certain embodiments, a RSPO3-binding agent (e.g., antibody) competes for specific binding to RSPO3 with an antibody that comprises a heavy chain comprising SEQ ID NO:48 and a light chain comprising SEQ ID NO:29. In certain embodiments, a RSPO3-binding agent (e.g., antibody) competes for specific binding to RSPO3 with an antibody that comprises a heavy chain comprising SEQ ID NO:49 and a light chain comprising SEQ ID NO:29. In certain embodiments, a RSPO3-binding agent (e.g., antibody) competes for specific binding to RSPO3 with an antibody that comprises a heavy chain comprising SEQ ID NO:64 and a light chain comprising SEQ ID NO:29. In certain embodiments, a RSPO3-binding agent (e.g., antibody) competes for specific binding to RSPO3 with an antibody that comprises a heavy chain comprising SEQ ID NO:69 and a light chain comprising SEQ ID NO:29. In certain embodiments, a RSPO3-binding agent (e.g., antibody) competes for specific binding to RSPO3 with an antibody that comprises a heavy chain comprising SEQ ID NO:48 and a light chain comprising SEQ ID NO:74. In certain embodiments, a RSPO3-binding agent (e.g., antibody) competes for specific binding to RSPO3 with an antibody that comprises a heavy chain comprising SEQ ID NO:49 and a light chain comprising SEQ ID NO:74. In certain embodiments, a RSPO3-binding agent (e.g., antibody) competes for specific binding to RSPO3 with an antibody that comprises a heavy chain comprising SEQ ID NO:64 and a light chain comprising SEQ ID NO:74. In certain embodiments, a RSPO3-binding agent (e.g., antibody) competes for specific binding to RSPO3 with an antibody that comprises a heavy chain comprising SEQ ID NO:69 and a light chain comprising SEQ ID NO:74. In certain embodiments, a RSPO3-binding agent (e.g., antibody) competes for specific binding to RSPO3 with an antibody that comprises a heavy chain comprising SEQ ID NO:48 and a light chain comprising SEQ ID NO:88. In certain embodiments, a RSPO3-binding agent (e.g., antibody) competes for specific binding to RSPO3 with an antibody that comprises a heavy chain comprising SEQ ID NO:49 and a light chain comprising SEQ ID NO:88. In certain embodiments, a RSPO3-binding agent (e.g., antibody) competes for specific binding to RSPO3 with an antibody that comprises a heavy chain comprising SEQ ID NO:64 and a light chain comprising SEQ ID NO:88. In certain embodiments, a RSPO3-binding agent (e.g., antibody) competes for specific binding to RSPO3 with an antibody that comprises a heavy chain comprising SEQ ID NO:69 and a light chain comprising SEQ ID NO:88.

In certain embodiments, a RSPO3-binding agent competes with antibody 131R002 or antibody 131R003 for specific binding to human RSPO3. In certain embodiments, a RSPO3-binding agent competes with a variant of antibody 131R003 for specific binding to human RSPO3. In certain embodiments, a RSPO3-binding agent competes with a humanized version of antibody 131R003 for specific binding to human RSPO3. In certain embodiments, a RSPO3-binding agent competes with antibody h131R005/131R007 for specific binding to human RSPO3. In certain embodiments, a RSPO3-binding agent competes with antibody h131R008 for specific binding to human RSPO3. In certain embodiments, a RSPO3-binding agent competes with antibody h131R006A or antibody h131R006B for specific binding to human RSPO3. In certain embodiments, a RSPO3-binding agent competes with antibody h131R010 for specific binding to human RSPO3. In certain embodiments, a RSPO3-binding agent competes with antibody h131R011 for specific binding to human RSPO3. In some embodiments, a RSPO3-binding agent or antibody competes for specific binding to RSPO3 in an in vitro competitive binding assay. In some embodiments, the RSPO3 is human RSPO3. In some embodiments, the RSPO3 is mouse RSPO3.

In certain embodiments, a RSPO3-binding agent (e.g., an antibody) binds the same epitope, or essentially the same epitope, on RSPO3 as an antibody of the invention. In certain embodiments, a RSPO3-binding agent (e.g., an antibody) binds the same epitope, or essentially the same epitope, on RSPO3 as antibody 131R002 or antibody 131R003. In certain embodiments, a RSPO3-binding agent (e.g., an antibody) binds the same epitope, or essentially the same epitope, on RSPO3 as a variant of antibody 131R003. In certain embodiments, a RSPO3-binding agent (e.g., an antibody) binds the same epitope, or essentially the same epitope, on RSPO3 as a humanized version of antibody 131R003. In certain embodiments, a RSPO3-binding agent (e.g., an antibody) binds the same epitope, or essentially the same epitope, on RSPO3 as antibody h131R006A or antibody h131R006B. In certain embodiments, a RSPO3-binding agent (e.g., an antibody) binds the same epitope, or essentially the same epitope, on RSPO3 as antibody h131R005/131R007. In certain embodiments, a RSPO3-binding agent (e.g., an antibody) binds the same epitope, or essentially the same epitope, on RSPO3 as antibody h131R008. In certain embodiments, a RSPO3-binding agent (e.g., an antibody) binds the same epitope, or essentially the same epitope, on RSPO3 as antibody h131R010. In certain embodiments, a RSPO3-binding agent (e.g., an antibody) binds the same epitope, or essentially the same epitope, on RSPO3 as antibody h131R011.

In another embodiment, a RSPO3-binding agent is an antibody that binds an epitope on RSPO3 that overlaps with the epitope on RSPO3 bound by an antibody of the invention. In some embodiments, the RSPO3-binding agent is an antibody that binds an epitope on RSPO3 that overlaps with the epitope on RSPO3 bound by antibody 131R002 or antibody 131R003. In another embodiment, the RSPO3-binding agent is an antibody that binds an epitope on RSPO3 that overlaps with the epitope on RSPO3 bound by a variant of antibody 131R003. In some embodiments, the RSPO3-binding agent is an antibody that binds an epitope on RSPO3 that overlaps with the epitope on RSPO3 bound by a humanized version of antibody 131R003. In certain embodiments, the RSPO3-binding agent is an antibody that binds an epitope on RSPO3 that overlaps with the epitope on RSPO3 bound by antibody h131R006A or antibody h131R006B. In certain embodiments, the RSPO3-binding agent is an antibody that binds an epitope on RSPO3 that overlaps with the epitope on RSPO3 bound by antibody h131R005/131R007. In certain embodiments, the RSPO3-binding agent is an antibody that binds an epitope on RSPO3 that overlaps with the epitope on RSPO3 bound by antibody h131R008. In certain embodiments, the RSPO3-binding agent is an antibody that binds an epitope on RSPO3 that overlaps with the epitope on RSPO3 bound by antibody h131R010. In certain embodiments, the RSPO3- binding agent is an antibody that binds an epitope on RSPO3 that overlaps with the epitope on RSPO3 bound by antibody h131R011.

In certain embodiments, the RSPO-binding agent (e.g., an antibody) described herein binds at least one human RSPO protein and modulates RSPO activity. In some embodiments, the RSPO-binding agent is a RSPO antagonist and decreases RSPO activity. In some embodiments, the RSPO-binding agent is a RSPO antagonist and decreases β-catenin activity.

In certain embodiments, a RSPO3-binding agent (e.g., an antibody) described herein binds human RSPO3 and modulates RSPO3 activity. In some embodiments, a RSPO3-binding agent is a RSPO3 antagonist and decreases RSPO3 activity. In some embodiments, a RSPO3-binding agent is a RSPO3 antagonist and decreases β-catenin activity.

In certain embodiments, the RSPO-binding agent (e.g., an antibody) is an antagonist of at least one human RSPO protein. In some embodiments, the RSPO-binding agent is an antagonist of at least one RSPO and inhibits RSPO activity. In certain embodiments, the RSPO-binding agent inhibits RSPO activity by at least about 10%, at least about 20%, at least about 30%, at least about 50%, at least about 75%, at least about 90%, or about 100%. In some embodiments, the RSPO-binding agent inhibits activity of one, two, three, or four RSPO proteins. In some embodiments, the RSPO-binding agent inhibits activity of human RSPO1, RSPO2, RSPO3, and/or RSPO4. In some embodiments, the RSPO-binding agent is a RSPO3-binding agent. In some embodiments, the RSPO3-binding agent inhibits RSPO3 activity. In certain embodiments, a RSPO3-binding agent that inhibits human RSPO3 activity is antibody 131R002, antibody 131R003, or a variant of 131R003. In certain embodiments, a RSPO3-binding agent that inhibits human RSPO3 activity is a humanized version of antibody 131R002, antibody 131R003, or a variant of 131R003. In certain embodiments, a RSPO3-binding agent that inhibits human RSPO3 activity is antibody h131R006A or antibody h131R006B. In certain embodiments, a RSPO3-binding agent that inhibits human RSPO3 activity is antibody h131R005/131R007. In certain embodiments, a RSPO3-binding agent that inhibits human RSPO3 activity is antibody h131R008. In certain embodiments, a RSPO3-binding agent that inhibits human RSPO3 activity is antibody h131R010. In certain embodiments, a RSPO3-binding agent that inhibits human RSPO3 activity is antibody h131R011.

In certain embodiments, the RSPO-binding agent (e.g., antibody) is an antagonist of at least one human RSPO protein. In certain embodiments, the RSPO-binding agent inhibits RSPO signaling by at least about 10%, at least about 20%, at least about 30%, at least about 50%, at least about 75%, at least about 90%, or about 100%. In some embodiments, the RSPO-binding agent inhibits signaling by one, two, three, or four RSPO proteins. In some embodiments, the RSPO-binding agent inhibits signaling of human RSPO1, RSPO2, RSPO3, and/or RSPO4. In some embodiments, the RSPO-binding agent is a RSPO3-binding agent. In some embodiments, the RSPO3-binding agent inhibits human RSPO3 signaling. In certain embodiments, a RSPO3-binding agent that inhibits RSPO3 signaling is antibody 131R002, antibody 131R003, or a variant of 131R003. In certain embodiments, a RSPO3-binding agent that inhibits RSPO3 signaling is a humanized version of antibody 131R002, antibody 131R003, or a variant of 131R003. In certain embodiments, a RSPO3-binding agent that inhibits human RSPO3 signaling is antibody h131R006A or antibody h131R006B. In certain embodiments, a RSPO3-binding agent that inhibits human RSPO3 signaling is antibody h131R005/131R007. In certain embodiments, a RSPO3-binding agent that inhibits human RSPO3 signaling is antibody h131R008. In certain embodiments, a RSPO3-binding agent that inhibits human RSPO3 signaling is antibody h131R010. In certain embodiments, a RSPO3-binding agent that inhibits human RSPO3 signaling is antibody h131R011.

In certain embodiments, the RSPO-binding agent (e.g., antibody) is an antagonist of β-catenin signaling. In certain embodiments, the RSPO-binding agent inhibits β-catenin signaling by at least about 10%, at least about 20%, at least about 30%, at least about 50%, at least about 75%, at least about 90%, or about 100%. In some embodiments, the RSPO-binding agent that inhibits β-catenin signaling is a RSPO3-binding agent. In some embodiments, the RSPO3-binding agent inhibits β-catenin signaling. In certain embodiments, a RSPO3-binding agent that inhibits β-catenin signaling is antibody 131R002, antibody 131R003, or a variant of 131R003. In certain embodiments, a RSPO3-binding agent that inhibits β-catenin signaling is a humanized version of antibody 131R002, antibody 131R003, or a variant of 131R003. In certain embodiments, a RSPO3-binding agent that inhibits β-catenin signaling is antibody h131R006A or antibody h131R0006B. In certain embodiments, a RSPO3-binding agent that inhibits β-catenin signaling is antibody h131R005/131R007. In certain embodiments, a RSPO3-binding agent that inhibits β-catenin signaling is antibody h131R008. In certain embodiments, a RSPO3-binding agent that inhibits β-catenin signaling is antibody h131R010. In certain embodiments, a RSPO3-binding agent that inhibits β-catenin signaling is antibody h131R011.

In certain embodiments, the RSPO-binding agent (e.g., antibody) inhibits binding of at least one RSPO protein to a receptor. In certain embodiments, the RSPO-binding agent inhibits binding of a human RSPO protein to one or more of its receptors. In some embodiments, the RSPO-binding agent inhibits binding of a RSPO protein to at least one LGR protein. In some embodiments, the RSPO-binding agent inhibits binding of a RSPO protein to LGR4, LGR5, and/or LGR6. In some embodiments, a RSPO3-binding agent inhibits binding of RSPO3 to LGR4. In some embodiments, a RSPO3-binding agent inhibits binding of RSPO3 to LGR5. In some embodiments, a RSPO3-binding agent inhibits binding of RSPO3 to LGR-6. In certain embodiments, the inhibition of binding of a RSPO-binding agent to at least one LGR protein is at least about 10%, at least about 25%, at least about 50%, at least about 75%, at least about 90%, or at least about 95%. In certain embodiments, a RSPO-binding agent that inhibits binding of at least one RSPO to at least one LGR protein further inhibits β-catenin signaling. In certain embodiments, a RSPO3-binding agent that inhibits binding of human RSPO3 to at least one LGR protein is antibody 131R002, antibody 131R003, or a variant of 131R003. In certain embodiments, a RSPO3-binding agent that inhibits binding of human RSPO3 to at least one LGR protein is a humanized version of antibody 131R002, antibody 131R003, or a variant of 131R003. In certain embodiments, a RSPO3-binding agent that inhibits binding of human RSPO3 to at least one LGR protein is antibody h131R006A or antibody h131R006B. In certain embodiments, a RSPO3-binding agent that inhibits binding of human RSPO3 to at least one LGR protein is antibody h131R005/131R007. In certain embodiments, a RSPO3-binding agent that inhibits binding of human RSPO3 to at least one LGR protein is antibody h131R008. In certain embodiments, a RSPO3-binding agent that inhibits binding of human RSPO3 to at least one LGR protein is antibody h131R010. In certain embodiments, a RSPO3-binding agent that inhibits binding of human RSPO3 to at least one LGR protein is antibody h131R011.

In certain embodiments, the RSPO-binding agent (e.g., antibody) blocks binding of at least one RSPO to a receptor. In certain embodiments, the RSPO-binding agent blocks binding of a human RSPO protein to one or more of its receptors. In some embodiments, the RSPO-binding agent blocks binding of a RSPO to at least one LGR protein. In some embodiments, the RSPO-binding agent blocks binding of at least one RSPO protein to LGR4, LGR5, and/or LGR6. In some embodiments, a RSPO3-binding agent blocks binding of RSPO3 to LGR4. In some embodiments, a RSPO3-binding agent blocks binding of RSPO3 to LGR5. In some embodiments, a RSPO3-binding agent blocks binding of RSPO3 to LGR6. In certain embodiments, the blocking of binding of a RSPO-binding agent to at least one LGR protein is at least about 10%, at least about 25%, at least about 50%, at least about 75%, at least about 90%, or at least about 95%. In certain embodiments, a RSPO-binding agent that blocks binding of at least one RSPO protein to at least one LGR protein further inhibits β-catenin signaling. In certain embodiments, a RSPO3-binding agent that blocks binding of human RSPO3 to at least one LGR protein is antibody 131R002, antibody 131R003, or a variant of 131R003. In certain embodiments, a RSPO3-binding agent that blocks binding of human RSPO3 to at least one LGR protein is a humanized version of antibody 131R002, antibody 131R003, or a variant of 131R003. In certain embodiments, a RSPO3-binding agent that blocks binding of human RSPO3 to at least one LGR protein is antibody h131R006A or antibody h131R006B. In certain embodiments, a RSPO3-binding agent that blocks binding of human RSPO3 to at least one LGR protein is antibody h131R005/131R007. In certain embodiments, a RSPO3-binding agent that blocks binding of human RSPO3 to at least one LGR protein is antibody h131R008. In certain embodiments, a RSPO3-binding agent that blocks binding of human RSPO3 to at least one LGR protein is antibody h131R010. In certain embodiments, a RSPO3-binding agent that blocks binding of human RSPO3 to at least one LGR protein is antibody h131R011.

In certain embodiments, the RSPO-binding agent (e.g., an antibody) inhibits β-catenin signaling. It is understood that a RSPO-binding agent that inhibits β-catenin signaling may, in certain embodiments, inhibit signaling by one or more receptors in the β-catenin signaling pathway but not necessarily inhibit signaling by all receptors. In certain alternative embodiments, β-catenin signaling by all human receptors may be inhibited. In certain embodiments, β-catenin signaling by one or more receptors selected from the group consisting of LGR4, LGR5, and LGR6 is inhibited. In certain embodiments, the inhibition of β-catenin signaling by a RSPO-binding agent is a reduction in the level of β-catenin signaling of at least about 10%, at least about 25%, at least about 50%, at least about 75%, at least about 90%, or at least about 95%. In some embodiments, a RSPO3-binding agent that inhibits β-catenin signaling is antibody 131R002, antibody 131R003, or a variant of 131R003. In some embodiments, a RSPO3-binding agent that inhibits β-catenin signaling is a humanized version of antibody 131R002, antibody 131R003, or a variant of 131R003. In some embodiments, a RSPO3-binding agent that inhibits β-catenin signaling is antibody h131R006A or antibody h131R006B. In some embodiments, a RSPO3-binding agent that inhibits β-catenin signaling is antibody h131R005/131R007. In some embodiments, a RSPO3-binding agent that inhibits β-catenin signaling is antibody h131R008. In some embodiments, a RSPO3-binding agent that inhibits β-catenin signaling is antibody h131R010. In some embodiments, a RSPO3-binding agent that inhibits β-catenin signaling is antibody h131R011.

In certain embodiments, the RSPO-binding agent (e.g., an antibody) inhibits activation of β-catenin. It is understood that a RSPO-binding agent that inhibits activation of β-catenin may, in certain embodiments, inhibit activation of β-catenin by one or more receptors, but not necessarily inhibit activation of β-catenin by all receptors. In certain alternative embodiments, activation of β-catenin by all human receptors may be inhibited. In certain embodiments, activation of β-catenin by one or more receptors selected from the group consisting of LGR4, LGR5, and LGR6 is inhibited. In certain embodiments, the inhibition of activation of β-catenin by a RSPO-binding agent is a reduction in the level of activation of β-catenin of at least about 10%, at least about 25%, at least about 50%, at least about 75%, at least about 90%, or at least about 95%. In some embodiments, a RSPO3-binding agent that inhibits activation of β-catenin is antibody 131R002, antibody 131R003, or a variant of 131R003. In some embodiments, a RSPO3-binding agent that inhibits activation of β-catenin is a humanized version of antibody 131R002, antibody 131R003, or a variant of 131R003. In some embodiments, a RSPO3-binding agent that inhibits activation of β-catenin is antibody 131R006A or antibody h131R006B. In some embodiments, a RSPO3-binding agent that inhibits activation of β-catenin is antibody h131R005/131R007. In some embodiments, a RSPO3-binding agent that inhibits activation of β-catenin is antibody h131R008. In some embodiments, a RSPO3-binding agent that inhibits activation of β-catenin is antibody h131R010. In some embodiments, a RSPO3-binding agent that inhibits activation of β-catenin is antibody h131R011.

In vivo and in vitro assays for determining whether a RSPO-binding agent (or candidate RSPO-binding agent) inhibits β-catenin signaling are known in the art. For example, cell-based, luciferase reporter assays utilizing a TCF/Luc reporter vector containing multiple copies of the TCF-binding domain upstream of a firefly luciferase reporter gene may be used to measure β-catenin signaling levels in vitro (Gazit et al., 1999, Oncogene, 18; 5959-66; TOPflash, Millipore, Billerica Mass.). The level of β-catenin signaling in the presence of one or more Wnts (e.g., Wnt(s) expressed by transfected cells or provided by Wnt-conditioned media) with or without a RSPO protein or RSPO-conditioned media in the presence of a RSPO-binding agent is compared to the level of signaling without the RSPO-binding agent present. In addition to the TCF/Luc reporter assay, the effect of a RSPO-binding agent (or candidate agent) on β-catenin signaling may be measured in vitro or in vivo by measuring the effect of the agent on the level of expression of β-catenin-regulated genes, such as c-myc (He et al., 1998, Science, 281:1509-12), cyclin D1 (Tetsu et al., 1999, Nature, 398:422-6) and/or fibronectin (Gradl et al. 1999, Mol. Cell. Biol., 19:5576-87). In certain embodiments, the effect of a RSPO-binding agent on β-catenin signaling may also be assessed by measuring the effect of the agent on the phosphorylation state of Dishevelled-1, Dishevelled-2, Dishevelled-3, LRP5, LRP6, and/or β-catenin.

In certain embodiments, the RSPO3-binding agents have one or more of the following effects: inhibit proliferation of tumor cells, inhibit tumor growth, reduce the tumorigenicity of a tumor, reduce the tumorigenicity of a tumor by reducing the frequency of cancer stem cells in the tumor, inhibit tumor growth, trigger cell death of tumor cells, induce cells in a tumor to differentiate, differentiate tumorigenic cells to a non-tumorigenic state, induce expression of differentiation markers in the tumor cells, prevent metastasis of tumor cells, decrease survival of tumor cells, or modulate angiogenesis.

In certain embodiments, the RSPO3-binding agents are capable of inhibiting tumor growth. In certain embodiments, the RSPO3-binding agents are capable of inhibiting tumor growth in vivo (e.g., in a xenograft mouse model, and/or in a human having cancer). In certain embodiments, tumor growth is inhibited at least about two-fold, about three-fold, about five-fold, about ten-fold, about 50-fold, about 100-fold, or about 1000-fold as compared to a untreated tumor.

In certain embodiments, the RSPO3-binding agents are capable of reducing the tumorigenicity of a tumor. In certain embodiments, the RSPO3-binding agent or antibody is capable of reducing the tumorigenicity of a tumor comprising cancer stem cells in an animal model, such as a mouse xenograft model. In certain embodiments, the RSPO3-binding agent or antibody is capable of reducing the tumorigenicity of a tumor by decreasing the number or frequency of cancer stem cells in the tumor. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236, U.S. Patent Publication No. 2008/0064049, and U.S. Patent Publication No. 2008/0178305.

In certain embodiments, the RSPO3-binding agents described herein have a circulating half-life in mice, cynomolgus monkeys, or humans of at least about 2 hours, at least about 5 hours, at least about 10 hours, at least about 24 hours, at least about 3 days, at least about 1 week, or at least about 2 weeks. In certain embodiments, the RSPO3-binding agent is an IgG (e.g., IgG1 or IgG2) antibody that has a circulating half-life in mice, cynomolgus monkeys, or humans of at least about 2 hours, at least about 5 hours, at least about 10 hours, at least about 24 hours, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g., U.S. Patent Publication Nos. 2005/0276799, 2007/0148164, and 2007/0122403). Known methods of increasing the circulating half-life of antibody fragments lacking the Fc region include such techniques as PEGylation.

In some embodiments, the RSPO3-binding agents are polyclonal antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, full-length recombinant protein, or fusion protein) using multiple subcutaneous or intraperitoneal injections. The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, the RSPO3-binding agents are monoclonal antibodies. Monoclonal antibodies can be prepared using hybridoma methods known to one of skill in the art (see e.g., Kohler and Milstein, 1975, Nature, 256:495-497). In some embodiments, using the hybridoma method, a mouse, hamster, or other appropriate host animal, is immunized as described above to elicit from lymphocytes the production of antibodies that specifically bind the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen may be identified by a variety of methods including, but not limited to, immunoprecipitation, immunoblotting, and in vitro binding assays (e.g., flow cytometry, FACS, ELISA, and radioimmunoassay). The hybridomas can be propagated either in vitro culture using standard methods (J. W. Goding, 1996, Monoclonal Antibodies: Principles and Practice, $3^{rd}$ Edition, Academic Press, San Diego, Calif.) or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In certain other embodiments, recombinant monoclonal antibodies, or fragments thereof, can be isolated from phage display libraries expressing variable domains or CDRs of a desired species (see e.g., McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can be modified, for example, by using recombinant DNA technology to generate alternative antibodies. In some embodiments, the constant domains of the light and heavy chains of, for example, a mouse monoclonal antibody can be substituted for those regions of, for example, a human antibody to generate a chimeric antibody, or for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, a monoclonal antibody against human RSPO3 is a humanized antibody. Typically, humanized antibodies are human immunoglobulins in which residues from the CDRs are replaced by residues from a CDR of a non-human species (e.g., mouse, rat, rabbit, hamster, etc.) that have the desired specificity, affinity, and/or binding capability using methods known to one skilled in the art. In some embodiments, the Fv framework region residues of a human immunoglobulin are replaced with the corresponding residues in an antibody from a non-human species that has the desired specificity, affinity, and/or binding capability. In some embodiments, a humanized antibody can be further modified by the substitution of additional residues either in the Fv framework region and/or within the replaced non-human residues to refine and optimize antibody specificity, affinity, and/ or capability. In general, a humanized antibody will comprise substantially all of at least one, and typically two or three, variable domain regions containing all, or substantially all, of the CDRs that correspond to the non-human immunoglobulin whereas all, or substantially all, of the framework regions are those of a human immunoglobulin consensus sequence. In some embodiments, a humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject. One skilled in the art would be able to obtain a functional humanized antibody with reduced immunogenicity following known techniques (see e.g., U.S. Pat. Nos. 5,225,539; 5,585,089; 5,693,761; and 5,693,762).

In certain embodiments, the RSPO3-binding agent is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated (see, e.g., Cole et al., 1985, Monoclonal Antibodies and Cancer Therapy, Alan R. Liss, p. 77; Boerner et al., 1991, J. Immunol., 147:86-95; and U.S. Pat. Nos. 5,750,373; 5,567,610 and 5,229,275). In some embodiments, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Alternatively, phage display technology can be used to produce human antibodies and antibody fragments in vitro, from immunoglobulin variable domain gene repertoires from unimmunized donors. Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, J. Mol. Bio., 376:1182-1200. Once antibodies are identified, affinity maturation strategies known in the art, including but not limited to, chain shuffling (Marks et al., 1992, Bio/Technology, 10:779-783) and site-directed mutagenesis, may be employed to generate high affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize at least one human RSPO protein. Bispecific antibodies are capable of specifically recognizing and binding at least two different antigens or epitopes. The different epitopes can either be within the same molecule (e.g., two epitopes on human RSPO3) or on different molecules (e.g., one epitope on RSPO3 and one epitope on RSPO2). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any binding agent (e.g., antibody) may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two binding agents (e.g., antibodies) in a common area (e.g., a tumor and/or tumor microenvironment). In some embodiments, a bispecific antibody has the ability to concentrate the actions of two binding agents (e.g., antibodies) to a common target (e.g., a tumor or a tumor cell). In some embodiments, a bispecific antibody has the ability to target the actions of two binding agents (e.g., antibodies) to more than one biological pathway or function.

In certain embodiments, the bispecific antibody specifically binds RSPO3 and a second target. In certain embodiments, the bispecific antibody specifically binds RSPO3 and a second human RSPO (e.g., RSPO1, RSPO2, or RSPO4). In certain embodiments, the bispecific antibody specifically binds RSPO3 and RSPO2. In some embodiments, the bispecific antibody is a monoclonal antibody. In some embodiments, the bispecific antibody is a humanized antibody. In some embodiments, the bispecific antibody is a human antibody. In some embodiments, the bispecific antibody is an IgG1 antibody. In some embodiments, the bispecific antibody is an IgG2 antibody. In some embodiments, the bispecific antibody has decreased toxicity and/or side effects. In some embodiments, the bispecific antibody has decreased toxicity and/or side effects as compared to a mixture of the two individual antibodies or the antibodies as single agents. In some embodiments, the bispecific antibody has an increased therapeutic index. In some embodiments, the bispecific antibody has an increased therapeutic index as compared to a mixture of the two individual antibodies or the antibodies as single agents.

In some embodiments, the antibodies can specifically recognize and bind a first antigen target, (e.g., RSPO3) as well as a second antigen target, such as an effector molecule on a leukocyte (e.g., CD2, CD3, CD28, CTLA-4, CD80, or CD86) or a Fc receptor (e.g., CD64, CD32, or CD16) so as to focus cellular defense mechanisms to the cell expressing and/or producing the first antigen target. In some embodiments, the antibodies can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA.

Techniques for making bispecific antibodies are known by those skilled in the art, see for example, Millstein et al., 1983, Nature, 305:537-539; Brennan et al., 1985, Science, 229:81;

Suresh et al., 1986, Methods in Enzymol., 121:120; Traunecker et al., 1991, EMBO J., 10:3655-3659; Shalaby et al., 1992, J. Exp. Med., 175:217-225; Kostelny et al., 1992, J. Immunol., 148:1547-1553; Gruber et al., 1994, J. Immunol., 152:5368; U.S. Pat. No. 5,731,168; International Publication No. WO 2009/089004; and U.S. Patent Publication No. 2011/0123532. In some embodiments, the bispecific antibodies comprise heavy chain constant regions with modifications in the amino acids which are part of the interface between the two heavy chains. In some embodiments, the bispecific antibodies can be generated using a "knobs-into-holes" strategy (see, e.g., U.S. Pat. No. 5,731,168; Ridgway et. al., 1996, Prot. Engin., 9:617-621). In some cases, the "knobs" and "holes" terminology is replaced with the terms "protuberances" and "cavities". In some embodiments, the bispecific antibodies may comprise variant hinge regions incapable of forming disulfide linkages between the heavy chains (see, e.g., WO 2006/028936). In some embodiments, the modifications may comprise changes in amino acids that result in altered electrostatic interactions. In some embodiments, the modifications may comprise changes in amino acids that result in altered hydrophobic/hydrophilic interactions.

Bispecific antibodies can be intact antibodies or antibody fragments comprising antigen-binding sites. Antibodies with more than two valencies are also contemplated. For example, trispecific antibodies can be prepared (Tutt et al., 1991, J. Immunol., 147:60). Thus, in certain embodiments the antibodies to RSPO3 are multispecific.

In certain embodiments, the antibodies (or other polypeptides) described herein may be monospecific. In certain embodiments, each of the one or more antigen-binding sites that an antibody contains is capable of binding (or binds) a homologous epitope on RSPO proteins. In certain embodiments, an antigen-binding site of a monospecific antibody described herein is capable of binding (or binds), for example, RSPO3 and RSPO2 (i.e., the same epitope is found on both RSPO3 and RSPO2 proteins).

In certain embodiments, the RSPO3-binding agent is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in and secreted from E. coli or other host cells, allowing for the production of large amounts of these fragments. In some embodiments, antibody fragments are isolated from antibody phage libraries as discussed herein. For example, methods can be used for the construction of Fab expression libraries (Huse et al., 1989, Science, 246:1275-1281) to allow rapid and effective identification of monoclonal Fab fragments with the desired specificity for a RSPO protein or derivatives, fragments, analogs or homologs thereof. In some embodiments, antibody fragments are linear antibody fragments. In certain embodiments, antibody fragments are monospecific or bispecific. In certain embodiments, the RSPO3-binding agent is a scFv. Various techniques can be used for the production of single-chain antibodies specific to one or more human RSPOs (see, e.g., U.S. Pat. No. 4,946,778).

It can further be desirable, especially in the case of antibody fragments, to modify an antibody in order to alter (e.g., increase or decrease) its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (see, e.g., U.S. Pat. No. 4,676,980). It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., human RSPO3). In this regard, the variable region may comprise or be derived from any type of mammal that can be induced to mount a humoral response and generate immunoglobulins against the desired antigen. As such, the variable region of the modified antibodies can be, for example, of human, murine, non-human primate (e.g. cynomolgus monkeys, macaques, etc.) or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs may be derived from an antibody of different class and often from an antibody from a different species. It may not be necessary to replace all of the CDRs with all of the CDRs from the donor variable region to transfer the antigen binding capacity of one variable domain to another. Rather, it may only be necessary to transfer those residues that are required to maintain the activity of the antigen-binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete the part of one or more constant region domains that control a specific effector function (e.g. complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In certain embodiments, the modified antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody thereby increasing cancer cell localization and/or tumor penetration. In other embodiments, the constant region modifications increase the serum half-life of the antibody. In other embodiments, the constant region modifications reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques.

In certain embodiments, a RSPO3-binding agent that is an antibody does not have one or more effector functions. For instance, in some embodiments, the antibody has no ADCC activity, and/or no complement-dependent cytotoxicity (CDC) activity. In certain embodiments, the antibody does not bind an Fc receptor, and/or complement factors. In certain embodiments, the antibody has no effector function.

The present invention further embraces variants and equivalents which are substantially homologous to the chimeric, humanized, and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another amino acid within the same general class such as, for example, one acidic amino acid with another acidic amino acid, one basic amino acid with another basic amino acid or one neutral amino acid by another neutral amino acid. What is intended by a conservative amino acid substitution is well known in the art and described herein.

Thus, the present invention provides methods for producing an antibody that binds RSPO3, including bispecific antibodies that specifically bind both RSPO3 and a second target (e.g., a human RSPO). In some embodiments, the method for producing an antibody that binds RSPO3 comprises using hybridoma techniques. In some embodiments, a method for producing an antibody that binds human RSPO3 is provided. In some embodiments, the method comprises using amino acids 22-272 of human RSPO3. In some embodiments, the method comprises using amino acids 22-272 of SEQ ID NO:3. In some embodiments, the method of generating an antibody that binds RSPO3 comprises screening a human phage library. The present invention further provides methods of identifying an antibody that binds RSPO3. In some embodiments, the antibody is identified by FACS screening for binding to RSPO3 or a portion thereof. In some embodiments, the antibody is identified by FACS screening for binding to RSPO3 and a second RSPO or a portion thereof. In some embodiments, the antibody is identified by FACS screening for binding to both RSPO3 and RSPO2 or a portion thereof. In some embodiments, the antibody is identified by screening using ELISA for binding to RSPO3. In some embodiments, the antibody is identified by screening using ELISA for binding to RSPO3 and a second RSPO. In some embodiments, the antibody is identified by screening using ELISA for binding to both RSPO3 and RSPO2. In some embodiments, the antibody is identified by screening by FACS for blocking of binding of RSPO3 to a human LGR protein. In some embodiments, the antibody is identified by screening for inhibition or blocking of β-catenin signaling.

In some embodiments, a method of generating an antibody to human RSPO3 protein comprises immunizing a mammal with a polypeptide comprising amino acids 22-272 of human RSPO3. In some embodiments, a method of generating an antibody to human RSPO3 protein comprises immunizing a mammal with a polypeptide comprising at least a portion of amino acids 22-272 of human RSPO3. In some embodiments, the method further comprises isolating antibodies or antibody-producing cells from the mammal. In some embodiments, a method of generating a monoclonal antibody which binds RSPO3 protein comprises: (a) immunizing a mammal with a polypeptide comprising at least a portion of amino acids 22-272 of human RSPO3; (b) isolating antibody producing cells from the immunized mammal; (c) fusing the antibody-producing cells with cells of a myeloma cell line to form hybridoma cells. In some embodiments, the method further comprises (d) selecting a hybridoma cell expressing an antibody that binds RSPO3 protein. In some embodiments, the at least a portion of amino acids 22-272 of human RSPO3 is selected from the group consisting of SEQ ID NOs:5-8. In some embodiments, the at least a portion of amino acids 22-272 of human RSPO3 is SEQ ID NO:5. In some embodiments, the at least a portion of amino acids 22-272 of human RSPO3 is SEQ ID NO:6 or SEQ ID NO:7. In some embodiments, the at least a portion of amino acids 22-272 of human RSPO3 is SEQ ID NO:6 and SEQ ID NO:7. In certain embodiments, the mammal is a mouse. In some embodiments, the antibody is selected using a polypeptide comprising at least a portion of amino acid 22-272 of human RSPO3. In certain embodiments, the polypeptide used for selection comprising at least a portion of amino acids 22-272 of human RSPO3 is selected from the group consisting of SEQ ID NOs:5-8. In some embodiments, the antibody binds RSPO3 and at least one other RSPO protein. In certain embodiments, the at least one other RSPO protein is selected from the group consisting of RSPO1, RSPO2, and RSPO4. In certain embodiments, the antibody binds RSPO3 and RSPO1. In certain embodiments, the antibody binds RSPO3 and RSPO2. In certain embodiments, the antibody binds RSPO3 and RSPO4. In certain embodiments, the antibody binds RSPO3, RSPO1, and RSPO2. In certain embodiments, the antibody binds RSPO3, RSPO1, and RSPO4. In certain embodiments, the antibody binds RSPO3, RSPO2, and RSPO4. In some embodiments, the antibody binds both human RSPO3 and mouse RSPO3.

In some embodiments, the antibody generated by the methods described herein is a RSPO antagonist, particularly a RSPO3 antagonist. In some embodiments, the antibody generated by the methods described herein inhibits β-catenin signaling.

In some embodiments, a method of producing an antibody to at least one human RSPO protein comprises identifying an antibody using a membrane-bound heterodimeric molecule comprising a single antigen-binding site. In some non-limiting embodiments, the antibody is identified using methods and polypeptides described in International Publication WO 2011/100566.

In some embodiments, a method of producing an antibody to at least one human RSPO protein comprises screening an antibody-expressing library for antibodies that bind a human RSPO protein. In some embodiments, the antibody-expressing library is a phage library. In some embodiments, the screening comprises panning. In some embodiments, the antibody-expressing library is a phage library.

In some embodiments, the antibody-expressing library is a mammalian cell library. In some embodiments, the antibody-expressing library is screened using at least a portion of amino acids 22-272 of human RSPO3. In some embodiments, antibodies identified in the first screening, are screened again using a different RSPO protein thereby identifying an antibody that binds RSPO3 and a second RSPO protein. In certain embodiments, the polypeptide used for screening comprises at least a portion of amino acids 22-272 of human RSPO3 selected from the group consisting of SEQ ID NOs:5-8. In some embodiments, the antibody identified in the screening binds RSPO3 and at least one other RSPO protein.

In certain embodiments, the at least one other RSPO protein is selected from the group consisting of RSPO1, RSPO2, and RSPO4. In certain embodiments, the antibody identified in the screening binds RSPO3 and RSPO1. In certain embodiments, the antibody identified in the screening binds RSPO3 and RSPO2. In certain embodiments, the antibody identified in the screening binds RSPO3 and RSPO4. In some embodiments, the antibody identified in the screening binds both human RSPO3 and mouse RSPO3. In some embodiments, the antibody identified in the screening is a RSPO3 antagonist. In some embodiments, the antibody identified in the screening inhibits β-catenin signaling induced by RSPO3.

In certain embodiments, the antibodies described herein are isolated. In certain embodiments, the antibodies described herein are substantially pure.

In some embodiments of the present invention, the RSPO3-binding agents are polypeptides. The polypeptides can be recombinant polypeptides, natural polypeptides, or synthetic polypeptides comprising an antibody, or fragment thereof, that bind RSPO3. It will be recognized in the art that some amino acid sequences of the invention can be varied without significant effect of the structure or function of the protein. Thus, the invention further includes variations of the polypeptides which show substantial activity or which include regions of an antibody, or fragment thereof, against human RSPO3. In some embodiments, amino acid sequence variations of RSPO-binding polypeptides include deletions, insertions, inversions, repeats, and/or other types of substitutions.

In certain embodiments, the polypeptides described herein are isolated. In certain embodiments, the polypeptides described herein are substantially pure.

The polypeptides, analogs and variants thereof, can be further modified to contain additional chemical moieties not normally part of the polypeptide. The derivatized moieties can improve or otherwise modulate the solubility, the biological half-life, and/or absorption of the polypeptide. The moieties can also reduce or eliminate undesirable side effects of the polypeptides and variants. An overview for chemical moieties can be found in Remington: The Science and Practice of Pharmacy, $22^{st}$ Edition, 2012, Pharmaceutical Press, London.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., 1984, PNAS, 81:5662-5066 and U.S. Pat. No. 4,588,585.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human RSPO3. For example, recombinant expression vectors can be replicable DNA constructs which have synthetic or cDNA-derived DNA fragments encoding a polypeptide chain of a RSPO-binding agent, such as an anti-RSPO antibody, or fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, in situations where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9 and their derivatives, and wider host range plasmids, such as M13 and other filamentous single-stranded DNA phages.

The RSPO-binding agents (e.g., polypeptides or antibodies) of the present invention can be expressed from one or more vectors. For example, in some embodiments, one heavy chain polypeptide is expressed by one vector, a second heavy chain polypeptide is expressed by a second vector and a light chain polypeptide is expressed by a third vector. In some embodiments, a first heavy chain polypeptide and a light chain polypeptide is expressed by one vector and a second heavy chain polypeptide is expressed by a second vector. In some embodiments, two heavy chain polypeptides are expressed by one vector and a light chain polypeptide is expressed by a second vector. In some embodiments, three polypeptides are expressed from one vector. Thus, in some embodiments, a first heavy chain polypeptide, a second heavy chain polypeptide, and a light chain polypeptide are expressed by a single vector.

Suitable host cells for expression of a RSPO3-binding polypeptide or antibody (or a RSPO protein to use as an antigen) include prokaryotes, yeast cells, insect cells, or higher eukaryotic cells under the control of appropriate promoters. Prokaryotes include gram-negative or gram-positive organisms, for example E. coli or Bacillus. Higher eukaryotic cells include established cell lines of mammalian origin as described below. Cell-free translation systems may also be employed. Appropriate cloning and expression vectors for use with bacterial, fungal, yeast, and mammalian cellular hosts are described in Pouwels et al., 1985, Cloning Vectors: A Laboratory Manual, Elsevier, New York, N.Y. Additional information regarding methods of protein production, including antibody production, can be found, e.g., in U.S. Patent Publication No. 2008/0187954, U.S. Pat. Nos. 6,413,746, 6,660,501; and International Patent Publication No. WO 04/009823.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art (see, e.g., Luckow and Summers, 1988, Bio/Technology, 6:47).

Thus, the present invention provides cells comprising the RSPO3-binding agents described herein. In some embodiments, the cells produce the RSPO3-binding agents described herein. In certain embodiments, the cells produce an antibody. In some embodiments, the cells produce an antibody that binds human RSPO3. In certain embodiments, the cells produce antibody 131R002. In certain embodiments, the cells produce antibody 131R003. In certain embodiments, the cells produce variants of antibody 131R003. In certain embodiments, the cells produce a humanized version of antibody 131R002, antibody 131R003, or variants of antibody 131R003. In some embodiments, the cells produce a chimeric version of antibody 131R002, antibody 131R003, or variants of antibody 131R003. In some embodiments, the cells produce antibody h131R006A or antibody h131R006B. In some embodiments, the cells produce antibody h131R005/131R007. In some embodiments, the cells produce antibody h131R008. In some embodiments, the cells produce antibody h131R010. In some embodiments, the cells produce antibody h131R011. In some embodiments, the cells produce a bispecific antibody that binds RSPO3. In some embodiments, the cells produce a bispecific antibody that binds RSPO3 and RSPO2. In some embodiments, the cell is a hybridoma cell. In some embodiments, the cell is a mammalian cell. In some embodiments, the cell is a prokaryotic cell. In some embodiments, the cell is an eukaryotic cell.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Affinity chromatography used for purifying immunoglobulins can include Protein A, Protein C, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a recombinant protein (e.g., a RSPO3-binding agent). Some or all of the foregoing purification steps, in various combinations, can be employed to provide a homogeneous recombinant protein.

In some embodiments, heterodimeric proteins such as bispecific antibodies are purified according the any of the methods described herein. In some embodiments, anti-RSPO bispecific antibodies are isolated and/or purified using at least one chromatography step. In some embodiments, the at least one chromatography step comprises affinity chromatography. In some embodiments, the at least one chromatography step further comprises anion exchange chromatography. In some embodiments, the isolated and/or purified antibody product comprises at least 90% heterodimeric antibody. In some embodiments, the isolated and/or purified antibody product comprises at least 95%, 96%, 97%, 98% or 99% heterodimeric antibody. In some embodiments, the isolated and/or purified antibody product comprises about 100% heterodimeric antibody.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005.

In certain embodiments, the RSPO3-binding agent is a polypeptide that is not an antibody. A variety of methods for identifying and producing non-antibody polypeptides that bind with high affinity to a protein target are known in the art. See, e.g., Skerra, 2007, Curr. Opin. Biotechnol., 18:295-304; Hosse et al., 2006, Protein Science, 15:14-27; Gill et al., 2006, Curr. Opin. Biotechnol., 17:653-658; Nygren, 2008, FEBS J., 275:2668-76; and Skerra, 2008, FEBS J., 275:2677-83. In certain embodiments, phage or mammalian display technology may be used to produce and/or identify a RSPO3-binding polypeptide. In certain embodiments, the polypeptide comprises a protein scaffold of a type selected from the group consisting of protein A, protein G, a lipocalin, a fibronectin domain, an ankyrin consensus repeat domain, and thioredoxin.

In certain embodiments, the RSPO3-binding agents or antibodies can be used in any one of a number of conjugated (i.e. an immunoconjugate or radioconjugate) or non-conjugated forms. In certain embodiments, the antibodies can be used in a non-conjugated form to harness the subject's natural defense mechanisms including complement-dependent cytotoxicity and antibody dependent cellular toxicity to eliminate malignant or cancer cells.

In some embodiments, the RSPO3-binding agent (e.g., an antibody or polypeptide) is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, Sapaonaria officinalis inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}Y$, $^{125}I$, $^{131}I$, $^{123}I$, $^{111}In$, $^{131}In$, $^{105}Rh$, $^{153}Sm$, $^{67}Cu$, $^{67}Ga$, $^{166}Ho$, $^{177}Lu$, $^{186}Re$, $^{188}Re$ and $^{212}Bi$. Conjugates of an antibody and one or more small molecule toxins, such as calicheamicins, maytansinoids, trichothenes, and CC1065, and the derivatives of these toxins that have toxin activity, can also be used. Conjugates of an antibody and cytotoxic agent may be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

III. Polynucleotides

In certain embodiments, the invention encompasses polynucleotides comprising polynucleotides that encode a polypeptide (or a fragment of a polypeptide) that specifically binds RSPO3. The term "polynucleotides that encode a polypeptide" encompasses a polynucleotide which includes only coding sequences for the polypeptide as well as a polynucleotide which includes additional coding and/or non-coding sequences. For example, in some embodiments, the invention provides a polynucleotide comprising a polynucleotide sequence that encodes an antibody to human RSPO3 or encodes a fragment of such an antibody (e.g., a fragment comprising the antigen-binding site). The polynucleotides of the invention can be in the form of RNA or in the form of DNA. DNA includes cDNA, genomic DNA, and synthetic DNA; and can be double-stranded or single-stranded, and if single stranded can be the coding strand or non-coding (antisense) strand.

In certain embodiments, the polynucleotide comprises a polynucleotide encoding a polypeptide comprising an amino acid sequence selected from the group consisting of: SEQ ID NO:15, SEQ ID NO:16, SEQ ID NO:17, SEQ ID NO:21, SEQ ID NO:22, SEQ ID NO:23, SEQ ID NO:27, SEQ ID NO:28, SEQ ID NO:29, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, SEQ ID NO:48, SEQ ID NO:49, SEQ ID NO:62, SEQ ID NO:63, SEQ ID NO:64, SEQ ID NO:68, SEQ ID NO:69, SEQ ID NO:72, SEQ ID NO:73, SEQ ID NO:74, SEQ ID NO:86, SEQ ID NO:87, and SEQ ID NO:88. In some embodiments, the polynucleotide comprises a polynucleotide sequence selected from the group consisting of: SEQ ID NO:18, SEQ ID NO:19, SEQ ID NO:20, SEQ ID NO:24, SEQ ID NO:25, SEQ ID NO:26, SEQ ID NO:30, SEQ ID NO:31, SEQ ID NO:32, SEQ ID NO:40, SEQ ID NO:43, SEQ ID NO:50, SEQ ID NO:51, SEQ ID NO:52, SEQ ID NO:53, SEQ ID NO:54, SEQ ID NO:55, SEQ ID NO:65, SEQ ID NO:66, SEQ ID NO:67, SEQ ID NO:70, SEQ ID NO:71, SEQ ID NO:75, SEQ ID NO:76, SEQ ID NO:77, SEQ ID NO:84, SEQ ID NO:85, SEQ ID NO:89, SEQ ID NO:90, SEQ ID NO:91, SEQ ID NO:92, SEQ ID NO:93, SEQ ID NO:94, and SEQ ID NO:95.

In some embodiments, a plasmid comprises a polynucleotide comprising SEQ ID NO:18. In some embodiments, a plasmid comprises a polynucleotide comprising SEQ ID NO:19. In some embodiments, a plasmid comprises a polynucleotide comprising SEQ ID NO:20. In some embodiments, a plasmid comprises a polynucleotide comprising SEQ ID NO:24. In some embodiments, a plasmid comprises a polynucleotide comprising SEQ ID NO:25. In some embodiments, a plasmid comprises a polynucleotide comprising SEQ ID NO:26. In some embodiments, a plasmid comprises a polynucleotide comprising SEQ ID NO:30. In some embodiments, a plasmid comprises a polynucleotide comprising SEQ ID NO:31. In some embodiments, a plasmid comprises a polynucleotide comprising SEQ ID NO:32. In some embodiments, a plasmid comprises a polynucleotide comprising SEQ ID NO:40. In some embodiments, a plasmid comprises a polynucleotide comprising SEQ ID NO:43. In some embodiments, a plasmid comprises a polynucleotide comprising SEQ ID NO:50. In some embodiments, a plasmid comprises a polynucleotide comprising SEQ ID NO:51. In some embodiments, a plasmid comprises a polynucleotide comprising SEQ ID NO:52. In some embodiments, a plasmid comprises a polynucleotide comprising SEQ ID NO:53. In some embodiments, a plasmid comprises a polynucleotide comprising SEQ ID NO:54. In some embodiments, a plasmid comprises a polynucleotide comprising SEQ ID NO:55. In some embodiments, a plasmid comprises a polynucleotide comprising SEQ ID NO:65. In some embodiments, a plasmid comprises a polynucleotide comprising SEQ ID NO:66. In some embodiments, a plasmid comprises a polynucleotide comprising SEQ ID NO:67. In some embodiments, a plasmid comprises a polynucleotide comprising SEQ ID NO:70. In some embodiments, a plasmid comprises a polynucleotide comprising SEQ ID NO:71. In some embodiments, a plasmid comprises a polynucleotide comprising SEQ ID NO:75. In some embodiments, a plasmid comprises a polynucleotide comprising SEQ ID NO:76. In some embodiments, a plasmid comprises a polynucleotide comprising SEQ ID NO:77. In some embodiments, a plasmid comprises a polynucleotide comprising SEQ ID NO:84. In some embodiments, a plasmid comprises a polynucleotide comprising SEQ ID NO:85. In some embodiments, a plasmid comprises a polynucleotide comprising SEQ ID NO:89. In some embodiments, a plasmid comprises a polynucleotide comprising SEQ ID NO:90. In some embodiments, a plasmid comprises a polynucleotide comprising SEQ ID NO:91. In some embodiments, a plasmid comprises a polynucleotide comprising SEQ ID NO:92. In some embodiments, a plasmid comprises a polynucleotide comprising SEQ ID NO:93. In some embodiments, a plasmid comprises a polynucleotide comprising SEQ ID NO:94. In some embodiments, a plasmid comprises a polynucleotide comprising SEQ ID NO:95.

In certain embodiments, the polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide comprising a sequence selected from the group consisting of SEQ ID NO:18, SEQ ID NO:19, SEQ ID NO:20, SEQ ID NO:24, SEQ ID NO:25, SEQ ID NO:26, SEQ ID NO:30, SEQ ID NO:31, SEQ ID NO:32, SEQ ID NO:40, SEQ ID NO:43, SEQ ID NO:50, SEQ ID NO:51, SEQ ID NO:52, SEQ ID NO:53, SEQ ID NO:54, SEQ ID NO:55, SEQ ID NO:65, SEQ ID NO:66, SEQ ID NO:67, SEQ ID NO:70, SEQ ID NO:71, SEQ ID NO:75, SEQ ID NO:76, SEQ ID NO:77, SEQ ID NO:84, SEQ ID NO:85, SEQ ID NO:89, SEQ ID NO:90, SEQ ID NO:91, SEQ ID NO:92, SEQ ID NO:93, SEQ ID NO:94, and SEQ ID NO:95. Also provided is a polynucleotide that comprises a polynucleotide that hybridizes to SEQ ID NO:18, SEQ ID NO:19, SEQ ID NO:20, SEQ ID NO:24, SEQ ID NO:25, SEQ ID NO:26, SEQ ID NO:30, SEQ ID NO:31, SEQ ID NO:32, SEQ ID NO:32, SEQ ID NO:40, SEQ ID NO:43, SEQ ID NO:50, SEQ ID NO:51, SEQ ID NO:52, SEQ ID NO:53, SEQ ID NO:54, SEQ ID NO:55, SEQ ID NO:65, SEQ ID NO:66, SEQ ID NO:67, SEQ ID NO:70, SEQ ID NO:71, SEQ ID NO:75, SEQ ID NO:76, SEQ ID NO:77, SEQ ID NO:84, SEQ ID NO:85, SEQ ID NO:89, SEQ ID NO:990, SEQ ID NO:91, SEQ ID NO:92, SEQ ID NO:93, SEQ ID NO:94, or SEQ ID NO:95. Also provided is a polynucleotide that comprises a polynucleotide that hybridizes to the complement of SEQ ID NO:18, SEQ ID NO:19, SEQ ID NO:20, SEQ ID NO:24, SEQ ID NO:25, SEQ ID NO:26, SEQ ID NO:30, SEQ ID NO:31, SEQ ID NO:32, SEQ ID NO:32, SEQ ID NO:40, SEQ ID NO:43, SEQ ID NO:50, SEQ ID NO:51, SEQ ID NO:52, SEQ ID NO:53, SEQ ID NO:54, SEQ ID NO:55, SEQ ID NO:65, SEQ ID NO:66, SEQ ID NO:67, SEQ ID NO:70, SEQ ID NO:71, SEQ ID NO:75, SEQ ID NO:76, SEQ ID NO:77, SEQ ID NO:84, SEQ ID NO:85, SEQ ID NO:89, SEQ ID NO:90, SEQ ID NO:91, SEQ ID NO:92, SEQ ID NO:93, SEQ ID NO:94, or SEQ ID NO:95. In certain embodiments, the hybridization is under conditions of high stringency.

In some embodiments, an antibody is encoded by a polynucleotide comprising SEQ ID NO:18 and SEQ ID NO:20. In some embodiments, an antibody is encoded by a polynucleotide comprising SEQ ID NO:19 and SEQ ID NO:20. In some embodiments, an antibody is encoded by a polynucleotide comprising SEQ ID NO:50 and SEQ ID NO:20. In some embodiments, an antibody is encoded by a polynucleotide comprising SEQ ID NO:51 and SEQ ID NO:20. In some embodiments, an antibody is encoded by a polynucleotide comprising SEQ ID NO:65 and SEQ ID NO:20. In some embodiments, an antibody is encoded by a polynucleotide comprising SEQ ID NO:18 and SEQ ID NO:75. In some embodiments, an antibody is encoded by a polynucleotide comprising SEQ ID NO:19 and SEQ ID NO:75. In some embodiments, an antibody is encoded by a polynucleotide comprising SEQ ID NO:50 and SEQ ID NO:75. In some embodiments, an antibody is encoded by a polynucleotide comprising SEQ ID NO:51 and SEQ ID NO:75. In some embodiments, an antibody is encoded by a polynucleotide comprising SEQ ID NO:65 and SEQ ID NO:75. In some embodiments, an antibody is encoded by a polynucleotide comprising SEQ ID NO:95 and SEQ ID NO:89. In some embodiments, an antibody is encoded by a polynucleotide comprising SEQ ID NO:92 and SEQ ID NO:89.

In some embodiments, an antibody is encoded by a polynucleotide comprising SEQ ID NO:24 and SEQ ID NO:26. In some embodiments, an antibody is encoded by a polynucleotide comprising SEQ ID NO:25 and SEQ ID NO:26. In some embodiments, an antibody is encoded by a polynucleotide comprising SEQ ID NO:40 and SEQ ID NO:26. In some embodiments, an antibody is encoded by a polynucleotide comprising SEQ ID NO:43 and SEQ ID NO:26. In some embodiments, an antibody is encoded by a polynucleotide comprising SEQ ID NO:52 and SEQ ID NO:26. In some embodiments, an antibody is encoded by a polynucleotide comprising SEQ ID NO:53 and SEQ ID NO:26. In some embodiments, an antibody is encoded by a polynucleotide comprising SEQ ID NO:66 and SEQ ID NO:26. In some embodiments, an antibody is encoded by a polynucleotide comprising SEQ ID NO:70 and SEQ ID NO:26. In some embodiments, an antibody is encoded by a polynucleotide comprising SEQ ID NO:24 and SEQ ID NO:76. In some embodiments, an antibody is encoded by a polynucleotide comprising SEQ ID NO:25 and SEQ ID NO:76. In some embodiments, an antibody is encoded by a polynucleotide comprising SEQ ID NO:40 and SEQ ID NO:76. In some embodiments, an antibody is encoded by a polynucleotide comprising SEQ ID NO:43 and SEQ ID NO:76. In some embodiments, an antibody is encoded by a polynucleotide comprising SEQ ID NO:52 and SEQ ID NO:76. In some embodiments, an antibody is encoded by a polynucleotide comprising SEQ ID NO:53 and SEQ ID NO:76. In some embodiments, an antibody is encoded by a polynucleotide comprising SEQ ID NO:66 and SEQ ID NO:76. In some embodiments, an antibody is encoded by a polynucleotide comprising SEQ ID NO:70 and SEQ ID NO:76. In some embodiments, an antibody is encoded by a polynucleotide comprising SEQ ID NO:84 and SEQ ID NO:90. In some embodiments, an antibody is encoded by a polynucleotide comprising SEQ ID NO:93 and SEQ ID NO:90.

In some embodiments, an antibody is encoded by a polynucleotide comprising SEQ ID NO:30 and SEQ ID NO:32. In some embodiments, an antibody is encoded by a polynucleotide comprising SEQ ID NO:31 and SEQ ID NO:32. In some embodiments, an antibody is encoded by a polynucleotide comprising SEQ ID NO:54 and SEQ ID NO:32. In some embodiments, an antibody is encoded by a polynucleotide comprising SEQ ID NO:55 and SEQ ID NO:32. In some embodiments, an antibody is encoded by a polynucleotide comprising SEQ ID NO:67 and SEQ ID NO:32. In some embodiments, an antibody is encoded by a polynucleotide comprising SEQ ID NO:71 and SEQ ID NO:32. In some embodiments, an antibody is encoded by a polynucleotide comprising SEQ ID NO:30 and SEQ ID NO:77. In some embodiments, an antibody is encoded by a polynucleotide comprising SEQ ID NO:31 and SEQ ID NO:77. In some embodiments, an antibody is encoded by a polynucleotide comprising SEQ ID NO:54 and SEQ ID NO:77. In some embodiments, an antibody is encoded by a polynucleotide comprising SEQ ID NO:55 and SEQ ID NO:77. In some embodiments, an antibody is encoded by a polynucleotide comprising SEQ ID NO:67 and SEQ ID NO:77. In some embodiments, an antibody is encoded by a polynucleotide comprising SEQ ID NO:71 and SEQ ID NO:77. In some embodiments, an antibody is encoded by a polynucleotide comprising SEQ ID NO:85 and SEQ ID NO:91. In some embodiments, an antibody is encoded by a polynucleotide comprising SEQ ID NO:94 and SEQ ID NO:91.

In certain embodiments, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:33) which can be used in conjunction with other affinity tags.

The present invention farther relates to variants of the hereinabove described polynucleotides encoding, for example, fragments, analogs, and/or derivatives.

In certain embodiments, the present invention provides polynucleotides comprising polynucleotides having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a RSPO3-binding agent (e.g., an antibody), or fragment thereof, described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that result in no change to the amino acid sequence of the polypeptide (due to the degeneracy of the genetic code). In some embodiments, nucleotide variants comprise nucleotide sequences which result in expression differences (e.g., increased or decreased expression) at the transcript level. Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heteromultimeric molecule. In some embodiments, at least one polynucleotide variant is produced (without changing the amino acid sequence of the encoded polypeptide) to increase production of a bispecific antibody.

In certain embodiments, the polynucleotides are isolated. In certain embodiments, the polynucleotides are substantially pure.

Vectors comprising the polynucleotides described herein are also provided. Cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

IV. Methods Of Use And Pharmaceutical Compositions

The RSPO3-binding agents (including polypeptides and antibodies) of the invention are useful in a variety of applications including, but not limited to, therapeutic treatment methods, such as the treatment of cancer. In certain embodiments, the agents are useful for inhibiting β-catenin signaling, inhibiting tumor growth, modulating angiogenesis, inhibiting angiogenesis, inducing differentiation, reducing tumor volume, reducing the frequency of cancer stem cells in a tumor, and/or reducing the tumorigenicity of a tumor. The methods of use may be in vitro, ex vivo, or in vivo methods. In certain embodiments, a RSPO3-binding agent or polypeptide or antibody is an antagonist of human RSPO3.

In certain embodiments, the RSPO3-binding agents are used in the treatment of a disease associated with activation of β-catenin, increased β-catenin signaling, and/or aberrant β-catenin signaling. In certain embodiments, the disease is a disease dependent upon β-catenin signaling. In certain embodiments, the RSPO3-binding agents are used in the treatment of disorders characterized by increased angiogenesis. In certain embodiments, the RSPO3-binding agents are used in the treatment of disorders characterized by increased levels of stem cells and/or progenitor cells. In some embodiments, the methods comprise administering a therapeutically effective amount of a RSPO3-binding agent (e.g., antibody) to a subject. In some embodiments, the subject is human.

The present invention provides methods for inhibiting growth of a tumor using the RSPO3-binding agents or antibodies described herein. In certain embodiments, the method of inhibiting growth of a tumor comprises contacting a cell with a RSPO3-binding agent (e.g., an antibody) in vitro. For example, an immortalized cell line or a cancer cell line is cultured in medium to which is added an anti-RSPO3 antibody or other agent to inhibit tumor growth. In some embodiments, tumor cells are isolated from a patient sample such as, for example, a tissue biopsy, pleural effusion, or blood sample and cultured in medium to which is added a RSPO3-binding agent to inhibit tumor growth.

In some embodiments, the method of inhibiting growth of a tumor comprises contacting the tumor or tumor cells with a RSPO3-binding agent (e.g., an antibody) in vivo. In certain embodiments, contacting a tumor or tumor cell with a RSPO3-binding agent is undertaken in an animal model. For example, a RSPO3-binding agent may be administered to immunocompromised mice (e.g. NOD/SCID mice) which have xenografts. In some embodiments, cancer cells or cancer stem cells are isolated from a patient sample such as, for example, a tissue biopsy, pleural effusion, or blood sample and injected into immunocompromised mice that are then administered a RSPO3-binding agent to inhibit tumor cell growth. In some embodiments, a RSPO3-binding agent is administered to the animal. In some embodiments, the RSPO3-binding agent is administered at the same time or shortly after introduction of tumorigenic cells into the animal to prevent tumor growth ("preventative model"). In some embodiments, the RSPO3-binding agent is administered as a therapeutic after tumors have grown to a specified size ("therapeutic model"). In some embodiments, the RSPO3-binding agent is an antibody. In some embodiments, the RSPO3-binding agent is an anti-RSPO3 antibody. In some embodiments, the anti-RSPO3 antibody is antibody 131R002. In some embodiments, the anti-RSPO3 antibody is a humanized version of antibody 131R002. In some embodiments, the anti-RSPO3 antibody is antibody 131R003. In some embodiments, the anti-RSPO3 antibody is a variant of antibody 131R003. In some embodiments, the anti-RSPO3 antibody is a humanized version of antibody 131R003. In some embodiments, the anti-RSPO3 antibody is a humanized version of a variant of antibody 131R003. In some embodiments, the anti-RSPO3 antibody is antibody h131R006A or antibody h131R006B. In some embodiments, the anti-RSPO3 antibody is antibody h131R005/131R007. In some embodiments, the anti-RSPO3 antibody is antibody h131R008. In some embodiments, the anti-RSPO3 antibody is antibody h131R010. In some embodiments, the anti-RSPO3 antibody is antibody h131R011.

in certain embodiments, the method of inhibiting growth of a tumor comprises administering to a subject a therapeutically effective amount of a RSPO3-binding agent, wherein the RSPO3-binding agent comprises a heavy chain CDR1 comprising KASGYTFTDYS (SEQ ID NO:9), KASGYTFT-SYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35), or TYFANNFD (SEQ ID NO:80). In some embodiments of the method, the RSPO3-binding agent further comprises a light chain CDR1 comprising QSVDYDGDSYM (SEQ ID NO:12) or KASQS-VDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83). In some embodiments, the RSPO3-binding agent comprises a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANY-FDY (SEQ ID NO:11), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In some embodiments, the RSPO3-binding agent comprises a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANN-FDY (SEQ ID NO:35), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In some embodiments, the RSPO3-binding agent comprises a heavy chain CDR1 comprising KASGYTFTSYTF (SEQ ID NO:34), a heavy chain CDR2 comprising IYPSNGDS (SEQ ID NO:10), and a heavy chain CDR3 comprising ATYFAN-NFDY (SEQ ID NO:35), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In some embodiments, the RSPO3-binding agent comprises a heavy chain CDR1 comprising KASGYTFTDYS (SEQ ID NO:9) or DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and/or a light chain CDR1 comprising KASQSVDYDGDSYMN (SEQ ID NO:81), a light chain CDR2 comprising AASNLES (SEQ ID NO:82), and a light chain CDR3 comprising QQSNEDPLTF (SEQ ID NO:83). In some embodiments, the RSPO3-binding agent comprises a heavy chain CDR1 comprising KASGYTFTDYS (SEQ ID NO:9) or DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and/or a light chain CDR1 comprising KASQSVDYDGDSYMN (SEQ ID NO:81), a light chain CDR2 comprising AASNLES (SEQ ID NO:82), and a light chain CDR3 comprising QQSNEDPLT (SEQ ID NO:14). In some embodiments, the RSPO3-binding agent comprises a heavy chain CDR1 comprising KASGYTFTDYS (SEQ ID NO:9) or DYSIH (SEQ ID NO:78), a heavy chain CDR2 comprising IYPSNGDS (SEQ ID NO:10), and a heavy chain CDR3 comprising TYFANNFD (SEQ ID NO:80), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14).

In certain embodiments, the method of inhibiting growth of a tumor comprises administering to a subject a therapeutically effective amount of a RSPO3-binding agent. In certain embodiments, the subject is a human. In certain embodiments, the subject has a tumor or has had a tumor which was removed. In some embodiments, the subject has a tumor with an elevated expression level of at least one RSPO protein (e.g., RSPO1, RSPO2, RSPO3, or RSPO4). In some embodiments, the subject has a tumor with a high expression level of at least one RSPO protein (e.g., RSPO1, RSPO2, RSPO3, or RSPO4). In some embodiments, the RSPO-binding agent is a RSPO3-binding agent. In some embodiments, the RSPO3-binding agent is an antibody. In some embodiments, the RSPO3-binding agent is antibody 131R002. In some embodiments, the anti-RSPO3 antibody is antibody 131R003. In some embodiments, the anti-RSPO3 antibody is a variant of antibody 131R003. In some embodiments, the anti-RSPO3 antibody is a humanized version of antibody 131R003. In some embodiments, the anti-RSPO3 antibody is a humanized version of a variant of antibody 131R003. In some embodiments, the RSPO3-binding agent is antibody h131R006A or antibody h131R006B. In some embodiments, the RSPO3-binding agent is antibody h131R005/131R007. In some embodiments, the RSPO3-binding agent is antibody h131R008. In some embodiments, the RSPO3-binding agent is antibody h131R1010. In some embodiments, the RSPO3-binding agent is antibody h131R01.

In certain embodiments, the tumor is a tumor in which β-catenin signaling is active. In some embodiments, the tumor is a tumor in which β-catenin signaling is aberrant. In certain embodiments, the tumor comprises an inactivating mutation (e.g., a truncating mutation) in the APC tumor suppressor gene. In certain embodiments, the tumor does not comprise an inactivating mutation in the APC tumor suppressor gene. In some embodiments, the tumor comprises a wild-type APC gene. In some embodiments, the tumor does not comprise an activating mutation in the β-catenin gene. In certain embodiments, a cancer for which a subject is being treated involves such a tumor.

In some embodiments, the tumor comprises a RSPO gene fusion. In some embodiments, the tumor comprises a RSPO2 gene fusion. In some embodiments, the tumor comprises a RSPO3 gene fusion.

In certain embodiments, the tumor expresses RSPO3 to which a RSPO3-binding agent or antibody binds. In certain embodiments, the tumor has elevated expression levels of RSPO1 or over-expresses RSPO1. In certain embodiments, the tumor has elevated expression levels of RSPO2 or over-expresses RSPO2. In certain embodiments, the tumor has elevated expression levels of RSPO3 or over-expresses RSPO3. The phrase "a tumor has elevated expression levels of" may refer to expression levels of a protein or expression levels of a nucleic acid. In general, the phrase "a tumor has elevated expression levels of" a protein or a gene (or similar phrases) refers to expression levels of a protein or a gene in a tumor as compared to expression levels of the same protein or the same gene in a reference sample or to a pre-determined expression level. In some embodiments, the reference sample is normal tissue of the same tissue type. In some embodiments, the reference sample is normal tissue of a group of tissue types. In some embodiments, the reference sample is a tumor or group of tumors of the same tissue type. In some embodiments, the reference sample is a tumor or group of tumors of a different tissue type. Thus in some embodiments, the expression levels of a protein or a gene in a tumor are "elevated" or "high" as compared to the average expression level of the protein or the gene within a group of tissue types. In some embodiments, the expression levels of a protein or a gene in a tumor are "elevated" or "high" as compared to the expression level of the protein or the gene in other tumors of the same tissue type or a different tissue type. In some embodiments, the tumor expresses "elevated" or "high" levels of RSPO1, RSPO2, RSPO3, and/or RSPO4 as compared to the RSPO levels expressed in normal tissue of the same tissue type. In some embodiments, the tumor expresses "elevated" or "high" levels of RSPO1, RSPO2, RSPO3, and/or RSPO4 as compared to a predetermined level.

In addition, the invention provides a method of inhibiting growth of a tumor in a subject, comprising administering a therapeutically effective amount of a RSPO3-binding agent to the subject. In certain embodiments, the tumor comprises cancer stem cells. In certain embodiments, the frequency of cancer stem cells in the tumor is reduced by administration of the RSPO3-binding agent. The invention also provides a method of reducing the frequency of cancer stem cells in a tumor, comprising contacting the tumor with an effective amount of a RSPO3-binding agent (e.g., an anti-RSPO3 antibody). In some embodiments, a method of reducing the frequency of cancer stem cells in a tumor in a subject, comprising administering to the subject a therapeutically effective amount of a RSPO3-binding agent (e.g., an anti-RSPO3 antibody) is provided. In some embodiments, the RSPO3-binding agent is an antibody. In some embodiments, the RSPO3-binding agent is an anti-RSPO3 antibody. In some embodiments, the anti-RSPO3 antibody is 131R002. In some embodiments, the anti-RSPO3 antibody is antibody 131R003. In some embodiments, the anti-RSPO3 antibody is a variant of antibody 131R003. In some embodiments, the anti-RSPO3 antibody is a humanized version of antibody 131R003. In some embodiments, the anti-RSPO3 antibody is a humanized version of a variant of antibody 131R003. In some embodiments, the anti-RSPO3 antibody is antibody h131R006A or antibody h131R006B. In some embodiments, the anti-RSPO3 antibody is antibody h131R005/131R007. In some embodiments, the anti-RSPO3 antibody is antibody h131R008. In some embodiments, the anti-RSPO3 antibody is antibody h131R010. In some embodiments, the anti-RSPO3 antibody is antibody h131R011.

In some embodiments, the tumor is a solid tumor. In certain embodiments, the tumor is a tumor selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. As used herein, "lung cancer" includes but is not limited to, small cell lung carcinoma and non-small cell lung carcinoma (NSCLC). In certain embodiments, the tumor is a colorectal tumor. In certain embodiments, the tumor is an ovarian tumor. In some embodiments, the tumor is a lung tumor. In certain embodiments, the tumor is a pancreatic tumor. In some embodiments, the tumor is a colorectal tumor that comprises an inactivating mutation in the APC gene. In some embodiments, the tumor is a colorectal tumor that does not comprise an inactivating mutation in the APC gene. In some embodiments, the tumor is a colorectal tumor that contains a RSPO gene fusion. In some embodiments, the tumor is a colorectal tumor that contains a RSPO2 gene fusion. In some embodiments, the tumor is a colorectal tumor that contains a RSPO3 gene fusion. In some embodiments, the tumor is an ovarian tumor with an elevated expression level of RSPO1. In some embodiments, the tumor is a pancreatic tumor with an elevated expression level of RSPO2. In some embodiments, the tumor is a colon tumor with an elevated expression level of RSPO2. In some embodiments, the tumor is a lung tumor with an elevated expression level of RSPO2. In some embodiments, the tumor is a lung tumor with an elevated expression level of RSPO3. In some embodiments, the tumor is an ovarian tumor with an elevated expression level of RSPO3. In some embodiments, the tumor is a breast tumor with an elevated expression level of RSPO3. In some embodiments, the tumor is a colorectal tumor with an elevated expression level of RSPO3.

The present invention further provides methods for treating cancer comprising administering a therapeutically effective amount of a RSPO3-binding agent to a subject. In certain embodiments, the cancer is characterized by cells expressing elevated levels of at least one RSPO protein as compared to expression levels of the same RSPO protein in a reference sample. As used herein, a "reference sample" includes but is not limited to, normal tissue, non-cancerous tissue of the same tissue type, tumor tissue of the same tissue type, and tumor tissue of a different tissue type. In certain embodiments, the cancer is characterized by cells expressing elevated levels of at least one RSPO protein as compared to a pre-determined level of the same RSPO protein. In some embodiments, determining the expression level of at least one RSPO is done prior to treatment. In some embodiments, determining the expression level of at least one RSPO is by immunohistochemistry. Thus, in certain embodiments, the cancer is characterized by cells expressing elevated levels of at least one RSPO protein as compared to expression levels of the same RSPO protein in normal tissue. In certain embodiments, the cancer is characterized by cells over-expressing RSPO1. In certain embodiments, the cancer is characterized by cells over-expressing RSPO2. In certain embodiments, the cancer is characterized by cells over-expressing RSPO3. In certain embodiments, the cancer over-expresses at least one RSPO protein selected from the group consisting of RSPO1, RSPO2, RSPO3, and/or RSPO4. In certain embodiments, the cancer is characterized by cells expressing β-catenin, wherein the RSPO3-binding agent (e.g., an antibody) interferes with RSPO3-induced β-catenin signaling and/or activation.

In some embodiments, the RSPO-binding agent binds RSPO3, and inhibits or reduces growth of the cancer. In some embodiments, the RSPO-binding agent binds RSPO3, interferes with RSPO3/LGR interactions, and inhibits or reduces growth of the cancer. In some embodiments, the RSPO-binding agent binds RSPO3, inhibits β-catenin activation, and inhibits or reduces growth of the cancer. In some embodiments, the RSPO-binding agent binds RSPO3, and reduces the frequency of cancer stem cells in the cancer. In some embodiments, the RSPO-binding agent is an antibody. In some embodiments, the RSPO-binding agent is an anti-RSPO3 antibody. In some embodiments, the anti-RSPO3 antibody is antibody 131R002. In some embodiments, the anti-RSPO3 antibody is antibody 131R003. In some embodiments, the anti-RSPO3 antibody is a variant of antibody 131R003. In some embodiments, the anti-RSPO antibody is a humanized version of antibody 131R002. In some embodiments, the anti-RSPO antibody is a humanized version of antibody 131R003. In some embodiments, the anti-RSPO antibody is a humanized version of a variant of antibody 131R003. In some embodiments, the anti-RSPO3 antibody is antibody h131R006A or antibody h131R006B. In some embodiments, the anti-RSPO3 antibody is antibody h131R005/131R007. In some embodiments, the anti-RSPO3 antibody is antibody h131R008. In some embodiments, the anti-RSPO3 antibody is antibody h131R010. In some embodiments, the anti-RSPO3 antibody is antibody h131R011.

The present invention provides for methods of treating cancer comprising administering a therapeutically effective amount of a RSPO3-binding agent to a subject (e.g., a subject in need of treatment). In certain embodiments, the method of treating cancer comprises administering to a subject a therapeutically effective amount of a RSPO3-binding agent, wherein the RSPO3-binding agent comprises a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSGYNQKFK (SEQ ID NO:79), and a heavy chain CDR3 comprising ATYFANYFDY (SEQ ID NO:11), ATYFANNFDY (SEQ ID NO:35), or TYFANNFD (SEQ ID NO:80). In some embodiments of the method, the RSPO3-binding agent further comprises a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83). In some embodiments, the RSPO3-binding agent comprises a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANYFDY (SEQ ID NO:11), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In some embodiments, the RSPO3-binding agent comprises a heavy chain CDR1 comprising KASGYTFTDYS (SEQ ID NO:9), a heavy chain CDR2 comprising IYPSNGDS (SEQ ID NO:10), and a heavy chain CDR3 comprising ATYFANNFDY (SEQ ID NO:35), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In some embodiments, the RSPO3-binding agent comprises a heavy chain CDR1 comprising KASGYTFTSYTF (SEQ ID NO:34), a heavy chain CDR2 comprising IYPSNGDS (SEQ ID NO:10), and a heavy chain CDR3 comprising ATYFANNFDY (SEQ ID NO:35), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In some embodiments, the RSPO3-binding agent comprises a heavy chain CDR1 comprising KASGYTFTDYS (SEQ ID NO:9) or DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and/or a light chain CDR1 comprising KASQSVDYDGDSYMN (SEQ ID NO:81), a light chain CDR2 comprising AASNLES (SEQ ID NO:82), and a light chain CDR3 comprising QQSNEDPLTF (SEQ ID NO:83). In some embodiments, the RSPO3-binding agent comprises a heavy chain CDR1 comprising KASGYTFTDYS (SEQ ID NO:9) or DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80), and/or a light chain CDR1 comprising KASQSVDYDGDSYMN (SEQ ID NO:81), a light chain CDR2 comprising AASNLES (SEQ ID NO:82), and a light chain CDR3 comprising QQSNEDPLT (SEQ ID NO:14). In some embodiments, the RSPO3-binding agent comprises a heavy chain CDR1 comprising KASGYTFTDYS (SEQ ID NO:9) or DYSIH (SEQ ID NO:78), a heavy chain CDR2 comprising IYPSNGDS (SEQ ID NO:10), and a heavy chain CDR3 comprising TYFANNFD (SEQ ID NO:80), and/or a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14). In certain embodiments, the subject is a human. In certain embodiments, the subject has a cancerous tumor. In certain embodiments, the subject has had a tumor removed. In some embodiments, a method of treating cancer comprises administering a therapeutically effective amount of a RSPO3-binding agent to a subject, wherein the subject has a tumor that has elevated expression of at least one RSPO protein as compared to a reference sample or a pre-determined level. In some embodiments, the subject has a lung tumor that has elevated expression of RSPO3 and is administered an anti-RSPO3 antibody.

The invention also provides a RSPO3-binding agent for use in a method of treating cancer, wherein the RSPO3-binding agent is an antibody described herein. The invention also provides the use of an RSPO3-binding agent (e.g., an antibody) described herein for the manufacture of a medicament for the treatment of cancer.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, bladder cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer.

In addition, the invention provides a method of reducing the tumorigenicity of a tumor in a subject, comprising administering to a subject a therapeutically effective amount of a RSPO3-binding agent. In certain embodiments, the tumor comprises cancer stem cells. In some embodiments, the tumorigenicity of a tumor is reduced by reducing the frequency of cancer stem cells in the tumor. In some embodiments, the methods comprise using the RSPO3-binding agents described herein. In certain embodiments, the frequency of cancer stem cells in the tumor is reduced by administration of a RSPO3-binding agent.

In certain embodiments, the methods further comprise a step of determining the expression level of at least one RSPO (i.e., protein or nucleic acid) in the tumor or cancer. In some embodiments, the step of determining the expression level of a RSPO in the tumor or cancer comprises determining the expression level of RSPO1, RSPO2, RSPO3, and/or RSPO4. In some embodiments, the expression level of RSPO1, RSPO2, RSPO3, and/or RSPO4 in a tumor or cancer is compared to the expression level of RSPO1, RSPO2, RSPO3, and/or RSPO4 in a reference sample. In some embodiments, the expression level of RSPO1, RSPO2, RSPO3, and/or RSPO4 in a tumor or cancer is compared to the expression level of RSPO1, RSPO2, RSPO3, and/or RSPO4 in normal tissue. In some embodiments, the level of expression of RSPO1, RSPO2, RSPO3, and/or RSPO4 in a tumor or cancer is compared to a pre-determined level of expression of RSPO1, RSPO2, RSPO3, and/or RSPO4. In some embodiments, the level of expression of RSPO1, RSPO2, RSPO3, and/or RSPO4 in a tumor or cancer is compared to a pre-determined level of expression of RSPO1, RSPO2, RSPO3, and/or RSPO4 in normal tissue. In some embodiments, the tumor has a high expression level of RSPO1. In some embodiments, the tumor has a high expression level of RSPO3. In general, the expression level of a RSPO (i.e., protein or nucleic acid) is compared to the expression level of the RSPO (i.e., protein or nucleic acid) in normal tissue of the same tissue type. However, in some embodiments, the expression level of a RSPO (i.e., protein or nucleic acid) is compared to the average expression level of the RSPO (i.e., protein or nucleic acid) within a group of tissue types. In some embodiments, the expression levels of a RSPO (i.e., protein or nucleic acid) in a tumor is compared to the expression level of the RSPO (i.e., protein or nucleic acid) in other tumors of the same tissue type or a different tissue type.

In some embodiments, determining the level of RSPO expression is done prior to treatment. In some embodiments, the subject is administered a RSPO3-binding agent or antibody describe herein if the tumor or cancer has an elevated expression level of RSPO as compared to the expression level of the same RSPO in a reference sample (e.g., normal tissue) or a pre-determined level. For example, in some embodiments, the subject is administered a RSPO3-binding agent (e.g., anti-RSPO3 antibody) if the tumor or cancer has an elevated expression level of RSPO3 (i.e., protein or nucleic acid) as compared to the expression level of RSPO3 in normal or control tissue.

In certain embodiments, the methods further comprise a step of determining if the tumor or cancer has an inactivating mutation in the APC gene. In some embodiments, the methods further comprise a step of determining if the tumor or cancer has an activating mutation in the β-catenin gene. In some embodiments, the methods further comprise a step of determining if the tumor or cancer has a RSPO gene fusion.

In addition, the invention provides a method of modulating angiogenesis, comprising administering to a subject a therapeutically effective amount of a RSPO3-binding agent. In some embodiments, the modulating angiogenesis comprises inhibiting angiogenesis. In some embodiments, the methods comprise using the RSPO3-binding agents described herein. In certain embodiments, the RSPO3-binding agent binds RSPO3 and inhibits or reduces angiogenesis. In certain embodiments, the inhibition and/or reduction of angiogenesis inhibits or reduces growth of a tumor or cancer. In some embodiments, the RSPO3-binding agent binds RSPO3 and promotes aberrant angiogenesis. In some embodiments, the RSPO3-binding agent binds RSPO3 and promotes unproductive angiogenesis. In certain embodiments, the aberrant angiogenesis or the unproductive angiogenesis inhibits or reduces growth of a tumor or cancer.

In addition, the present invention provides methods of identifying a human subject for treatment with a RSPO-binding agent, comprising determining if the subject has a tumor that has an elevated expression level of RSPO (i.e., protein or nucleic acid) as compared to expression of the same RSPO (i.e., protein or nucleic acid) in normal tissue, in a reference sample, or to a pre-determined level of the RSPO protein. In some embodiments, a method of identifying a human subject for treatment with a RSPO3-binding agent comprises determining if the subject has a tumor that has an elevated expression level of RSPO3 as compared to a reference sample or a pre-determined level of RSPO3. In some embodiments, a method of identifying a human subject for treatment with a RSPO3-binding agent comprises: obtaining a tumor sample from the subject, and determining if the tumor has an elevated expression level of RSPO3 as compared to a reference sample or a pre-determined level of RSPO3. In some embodiments, if the tumor has an elevated expression level of RSPO3, the subject is selected for treatment with an antibody that specifically binds RSPO3. In some embodiments, if selected for treatment, the subject is administered a RSPO3-binding agent or antibody describe herein. In some embodiments, if the tumor has an elevated expression level of more than one RSPO (i.e., protein or nucleic acid), the subject is administered a RSPO-binding agent that binds the RSPO with the highest level of expression. In certain embodiments, the subject has had a tumor removed. For example, in some embodiments, the expression level of RSPO1, RSPO2, RSPO3, and/or RSPO4 in a tumor is determined, if the tumor has an elevated level of RSPO3 expression as compared to the level of RSPO3 in normal tissue, the subject is selected for treatment with an antibody that specifically binds RSPO3. If selected for treatment, the subject is administered an anti-RSPO3 antibody describe herein. In some embodiments, the RSPO3-binding agent is antibody 131R002. In some embodiments, the RSPO3-binding agent is antibody 131R003. In some embodiments, the RSPO3-binding agent is a variant of antibody 131R003. In some embodiments, the RSPO3-binding agent is a humanized form of antibody 131R003. In some embodiments, the RSPO3-binding agent is a humanized form of a variant of antibody 131R003. In some embodiments, the RSPO3-binding agent is antibody h131R006A or antibody h131R006B. In some embodiments, the RSPO3-binding agent is antibody h131R005/131R007. In some embodiments, the RSPO3-binding agent is antibody h131R008. In some embodiments, the RSPO3-binding agent is antibody h131R010. In some embodiments, the RSPO3-binding agent is antibody h131R011.

The present invention provides methods of selecting a human subject for treatment with a RSPO-binding agent, comprising determining if the subject has a tumor that has an elevated expression level of at least one RSPO (i.e., protein or nucleic acid), as compared to expression of the same RSPO in normal tissue or as compared to a predetermined level, wherein if the tumor has an elevated expression level of at least one RSPO, the subject is selected for treatment with an antibody that specifically binds the RSPO with the elevated expression level. In some embodiments, if selected for treatment, the subject is administered a RSPO-binding agent or antibody describe herein. In some embodiments, a method of selecting a human subject for treatment with an antibody that specifically binds RSPO3 comprises: determining if the subject has a tumor that has an elevated expression level of RSPO3 as compared to a reference sample or a pre-determined level of RSPO3. In some embodiments, a method of selecting a human subject for treatment with an antibody that specifically binds RSPO3 comprises obtaining a tumor sample from the subject, and determining if the tumor has an elevated expression level of RSPO3 as compared to a reference sample or a pre-determined level of RSPO3. In some embodiments, a method of selecting a human subject for treatment with an antibody that specifically binds RSPO3, comprises determining if the subject has a tumor that has an elevated expression level of RSPO3 as compared to a reference sample or a pre-determined level of RSPO3, wherein if the tumor has an elevated expression level of RSPO3 the subject is selected for treatment with the antibody. In some embodiments, a method of selecting a human subject for treatment with an antibody that specifically binds RSPO3, comprises obtaining a tumor sample from the subject, and determining if the tumor has an elevated expression level of RSPO3 as compared to a reference sample or a pre-determined level of RSPO3, wherein if the tumor has an elevated expression level of RSPO3 the subject is selected for treatment with the antibody. In certain embodiments, the subject has had a tumor removed. In some embodiments, the RSPO-binding agent is a RSPO3-binding agent. In some embodiments, the RSPO3-binding agent is an anti-RSPO3 antibody. In some embodiments, the anti-RSPO3 antibody is antibody 131R002. In some embodiments, the anti-RSPO3 antibody is antibody 131R003. In some embodiments, the anti-RSPO3 antibody is a variant of antibody 131R003. In some embodiments, the anti-RSPO3 antibody is a humanized version of antibody 131R002. In some embodiments, the anti-RSPO3 antibody is a humanized version of antibody 131R003. In some embodiments, the anti-RSPO3 antibody is a humanized version of a variant of antibody 131R003. In some embodiments, the anti-RSPO3 antibody is antibody h131R006A or h131R006B. In some embodiments, the anti-RSPO3 antibody is antibody h131R005/131R007. In some embodiments, the anti-RSPO3 antibody is antibody h131R008. In some embodiments, the anti-RSPO3 antibody is antibody h131R010. In some embodiments, the anti-RSPO3 antibody is antibody h131R011.

The present invention also provides methods of treating cancer in a human subject, comprising: (a) selecting a subject for treatment based, at least in part, on the subject having a cancer that has an elevated level of a RSPO, and (b) administering to the subject a therapeutically effective amount of a RSPO3-binding agent described herein. In some embodiments, the RSPO3-binding agent is antibody 131R002. In some embodiments, the RSPO3-binding agent is antibody 131R003. In some embodiments, the RSPO3-binding agent is a variant of antibody 131R003. In some embodiments, the anti-RSPO3 antibody is a humanized version of antibody 131R002. In some embodiments, the anti-RSPO3 antibody is a humanized version of antibody 131R003. In some embodiments, the anti-RSPO3 antibody is a humanized version of a variant of antibody 131R003. In some embodiments, the anti-RSPO3 antibody is antibody h131R006A or h131R006B. In some embodiments, the anti-RSPO3 antibody is antibody h131R005/131R007. In some embodiments, the anti-RSPO3 antibody is antibody h131R008. In some embodiments, the anti-RSPO3 antibody is antibody h131R010. In some embodiments, the anti-RSPO3 antibody is antibody h131R011.

Methods for determining the level of RSPO expression in a cell, tumor or cancer are known by those of skill in the art. For nucleic acid expression these methods include, but are not limited to, PCR-based assays, microarray analyses and nucleotide sequencing (e.g., NextGen sequencing). For protein expression these methods include, but are not limited to, Western blot analysis, protein arrays, ELISAs, immunohistochemistry (IHC) assays, and FACS.

The present invention provides methods of identifying a human subject for treatment with a RSPO3-binding agent, comprising obtaining a tumor sample from the subject, and determining if the tumor has a RSPO gene fusion. In some embodiments, a method of identifying a human subject for treatment with a RSPO3-binding agent comprises: determining if the subject has a tumor that has a RSPO gene fusion, wherein if the tumor has a RSPO gene fusion, then the subject is selected for treatment with the antibody. In some embodiments, a method of identifying a human subject for treatment with a RSPO3-binding agent comprises: (a) obtaining a tumor sample from the subject, and (b) determining if the tumor has a RSPO gene fusion, wherein if the tumor has a RSPO gene fusion, then the subject is selected for treatment with the antibody. In some embodiments, a method of selecting a human subject for treatment with an antibody that specifically binds RSPO3, comprises determining if the subject has a tumor that has a RSPO gene fusion.

The present invention also provides methods of selecting a human subject for treatment with a RSPO-binding agent, comprising determining if the subject has a tumor that has a RSPO gene fusion, wherein if the tumor has a RSPO gene fusion, the subject is selected for treatment with an antibody that specifically binds a RSPO protein. In some embodiments, a method of selecting a human subject for treatment with an antibody that specifically binds RSPO3 comprises determining if the subject has a tumor that has a RSPO gene fusion. In some embodiments, a method of selecting a human subject for treatment with an antibody that specifically binds RSPO3, comprises obtaining a tumor sample from the subject, and determining if the tumor has a RSPO gene fusion. In some embodiments, a method of selecting a human subject for treatment with an antibody that specifically binds RSPO3, comprises determining if the subject has a tumor that has a RSPO gene fusion, wherein if the tumor has a RSPO gene fusion the subject is selected for treatment with the antibody. In some embodiments, a method of selecting a human subject for treatment with an antibody that specifically binds RSPO3, comprises obtaining a tumor sample from the subject, and determining if the tumor has a RSPO gene fusion, wherein if the tumor has a RSPO gene fusion the subject is selected for treatment with the antibody. In some embodiments, the RSPO gene fusion is a RSPO2 gene fusion. In some embodiments, the RSPO gene fusion is a RSPO3 gene fusion. In some embodiments, if selected for treatment, the subject is administered a RSPO-binding agent or antibody describe herein. In certain embodiments, the subject has had a tumor removed. In some embodiments, the RSPO-binding agent is a RSPO3-binding agent. In some embodiments, the RSPO3-binding agent is an anti-RSPO3 antibody. In some embodiments, the anti-RSPO3 antibody is antibody 131R002. In some embodiments, the anti-RSPO3 antibody is antibody 131R003. In some embodiments, the anti-RSPO3 antibody is a variant of antibody 131R003. In some embodiments, the anti-RSPO3 antibody is a humanized version of antibody 131R002. In some embodiments, the anti-RSPO3 antibody is a humanized version of antibody 131R003. In some embodiments, the anti-RSPO3 antibody is a humanized version of a variant of antibody 131R003. In some embodiments, the anti-RSPO3 antibody is antibody h131R006A or h131R006B. In some embodiments, the anti-RSPO3 antibody is antibody h131R005/131R007. In some embodiments, the anti-RSPO3 antibody is antibody h131R008. In some embodiments, the anti-RSPO3 antibody is antibody h131R010. In some embodiments, the anti-RSPO3 antibody is antibody h131R011.

The present invention also provides methods of treating cancer in a human subject, comprising: (a) selecting a subject for treatment based, at least in part, on the subject having a cancer that has a RSPO gene fusion, and (b) administering to the subject a therapeutically effective amount of a RSPO3-binding agent described herein. In some embodiments, the RSPO3-binding agent is antibody 131R002. In some embodiments, the RSPO3-binding agent is antibody 131R003. In some embodiments, the RSPO3-binding agent is a variant of antibody 131R003. In some embodiments, the anti-RSPO3 antibody is a humanized version of antibody 131R002. In some embodiments, the anti-RSPO3 antibody is a humanized version of antibody 131R003. In some embodiments, the anti-RSPO3 antibody is a humanized version of a variant of antibody 131R003. In some embodiments, the anti-RSPO3 antibody is antibody h131R006A or h131R006B. In some embodiments, the anti-RSPO3 antibody is antibody h131R005/131R007. In some embodiments, the anti-RSPO3 antibody is antibody h131R008. In some embodiments, the anti-RSPO3 antibody is antibody h131R010. In some embodiments, the anti-RSPO3 antibody is antibody h131R011.

Methods for determining whether a tumor has a RSPO gene fusion are known by those of skill in the art. Methods may include but are not limited to, PCR-based assays, microarray analyses, and nucleotide sequencing (e.g., Next-Gen sequencing, whole-genome sequencing (WGS)).

Methods for determining whether a tumor or cancer has an elevated level of RSPO expression or has a RSPO gene fusion can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Methods of treating a disease or disorder in a subject, wherein the disease or disorder is associated with aberrant (e.g., increased levels) β-catenin signaling are further provided. Methods of treating a disease or disorder in a subject, wherein the disease or disorder is characterized by an increased level of stein cells and/or progenitor cells are further provided. In some embodiments, the treatment methods comprise administering a therapeutically effective amount of a RSPO-binding agent, polypeptide, or antibody to the subject. In some embodiments, the RSPO-binding agent is a RSPO3-binding agent. In some embodiments, the RSPO3-binding agent is an antibody. In some embodiments, the RSPO3-binding agent is antibody 131R002. In some embodiments, the RSPO3-binding agent is antibody 131R003. In some embodiments, the RSPO3-binding agent is a variant of antibody 131R003. In some embodiments, the RSPO3-binding agent is a humanized version of antibody 131R002. In some embodiments, the RSPO3-binding agent is a humanized version of antibody 131R003. In some embodiments, the RSPO3-binding agent is a humanized version of a variant of antibody 131R003. In some embodiments, the RSPO3-binding agent is antibody h131R006A or antibody h131R006B. In some embodiments, the RSPO3-binding agent is antibody h131R005/131R007. In some embodiments, the RSPO3-binding agent is antibody h131R008. In some embodiments, the RSPO3-binding agent is antibody h131R010. In some embodiments, the RSPO3-binding agent is antibody h131R011.

The invention also provides a method of inhibiting β-catenin signaling in a cell comprising contacting the cell with an effective amount of a RSPO-binding agent. In certain embodiments, the cell is a tumor cell. In certain embodiments, the method is an in vivo method wherein the step of contacting the cell with the RSPO3-binding agent comprises administering a therapeutically effective amount of the RSPO3-binding agent to the subject. In some embodiments, the method is an in vitro or ex vivo method. In certain embodiments, the RSPO-binding agent inhibits β-catenin signaling. In some embodiments, the RSPO-binding agent inhibits activation of β-catenin. In certain embodiments, the RSPO-binding agent interferes with a RSPO/LGR interaction. In certain embodiments, the LGR is LGR4, LGR5, and/or LGR6. In certain embodiments, the LGR is LGR4. In certain embodiments, the LGR is LGR5. In certain embodiments, the LGR is LGR6. In some embodiments, the RSPO-binding agent is a RSPO3-binding agent. In some embodiments, the RSPO3-binding agent is an antibody. In some embodiments, the RSPO3-binding agent is antibody 131R002. In some embodiments, the RSPO3-binding agent is antibody 131R003. In some embodiments, the RSPO3-binding agent is a variant of antibody 131R003. In some embodiments, the RSPO3-binding agent is a humanized version of antibody 131R002. In some embodiments, the RSPO3-binding agent is a humanized version of antibody 131R003. In some embodiments, the RSPO3-binding agent is a humanized version of a variant of antibody 131R003. In some embodiments, the RSPO3-binding agent is antibody h131R006A or antibody h131R006B. In some embodiments, the RSPO3-binding agent is antibody h131R005/131R007. In some embodiments, the RSPO3-binding agent is antibody h131R008. In some embodiments, the RSPO3-binding agent is antibody h131R010. In some embodiments, the RSPO3-binding agent is antibody h131R011.

The use of the RSPO-binding agents, polypeptides, or antibodies described herein to induce the differentiation of cells, including, but not limited to tumor cells, is also provided. In some embodiments, methods of inducing cells to differentiate comprise contacting the cells with an effective amount of a RSPO-binding agent (e.g., an anti-RSPO antibody) described herein. In certain embodiments, methods of inducing cells in a tumor in a subject to differentiate comprise administering a therapeutically effective amount of a RSPO-binding agent, polypeptide, or antibody to the subject. In some embodiments, methods for inducing differentiation markers on tumor cells comprise administering a therapeutically effective amount of a RSPO-binding agent, polypeptide, or antibody. In some embodiments, the tumor is a solid tumor. In some embodiments, the tumor is selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is an ovarian tumor. In certain other embodiments, the tumor is a colon tumor. In some embodiments, the tumor is a lung tumor. In certain embodiments, the method is an in vivo method. In certain embodiments, the method is an in vitro method. In some embodiments, the RSPO-binding agent is a RSPO3-binding agent. In some embodiments, the RSPO3-binding agent is an antibody. In some embodiments, the RSPO3-binding agent is antibody 131R002. In some embodiments, the RSPO3-binding agent is antibody 131R003. In some embodiments, the RSPO3-binding agent is a variant of antibody 131R003. In some embodiments, the RSPO3-binding agent is a humanized version of antibody 131R002. In some embodiments, the RSPO3-binding agent is a humanized version of antibody 131R003. In some embodiments, the RSPO3-binding agent is a humanized version of a variant of antibody 131R003. In some embodiments, the RSPO3-binding agent is antibody h131R006A or antibody h131R006B. In some embodiments, the RSPO3-binding agent is antibody h131R005/131R007. In some embodiments, the RSPO3-binding agent is antibody h131R008. In some embodiments, the RSPO3-binding agent is antibody h131R010. In some embodiments, the RSPO3-binding agent is antibody h1131R011.

The invention further provides methods of differentiating tumorigenic cells into non-tumorigenic cells comprising contacting the tumorigenic cells with a RSPO-binding agent. In some embodiments, the method comprises administering the RSPO-binding agent to a subject that has a tumor comprising tumorigenic cells or that has had such a tumor removed. In certain embodiments, the tumorigenic cells are ovarian tumor cells. In certain embodiments, the tumorigenic cells are colon tumor cells. In some embodiments, the tumorigenic cells are lung tumor cells. In some embodiments, the RSPO-binding agent is a RSPO3-binding agent. In some embodiments, the RSPO3-binding agent is an antibody. In some embodiments, the RSPO3-binding agent is antibody 131R002. In some embodiments, the RSPO3-binding agent is antibody 131R003. In some embodiments, the RSPO3-binding agent is a variant of antibody 131R003. In some embodiments, the RSPO3-binding agent is a humanized version of antibody 131R002. In some embodiments, the RSPO3-binding agent is a humanized version of antibody 131R003. In some embodiments, the RSPO3-binding agent is a humanized version of a variant of antibody 131R003. In some embodiments, the RSPO3-binding agent is antibody h131R006A or antibody h131R006B. In some embodiments, the RSPO3-binding agent is antibody h131R005/131R007. In some embodiments, the RSPO3-binding agent is antibody h131R008. In some embodiments, the RSPO3-binding agent is antibody h131R010. In some embodiments, the RSPO3-binding agent is antibody h131R011.

In certain embodiments, the disease treated with the RSPO3-binding agents described herein is not a cancer. For example, the disease may be a metabolic disorder such as obesity or diabetes (e.g., type II diabetes) (Jin T., 2008, Diabetologia, 51:1771-80). Alternatively, the disease may be a bone disorder such as osteoporosis, osteoarthritis, or rheumatoid arthritis (Corr M., 2008, Nat. Clin. Pract. Rheumatol., 4:550-6; Day et al., 2008, Bone Joint Surg. Am., 90 Suppl 1:19-24). The disease may also be a kidney disorder, such as a polycystic kidney disease (Harris et al., 2009, Ann. Rev. Med., 60:321-337; Schmidt-Ott et al., 2008, Kidney Int., 74:1004-8; Benzing et al., 2007, J. Am. Soc. Nephrol., 18:1389-98). Alternatively, eye disorders including, but not limited to, macular degeneration and familial exudative vitreoretinopathy may be treated (Lad et al., 2009, Stem Cells Dev., 18:7-16). Cardiovascular disorders, including myocardial infarction, atherosclerosis, and valve disorders, may also be treated (Al-Aly Z., 2008, Transl. Res., 151:233-9; Kobayashi et al., 2009, Nat. Cell Biol., 11:46-55; van Gijn et al., 2002, Cardiovasc. Res., 55:16-24; Christman et al., 2008, Am. J. Physiol. Heart Circ. Physiol., 294:H2864-70). In some embodiments, the disease is a pulmonary disorder such as idiopathic pulmonary arterial hypertension or pulmonary fibrosis (Laumanns et al., 2008, Am. J. Respir. Cell Mol. Biol., 2009, 40:683-691; Königshoff et al., 2008, PLoS ONE, 3:e2142). In some embodiments, the disease treated with the RSPO3-binding agent is a liver disease, such as cirrhosis or liver fibrosis (Cheng et al., 2008, Am. J. Physiol. Gastrointest. Liver Physiol., 294:G39-49).

The present invention further provides pharmaceutical compositions comprising the RSPO3-binding agents described herein. In certain embodiments, the pharmaceutical compositions further comprise a pharmaceutically acceptable vehicle. In some embodiments, these pharmaceutical compositions find use in inhibiting tumor growth and treating cancer in a subject (e.g., a human patient).

In certain embodiments, formulations are prepared for storage and use by combining a purified antibody or agent of the present invention with a pharmaceutically acceptable vehicle (e.g., a carrier or excipient). Suitable pharmaceutically acceptable vehicles include, but are not limited to, non-toxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington*: The Science and Practice of Pharmacy, $22^{st}$ Edition, 2012, Pharmaceutical Press, London.)

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid pre-formulation composition containing a homogeneous mixture of a compound of the present invention, or a non-toxic pharmaceutically acceptable salt thereof. The solid pre-formulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The RSPO3-binding agents or antibodies described herein can also be entrapped in microcapsules. Such microcapsules are prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy*, $22^{st}$ Edition, 2012, Pharmaceutical Press, London.

In certain embodiments, pharmaceutical formulations include a RSPO3-binding agent (e.g., an antibody) of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations can be produced. Suitable examples of sustained-release preparations include semi-permeable matrices of solid hydrophobic polymers containing a RSPO3-binding agent (e.g., an antibody), where the matrices are in the form of shaped articles (e.g., films or microcapsules). Examples of sustained-release matrices include polyesters, hydrogels such as poly (2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering a RSPO3-binding agent (e.g., an antibody), the method or treatment further comprises administering at least one additional therapeutic agent. An additional therapeutic agent can be administered prior to, concurrently with, and/or subsequently to, administration of the RSPO3-binding agent. Pharmaceutical compositions comprising a RSPO3-binding agent and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistant cancer cells will develop. In some embodiments, combination therapy comprises a therapeutic agent that affects (e.g., inhibits or kills) non-tumorigenic cells and a therapeutic agent that affects (e.g., inhibits or kills) tumorigenic CSCs.

In some embodiments, the combination of a RSPO3-binding agent and at least one additional therapeutic agent results in additive or synergistic results. In some embodiments, the combination therapy results in an increase in the therapeutic index of the RSPO3-binding agent. In some embodiments, the combination therapy results in an increase in the therapeutic index of the additional agent(s). In some embodiments, the combination therapy results in a decrease in the toxicity and/or side effects of the RSPO3-binding agent. In some embodiments, the combination therapy results in a decrease in the toxicity and/or side effects of the additional agent(s).

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor. In some embodiments, the second therapeutic agent is a platinum complex such as carboplatin or cisplatin. In some embodiments, the additional therapeutic agent is a platinum complex in combination with a taxane.

Therapeutic agents that may be administered in combination with the RSPO3-binding agents include chemotherapeutic agents. Thus, in some embodiments, the method or treatment involves the administration of a RSPO3-binding agent or antibody of the present invention in combination with a chemotherapeutic agent or cocktail of multiple different chemotherapeutic agents. Treatment with a RSPO3-binding agent (e.g., an antibody) can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book*, $4^{th}$ Edition, 2008, M. C. Perry, Editor, Lippincott, Williams &. Wilkins, Philadelphia, Pa.

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin. In certain embodiments, the additional therapeutic agent is paclitaxel (taxol). In some embodiments, a method comprises administering anti-RSPO3 antibody 131R002, 131R003, a variant of 131R003, 131R006A, 131R006B, 131R005/131R007, or 131R008 in combination with cisplatin.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan. Thus, in some embodiments, a method comprises administering a RSPO3-binding agent in combination with a topoisomerase inhibitor. In some embodiments, a method comprises administering anti-RSPO3 antibody 131R002, 131R003, a variant of 131R003, a humanized version of 131R003, h131R006A, h131R006B, h131R005/131R007, h131R008, h131R010, or h131R011 in combination with irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine. Thus, in some embodiments, a method comprises administering a RSPO3-binding agent in combination with an anti-metabolite. In some embodiments, a method comprises administering anti-RSPO3 antibody 131R002, 131R003, a variant of 131R003, a humanized version of 131R003, h131R006A, h131R006B, h131R005/131R007, h131R008, h131R010, or h131R011 in combination with gemcitabine. In some embodiments, a method comprises administering anti-RSPO3 antibody 131R002, 131R003, a variant of 131R003, a humanized version of 131R003, h131R006A, h131R006B, h131R005/131R007, h131R008, h131R010, or h131R011 in combination with pemetrexed.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, where the chemotherapeutic agent administered in combination with a RSPO-binding agent is an anti-mitotic agent, the cancer or tumor being treated is breast cancer or a breast tumor. In some embodiments, a method comprises administering anti-RSPO3 antibody 131R002, 131R003, a variant of 131R003, a humanized version of 131R003, h131R006A, h131R006B, h131R005/131R007, h131R008, h131R010, or h131R011 in combination with paclitaxel. In some embodiments, a method comprises administering anti-RSPO3 antibody 131R002, 131R003, a variant of 131R003, a humanized version of 131R003, h131R006A, h131R006B, h131R005/131R007, h131R008, h131R010, or h131R011 in combination with nab-paclitaxel (ABRAXANE). In some embodiments, a method comprises administering anti-RSPO3 antibody 131R002, 131R003, a variant of 131R003, a humanized version of 131R003, h131R006A, h131R006B, h31R005/131R007, h131R008, h131R010, or h131R011 in combination with gemcitabine and nab-paclitaxel (ABRAXANE).

In some embodiments, an additional therapeutic agent comprises an agent such as a small molecule. For example, treatment can involve the combined administration of a RSPO3-binding agent (e.g. an antibody) of the present invention with a small molecule that acts as an inhibitor against additional tumor-associated antigens including, but not limited to, EGFR, ErbB2, HER2, and/or VEGF. In certain embodiments, the additional therapeutic agent is a small molecule that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is a molecule that inhibits β-catenin signaling.

In some embodiments, an additional therapeutic agent comprises a biological molecule, such as an antibody. For example, treatment can involve the combined administration of a RSPO3-binding agent (e.g. an antibody) of the present invention with other antibodies against additional tumor-associated antigens including, but not limited to, antibodies that bind EGFR, ErbB2, HER2, and/or VEGF. In some embodiments, the additional therapeutic agent is an antibody that binds a second RSPO, e.g., RSPO1, RSPO2, and/or RSPO4. In some embodiments, the additional therapeutic agent is an anti-RSPO2 antibody. In some embodiments, the additional therapeutic agent is an anti-RSPO1 antibody. In certain embodiments, the additional therapeutic agent is an antibody specific for an anti-cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), trastuzumab (HERCEPTIN), panitumumab (VECTBIX), or cetuximab (ERBITUX).

In some embodiments, the methods described herein comprise administering a therapeutically effective amount of a RSPO3-binding agent in combination with Wnt pathway inhibitors. In some embodiments, the Wnt pathway inhibitors are frizzled (FZD) protein binding agents, "FZD-binding agents". Non-limiting examples of FZD-binding agents can be found in U.S. Pat. No. 7,982,013, which is incorporated by reference herein in its entirety. FZD-binding agents may include, but are not limited to, anti-FZD antibodies. In some embodiments, a method comprises administering a RSPO-binding agent in combination with an anti-FZD antibody. In some embodiments, a method comprises administering a RSPO-binding agent in combination with the anti-FZD antibody 18R5. In some embodiments, the Wnt pathway inhibitors are Wnt protein binding agents, "Wnt-binding agents". Nonlimiting examples of Wnt-binding agents can be found in U.S. Pat. Nos. 7,723,477 and 7,947,277; and International Publications WO 2011/088127 and WO 2011/088123, which are incorporated by reference herein in their entirety. Wnt-binding agents may include, but are not limited to, anti-Wnt antibodies and FZD-Fc soluble receptors. In some embodiments, a method comprises administering a RSPO3-binding agent in combination with a FZD-Fc soluble receptor. In some embodiments, a method comprises administering a RSPO3-binding agent in combination with a FZD8-Fc soluble receptor. In some embodiments, a method comprises administering a RSPO3-binding agent in combination with an anti-FZD antibody. In some embodiments, a method comprises administering anti-RSPO3 antibodies 131R002, 131R003, a variant of 131R003, a humanized version of 131R003, h131R006A, h131R006B, h131R005/131R007, h131R008, h131R010, or h131R011 in combination with an anti-FZD antibody. In some embodiments, a method comprises administering anti-RSPO3 antibodies 131R002, 131R003, a variant of 131R003, a humanized version of 131R003, h131R006A, h131R006B, h131R005/131R007, h131R008, h131R010, or h131R011 in combination with anti-FZD antibody 18R5. In some embodiments, a method comprises administering anti-RSPO3 antibodies 131R002, 131R003, a variant of 131R003, a humanized version of 131R003, h131R006A, h131R006B, h131R005/131R007, h131R008, h131R010, or h131R011 in combination with a FZD-Fc soluble receptor. In some embodiments, a method comprises administering anti-RSPO3 antibodies 131R002, 131R003, a variant of 131R003, a humanized version of 131R003, h131R006A, h131R006B, h131R005/131R007, h131R008, h131R010, or h131R011 in combination with a FZD8-Fc soluble receptor.

In some embodiments, the methods described herein comprise administering a therapeutically effective amount of a RSPO-binding agent in combination with more than one additional therapeutic agent. Thus, in some embodiments, a method comprises administering a RSPO-binding agent in combination with a chemotherapeutic agent and a Wnt pathway inhibitor. In some embodiments, a method comprises administering a RSPO3-binding agent in combination with a chemotherapeutic agent and a Wnt pathway inhibitor. In some embodiments, a method comprises administering a RSPO3-binding agent in combination with a chemotherapeutic agent and anti-FZD antibody 18R5. In some embodiments, a method comprises administering a RSPO3-binding agent in combination with a chemotherapeutic agent and a FZD8-Fc soluble receptor. In some embodiments, a method comprises administering a RSPO3-binding agent in combination with gemcitabine and a Wnt pathway inhibitor. In some embodiments, a method comprises administering anti-RSPO3 antibodies 131R002, 131R003, a variant of 131R003, a humanized version of 131R003, h131R006A, h131R006B, h131R005/131R007, h131R008, h131R010, or h131R011 in combination with gemcitabine and anti-FZD antibody 18R5. In some embodiments, a method comprises administering anti-RSPO3 antibodies 131R002, 131R003, a variant of 131R003, a humanized version of 131R003, h131R006A, h131R006B, h131R005/131R007, h131R008, h131R010, or h131R011 in combination with gemcitabine and FZD8-Fc soluble receptor.

Furthermore, treatment with a RSPO3-binding agent described herein can include combination treatment with other biologic molecules, such as one or more cytokines (e.g., lymphokines, interleukins, tumor necrosis factors, and/or growth factors) or can be accompanied by surgical removal of tumors, cancer cells or any other therapy deemed necessary by a treating physician.

In certain embodiments, the treatment involves the administration of a RSPO3-binding agent (e.g. an antibody) of the present invention in combination with radiation therapy. Treatment with a RSPO3-binding agent can occur prior to, concurrently with, or subsequent to administration of radiation therapy. Dosing schedules for such radiation therapy can be determined by the skilled medical practitioner.

Combined administration can include co-administration, either in a single pharmaceutical formulation or using separate formulations, or consecutive administration in either order but generally within a time period such that all active agents can exert their biological activities simultaneously.

It will be appreciated that the combination of a RSPO3-binding agent and at least one additional therapeutic agent may be administered in any order or concurrently. In some embodiments, the RSPO3-binding agent will be administered to patients that have previously undergone treatment with a second therapeutic agent. In certain other embodiments, the RSPO3-binding agent and a second therapeutic agent will be administered substantially simultaneously or concurrently. For example, a subject may be given a RSPO3-binding agent (e.g., an antibody) while undergoing a course of treatment with a second therapeutic agent (e.g., chemotherapy). In certain embodiments, a RSPO3-binding agent will be administered within 1 year of the treatment with a second therapeutic agent. In certain alternative embodiments, a RSPO3-binding agent will be administered within 10, 8, 6, 4, or 2 months of any treatment with a second therapeutic agent. In certain other embodiments, a RSPO3-binding agent will be administered within 4, 3, 2, or 1 weeks of any treatment with a second therapeutic agent. In some embodiments, a RSPO3-binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of an RSPO3-binding agent (e.g., an antibody) of the present invention depends on the type of disease to be treated, the severity and course of the disease, the responsiveness of the disease, whether the RSPO3-binding agent or antibody is administered for therapeutic or preventative purposes, previous therapy, the patient's clinical history, and so on, all at the discretion of the treating physician. The RSPO3-binding agent or antibody can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody or agent. The administering physician can easily determine optimum dosages, dosing methodologies, and repetition rates. In certain embodiments, dosage is from 0.01 μg to 100 mg/kg of body weight, from 0.1 μg to 100 mg/kg of body weight, from 1μg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the antibody or other RSPO3-binding agent is from about 0.1 mg to about 20 mg/kg of body weight. In certain embodiments, dosage can be given once or more daily, weekly, monthly, or yearly. In certain embodiments, the antibody or other RSPO3-binding agent is given once every week, once every two weeks or once every three weeks.

In some embodiments, a RSPO3-binding agent (e.g., an antibody) may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

Thus, the present invention provides methods of treating cancer in a subject comprising using an intermittent dosing strategy for administering one or more agents, which may reduce side effects and/or toxicities associated with administration of a RSPO3-binding agent, chemotherapeutic agent, etc. In some embodiments, a method for treating cancer in a human subject comprises administering to the subject a therapeutically effective dose of a RSPO3-binding agent in combination with a therapeutically effective dose of a chemotherapeutic agent, wherein one or both of the agents are administered according to an intermittent dosing strategy. In some embodiments, the intermittent dosing strategy comprises administering an initial dose of a RSPO3-binding agent to the subject, and administering subsequent doses of the RSPO3-binding agent about once every 2 weeks. In some embodiments, the intermittent dosing strategy comprises administering an initial dose of a RSPO3-binding agent to the subject, and administering subsequent doses of the RSPO3-binding agent about once every 3 weeks. In some embodiments, the intermittent dosing strategy comprises administering an initial dose of a RSPO3-binding agent to the subject, and administering subsequent doses of the RSPO3-binding agent about once every 4 weeks. In some embodiments, the RSPO3-binding agent is administered using an intermittent dosing strategy and the chemotherapeutic agent is administered weekly.

V. Kits comprising RSPO-binding agents

The present invention provides kits that comprise the RSPO3-binding agents (e.g., antibodies) described herein and that can be used to perform the methods described herein. In certain embodiments, a kit comprises at least one purified antibody against at least one human RSPO protein in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed RSPO3-binding agents of the present invention can be readily incorporated into one of the established kit formats which are well known in the art.

Further provided are kits comprising a RSPO3-binding agent (e.g., an anti-RSPO3 antibody), as well as at least one additional therapeutic agent. In certain embodiments, the second (or more) therapeutic agent is a chemotherapeutic agent. In certain embodiments, the second (or more) therapeutic agent is a Wnt pathway inhibitor. In certain embodiments, the second (or more) therapeutic agent is an angiogenesis inhibitor.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

Expression of RSPO and LGR in Human Tumors mRNA from normal tissue, benign tumor and malignant tumor samples of a large number of human patients was analyzed by microarray analysis (Genelogic BioExpress Datasuite). This data revealed elevated expression levels of RSPO1 in malignant tissue relative to normal tissue in several tumor types including kidney, endometrial, and ovarian. RSPO1 was noted to be frequently over-expressed in ovarian cancer (FIG. 1A and FIG. 1B). In addition, this data suggested elevated expression levels of RSPO3 in malignant tissue relative to normal tissue in several tumor types including ovarian, eration of labeled cRNA. The processed RNA was hybridized to Affymetrix HG-U133 plus 2.0 microarrays (Affymetrix, Santa Clara, Calif.) as outlined in the manufacturer's technical manuals. After hybridization, the microarrays were washed, scanned, and analyzed. Scanned array background adjustment and signal intensity normalization were performed using the GCRMA algorithm (Bioconductor, www.bioconductor.org).

Particular human RSPOs and human LGRs were evaluated—RSPO1 (241450_at), RSPO2 (1554012_at), RSPO3 (228186_s_at), RSPO4 (237423_at), LGR4 (218326_s_at), LGR5 (210393_at) and LGR6 (227819_at). Microarray analysis showed that, while LGR4 and LGR6 were broadly expressed in almost all tumors, many tumors were found to greatly over-express only particular RSPO family members and LGR5 (Table 2), although these expression levels were not compared to expression levels in normal tissue. Generally there is only a single RSPO family member that is highly expressed in a given tumor, suggesting that there may be functional redundancy within the RSPO family.

TABLE 2

| Tumor | RSPO1 | RSPO2 | RSPO3 | RSPO4 | LGR4 | LGR5 | LGR6 |
|---|---|---|---|---|---|---|---|
| Breast tumor | | | | | | | |
| B34 | 4.79 | 4.93 | 303.31 | 4.41 | | | |
| B39 | 20.59 | 588.88 | 22.60 | 4.40 | | | |
| B60 | 4.60 | 4.92 | 10.89 | 64.79 | | | |
| B02 | 4.60 | 4.92 | 692.34 | 4.41 | 2678.95 | 4.28 | 50.88 |
| B03 | 5.56 | 4.89 | 1870.42 | 4.41 | 686.47 | 30.78 | 73.49 |
| B06 | 4.60 | 4.91 | 4.51 | 120.72 | 274.54 | 4.26 | 20.77 |
| B59 | 4.60 | 4.91 | 4.53 | 1158.11 | 200.48 | 4.26 | 6467.15 |
| Colon tumors | | | | | | | |
| C11 | 4.63 | 4.98 | 4.56 | 4.43 | 3852.26 | 6.22 | 11.31 |
| C17 | 4.64 | 5.00 | 4.57 | 4.44 | 2822.46 | 62.34 | 43.94 |
| C18 | 4.63 | 4.95 | 13.83 | 4.42 | 2454.15 | 4.29 | 723.15 |
| C27 | 6.66 | 980.49 | 4.75 | 4.40 | 5083.84 | 4.30 | 20.82 |
| Lung tumors | | | | | | | |
| LU02 | 4.62 | 15190.40 | 4.55 | 4.43 | 13.95 | 4.29 | 14.56 |
| LU11 | 4.60 | 4.92 | 4.53 | 4.41 | 999.55 | 4.27 | 146.67 |
| LU25 | 4.64 | 5.56 | 11123.06 | 4.44 | 1208.92 | 4.29 | 41089 |
| LU33 | 4.64 | 5.01 | 12.02 | 62.98 | 329.62 | 4.30 | 20.96 |
| LU45 | 4.64 | 4.99 | 4.62 | 4.44 | 3877.47 | 4.29 | 4.86 |
| Melanoma tumors | | | | | | | |
| M06 | 4.73 | 21.80 | 4.65 | 4.50 | 1077.93 | 4.34 | 3.90 |
| Ovarian tumors | | | | | | | |
| OV12 | 4.72 | 5.12 | 4.64 | 460.40 | 5383.63 | 1152.73 | 115.04 |
| OV19 | 960.19 | 4.74 | 69.77 | 20.90 | 494.67 | 5.72 | 4302.78 |
| OV22 | 4.66 | 5.10 | 132.85 | 37.43 | 3743.91 | 482.33 | 812.05 |
| OV27 | 4.55 | 4.86 | 125.78 | 4.92 | | | |
| OV38 | 9.19 | 4.83 | 3439.88 | 16.35 | 1528.12 | 4.24 | 19.49 |
| Pancreatic tumors | | | | | | | |
| PN07 | 4.58 | 689.52 | 4.51 | 4.40 | 6777.41 | 4.28 | 746.38 |
| PN18 | 4.72 | 2508.47 | 4.65 | 4.50 | 6750.73 | 51.15 | 564.94 | pancreas, and lung (FIG. 1-E and FIG. 1F). In addition, it was found that LGR5 and LGR6 were over-expressed in malignant breast tumors, colon tumors, lung tumors, and ovarian tumors relative to normal tissue, while LGR4 was over-expressed in lung tumors. LGR5 and LGR6 over-expression appeared to be restricted to triple-negative (ER$^{neg}$PR$^{neg}$HER2$^{neg}$) breast tumors relative to other breast tumor subtypes.

RNA was isolated from a series of human tumors grown in murine xenografts. The RNA samples were prepared and processed using established Affymetrix protocols for the gen-

Example 2

Binding of RSPO Proteins to LGR5PGP

A cell surface LGR5 protein was generated by ligating amino acids 22-564 of human LGR5 to an N-terminal FLAG tag and to the transmembrane domain of CD4 and a C-terminal GFP protein tag using standard recombinant DNA techniques (FLAG-LGR5-CD4TM-GFP). RSPO-Fc constructs were generated using standard recombinant DNA techniques. Specifically, full-length human RSPO1, RSPO2, RSPO3 and RSPO4 were ligated in-frame to a human Fc region and the recombinant RSPO-Fc proteins were expressed in insect cells using baculovirus. The fusion proteins were purified from the insect medium using protein A chromatography.

HEK-293 cells were transiently transfected with the FLAG-LGR5-CD4TM-GFP construct. After 48 hours, transfected cells were suspended in ice cold PBS containing 2% FBS and heparin and incubated on ice in the presence of 10 μg/ml RSPO1-Fc, RSPO2-Fc, RSPO3-Fc, RSPO4-Fc, or FZD8-Fc fusion proteins for 15 minutes. A second incubation with 100 μl PE-conjugated anti-human Fc secondary antibody was performed to detect cells bound by the Fc fusion proteins. Cells were incubated with an anti-FLAG antibody (Sigma-Aldrich, St. Louis, Mo.) as a positive control and with an anti-PE antibody as a negative control. The cells were analyzed on a FACSCalibur instrument (BD Biosciences, San Jose, Calif.) and the data was processed using FlowJo software.

Figure 2:
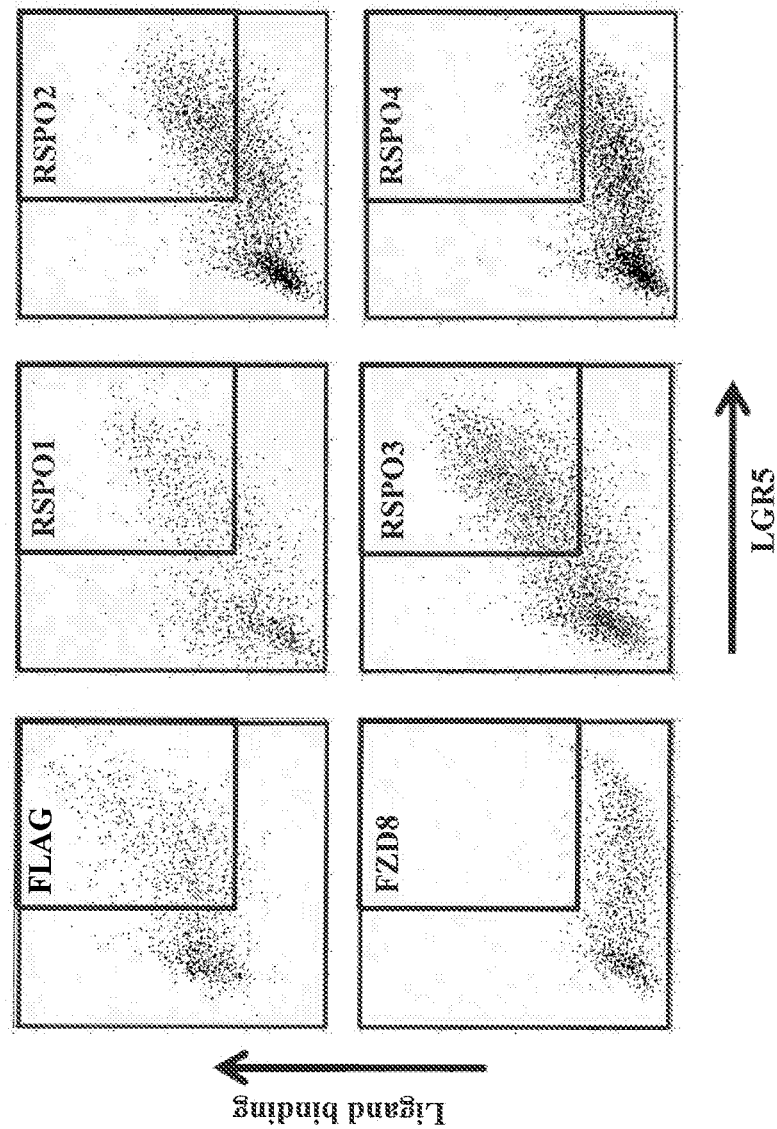
FIG. 2. Binding studies of RSPO proteins and LGR5. FACS analysis of HEK-293 cells expressing LGR5. HEK-293 cells were transiently transfected with a cDNA expression vector encoding FLAG-LGR5-CD4TM-GFP and then subsequently mixed with soluble RSPO1-Fc, RSPO2-Fc, RSPO3-Fc, or RSPO4-Fc fusion proteins. An anti-FLAG antibody was used as a positive control, and soluble FZD8-Fc was used as a negative control. Specific binding is indicated by the presence of signal within the dark lined box overlay on each FACS plot.

As shown in FIG. 2, RSPO1, RSPO2, RSPO3 and RSPO4 all bound to LGR5 expressed on the surface of the HEK-293 cells, while FZD8, the negative control, did not bind LGR5.

Binding affinities between RSPO proteins and LGR5 were analyzed by surface plasmon resonance. A soluble LGR5-Fc construct was generated using standard recombinant DNA techniques. Specifically, amino acids 1-564 of human LGR5 were ligated in frame to human Fc and the recombinant LGR5-Fc fusion protein was expressed in insect cells using baculovirus. The LGR5-Fc fusion protein was purified from the insect medium using protein A chromatography. Cleavage of the LGR5 signal sequence results in a mature LGR5-Fc fusion protein containing amino acids 22-564 of LGR5. Recombinant RSPO1-Fc, RSPO2-Fc, RSPO3-Fc and RSPO4-Fc fusion proteins were immobilized on CM5 chips using standard amine-based chemistry (NHS/EDC). Two-fold dilutions of soluble LGR5-Fc were injected over the chip surface (100 nM to 0.78 nM). Kinetic data were collected over time using a Biacore 2000 system from Biacore Life Sciences (GE Healthcare) and the data were fit using the simultaneous global fit equation to yield affinity constants ($K_D$ values) for each RSPO protein (Table 3).

TABLE 3

|  | LGR5 (nM) |
|---|---|
| RSPO1 | 110 |
| RSPO2 | 14 |
| RSPO3 | <1.0 |
| RSPO4 | 73 |

Human RSPO1, RSPO2, RSPO3 and RSPO4 all bound to LGR5, demonstrating that RSPO proteins may be ligands for LGR proteins.

Example 3

Identification of Anti-RSPO3 Antibodies

A mammalian cell antibody library was screened and two anti-RSPO3 antibodies, 131R002 and 131R003, were identified. Sequence data subsequently demonstrated that antibodies 131R002 and 131R003 have the same light chain sequence but different heavy chain sequences.

The $K_D$s of antibodies 131R002 and 131R003 were determined using a Biacore 2000 system from Biacore Life-Sciences (GE Healthcare). Recombinant human RSPO3 protein was biotinylated and captured on streptavidin-coated chips (GE Healthcare) with coating densities of 400-700 ru. The antibodies were serially diluted 2-fold from 100 nM to 0.78 nM in HBS-P (0.01M HEPES pH 7.4, 0.15M NaCl, 0.005% v/v Surfactant P20) and were injected over the chip surface. Kinetic data were collected over time and were fit using the simultaneous global fit equation to yield affinity constants ($K_D$ values) for each antibody.

Antibody 131R002 had an affinity constant ($K_D$) for human RSPO3 of 8.2 nM and antibody 131R003 had a $K_D$ for human RSPO3 of 7.3 nM.

Example 4

In Vitro Testing for Inhibition of β-Catenin Activity by Anti-RSPO3 Antibodies

HEK-293 cells were transfected with a 6×TCF-luciferase reporter vector (TOPflash, Millipore, Billerica, Mass.). After 24-48 hrs, the transfected HEK-293 cells were incubated with a combination of WNT3a (5 ng/ml) and human RSPO3 (10 ng/ml, R&D BioSystems, Minneapolis, Minn.) in the presence of anti-RSPO3 antibodies 131R002 and 131R003. Antibodies 131R002 and 131R003 were added to the cells in 4-fold serial dilutions from 20 μg/ml to 0.02 μml. As controls, cells were incubated with a combination of WNT3a and RSPO3, WNT3a only, RSPO3 only, or with no addition. The cells were incubated for 16 hours and luciferase activity was measured using Steady-Glo® Luciferase Assay System according to the manufacturer's instructions (Promega, Madison, Wis.).

Figure 3:
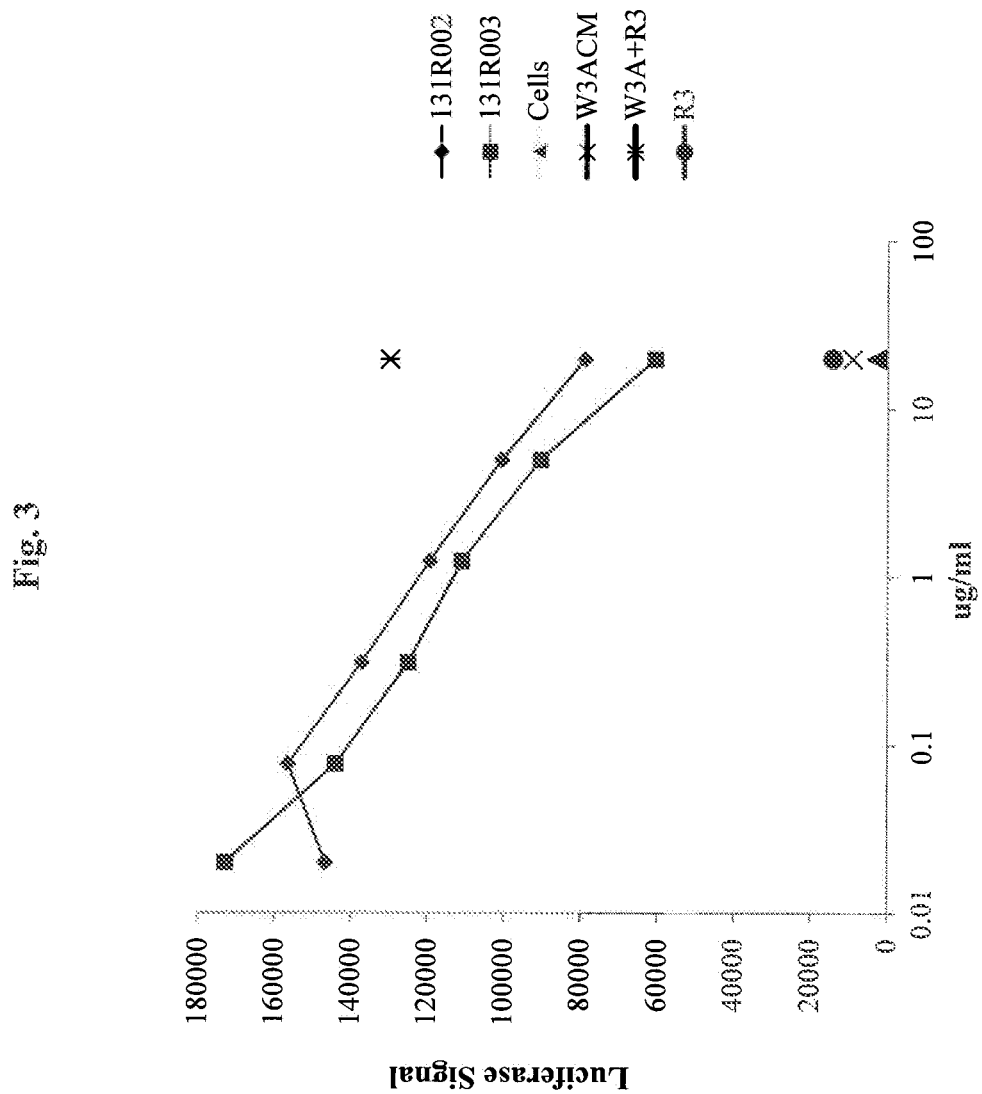
FIG. 3. Anti-RSPO3 antibodies inhibit β-catenin signaling induced by RSPO3 and WNT3A. A TOPflash luciferase reporter assay was used to measure β-catenin signaling in HEK-293 cells after exposure to a combination of WNT3a (5 ng/ml) and RSPO3 (10 ng/ml) and in the presence of increasing concentrations of anti-RSPO3 antibodies (131R002 or 131R003). Antibodies were used as 4-fold serial dilutions from 20 µg/ml to 0.02 µg/ml. Controls included exposure to control medium (no WNT3a and no RSPO), WNT3a alone, or a combination of WNT3a and RSPO3 in the absence of antibody.

As shown in FIG. 3, anti-RSPO3 antibodies 131R002 and 131R003 each reduced RSPO3-induced β-catenin signaling in a dose-dependent manner. These results demonstrated that antibodies 131R002 and 131R003 are specific inhibitors of RSPO3 and are capable of reducing and/or blocking RSPO3-induced β-catenin signaling.

Example 5

Affinity Maturation and Humanization of RSPO3 Antibodies

Anti-RSPO3 antibody 131R003 was affinity matured and several variants were identified. One 131R003 variant had an altered heavy chain CDR1 (SEQ ID NO:34) as compared to parental 131R003 antibody. A second variant had an altered heavy chain CDR3 (SEQ ID NO:35) as compared to parental 131R003. An additional variant was generated that comprised both the altered heavy chain CDR1 and CDR3 as compared to parental 131R003.

HEK-293 cells were transfected with a 6×TCF-luciferase reporter vector (TOPflash, Millipore, Billerica, Mass.). After 24-48 hrs, the transfected HEK-293 cells were incubated with a combination of WNT3a and human RSPO3 in the presence of anti-RSPO3 antibodies 131R003, 131R003CDR1 variant and 131R003CDR3 variant. 131R003, 131R003CDR1 variant, and 131R003CDR3 variant were added to the cells in 5-fold serial dilutions from 20 μg/ml to 0.006 μg/ml. As controls, cells were incubated with a combination of WNT3a and RSPO3, WNT3a only, RSPO3 only, a control antibody, or with no addition. The cells were incubated for 16 hours and luciferase activity was measured using Steady-Glo® Luciferase Assay System according to the manufacturer's instructions (Promega, Madison, Wis.).

Figure 4:
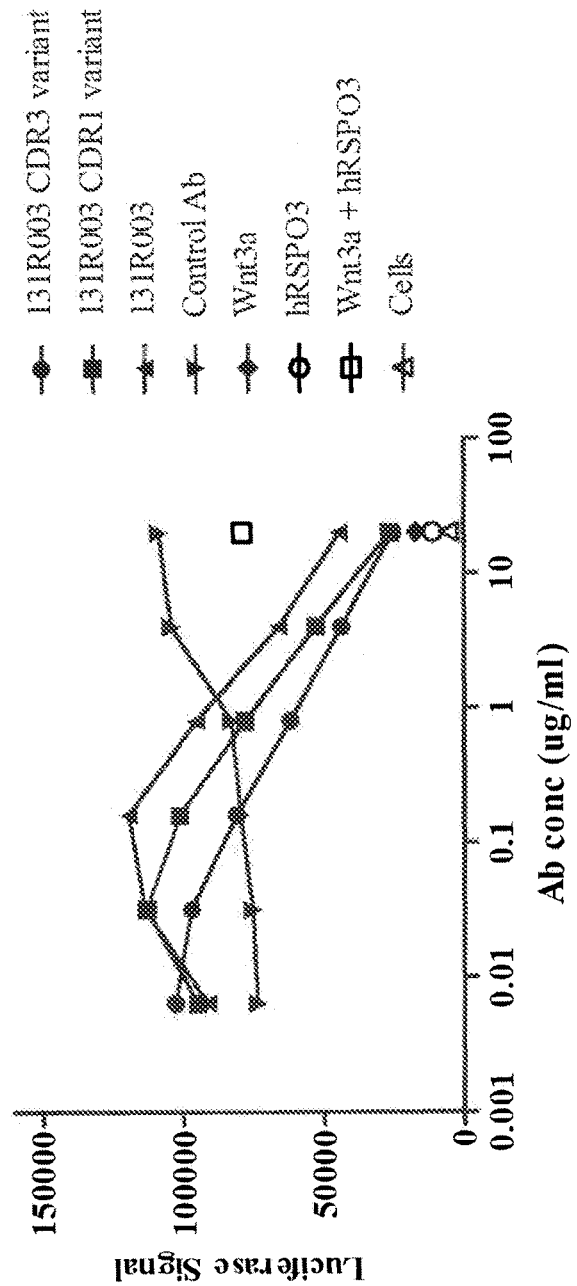
FIG. 4. Affinity-matured 131R003 antibody variants inhibit β-catenin signaling induced by RSPO3 and WNT3A. A TOPflash luciferase reporter assay was used to measure β-catenin signaling in HEK-293 cells after exposure to a combination of WNT3a and RSPO3 and in the presence of increasing concentrations of anti-RSPO3 antibodies (131R003 (-▲-), 131R003CDR1 variant (-■-), or 131R003 CDR3 variant (-●-)). Antibodies were used as 5-fold serial dilutions from 20 µg/ml to 0.006 µg/ml. Controls included exposure to control medium (no WNT3a and no RSPO)/cells only (-Δ-), a control antibody (-▼-), WNT3a alone (-♦-), or a combination of WNT3a and RSPO3 in the absence of antibody (-□-).

As shown in FIG. 4, anti-RSPO3 antibodies 131R003CDR1 variant and 131R003CDR3 variant each reduced RSPO3-induced β-catenin signaling in a dose-dependent manner and at lower concentrations than parental 131R003. These results demonstrated that the 131R003 variants retained the characteristics of parental 131R003, i.e., they were specific inhibitors of RSPO3 and were capable of reducing and/or blocking RSPO3-induced β-catenin signaling. In addition, these results demonstrated that the 131R003 variants had better activity than parental 131R003.

Humanized forms of 131R003 variants were generated using standard techniques. Humanized antibodies h131R005, h131R007, h131R008, h131R010, h131R011 comprise an altered heavy chain CDR3 as compared to parental 131R003 antibody. Humanized 131R006B comprises an altered heavy chain CDR3 as compared to parental 131R003 antibody. Antibodies h131R005/131R007, h131R010, and h131R011 comprise several amino acid substitutions in framework region 3 as compared to antibody 131R006B. Antibodies h131R005/131R007, h131R006, and h131R011 are IgG2 antibodies. Antibodies h131R008 and h131R010 are IgG1 antibodies. Antibodies h131R005/131R007, h31R010, and h131R011 comprise the same heavy chain variable region. Antibodies h131R010 and h131R011 comprise the same light chain variable region, which is different than the light chain variable region of h131R005/131R007.

A plasmid encoding the heavy chain of the 131R010 antibody was deposited with American Type Culture Collection (ATCC), 10801 University Boulevard, Manassas, Va., USA, under the conditions of the Budapest Treaty on Jun. 18, 2013, and assigned ATCC deposit designation number PTA-120420. A plasmid encoding the light chain of the 131R010 antibody was deposited with ATCC, 10801 University Boulevard, Manassas, Va., USA, under the conditions of the Budapest Treaty on Jun. 18, 2013, and assigned ATCC deposit designation number PTA-120421.

Example 6

Inhibition of Ovarian Tumor Growth In Vivo by Anti-RSPO Antibodies

Dissociated OMP-OV38 ovarian tumor cells ($1 \times 10^5$ cells) were injected in to 6-8 week old NOD/SCID mice. Tumors were allowed to grow for 39 days until they reached an average volume of 150 mm$^3$. The mice were randomized (n=8 per group) and treated with a combination of anti-RSPO1 antibody 89M5 and anti-RSPO3 antibody 131R003, a combination of anti-RSPO1 antibody 89M5, anti-RSPO3 antibody 131R003, and taxol, taxol as a single agent, or a control antibody. Antibodies were dosed at 20 mg/kg once a week, and taxol was dosed at 15 mg/ml once a week. Administration of the antibodies and taxol was performed via injection into the intraperitoneal cavity. Tumor growth was monitored and tumor volumes were measured with electronic calipers at the indicated time points. Data are expressed as mean±S.E.M.

Figure 5:
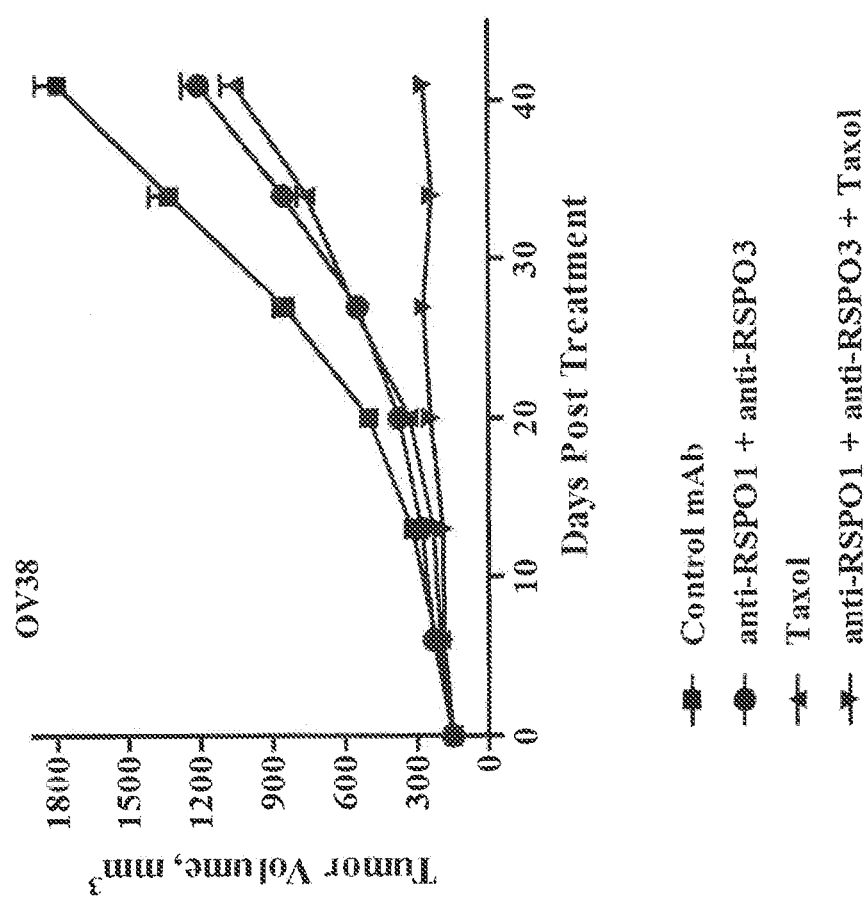
FIG. 5. Inhibition of tumor growth with anti-RSPO antibodies. OV38 ovarian tumor cells were injected subcutaneously into NOD/SCID mice. Mice were treated with a combination of anti-RSPO 1 antibody 89M5 and anti-RSPO3 antibody 131R003 (-●-), taxol (-▲-), a combination of anti-RSPO1 antibody 89M5, anti-RSPO3 antibody 131R003, and taxol (-▼-), or a control antibody (-■-). Data is shown as tumor volume ($mm^3$) over days post-treatment.

As shown in FIG. 5, a combination of anti-RSPO1 and anti-RSPO3 antibodies inhibited OMP-OV38 ovarian tumor growth. Surprisingly, a combination of anti-RSPO1 antibody 89M5, anti-RSPO3 antibody 131R002, and taxol inhibited tumor growth to a significantly greater level than taxol alone or the antibody combination alone.

Dissociated OMP-OV38 ovarian tumor cells ($1 \times 10^5$ cells) were injected in to 6-8 week old NOD/SCID mice. Tumors were allowed to grow for 35 days until they reached an average volume of 140 mm$^3$. The mice were randomized (n=10 per group) and treated with anti-RSPO3 antibody 131R002, anti-RSPO1 antibody 89M5, taxol, a combination of 89M5 and taxol, a combination of 131R002 and taxol, a combination of 89M5 and 131R002, a combination of 89M5, 131R002 and taxol, or a control antibody. Antibodies were dosed at 20 mg/kg once a week, and taxol was dosed at 15 mg/ml once a week through day 46 and subsequently dosed at 7.5 mg/kg. Administration of the antibodies and taxol was performed via injection into the intraperitoneal cavity. Tumor growth was monitored and rumor volumes were measured with electronic calipers at the indicated time points. Data are expressed as mean±S.E.M.

As shown in FIG. 6, a combination of anti-RSPO1 antibody 89M5 and anti-RSPO3 antibody 131R002 inhibited OMP-OV38 ovarian tumor growth as compared to control antibody. Combinations of anti-RSPO1 antibody 89M5 and taxol or anti-RSPO3 antibody 131R002 and taxol had no effect relative to taxol alone. However, surprisingly a combination of anti-RSPO1 89M5, anti-RSPO3 antibody 131R002, and taxol showed activity that was greater than taxol alone.

Example 7

Inhibition of Lung Tumor Growth In Vivo by Anti-RSPO3 Antibodies

In OMP-LU45 non-small cell lung tumors, it has been observed that $CD201^+$ cells are more tumorigenic than $CD201^-$ cells. Furthermore, RSPO3 was found to be highly expressed in the $CD201^+$ cell population. Dissociated and sorted OMP-LU45 $CD44^+CD201^+$ lung tumor cells ($5 \times 10^4$ cells) were injected into 6-8 week old NOD/SCID mice. Tumors were allowed to grow for 38 days until they reached an average volume of 140 mm$^3$. The mice were randomized (n=10 per group) and treated with anti-RSPO3 antibody 131R002 or a control antibody. Antibodies were dosed at 25 mg/kg once a week and administration of the antibodies was performed via injection into the intraperitoneal cavity. Tumor growth was monitored and tumor volumes were measured with electronic calipers at the indicated time points. Data are expressed as mean±S.E.M.

In a study with a second lung tumor, dissociated OMP-LU25 lung tumor cells ($5 \times 10^4$ cells) were injected into 6-8 week old NOD/SCID mice. Tumors were allowed to grow for 48 days until they reached an average volume of 110 mm$^3$. The mice were randomized (n=9 per group) and treated with anti-RSPO3 antibody 131R002 or a control antibody. Antibodies were dosed at 25 mg/kg once a week and administration of the antibodies was performed via injection into the intraperitoneal cavity. Tumor growth was monitored and tumor volumes were measured with electronic calipers at the indicated time points. Data are expressed as mean±S.E.M.

Figures 7A, 7B:
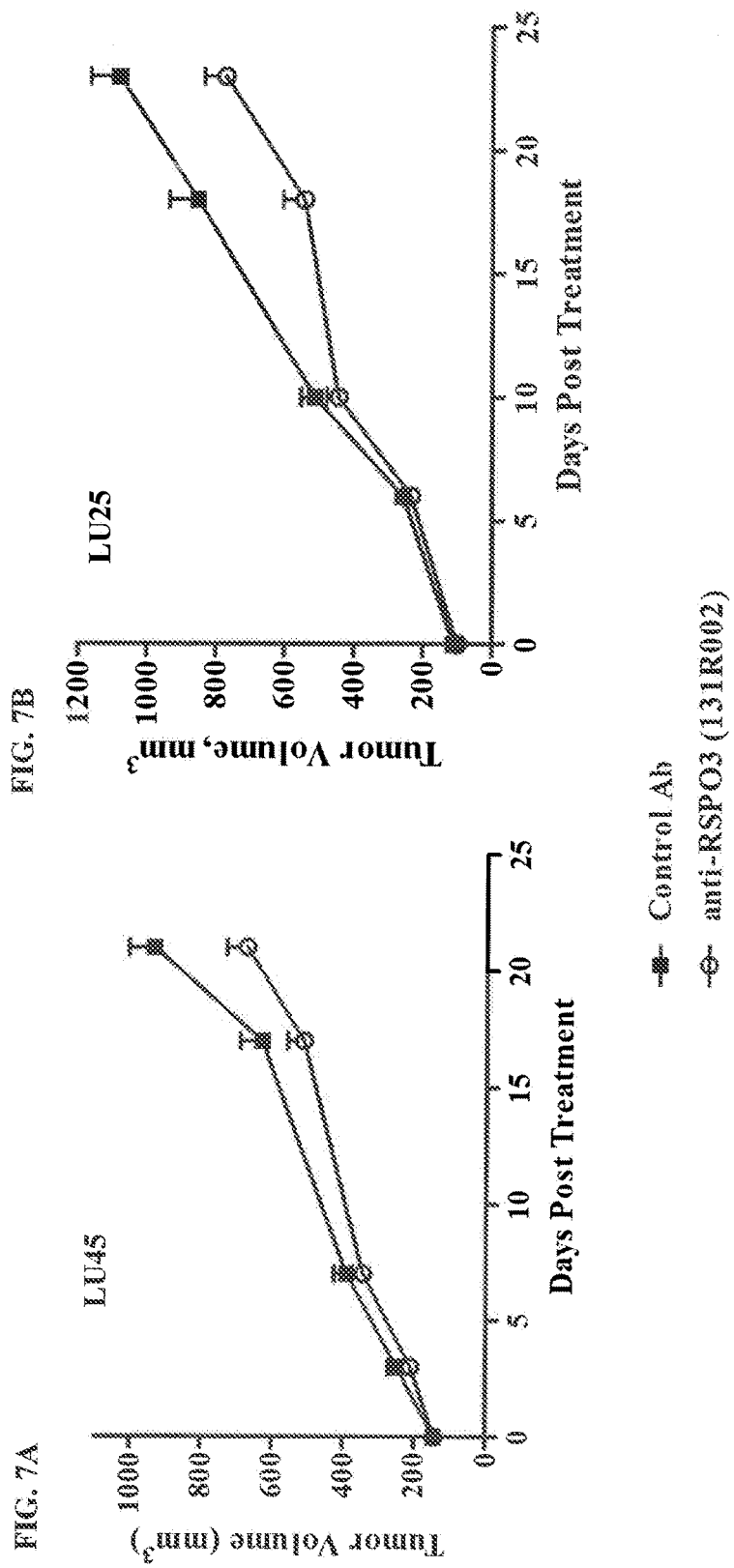
FIG. 7A. Inhibition of tumor growth with anti-RSPO3 antibodies. LU45 lung tumor cells were injected subcutaneously into NOD/SCID mice. Mice were treated with anti-RSPO3 antibody 131R002 (-○-) or a control antibody (-■-).
FIG. 7B. Inhibition of tumor growth with anti-RSPO3 antibodies. LU25 lung tumor cells were injected subcutaneously into NOD/SCID mice. Mice were treated with anti-RSPO3 antibody 131R002 (-○-) or a control antibody (-■-). Data is shown as tumor volume ($mm^3$) over days post-treatment.

As shown in FIGS. 7A and 7B, anti-RSPO antibody 131R002 inhibited growth of both lung tumors OMP-LU45 and OMP-LU25 as compared to a control antibody.

Example 8

Inhibition of β-Catenin Activity by Anti-RSPO3 Antibodies

HEK-293 cells were transfected with a 6×TCF-luciferase reporter vector (TOPflash, Millipore, Billerica, Mass.). After 24-48 hrs, the transfected HEK-293 cells were incubated with a combination of WNT3a conditioned medium (5 ng/ml) and human RSPO3 (10 ng/ml, R&D BioSystems) in the presence of anti-RSPO3 antibodies 131R002, 131R006B, or 131R007. Antibodies 131R002, 131R006 or 131R007 were added to the cells in 5-fold serial dilutions from 20 µg/ml to 0.0064 µg/ml. As controls, cells were incubated with WNT3a conditioned medium alone, a combination of WNT3a conditioned medium and human RSPO3, or with no addition to cells. The cells were incubated for 16 hours and luciferase activity was measured using Steady-Glo® Luciferase Assay System according to the manufacturer's instructions (Promega, Madison, Wis.).

As shown in FIG. 8, all three anti-RSPO3 antibodies reduced WNT3a/RSPO3-induced β-catenin signaling in a dose-dependent manner. The humanized antibodies 131R006B and 131R007 appeared to have a greater ability to inhibit β-catenin activity than antibody 131R002. These results demonstrated that humanized antibodies 131R006B and 131R007 are stronger inhibitors of RSPO3 than 131R002 and are capable of reducing and/or blocking WNT3a/RSPO3-induced β-catenin signaling.

Example 9

Inhibition of RSPO3 Binding to LGR5

HEK-293T cells were transfected with a cDNA expression vector that encoded the extracellular domain of human LGR5 (FLAG-LGR5-CD4TM-GFP). Transfected cells were incubated with recombinant RSPO3-biotin fusion protein in the presence of anti-RSPO3 antibodies 131R006B or 131R007. Cells were incubated without antibody as a control. Cells were washed in PBS and binding of RSPO3 to LGR5-expressing transfected cells was determined by addition of PE-conjugated streptavidin and analysis by flow cytometry.

Figure 9:
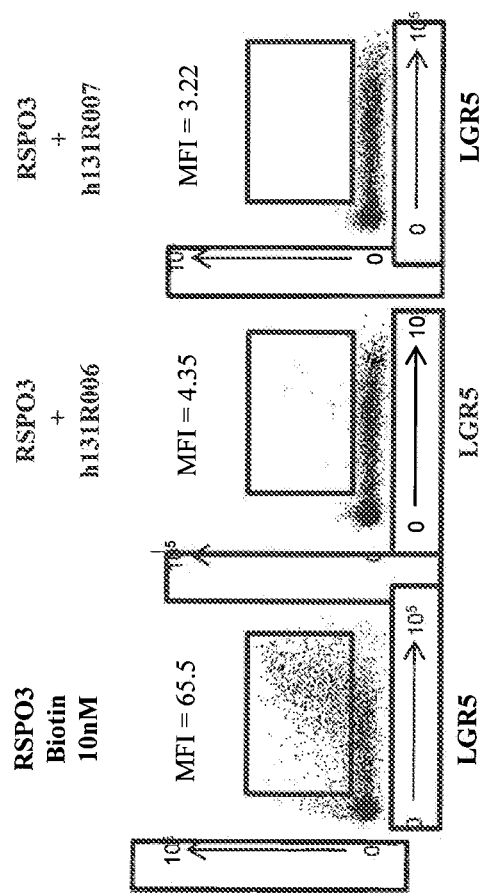
FIG. 9. Inhibition of RSPO3 and LGR5 interaction by anti-RSPO3 antibodies. FACS analysis of HEK-293T cells expressing LGR5. HEK-293T cells were transiently transfected with a cDNA expression vector encoding the extracellular domain of human LGR5 (FLAG-LGR5-CD4TM-GFP) and then subsequently mixed with RSPO3-biotin fusion protein in combination with anti-RSPO3 antibodies 131R006 or 131R007. Binding was detected with PE-conjugated streptavidin. Relative RSPO3-biotin binding is shown on the y-axis and expression of the FLAG-LGR5-CD4TM-GFP fusion protein is indicated on the x-axis. Positive binding is indicated by the presence of signal within the dark lined box overlay on each FACS plot.

As shown in FIG. 9, anti-RSPO3 antibodies 131R006B and 131R007 were highly effective in blocking binding of RSPO3 to LGR5-expressing cells.

Example 10

Binding Affinities of RSPO3 Antibodies

The $K_D$ of RSPO3 antibodies 131R002, 131R003, 131R003CDR3 variant, h131R007, h131R008, and h131R011 were determined using a Biacore 2000 system from Biacore LifeSciences (GE Healthcare). The method used was different than described in Example 3. A goat anti-human IgG antibody was coupled to a carboxymethyl-dextran (CM5) SPR chip using standard amine-based chemistry (NHS/EDC) and blocked with ethanolamine. Antibodies (purified antibody or culture supernatant) were diluted to a concentration of 10 μg/ml in HBS-P-BSA (0.01M HEPES pH7.4, 0.15M NaCl, 0.005% v/v Polysorbate 20, 100 μg/ml BSA) and captured onto the chip via the anti-human IgG antibody. Human RSPO3 (R&D Systems) was serially diluted 2-fold from 300 nM to 37.5 nM in HBS-P-BSA and injected sequentially over the captured anti-RSPO3 antibodies. RSPO3 association and dissociation was measured at each concentration. After each antigen injection 5 μl of 100 mM $H_3PO_4$ was injected to remove the antigen-antibody complex and a subsequent injection performed. Kinetic data were collected over time and were fit using the simultaneous global fit equation to yield affinity constants ($K_D$ values) for each antibody (Table 4).

TABLE 4

| RSPO3 Antibody | $K_D$ |
|---|---|
| 131R002 (IgG2) | 1.3 nM |
| 131R003 (IgG2) | 1.9 nM |
| 131R003 CDR3 variant (IgG2) | 1.7 nM |
| h131R007 (IgG2) | 654 pM |
| h131R008 (IgG1) | 876 pM |
| h131R010 (IgG1) | ND |
| h131R011 (IgG2) | 686 pM |

In additional experiments, antibody h131R008 was shown to have a $K_D$ as low as 448 pM for human RSPO3, no detectable binding to human RSPO1 or RSPO2, and weak binding to human RSPO4. Antibody h131R008 was shown to have a $K_D$ of 248 pM for murine RSPO3, no detectable binding to murine RSPO1 or RSPO2 and weak binding to murine RSPO4.

Example 11

Inhibition of Lung Tumor Growth In Vivo by Anti-RSPO3 Antibodies

The non-small cell lung cancer (NSCLC) cell line NCI-H2030 was selected for testing based on a high level of RPSO3 expression in microarray data. NCI-H2030 cells ($1 \times 10^6$) were injected into NOD-SCID mice. Tumors were allowed to grow for approximately 60 days until they reached an average volume of 100 mm³. Tumor-bearing mice were randomized into 4 groups (n=7-9 per group). Tumor-bearing mice were treated with anti-RSPO3 antibody 131R002, carboplatin, a combination of anti-RSPO3 antibody 131R002 and carboplatin, or a control antibody. Antibodies were dosed at 25 mg/kg once a week. Carboplatin was dosed at 50 mg/kg once a week. Tumor growth was monitored and tumor volumes were measured with electronic calipers on the indicated days post-treatment.

Figure 10:
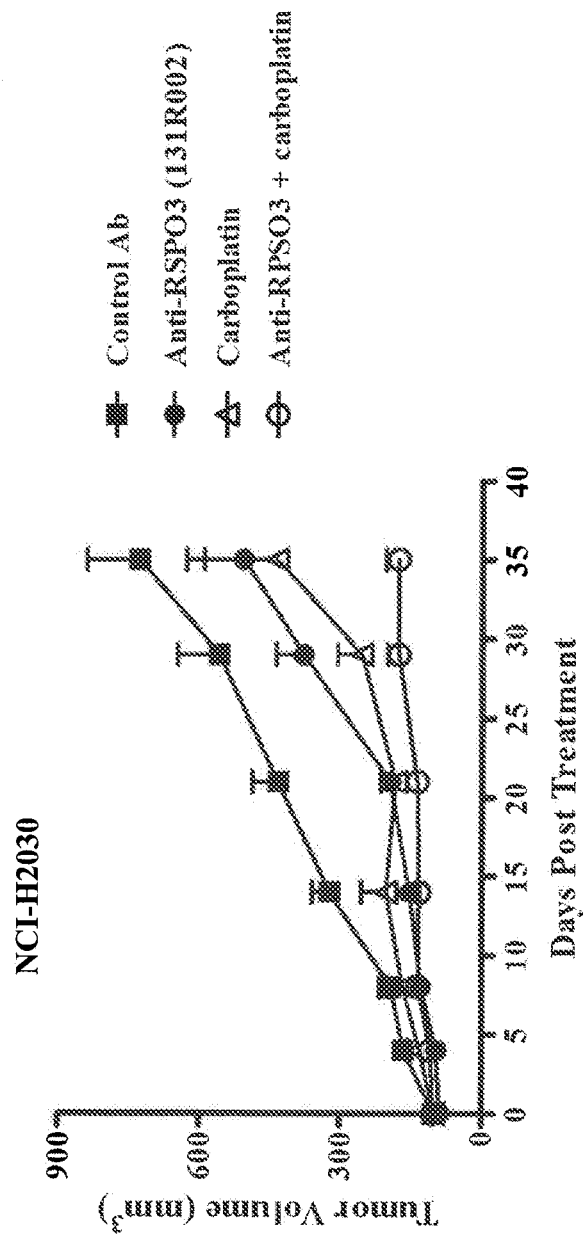
FIG. 10. Inhibition of tumor growth with anti-RSPO antibodies. NCI-H2030 cells were injected subcutaneously into NOD/SCID mice. Mice were treated with anti-RSPO3 antibody 131R002 (-●-), carboplatin alone (-Δ-), a combination of anti-RSPO3 antibody 131R002 and carboplatin (-○-), or a control antibody (-■-). Data is shown as tumor volume (mm³) over days post-treatment.

As shown in FIG. 10, treatment with anti-RSPO3 antibody in combination with carboplatin inhibited NCI-H2030 tumor growth better than carboplatin alone or the antibody alone.

OMP-LU102 is a patient-derived non-small cell lung cancer (NSCLC) xenograft that was selected for testing based on a high level of RPSO3 expression in microarray data. OMP-LU102 lung tumor cells ($1 \times 10^5$) were injected into NOD-SCID mice. Tumors were allowed to grow for 22 days until they reached an average volume of 90 mm³. Tumor-bearing mice were randomized into 4 groups (n=10 per group). Tumor-bearing mice were treated with anti-RSPO3 antibody 131R002, carboplatin, a combination of anti-RSPO3 antibody 131R002 and carboplatin, or a control antibody. Antibodies were dosed at 25 mg/kg once a week. Carboplatin was dosed at 50 mg/kg once a week. Tumor growth was monitored and tumor volumes were measured with electronic calipers on the indicated days post-treatment.

Figure 11A:
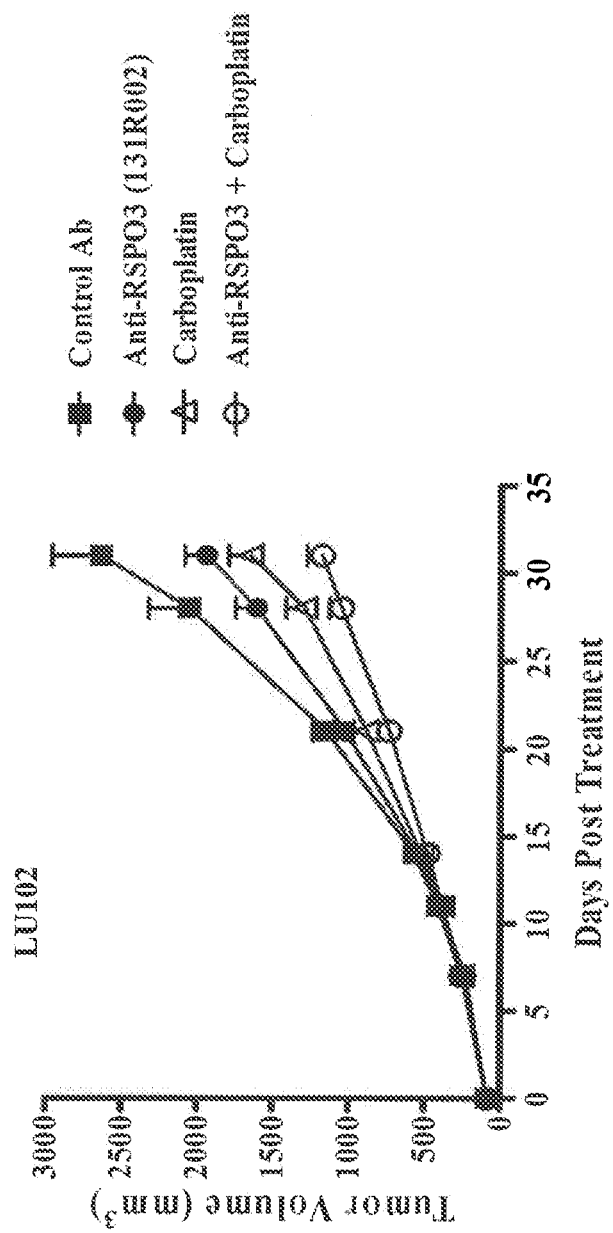
FIG. 11A. Inhibition of tumor growth with anti-RSPO antibodies. LU102 lung tumor cells were injected subcutaneously into NOD/SCID mice. Mice were treated with anti-RSPO3 antibody 131R002 (-●-), carboplatin alone (-Δ-), a combination of anti-RSPO3 antibody 131R002 and carboplatin (-○-), or a control antibody (-■-). Data is shown as tumor volume (mm³) over days post-treatment.

As shown in FIG. 11A, treatment with anti-RSPO3 antibody inhibited OMP-LU102 lung tumor growth as a single agent but had much greater effect in combination with carboplatin.

RNA was prepared from tumors from each of the four experimental groups following the treatment. Gene expression was characterized by microarray analysis. Gene set enrichment analysis indicated that anti-RSPO3 antibody treatment (either as a single agent or in combination with carboplatin) inhibited the expression of various gene sets characteristic of normal stem cells or cancer stem cells as shown in FIG. 11B. Treatment with carboplatin alone did not have this effect on gene expression.

Example 12

Inhibition of Pancreatic Tumor Growth In Vivo by Anti-RSPO3 Antibodies

OMP-PN35 is patient-derived pancreatic ductal adenocaricoma (PDAC) xenograft that was selected for testing based on high level of RPSO3 expression in microarray data. OMP-PN35 ($1 \times 10^5$) tumor cells were injected into NOD-SCID mice. Tumors were allowed to grow for 30 days until they reached an average volume of 90 mm³. Tumor-bearing mice were randomized into 4 groups (n=10 per group). Tumor-bearing mice were treated with anti-RSPO3 antibody 131R002, gemcitabine plus nab-paclitaxel (ABRAXANE), a combination of anti-RSPO3 antibody and gemcitabine and nab-paclitaxel (ABRAXANE). Antibodies were dosed at 25 mg/kg once a week. Gemcitabine was dosed at 20 mg/kg once a week and nab-paclitaxel (ABRAXANE) was dosed at 30 mg/kg once a week. Tumor growth was monitored and tumor volumes were measured with electronic calipers on the indicated days post-treatment.

In FIG. 12A the results from all four treatment groups are shown and in FIG. 12B only the combination treatments are shown on an expanded scale. FIGS. 12A and 12B show that anti-RSPO3 antibody in combination with gemcitabine and nab-paclitaxel (ABRAXANE) inhibited OMP-PN35 pancreatic tumor growth better than gemcitabine and nab-paclitaxel (ABRAXANE) alone.

Example 13

Inhibition of β-Catenin Activity by Anti-RSPO3 Antibodies

HEK-293 cells were transfected with a 6×TCF-luciferase reporter vector (TOPflash, Millipore, Billerica, Mass.). After 24-48 hrs, the transfected HEK-293 cells were incubated with a combination of WNT3a conditioned medium (5 ng/ml) and human RSPO3 (2 ng/ml, R&D BioSystems) in the presence of anti-RSPO3 antibodies h131R007 or h131R010. Antibodies h131R007 or h131R010 were added to the cells in 5-fold serial dilutions from 20 μg/ml to 0.0064 μg/ml. As controls, cells were incubated with WNT3a conditioned medium alone, a combination of WNT3a conditioned medium and human RSPO3, or with no addition to cells. The cells were incubated for 16 hours and luciferase activity was measured using Steady-Glo® Luciferase Assay System according to the manufacturer's instructions (Promega, Madison, Wis.).

Figure 13:
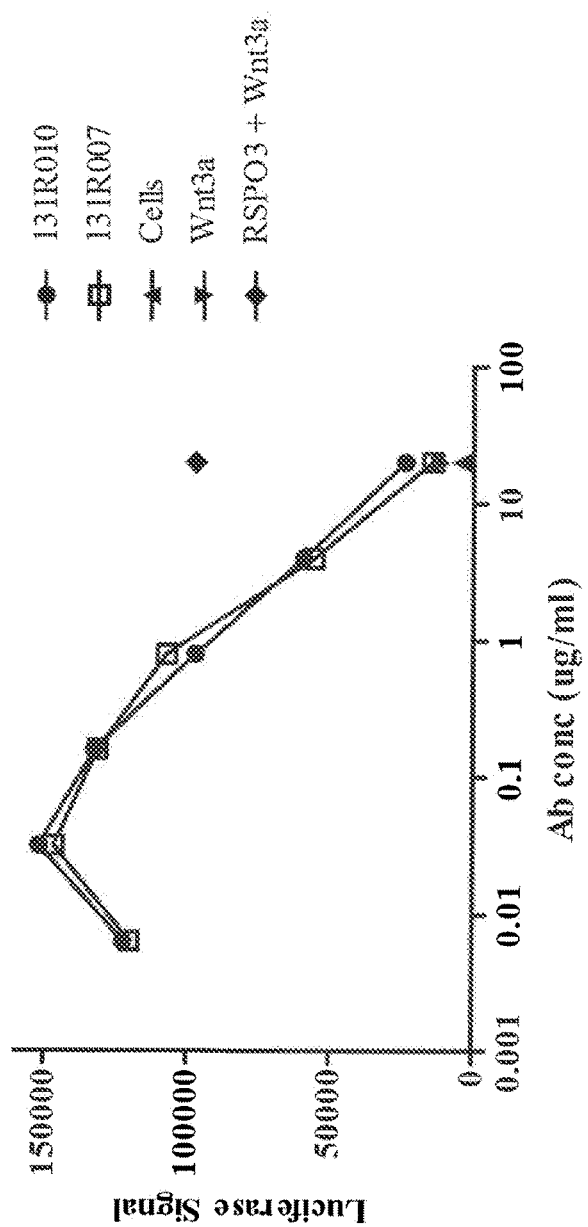
FIG. 13. Inhibition of β-catenin signaling induced by RSPO3 and WNT3A. A TOPflash luciferase reporter assay was used to measure β-catenin signaling in HEK-293T cells after exposure to a combination of WNT3a and human RSPO3 and in the presence of increasing concentrations of anti-RSPO3 antibody 131R007 (-□-) or 131R010 (-●-). Antibodies were used as 5-fold serial dilutions from 20 µg/ml to 0.0064 µg/ml. Controls included exposure to control medium (no WNT3a and no RSPO/cells (-▲-)), WNT3a alone (-▼-), or a combination of WNT3a and human RSPO3 in the absence of antibody (-◆-).

As shown in FIG. 13, antibody h131R010 reduced WNT3a/RSPO3-induced β-catenin signaling in a dose-dependent manner and to a similar extent as h131R007. Since h131R010 inhibited β-catenin signaling to the same extent as h131R007, it is clear that activity of the anti-RSPO3 antibody was not affected by conversion to an IgG1 isotype.

Example 14

Inhibition of Lung Tumor Growth In Vivo by Anti-RSPO3 Antibodies

OMP-LU25 is a patient-derived non small cell lung cancer (NSCLC) xenograft that was selected for testing based on high level of RPSO3 expression in microarray data. OMP-LU25 tumor cells ($5 \times 10^4$) were injected into NOD-SCID mice. Tumors were allowed to grow for 33 days until they reached an average volume of 120 mm³. Tumor-bearing mice were randomized into 4 groups (n=9 per group). Tumor-bearing mice were treated with either control antibody, anti-RSPO3 antibody 131R008, paclitaxel, or the combination of anti-RSPO3 antibody 131R008 and paclitaxel. Antibodies were dosed weekly at 20 mg/kg. Paclitaxel was dosed weekly at 15 mg/kg. Tumor growth was monitored and tumor volumes were measured with electronic calipers on the indicated days post-treatment.

Figure 14:
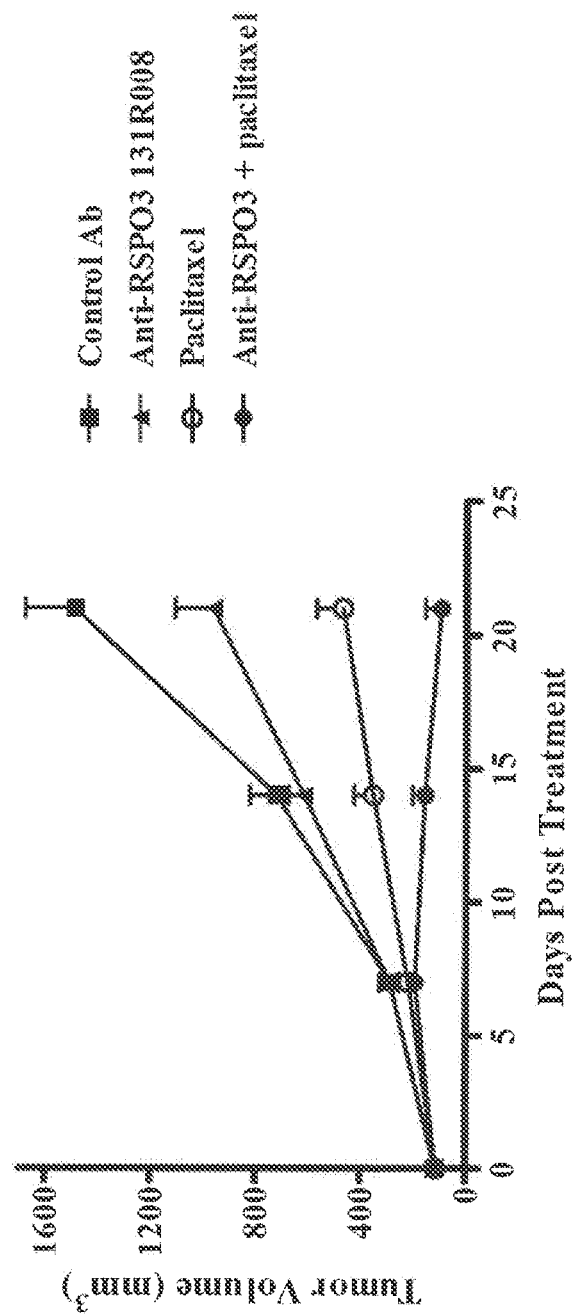
FIG. 14. Inhibition of tumor growth with anti-RSPO antibodies. LU25 NSCLC lung tumor cells were injected subcutaneously into NOD/SCID mice. Mice were treated with anti-RSPO3 antibody 131R008 (-▲-), paclitaxel alone (-○-), a combination of anti-RSPO3 antibody 131R008 and paclitaxel (-●-), or a control antibody (-■-). Data is shown as tumor volume (mm³) over days post-treatment.

As shown in FIG. 14, anti-RSPO3 antibody 131R008 inhibited OMP-LU25 tumor growth as a single agent and in combination with chemotherapy. Furthermore, the combination of anti-RSPO3 antibody 131R008 with paclitaxel led to tumor regression.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The sequences disclosed in the application are:

```
Human RSPO1 protein sequence with signal sequence
                                                                        (SEQ ID NO: 1)
MRLGLCVVALVLSWTHLTISSRGIKGKRQRRISAEGSQACAKGCELCSEVNGCLKCSPKL

FILLERNDIRQVGVCLPSCPPGYFDARNPDMNKCIKCKIEHCEACFSHNFCTKCKEGLYL

HKGRCYPACPEGSSAANGTMECSSPAQCEMSEWSPWGPCSKKQQLCGFRRGSEERTRRVL

HAPVGDHAACSDTKETRRCTVRRVPCPEGQKRRKGGQGRRENANRNLARKESKEAGAGSR

RRKGQQQQQQQGTVGPLTSAGPA

Human RSPO2 protein sequence with signal sequence
                                                                        (SEQ ID NO: 2)
MQFRLFSFALIILNCMDYSHCQGNRWRRSKRASYVSNPICKGCLSCSKDNGCSRCQQKLF

FFLRREGMRQYGECLHSCPSGYYGHRAPDMNRCARCRIENCDSCFSKDFCTKCKVGFYLH

RGRCFDECPDGFAPLEETMECVEGCEVGHWSEWGTCSRNNRTCGFKWGLETRTRQIVKKP

VICTIPCPTIAESRRCKMTMRHCPGGKRTPKAKEKRNKKKKRKLIERAQEQHSVFLATDR

ANQ

Human RSPO3 protein sequence with signal sequence
                                                                        (SEQ ID NO: 3)
MHLRLISWLFIILNFMEYIGSQNASRGRRQRRMHPNVSQGCQGGCATCSDYNGCLSCKPR

LFFALERIGMKQIGVCLSSCPSGYYGTRYPDINKCTKCKADCDTCFNKNFCTKCKSGFYL

HLGKCLDNCPEGLEANNHTMECVSIVHCEVSEWNPWSPCTKKGKTCGFKRGTETRVREII

QHPSAKGNLCPPTNETRKCTVQRKKCQKGERGKKGRERKRKKPNKGESKEAIPDSKSLES

SKEIPEQRENKQQQKKRKVQDKQKSVSVSTVH
```

-continued

Human RSPO4 protein sequence with signal sequence
(SEQ ID NO: 4)
MRAPLCLLLLVAHAVDMLALNRRKKQVGTGLGGNCTGCIICSEENGCSTCQQRLFLFIRR

EGIRQYGKCLHDCPPGYFGIRGQEVNRCKKCGATCESCFSQDFCIRCKRQFYLYKGKCLP

TCPPGTLAHQNTRECQGECELGPWGGWSPCTHNGKTCGSAWGLESRVREAGRAGHEEAAT

CQVLSESRKCPIQRPCPGERSPGQKKGRKDRRPRKDRKLDRRLDVRPRQPGLQP

Human RSPO3 protein sequence without predicted signal sequence
(SEQ ID NO: 5)
QNASRGRRQRRMHPNVSQGCQGGCATCSDYNGCLSCKPRLFFALERIGMKQIGVCLSSCP

SGYYGTRYPDINKCTKCKADCDTCFNKNFCTKCKSGFYLHLGKCLDNCPEGLEANNHTME

CVSIVHCEVSEWNPWSPCTKKGKTCGFKRGTETRVREIIQHPSAKGNLCPPTNETRKCTV

QRKKCQKGERGKKGRERKRKKPNKGESKEAIPDSKSLESSKEIPEQRENKQQQKKRKVQD

KQKSVSVSTVH

Human RSPO3 furin-like domain 1
(SEQ ID NO: 6)
PNVSQGCQGGCATCSDYNGCLSCKPRLFFALERIGMKQIGVCLSSCPSGYYG Human RSPO3 furin-like domain 2
(SEQ ID NO: 7)
INKCTKCKADCDTCFNKNFCTKCKSGFYLHLGKCLDNCPEGLEA Human RSPO3 thrombospondin domain
(SEQ ID NO: 8)
HCEVSEWNPWSPCTKKGKTCGFKRGTETRVREIIQHPSAKGNLCPPTNETRKCTVQRKKCQ 131R002/131R003 Heavy chain CDR1
(SEQ ID NO: 9)
KASGYTFTDYS 131R002/131R003 Heavy chain CDR2
(SEQ ID NO: 10)
IYPSNGDS 131R002/131R003 Heavy chain CDR3
(SEQ ID NO: 11)
ATYFANYFDY 131R002/131R003 Light chain CDR1
(SEQ ID NO: 12)
QSVDYDGDSYM 131R002/131R003 Light chain CDR2
(SEQ ID NO: 13)
AAS 131R002/131R003 Light chain CDR3
(SEQ ID NO: 14)
QQSNEDPLT 131R002 Heavy chain variable region
(SEQ ID NO: 15)
QVQLQESGPELVKPGASVKISCKASGYTFTDYSIHWVKQNHGKSLDWIGYIYPSNGDSGYN

QKFKNRATLTVDTSSSTAYLEVRRLTFEDSAVYYCATYFANYFDYWGQGTTLTVSSAST

131R003 Heavy chain variable region
(SEQ ID NO: 16)
QVQLKQSGPELVKPGASVKISCKASGYTFTDYSIHWVKQNHGKSLDWIGYIYPSNGDSGYN

QKFKNRATLTVDTSYSTAYLEVRRLTFEDSAVYYCATYFANYFDYWGQGTTLTVSSAST

131R002/131R003 Light chain variable region
(SEQ ID NO: 17)
DIVLTQSPASLAVSLGQRATISCKASQSVDYDGDSYMNWYQQKPGQPPKLLIYAASNLESG

IPARFSGSGSGTDFTLNIHPVEEEDAATYYCQQSNEDPLTFGAGTKLELKR

131R002 Heavy chain variable region nucleotide sequence
(SEQ ID NO: 18)
CAGGTACAATTGCAAGAATCCGGACCCGAACTTGTGAAGCCCGGAGCGTCAGTCAAGATC
TCGTGTAAGGCCAGCGGGTACACCTTTACGGATTATTCGATCCATTGGGTAAAACAGANT
CACGGGAAGTCGCTCGACTGGATTGGTTATATCTACCCGTCCAACGGTGATTCGGGATAC
AACCAGAAGTTCAAAAATCGGGCCACACTTACAGTGGACACATCGTCGTCAACTGCATAT
CTCGAGGTCCGCAGACTGACGTTTGAGGACTCAGCTGTCTACTATTGCGCGACTTATTTC
GCCAACTACTTCGATTACTGGGGCCAGGGGACGACACTGACGGTCAGCTCCGCGAGCACC 131R003 Heavy chain variable region nucleotide sequence
(SEQ ID NO: 19)
CAGGTGCAACTTAAACAGTCGGGGCCTGAGTTGGTCAAACCAGGAGCCTCAGTAAAGATT
AGCTGCAAAGCATCAGGTTATACCTTTACGGATTACTCGATCCACTGGGTGAAGCAGAAC
CACGGAAAGTCACTGGATTGGATCGGGTACATCTACCCCTCGAATGGAGATTCGGGGTAT
AACCAAAAGTTCAAAAACCGGGCCACGCTGACTGTGGACACGTCGTATTCCACCGCATAT
TTGGAAGTCCGCAGACTCACGTTCGAGGACTCCGCGGTATACTATTGTGCCACATACTTT
GCGAATTACTTTGACTACTGGGGTCAGGGCACAACGCTTACTGTCTCCAGCGCGTCAACA 131R002/131R003 Light chain variable region nucleotide sequence
(SEQ ID NO: 20)
GACATCGTGCTCACACAGAGCCCTGCATCGCTCGCAGTATCGCTTGGTCAGCGAGCGACC
ATTTCATGCAAAGCGTCACAATCGGTAGATTACGACGGAGACTCCTACATGAACTGGTAT
CAGCAGAAACCAGGGCAGCCCCCGAAGTTGCTCATCTACGCCGCGTCCAATCTGGAGTCA
GGCATTCCCGCCAGATTCAGCGGGAGCGGGTCAGGAACGGATTTTACCCTCAATATCCAT
CCGGTAGAGGAGGAAGATGCGGCGACTTACTATTGTCAGCAGTCGAATGAGGACCCACTC
ACGTTCGGGGCTGGAACAAAACTGGAACTTAAACGG 131R002 Heavy chain amino acid sequence with predicted signal sequence underlined
(SEQ ID NO: 21)
<u>MKHLWFFLLLLVAAPRWVLS</u>QVQLQESGPELVKPGASVKISCKASGYTFTDYSIHWVKQNH
GKSLDWIGYIYPSNGDSGYNQKFKNRATLTVDTSSSTAYLEVRRLTFEDSAVYYCATYFA
NYFDYWGQGTTLTVSSASTKGPSVFPLAPCSRSTSESTAALGCLVKDYFPEPVTVSWNSG
ALTSGVHTFPAVLQSSGLYSLSSVVTVPSSNFGTQTYTCNVDHKPSNTKVDKTVERKCCV
ECPPCPAPPVAGPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEKTISKTKGQPRE
PQVYTLPPSREEMTKNQVSLTCLVKGFYPSDIAVEWESNGQPENNYKTTPPMLDSDGSFF
LYSKLTVDKSRWQQGNVFSCSVMHEALHNHYTQKSLSLSPGK 131R003 Heavy chain amino acid sequence with predicted signal sequence underlined
(SEQ ID NO: 22)
<u>MKHLWFFLLLLVAAPRWVLS</u>QVQLKQSGPELVKPGASVKISCKASGYTFTDYSIHWVKQNH
GKSLDWIGYIYPSNGDSGYNQKFKNRATLTVDTSYSTAYLEVRRLTFEDSAVYYCATYFA
NYFDYWGQGTTLTVSSASTKGPSVFPLAPCSRSTSESTAALGCLVKDYFPEPVTVSWNSG
ALTSGVHTFPAVLQSSGLYSLSSVVTVPSSNFGTQTYTCNVDHKPSNTKVDKTVERKCCV
ECPPCPAPPVAGPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEKTISKTKGQPRE
PQVYTLPPSREEMTKNQVSLTCLVKGFYPSDIAVEWESNGQPENNYKTTPPMLDSDGSFF
LYSKLTVDKSRWQQGNVFSCSVMHEALHNHYTQKSLSLSPGK -continued 131R002/131R003 Light chain amino acid sequence with predicted signal sequence underlined (SEQ ID NO: 23)

<u>MKHLWFFLLLVAAPRWVLS</u>DIVLTQSPASLAVSLGQRATISCKASQSVDYDGDSYMNWYQ

QKPGQPPKLLIYAASNLESGIPARFSGSGSGTDFTLNIHPVEEEDAATYYCQQSNEDPLT

FGAGTKLELKRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC

131R002 Heavy chain nucleotide sequence with predicted signal sequence (SEQ ID NO: 24)

ATGAAACACTTGTGGTTCTTTCTTTTGCTGGTGGCAGCGCCTAGGTGGGTGCTCAGCCAG

GTACAATTGCAAGAATCCGGACCCGAACTTGTGAAGCCCGGAGCGTCAGTCAAGATCTCG

TGTAAGGCCAGCGGGTACACCTTTACGGATTATTCGATCCATTGGGTAAAACAGAATCAC

GGGAAGTCGCTCGACTGGATTGGTTATATCTACCCGTCCAACGGTGATTCGGGATACAAC

CAGAAGTTCAAAAATCGGGCCACACTTACAGTGGACACATCGTCGTCAACTGCATATCTC

GAGGTCCGCAGACTGACGTTTGAGGACTCAGCTGTCTACTATTGCGCGAATTATTTCGCC

AACTACTTCGATTACTGGGGCCAGGGGACGACACTGACGGTCAGCTCCGCGAGCACCAAG

GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

GCCCTGACCTCTGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

CTGACCGTGGTGCACCAGGACTGGCTGAACGGCAAAGAATACAAGTGCAAGGTGTCCAAC

AAGGGCCTGCCCTGCCCCTATCGAAAAGACCATCTCTAAGACCAAGGGCCAGCCTCGCGAG

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGA

131R003 Heavy chain nucleotide sequence with predicted signal sequence (SEQ ID NO: 25)

ATGAAGCATCTTTGGTTCTTCCTGCTCTTGGTGGCTGCGCCGAGGTGGGTGCTCAGCCAG

GTGCAACTTAAACAGTCGGGGCCTGAGTTGGTCAAACCAGGAGCCTCAGTAAAGATTAGC

TGCAAAGCATCAGGTTATACCTTTACGGATTACTCGATCCACTGGGTGAAGCAGAACCAC

GGAAAGTCACTGGATTGGATCGGGTACATCTACCCCTCGAATGGAGATTCGGGGTATAAC

CAAAAGTTCAAAAACCGGGCCACGCTGACTGTGGACACGTCGTATTCCACCGCATATTTG

GAAGTCCGCAGACTCACGTTCGAGGACTCCGCGGTATACTATTGTGCCACATACTTTGCG

AATTACTTTGACTACTGGGGTCAGGGCACAACGCTTACTGTCTCCAGCGCGTCAACAAAG

GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

-continued

```
GCCCTGACCTCTGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

CTGACCGTGGTGCACCAGGACTGGCTGAACGGCAAAGAATACAAGTGCAAGGTGTCCAAC

AAGGGCCTGCCTGCCCCTATCGAAAAGACCATCTCTAAGACCAAGGGCCAGCCTCGCQAG

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGA

131R002/131R003 Light chain nucleotide sequence with predicted signal sequence
                                                                                   (SEQ ID NO: 26)
ATGAAGCACCTCTGGTTCTTTCTTCTTCTGGTCGCAGCGCCGAGATGGGTACTTAGCGAC

ATCGTGCTCACACAGAGCCCTGCATCGCTCGCAGTATCGCTTGGTCAGCGAGCGACCATT

TCATGCAAAGCGTCACAATCGGTAGATTACGACGGAGACTCCTACATGAACTGGTATCAG

CAGAAACCAGGGCAGCCCCCGAAGTTGCTCATCTACGCCGCGTCCAATCTGGAGTCAGGC

ATTCCCGCCAGATTCAGCGGGAGCGGGTCAGGAACGGATTTTACCCTCAATATCCATCCG

GTAGAGGAGGAAGATGCGGCGACTTACTATTGTCAGCAGTCGAATGAGGACCCACTCACG

TTCGGGGCTGGAACAAAACTGGAACTTAAACGGACTGTGGCGGCTCCCTCAGTGTTCATC

TTCCCTCCCTCCGACGAACAATTGAAGTCGGGTACTGCCTCCGTCGTCTGTTTGTTGAAC

AACTTTTATCCGAGGGAAGCCAAGGTGCAGTGGAAGGTGGATAATGCGCTGCAGAGCGGT

AACTCGCAAGAGTCAGTCACAGAGCAAGACTCGAAGGATTCGACGTATTCGCTCAGCAGC

ACATTGACGCTGTCGAAGGCAGATTACGAGAAACACAAGGTGTACGCGTGCGAGGTCACC

CATCAGGGATTGTCGTCACCCGTGACGAAATCCTTTAACCGCGGAGAATGCTGA

131R002 Heavy chain amino acid sequence without predicted signal sequence
                                                                                   (SEQ ID NO: 27)
QVQLQESGPELVKPGASVKISCKASGYTFTDYSIHWVKQNHGKSLDWIGYIYPSNGDSGY

NQKFKNRATLTVDTSSSTAYLEVRRLTFEDSAVYYCATYFANYFDYWGQGTTLTVSSAST

KGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDKSRWQQGNVFS

CSVMHEALHNHYTQKSLSLSPGK

131R003 Heavy chain amino acid sequence without predicted signal sequence
                                                                                   (SEQ ID NO: 28)
QVQLKQSGPELVKPGASVKISCKASGYTFTDYSIHWVKQNHGKSLDWIGYIYPSNGDSGY

NQKFKNRATLTVDTSYSTAYLEVRRLTFEDSAVYYCATYFANYFDYWGQGTTLTVSSAST

KGPSVFPLAPCSPSTSESTAALGCLVKDYFPEPVTVSWNSGALTSGVHTFPAVLQSSGLY
```

-continued

SLSSVVTVPSSNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDKSRWQQGNVFS

CSVMHEALHNHYTQKSLSLSPGK

131R002/131R003 Light chain amino acid sequence without predicted signal sequence (SEQ ID NO: 29)

DIVLTQSPASLAVSLGQRATISCKASQSVDYDGDSYMNWYQQKPGQPPKLLIYAASNLES

GIPARFSGSGSGTDFTLNIHPVEEEDAATYYCQQSNEDPLTFGAGTKLELKRTVAAPSVF

IFPPSDEQLK$GTASVVCLLNNFYPREAKVQWKVDNALQSGNSQESVTEQDSKDSTYSLS

STLTLSKADYEKHKVYACEVTHQGLSSPVTKSFNRGEC

131R002 Heavy chain amino acid sequence without predicted signal sequence (SEQ ID NO: 30)

CAGGTACAATTGCAAGAATCCGGACCCGAACTTGTGAAGCCCGGAGCGTCAGTCAAGATC

TCGTGTAAGGCCAGCGGGTACACCTTTACGGATTATTCGATCCATTGGGTAAAACAGAAT

CACGGGAAGTCGCTCGACTGGATTGGTTATATCTACCCGTCCAACGGTGATTCGGGATAC

AACCAGAAGTTCAAAAATCGGGCCACACTTACAGTGGACACATCGTCGTCAACTGCATAT

CTCGAGGTCCGCAGACTGACGTTTGAGGACTCAGCTGTCTACTATTGCGCGACTTATTTC

GCCAACTACTTCGATTACTGGGGCCAGGGGACGACACTGACGGTCAGCTCCGCGAGCACC

AAGGGCCCCTCCGTGTTCCCTCTGGCCCCTTGCTCCCGGTCCACCTCTGAGTCTACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCTGCCGTGCTGCAGTCCTCCGGCCTGTAC

TCCCTGTCCTCCGTGGTGACCGTGCCTTCCTCCAACTTCGGCACCCAGACCTACACCTGC

AACGTGGACCACAAGCCTTCCAACACCAAGGTGGACAAGACCGTGGAGCGGAAGTGCTGC

GTGGAGTGCCCTCCTTGTCCTGCTCCTCCTGTGGCTGGCCCTTCTGTGTTCCTGTTCCCT

CCTAAGCCTAAGGACACCCTGATGATCTCCCGGACCCCTGAAGTGACCTGCGTGGTGGTG

GACGTGTCCCACGAGGACCCTGAGGTGCAGTTCAATTGGTACGTGGACGGCGTGGAGGTG

CACAACGCCAAGACCAAGCCTCGGGAGGAACAGTTCAACTCCACCTTCCGGGTGGTGTCT

GTGCTGACCGTGGTGCACCAGGACTGGCTGAACGGCAAAGAATACAAGTGCAAGGTGTCC

AACAAGGGCCTGCCTGCCCCTATCGAAAAGACCATCTCTAAGACCAAGGGCCAGCCTCGC

GAGCCTCAGGTCTACACCCTGCCTCCTAGCCGGGAGGAAATGACCAAGAACCAGGTGTCC

CTGACCTGTCTGGTGAAGGGCTTCTACCCTTCCGATATCGCCGTGGAGTGGGAGTCTAAC

GGCCAGCCTGAGAACAACTACAAGACCACCCCTCCTATGCTGGACTCCGACGGCTCCTTC

TTCCTGTACTCCAAGCTGACAGTGGACAAGTCCCGGTGGCAGCAGGGCAACGTGTTCTCC

TGCTCCGTGATGCACGAGGCCCTGCACAACCACTACACCCAGAAGTCCCTGTCCCTGTCT

CCTGGCAAGTGA

131R003 Heavy chain amino acid sequence without predicted signal sequence (SEQ ID NO: 31)

CAGGTGCAACTTAAACAGTCGGGGCCTGAGTTGGTCAAACCAGGAGCCTCAGTAAAGATT

AGCTGCAAAGCATCAGGTTATACCTTTACGGATTACTCGATCCACTGGGTGAAGCAGAAC

CACGGAAAGTCACTGGATTGGATCGGGTACATCTACCCCTCGAATGGAGATTCGGGGTAT

AACCAAAAGTTCAAAAACCGGGCCACGCTGACTGTGGACACGTCGTATTCCACCGCATAT

TTGGAAGTCCGCAGACTCACGTTCGAGGACTCCGCGGTATACTATTGTGCCACATACTTT

```
GCGAATTACTTTGACTACTGGGGTCAGGGCACAACGCTTACTGTCTCCAGCGCGTCAACA

AAGGGCCCCTCCGTGTTCCCTCTGGCCCCTTGCTCCCGGTCCACCTCTGAGTCTACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCTGCCGTGCTGCAGTCCTCCGGCCTGTAC

TCCCTGTCCTCCGTGGTGACCGTGCCTTCCTCCAACTTCGGCACCCAGACCTACACCTGC

AACGTGGACCACAAGCCTTCCAACACCAAGGTGGACAAGACCGTGGAGCGGAAGTGCTGC

GTGGAGTGCCCTCCTTGTCCTGCTCCTCCTGTGGCTGGCCCTTCTGTGTTCCTGTTCCCT

CCTAAGCCTAAGGACACCCTGATGATCTCCCGGACCCCTGAAGTGACCTGCGTGGTGGTG

GACGTGTCCCACGAGGACCCTGAGGTGCAGTTCAATTGGTACGTGGACGGCGTGGAGGTG

CACAACGCCAAGACCAAGCCTCGGGAGGAACAGTTCAACTCCACCTTCCGGGTGGTGTCT

GTGCTGACCGTGGTGCACCAGGACTGGCTGAACGGCAAAGAATACAAGTGCAAGGTGTCC

AACAAGGGCCTGCCTGCCCCTATCGAAAAGACCATCTCTAAGACCAAGGGCCAGCCTCGC

GAGCCTCAGGTCTACACCCTGCCTCCTAGCCGGGAGGAAATGACCAAGAACCAGGTGTCC

CTGACCTGTCTGGTGAAGGGCTTCTACCCTTCCGATATCGCCGTGGAGTGGGAGTCTAAC

GGCCAGCCTGAGAACAACTACAAGACCACCCCTCCTATGCTGGACTCCGACGGCTCCTTC

TTCCTGTACTCCAAGCTGACAGTGGACAAGTCCCGGTGGCAGCAGGGCAACGTGTTCTCC

TGCTCCGTGATGCACGAGGCCCTGCACAACCACTACACCCAGAAGTCCCTGTCCCTGTCT

CCTGGCAAGTGA

131R002/131R003 Light chain amino acid sequence without predicted signal sequence
                                                                          (SEQ ID NO: 32)
GACATCGTGCTCACACAGAGCCCTGCATCGCTCGCAGTATCGCTTGGTCAGCGAGCGACC

ATTTCATGCAAAGCGTCACAATCGGTAGATTACGACGGAGACTCCTACATGAACTGGTAT

CAGCAGAAACCAGGGCAGCCCCCGAAGTTGCTCATCTACGCCGCGTCCAATCTGGAGTCA

GGCATTCCCGCCAGATTCAGCGGGAGCGGGTCAGGAACGGATTTTACCCTCAATATCCAT

CCGGTAGAGGAGGAAGATGCGGCGACTTACTATTGTCAGCAGTCGAATGAGGACCCACTC

ACGTTCGGGGCTGGAACAAAACTGGAACTTAAACGGACTGTGGCGGCTCCCTCAGTGTTC

ATCTTCCCTCCCTCCGACGAACAATTGAAGTCGGGTACTGCCTCCGTCGTCTGTTTGTTG

AACAACTTTTATCCGAGGGAAGCCAAGGTGCAGTGGAAGGTGGATAATGCGCTGCAGAGC

GGTAACTCGCAAGAGTCAGTCACAGAGCAAGACTCGAAGGATTCGACGTATTCGCTCAGC

AGCACATTGACGCTGTCGAAGGCAGATTACGAGAAACACAAGGTGTACGCGTGCGAGGTC

ACCCATCAGGGATTGTCGTCACCCGTGACGAAATCCTTTAACCGCGGAGAATGCTGA

FLAG Tag
                                                                          (SEQ ID NO: 33)
DYKDDDDK

131R003 Heavy chain CDR1 variant
                                                                          (SEQ ID NO: 34)
KASGYTFTSYTF 131R003 Heavy chain CDR3 variant
                                                                          (SEQ ID NO: 35)
ATYFANNEDY 131R003 Heavy chain variable region - Variant 1
                                                                          (SEQ ID NO: 36)
QVQLKQSGPELVKPGASVKISCKASGYTFTDYSIHWVKQNHGKSLDWIGYIYPSNGDSGY

NQKFKNRATLTVDTSYSTAYLEVRRLTFEDSAVYYCATYFANNEDYWGQGTTLTVSS
```

131R003 Heavy chain variable region - Variant 2

(SEQ ID NO: 37)

QVQLKQSGPELVKPGASVKISCKASGYTFTSYTFHWVKQNHGKSLDWIGYIYPSNGDSGY

NQKFKNRATLTVDTSYSTAYLEVRRLTFEDSAVYYCATYFANNFDYWGQGTTLTVSS

131R003 Heavy chain - Variant 1 with predicted signal sequence underlined (SEQ ID NO: 38)

<u>MKHLWFFLLLLVAAPRWVLS</u>QVQLKQSGPELVKPGASVKISCKASGYTFTDYSIHWVKQNH

GKSLDWIGYIYPSNGDSGYNQKFKNRATLTVDTSYSTAYLEVRRLTFEDSAVYYCATYFA

NNFDYWGQGTTLTVSSASTKGPSVFPLAPCSRSTSESTAALGCLVKDYFPEPVTVSWNSG

ALTSGVHTFPAVLQSSGLYSLSSVVTVPSSNFGTQTYTCNVDHKPSNTKVDKTVERKCCV

ECPPCPAPPVAGPSVFLFPPKPKDTLMISRTPEVTCVVVDVSHEDPEVQFNWYVDGVEVH

NAKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK

131R003 Heavy chain - Variant 1 without predicted signal sequence (SEQ ID NO: 39)

QVQLKQSGPELVKPGASVKISCKASGYTFTDYSIHWVKQNHGKSLDWIGYIYPSNGDSGY

NQKFKNRATLTVDTSYSTAYLEVRRLTFEDSAVYYCATYFANNFDYWGQGTTLTVSSAST

KGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPSREEMTKNQTS

LTCLVKGFYPSDEAVEWESNGQPENNYKTTPPMLDSDGSFFLYSKLTVDKSRWQQGNVFS

CSVMHEALHNHYTQKSLSLSPGK

131R003 Heavy chain - Variant 1 nucleic acid with predicted signal sequence (SEQ ID NO: 40)

ATGAAGCATCTTTGGTTCTTCCTGCTCTTGGTGGCTGCGCCGAGGTGGGTGCTCAGCCAG

GTGCAACTTAAACAGTCGGGGCCTGAGTTGGTCAAACCAGGAGCCTCAGTAAAGATTAGC

TGCAAAGCATCAGGTTATACCTTTACGGATTACTCGATCCACTGGGTGAAGCAGAACCAC

GGAAAGTCACTGGATTGGATCGGGTACATCTACCCCTCGAATGGAGATTCGGGGTATAAC

CAAAAGTTCAAAAACCGGGCCACGCTGACTGTGGACACGTCGTATTCCACCGCATATTTG

GAAGTCCGCAGACTCACGTTCGAGGACTCCGCGGTATACTATTGTGCCACATACTTTGCG

AATAACTTTGACTACTGGGGTCAGGGCACAACGCTTACTGTCTCCAGCGCGTCAACAAAG

GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

GCCCTGACCTCTGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

CTGACCGTGGTGCACCAGGACTGGCTGAACGGCAAGGAATACAAGTGCAAGGTGTCCAAC

AAGGGCCTGCCTGCCCCTATCGAAAAGACCATCTCTAAGACCAAGGGCCAGCCTCGCGAG

-continued

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGA

131R003 Heavy chain - Variant 2 with predicted signal sequence underlined (SEQ ID NO: 41)

<u>MKHLWFFLLLLVAAPRWVLS</u>QVQLKQSGPELVKPGASVKISCKASGYTFTSYTFHWVKQNH

GKSLDWIGYIYPSNGDSGYNQKFKNRATLTVDTSYSTAYLEVRRLTFEDSAVYYCATYFA

NNFDYWGQGTTLTVSSASTKGPSVFPLAPCSRSTSESTAALGCLVKDYFPEPVTVSWNSG

ALTSGVHTFPAVLQSSGLYSLSSVVTVPSSNFGTQTYTCNVDHKPSNTKVDKTVERKCCV

ECPPCPAPPVAGPSVFLFPPKPKDTLMISRTPEVTCVVVDVSHEDPEVQFNWYVDGVEVH

NAKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK

131R003 Heavy chain - Variant 2 without predicted signal sequence (SEQ ID NO: 42)

QVQLKQSGPELVKPGASVKISCKASGYTFTSYTFHWVKQNHGKSLDWIGYIYPSNGDSGY

NQKFKNRATLTVDTSYSTAYLEVRRLTFEDSAVYYCATYFANNFDYWGQGTTLTVSSAST

KGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDKSRWQQGNVFS

CSVMHEALHNHYTQKSLSLSPGK

131R003 Heavy chain - Variant 2 nucleic acid with predicted signal sequence (SEQ ID NO: 43)

ATGAAGCATCTTTGGTTCTTCCTGCTCTTGGTGGCTGCGCCGAGGTGGGTGCTCAGCCAG

GTGCAACTTAAACAGTCGGGGCCTGAGTTGGTCAAACCAGGAGCCTCAGTAAAGATTAGC

TGCAAAGCATCAGGATACACCTTCACTAGCTATACATTCCACTGGGTGAAGCAGAACCAC

GGAAAGTCACTGGATTGGATCGGGTACATCTACCCCTCGAATGGAGATTCGGGGTATAAC

CAAAAGTTCAAAAACCGGGCCACGCTGACTGTGGACACGTCGTATTCCACCGCATATTTG

GAAGTCCGCAGACTCACGTTCGAGGACTCCGCGGTATACTATTGTGCCACATACTTTGCG

AATAACTTTGACTACTGGGGTCAGGGCACAACGCTTACTGTCTCCAGCGCGTCAACAAAG

GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

GCCCTGACCTCGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

-continued

```
CTGACCGTGGTGCACCAGGACTGGCTGAACGGCAAAGAATACAAGTGCAAGGTGTCCAAC

AAGGGCCTGCCTGCCCCTATCGAAAAGACCATCTCTAAGACCAAGGGCCAGCCTCGCGAG

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGA
```

Humanized 131R003 Antibodies
Humanized 131R005/131R007/131R008/131R010/131R011 Heavy chain variable region (SEQ ID NO: 44)

```
QVQLVQSGAEVKKPGASVKVSCKASGYTFTDYSIHWVRQAPGQGLEWIGYIYPSNGDSGY

NQKFKNRVTMTRDTSTSTAYMELSRLRSEDTAVYYCATYFANNFDYWGQGTTLTVSS
```

Humanized 131R006A Heavy chain variable region (SEQ ID NO: 45)

```
QVQLVQSGAEVKKPGASVKVSCKASGYTFTSYTFHWVRQAPGQGLEWIGYIYPSNGDSGY

NQKFKNRVTMTRDTSTSTAYMELSRLRSEDTAVYYCATYFANNFDYWGQGTTLTVSS
```

Humanized 131R005/131R007/131R011 Heavy chain (IgG2) with predicted signal sequence underlined (SEQ ID NO: 46)

```
MKHLWFFLLLVAAPRWVLSQVQLVQSGAEVKKPGASVKVSCKASGYTFTDYSIHWVRQAP

GQGLEWIGYIYPSNGDSGYNQKFKNRVTMTRDTSTSTAYMELSRLRSEDTAVYYCATYFA

NNFDYWGQGTTLTVSSASTKGPSVFPLAPCSRSTSESTAALGCLVKDYFPEPVTVSWNSG

ALTSGVHTFPAVLQSSGLYSLSSVVTVPSSNFGTQTYTCNVDHKPSNTKVDKTVERKCCV

ECPPCPAPPVAGPSVFLFPPKPKDTLMISRTPEVTCVVVDVSHEDPEVQFNWYVDGVEVH

NAKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK
```

Humanized 131R006A Heavy chain with predicted signal sequence underlined (SEQ ID NO: 47)

```
MKHLWFFLLLVAAPRWVLSQVQLVQSGAEVKKPGASVKVSCKASGYTFTSYTFHWVRQAP

GQGLEWIGYIYPSNGDSGYNQKFKNRVTMTRDTSTSTAYMELSRLRSEDTAVYYCATYFA

NNFDYWGQGTTLTVSSASTKGPSVFPLAPCSRSTSESTAALGCLVKDYFPEPVTVSWNSG

ALTSGVHTFPAVLQSSGLYSLSSVVTVPSSNFGTQTYTCNVDHKPSNTKVDKTVERKCCV

ECPPCPAPPVAGPSVFLFPPKPKDTLMISRTPEVTCVVVDVSHEDPEVQFNWYVDGVEVH

NAKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK
```

Humanized 131R005/131R007/131R011 Heavy chain (IgG2) without predicted signal sequence (SEQ ID NO: 48)

```
QVQLVQSGAEVKKPGASVKVSCKASGYTFTDYSIHWVRQAPGQGLEWIGYIYPSNGDSGY

NQKFKNRVTMTRDTSTSTAYMELSRLRSEDTAVYYCATYFANNFDYWGQGTTLTVSSAST

KGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPSREEMTKNQVS
```

-continued

LTCLVKGFYPSDIAVEWESNGQPENNYKTTPPMLDSDGSFFLYSKLTVDKSRWQQGNVFS

CSVMHEALHNHYTQKSLSLSPGK

Humanized 131R006A Heavy chain without predicted signal sequence (SEQ ID NO: 49)

QVQLVQSGAEVKKPGASVKVSCKASGYTFTSYTFHWVRQAPGQGLEWIGYIYPSNGDSGY

NQKFKNRVTMTRDTSTSTAYMELSRLRSEDTAVYYCATYFANNFDYWGQGTTLTVSSAST

KGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPSREEMTKNQVS

LTCLVKGFYPSDIATEWESNGQPENNYKTTPPMLDSDGSFFLYSKLTVDKSRWQQGNVFS

CSVMHEALHNHYTQKSLSLSPGK

Humanized 131R005/131R007 Heavy chain variable region nucleic acid (SEQ ID NO: 50)

CAAGTCCAATTGGTCCAGAGCGGTGCCGAAGTGAAGAAACCGGGAGCTTCCGTGAAAGTG

AGCTGCAAGGCTTCTGGATACACCTTCACTGACTATTCAATCCACTGGGTGAGACAGGCA

CCTGGTCAGGGACTGGAGTGGATTGGATACATCTACCCCTCAAATGGGGACTCTGGCTAC

AACCAAAAGTTCAAGAACCGGGTGACTATGACCAGAGATACCTCAACATCTACTGCCTAC

ATGGAACTCAGCAGGCTGCGCTCAGAGGACACCGCAGTGTATTACTGTGCCACCTACTTC

GCTAATAACTTCGACTATTGGGGCAGGGCACCACCCTGACTGTCAGCTCA

Humanized 131R006A Heavy chain variable region nucleic acid (SEQ ID NO: 51)

CAAGTCCAATTGGTCCAGAGCGGTGCCGAAGTGAAGAAACCGGGAGCTTCCGTGAAAGTG

AGCTGCAAGGCTTCTGGATACACCTTCACTAGCTATACATTCCACTGGGTGAGACAGGCA

CCTGGTCAGGGACTGGAGTGGATTGGATACATCTACCCCTCAAATGGGGACTCTGGCTAC

AACCAAAAGTTCAAGAACCGGGTGACTATGACCAGAGATACCTCAACATCTACTGCCTAC

ATGGAACTCAGCAGGCTGCGCTCAGAGGACACCGCAGTGTATTACTGTGCCACCTACTTC

GCTAATAACTTCGACTATTGGGGCAGGGCACCACCCTGACTGTCAGCTCA

Humanized 131R005/131R007 Heavy chain nucleic acid with predicted signal sequence (SEQ ID NO: 52)

ATGAAGCATCTGTGGTTTTTCCTCCTCCTTGTCGCCGCTCCACGCTGGGTGCTTTCCCAA

GTCCAATTGGTCCAGAGCGGTGCCGAAGTGAAGAAACCGGGAGCTTCCGTGAAAGTGAGC

TGCAAGGCTTCTGGATACACCTTCACTGACTATTCAATCCACTGGGTGAGACAGGCACCT

GGTCAGGGACTGGAGTGGATTGGATACATCTACCCCTCAAATGGGGACTCTGGCTACAAC

CAAAAGTTCAAGAACCGGGTGACTATGACCAGAGATACCTCAACATCTACTGCCTACATG

GAACTCAGCAGGCTGCGCTCAGAGGACACCGCAGTGTATTACTGTGCCACCTACTTCGCT

AATAACTTCGACTATTGGGGCAGGGCACCACCCTGACTGTCAGCTCAGCCTCAACCAAG

GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

GCCCTGACCTCTGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

-continued

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

CTGACCGTGGTGCACCAGGACTGGCTGAACGGCAAAGAATACAAGTGCAAGGTGTCCAAC

AAGGGCCTGCCTGCCCCTATCGAAAAGACCATCTCTAAGACCAAGGGCCAGCCTCGCGAG

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGA

Humanized 131R006A Heavy chain nucleic acid with predicted signal sequence
(SEQ ID NO: 53)
ATGAAGCATCTGTGGTTTTTCCTCCTCCTTGTCGCCGCTCCACGCTGGGTGCTTTCCCAA

GTCCAATTGGTCCAGAGCGGTGCCGAAGTGAAGAAACCGGGAGCTTCCGTGAAAGTGAGC

TGCAAGGCTTCTGGATACACCTTCACTAGCTATACATTCCACTGGGTGAGACAGGCACCT

GGTCAGGGACTGGAGTGGATTGGATACATCTACCCCTCAAATGGGGACTCTGGCTACAAC

CAAAAGTTCAAGAACCGGGTGACTATGACCAGAGATACCTCAACATCTACTGCCTACATG

GAACTCAGCAGGCTGCGCTCAGAGGACACCGCAGTGTATTACTGTGCCACCTACTTCGCT

AATAACTTCGACTATTGGGGCAGGGCACCACCCTGACTGTCAGCTCAGCCTCAACCAAG

GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

GCCCTGACCTCTGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

CTGACCGTGGTGCACCAGGACTGGCTGAACGGCAAAGAATACAAGTGCAAGGTGTCCAAC

AAGGGCCTGCCTGCCCCTATCGAAAAGACCATCTCTAAGACCAAGGGCCAGCCTCGCGAG

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGA

Humanized 131R005/131R007 Heavy chain nucleic acid without predicted signal sequence
(SEQ ID NO: 54)
CAAGTCCAATTGGTCCAGAGCGGTGCCGAAGTGAAGAAACCGGGAGCTTCCGTGAAAGTG

AGCTGCAAGGCTTCTGGATACACCTTCACTGACTATTCAATCCACTGGGTGAGACAGGCA

CCTGGTCAGGGACTGGAGTGGATTGGATACATCTACCCCTCAAATGGGGACTCTGGCTAC

AACCAAAAGTTCAAGAACCGGGTGACTATGACCAGAGATACCTCAACATCTACTGCCTAC

ATGGAACTCAGCAGGCTGCGCTCAGAGGACACCGCAGTGTATTACTGTGCCACCTACTTC

-continued

```
GCTAATAACTTCGACTATTGGGGGCAGGGCACCACCCTGACTGTCAGCTCAGCCTCAACC

AAGGGCCCCTCCGTGTTCCCTCTGGCCCCTTGCTCCCGGTCCACCTCTGAGTCTACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCTGCCGTGCTGCAGTCCTCCGGCCTGTAC

TCCCTGTCCTCCGTGGTGACCGTGCCTTCCTCCAACTTCGGCACCCAGACCTACACCTGC

AACGTGGACCACAAGCCTTCCAACACCAAGGTGGACAAGACCGTGGAGCGGAAGTGCTGC

GTGGAGTGCCCTCCTTGTCCTGCTCCTCCTGTGGCTGGCCCTTCTGTGTTCCTGTTCCCT

CCTAAGCCTAAGGACACCCTGATGATCTCCCGGACCCCTGAAGTGACCTGCGTGGTGGTG

GACGTGTCCCACGAGGACCCTGAGGTGCAGTTCAATTGGTACGTGGACGGCGTGGAGGTG

CACAACGCCAAGACCAAGCCTCGGGAGGAACAGTTCAACTCCACCTTCCGGGTGGTGTCT

GTGCTGACCGTGGTGCACCAGGACTGGCTGAACGGCAAAGAATACAAGTGCAAGGTGTCC

AACAAGGGCCTGCCTGCCCCTATCGAAAAGACCATCTCTAAGACCAAGGGCCAGCCTCGC

GAGCCTCAGGTCTACACCCTGCCTCCTAGCCGGGAGGAAATGACCAAGAACCAGGTGTCC

CTGACCTGTCTGGTGAAGGGCTTCTACCCTTCCGATATCGCCGTGGAGTGGGAGTCTAAC

GGCCAGCCTGAGAACAACTACAAGACCACCCCTCCTATGCTGGACTCCGACGGCTCCTTC

TTCCTGTACTCCAAGCTGACAGTGGACAAGTCCCGGTGGCAGCAGGGCAACGTGTTCTCC

TGCTCCGTGATGCACGAGGCCCTGCACAACCACTACACCCAGAAGTCCCTGTCCCTGTCT

CCTGGCAAGTGA
```

Humanized 131R006A Heavy chain - nucleic acid without predicted signal sequence
(SEQ ID NO: 55)

```
CAAGTCCAATTGGTCCAGAGCGGTGCCGAAGTGAAGAAACCGGGAGCTTCCGTGAAAGTG

AGCTGCAAGGCTTCTGGATACACCTTCACTAGCTATACATTCCACTGGGTGAGACAGGCA

CCTGGTCAGGGACTGGAGTGGATTGGATACATCTACCCCTCAAATGGGGACTCTGGCTAC

AACCAAAAGTTCAAGAACCGGGTGACTATGACCAGAGATACCTCAACATCTACTGCCTAC

ATGGAACTCAGCAGGCTGCGCTCAGAGGACACCGCAGTGTATTACTGTGCCACCTACTTC

GCTAATAACTTCGACTATTGGGGGCAGGGCACCACCCTGACTGTCAGCTCAGCCTCAACC

AAGGGCCCCTCCGTGTTCCCTCTGGCCCCTTGCTCCCGGTCCACCTCTGAGTCTACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCTGCCGTGCTGCAGTCCTCCGGCCTGTAC

TCCCTGTCCTCCGTGGTGACCGTGCCTTCCTCCAACTTCGGCACCCAGACCTACACCTGC

AACGTGGACCACAAGCCTTCCAACACCAAGGTGGACAAGACCGTGGAGCGGAAGTGCTGC

GTGGAGTGCCCTCCTTGTCCTGCTCCTCCTGTGGCTGGCCCTTCTGTGTTCCTGTTCCCT

CCTAAGCCTAAGGACACCCTGATGATCTCCCGGACCCCTGAAGTGACCTGCGTGGTGGTG

GACGTGTCCCACGAGGACCCTGAGGTGCAGTTCAATTGGTACGTGGACGGCGTGGAGGTG

CACAACGCCAAGACCAAGCCTCGGGAGGAACAGTTCAACTCCACCTTCCGGGTGGTGTCT

GTGCTGACCGTGGTGCACCAGGACTGGCTGAACGGCAAAGAATACAAGTGCAAGGTGTCC

AACAAGGGCCTGCCTGCCCCTATCGAAAAGACCATCTCTAAGACCAAGGGCCAGCCTCGC

GAGCCTCAGGTCTACACCCTGCCTCCTAGCCGGGAGGAAATGACCAAGAACCAGGTGTCC

CTGACCTGTCTGGTGAAGGGCTTCTACCCTTCCGATATCGCCGTGGAGTGGGAGTCTAAC

GGCCAGCCTGAGAACAACTACAAGACCACCCCTCCTATGCTGGACTCCGACGGCTCCTTC

TTCCTGTACTCCAAGCTGACAGTGGACAAGTCCCGGTGGCAGCAGGGCAACGTGTTCTCC
```

```
TGCTCCGTGATGCACGAGGCCCTGCACAACCACTACACCCAGAAGTCCCTGTCCCTGTCT

CCTGGCAAGTGA
```

Human IgG1 Heavy chain constant region (SEQ ID NO: 56)

```
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK
```

Human IgG2 Heavy chain constant region (SEQ ID NO: 57)

```
ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKLTVDKSRWQQGN

VFSCSVMHEALHNHYTQKSLSLSPGK
```

Human IgG3 Heavy chain constant region (SEQ ID NO: 58)

```
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSC

DTPPPCPRCPEPKSCDTPPPCPRCPEPKSCDTPPPCPRCPAPELLGGPSVFLFPPKPKDT

LMISRTPEVTCVVVDVSHEDPEVQFKWYVDGVEVHNAKTKPREEQYNSTFRVVSVLTVLH

QDWLNGKEYKCKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQGNIFSCSVMHE

ALHNRFTQKSLSLSPGK
```

Human IgG4 Heavy chain constant region (SEQ ID NO: 59)

```
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLGK
```

Human IgG2 Heavy chain constant region (13A Chain variant) (SEQ ID NO: 60)

```
ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREKMTKN

QVSLTCLVKGFYPSDIAVEWESNGQPENNYKTTPPMLKSDGSFFLYSKLTVDKSRWQQGN

VFSCSVMHEALHNHYTQKSLSLSPGK
```

Human IgG2 Heavy chain constant region (13B Chain variant) (SEQ ID NO: 61)

```
ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSVF
```

-continued

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKN

QVSLTCLVEGFYPSDIAVEWESNGQPENNYKTTPPMLDSDGSFFLYSELTVDKSRWQQGN

VFSCSVMHEALHNHYTQKSLSLSPGK

Humanized 131R006B Heavy chain variable region (SEQ ID NO: 62)

QVQLVQSGAEVKKPGASVKVSCKASGYTFTDYSIHWVRQAPGQGLEWIGYIYPSNGDSGY

NQKFKNRVTMTVDTSYSTAYMELSRLRSEDTAVYYCATYFANNFDYWGQGTTLTVSS

Humanized 131R006B Heavy chain with predicted signal sequence underlined (SEQ ID NO: 63)

<u>MKHLWFFLLLVAAPRWVLS</u>QVQLVQSGAEVKKPGASVKVSCKASGYTFTDYSIHWVRQAP

GQGLEWIGYIYPSNGDSGYNQKFKNRVTMTVDTSYSTAYMELSRLRSEDTAVYYCATYFA

NNFDYWGQGTTLTVSSASTKGPSVFPLAPCSRSTSESTAALGCLVKDYFPEPVTVSWNSG

ALTSGVHTFPAVLQSSGLYSLSSVVTVPSSNFGTQTYTCNVDHKPSNTKVDKTVERKCCV

ECPPCPAPPVAGPSVFLFPPKPKDTLMISRTPEVTCVVVDVSHEDPEVQFNWYVDGVEVH

NAKTKPREEQFNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK

Humanized 131R006B Heavy chain without predicted signal sequence (SEQ ID NO: 64)

QVQLVQSGAEVKKPGASVKVSCKASGYTFTDYSIHWVRQAPGQGLEWIGYIYPSNGDSGY

NQKFKNRVTMTVDTSYSTAYMELSRLRSEDTAVYYCATYFANNFDYWGQGTTLTVSSAST

KGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDKSRWQQGNVFS

CSVMHEALHNHYTQKSLSLSPGK

Humanized 131R0068 Heavy chain variable region nucleic acid (SEQ ID NO: 65)

CAAGTCCAATTGGTCCAGAGCGGTGCCGAAGTGAAGAAACCGGGAGCTTCCGTGAAAGTG

AGCTGCAAGGCTTCTGGATACACCTTCACTGACTATTCAATCCACTGGGTGAGACAGGCA

CCTGGTCAGGGACTGGAGTGGATTGGATACATCTACCCCTCAAATGGGGACTCTGGCTAC

AACCAAAAGTTCAAGAACCGGGTGACTATGACCGTGGATACCTCATACTCTACTGCCTAC

ATGGAACTCAGCAGGCTGCGCTCAGAGGACACCGCAGTGTATTACTGTGCCACCTACTTC

GCTAATAACTTCGACTATTGGGGGCAGGGCACCACCCTGACTGTCAGCTCA

Humanized 131R006B Heavy chain nucleic acid with sequence signal (SEQ ID NO: 66)

ATGAAGCATCTGTGGTTTTTCCTCCTCCTTGTCGCCGCTCCACGCTGGGTGCTTTCCCAA

GTCCAATTGGTCCAGAGCGGTGCCGAAGTGAAGAAACCGGGAGCTTCCGTGAAAGTGAGC

TGCAAGGCTTCTGGATACACCTTCACTGACTATTCAATCCACTGGGTGAGACAGGCACCT

GGTCAGGGACTGGAGTGGATTGGATACATCTACCCCTCAAATGGGGACTCTGGCTACAAC

CAAAAGTTCAAGAACCGGGTGACTATGACCGTGGATACCTCATACTCTACTGCCTACATG

GAACTCAGCAGGCTGCGCTCAGAGGACACCGCAGTGTATTACTGTGCCACCTACTTCGCT

AATAACTTCGACTATTGGGGGCAGGGCACCACCCTGACTGTCAGCTCAGCCTCAACCAAG

-continued

```
GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

GCCCTGACCTCTGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

CTGACCGTGGTGCACCAGGACTGGCTGAACGGCAAAGAATACAAGTGCAAGGTGTCCAAC

AAGGGCCTGCCTGCCCCTATCGAAAAGACCATCTCTAAGACCAAGGGCCAGCCTCGCGAG

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGA
```

Humanized 131R006B Heavy chain nucleic acid without predicted sequence signal (SEQ ID NO: 67)

```
CAAGTCCAATTGGTCCAGAGCGGTGCCGAAGTGAAGAAACCGGGAGCTTCCGTGAAAGTG

AGCTGCAAGGCTTCTGGATACACCTTCACTGACTATTCAATCCACTGGGTGAGACAGGCA

CCTGGTCAGGGACTGGAGTGGATTGGATACATCTACCCCTCAAATGGGGACTCTGGCTAC

AACCAAAAGTTCAAGAACCGGGTGACTATGACCGTGGATACCTCATACTCTACTGCCTAC

ATGGAACTCAGCAGGCTGCGCTCAGAGGACACCGCAGTGTATTACTGTGCCACCTACTTC

GCTAATAACTTCGACTATTGGGGCAGGGCACCACCCTGACTGTCAGCTCAGCCTCAACC

AAGGGCCCCTCCGTGTTCCCTCTGGCCCCTTGCTCCCGGTCCACCTCTGAGTCTACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCTGCCGTGCTGCAGTCCTCCGGCCTGTAC

TCCCTGTCCTCCGTGGTGACCGTGCCTTCCTCCAACTTCGGCACCCAGACCTACACCTGC

AACGTGGACCACAAGCCTTCCAACACCAAGGTGGACAAGACCGTGGAGCGGAAGTGCTGC

GTGGAGTGCCCTCCTTGTCCTGCTCCTCCTGTGGCTGGCCCTTCTGTGTTCCTGTTCCCT

CCTAAGCCTAAGGACACCCTGATGATCTCCCGGACCCCTGAAGTGACCTGCGTGGTGGTG

GACGTGTCCCACGAGGACCCTGAGGTGCAGTTCAATTGGTACGTGGACGGCGTGGAGGTG

CACAACGCCAAGACCAAGCCTCGGGAGGAACAGTTCAACTCCACCTTCCGGGTGGTGTCT

GTGCTGACCGTGGTGCACCAGGACTGGCTGAACGGCAAAGAATACAAGTGCAAGGTGTCC

AACAAGGGCCTGCCTGCCCCTATCGAAAAGACCATCTCTAAGACCAAGGGCCAGCCTCGC

GAGCCTCAGGTCTACACCCTGCCTCCTAGCCGGGAGGAAATGACCAAGAACCAGGTGTCC

CTGACCTGTCTGGTGAAGGGCTTCTACCCTTCCGATATCGCCGTGGAGTGGGAGTCTAAC

GGCCAGCCTGAGAACAACTACAAGACCACCCCTCCTATGCTGGACTCCGACGGCTCCTTC

TTCCTGTACTCCAAGCTGACAGTGGACAAGTCCCGGTGGCAGCAGGGCAACGTGTTCTCC

TGCTCCGTGATGCACGAGGCCCTGCACAACCACTACACCCAGAAGTCCCTGTCCCTGTCT

CCTGGCAAGTGA
```

-continued

Humanized 131R008/131R010 Heavy chain (IgG1) with predicted signal sequence underlined
(SEQ ID NO: 68)
<u>MKHLWFFLLLVAAPRWVLS</u>QVQLVQSGAEVKKPGASVKVSCKASGYTFTDYSIHWVRQAP
GQGLEWIGYIYPSNGDSGYNQKFKNRVTMTRDTSTSTAYMELSRLRSEDTAVYYCATYFA
NNFDYWGQGTTLTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKSCD
KTHTCPPCPAPELLGGPSVFLFPPKPKDTLMISRTPEVTCVVVDVSHEDPEVKFNWYNDG
VEVHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK Humanized 131R008/131R010 Heavy chain (IgG1) without predicted signal sequence
(SEQ ID NO: 69)
QVQLVQSGAEVKKPGASVKVSCKASGYTFTDYSIHWVRQAPGQGLEWIGYIYPSNGDSGY
NQKFKNRVTMTRDTSTSTAYMELSRLRSEDTAVYYCATYFANNFDYWGQGTTLTVSSAST
KGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK Humanized 131R008 Heavy chain (IgG1) with signal sequence nucleic acid
(SEQ ID NO: 70)
ATGAAGCATCTGTGGTTTTTCCTCCTCCTTGTCGCCGCTCCACGCTGGGTGCTTTCCCAA
GTCCAATTGGTCCAGAGCGGTGCCGAAGTGAAGAAACCGGGAGCTTCCGTGAAAGTGAGC
TGCAAGGCTTCTGGATACACCTTCACTGACTATTCAATCCACTGGGTGAGACAGGCACCT
GGTCAGGGACTGGAGTGGATTGGATACATCTACCCCTCAAATGGGGACTCTGGCTACAAC
CAAAAGTTCAAGAACCGGGTGACTATGACCAGAGATACCTCAACATCTACTGCCTACATG
GAACTCAGCAGGCTGCGCTCAGAGGACACCGCAGTGTATTACTGTGCCACCTACTTCGCT
AATAACTTCGACTATTGGGGCAGGGCACCACCCTGACTGTCAGCTCAGCCTCAACCAAG
GGCCCCTCCGTGTTCCCTCTGGCCCCTTCCTCCAAGTCCACCTCCGGCGGCACCGCCGCT
CTGGGCTGCCTGGTGAAGGACTACTTCCCTGAGCCTGTGACCGTGTCCTGGAACTCTGGC
GCCCTGACCTCTGGCGTGCACACCTTCCCAGCCGTGCTGCAGTCCTCCGGCCTGTACTCC
CTGTCCTCCGTGGTGACCGTGCCTTCCTCCTCCCTGGGCACCCAGACCTACATCTGCAAC
GTGAACCACAAGCCTTCCAACACCAAGGTGGACAAGCGGGTGGAGCCTAAGTCCTGCGAC
AAGACCCACACCTGCCCTCCCTGCCCTGCCCCTGAGCTGCTGGGCGGACCTTCCGTGTTC
CTGTTCCCTCCTAAGCCTAAGGACACCCTGATGATCTCCCGGACCCCTGAGGTGACCTGC
GTGGTGGTGGACGTGTCCCACGAGGATCCTGAGGTGAAGTTCAATTGGTACGTGGACGGC
GTGGAGGTGCACAACGCTAAGACCAAGCCAAGGGAGGAGCAGTACAACTCCACCTACCGG
GTGGTGTCTGTGCTGACCGTGCTGCACCAGGACTGGCTGAACGGCAAAGAATACAAGTGC
AAGGTCTCCAACAAGGCCCTGCCCGCTCCCATCGAGAAAACCATCTCCAAGGCCAAGGGC
CAGCCTCGCGAGCCTCAGGTGTACACCCTGCCACCCAGCCGGGAGGAGATGACCAAGAAC
CAGGTGTCCCTGACCTGTCTGGTGAAGGGCTTCTACCCTTCCGATATCGCCGTGGAGTGG
GAGTCTAACGGCCAGCCCGAGAACAACTACAAGACCACCCCTCCTGTGCTGGACTCCGAC

```
GGCTCCTTCTTCCTGTACTCCAAGCTGACCGTGGACAAGTCCCGGTGGCAGCAGGGCAAC

GTGTTCTCCTGCTCCGTGATGCACGAGGCCCTGCACAACCACTACACCCAGAAGAGCCTG

TCTCTGTCTCCTGGCAAGTGA
```

Humanized 131R008 Heavy chain (IgG1) without predicted signal sequence nucleic acid
(SEQ ID NO: 71)

```
CAAGTCCAATTGGTCCAGAGCGGTGCCGAAGTGAAGAAACCGGGAGCTTCCGTGAAAGTG

AGCTGCAAGGCTTCTGGATACACCTTCACTGACTATTCAATCCACTGGGTGAGACAGGCA

CCTGGTCAGGGACTGGAGTGGATTGGATACATCTACCCCTCAAATGGGGACTCTGGCTAC

AACCAAAAGTTCAAGAACCGGGTGACTATGACCAGAGATACCTCAACATCTACTGCCTAC

ATGGAACTCAGCAGGCTGCGCTCAGAGGACACCGCAGTGTATTACTGTGCCACCTACTTC

GCTAATAACTTCGACTATTGGGGCAGGGCACCACCCTGACTGTCAGCTCAGCCTCAACC

AAGGGCCCCTCCGTGTTCCCTCTGGCCCCTTCCTCCAAGTCCACCTCCGGCGGCACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCAGCCGTGCTGCAGTCCTCCGGCCTGTAC

TCCCTGTCCTCCGTGGTGACCGTGCCTTCCTCCTCCCTGGGCACCCAGACCTACATCTGC

AACGTGAACCACAAGCCTTCCAACACCAAGGTGGACAAGCGGGTGGAGCCTAAGTCCTGC

GACAAGACCCACACCTGCCCTCCTGCCCTGCCCCTGAGCTGCTGGGCGGACCTTCCGTG

TTCCTGTTCCCTCCTAAGCCTAAGGACACCCTGATGATCTCCCGGACCCCTGAGGTGACC

TGCGTGGTGGTGGACGTGTCCCACGAGGATCCTGAGGTGAAGTTCAATTGGTACGTGGAC

GGCGTGGAGGTGCACAACGCTAAGACCAAGCCAAGGGAGGAGCAGTACAACTCCACCTAC

CGGGTGGTGTCTGTGCTGACCGTGCTGCACCAGGACTGGCTGAACGGCAAAGAATACAAG

TGCAAGGTCTCCAACAAGGCCCTGCCCGCTCCCATCGAGAAAACCATCTCCAAGGCCAAG

GGCCAGCCTCGCGAGCCTCAGGTGTACACCCTGCCACCCAGCCGGGAGGAGATGACCAAG

AACCAGGTGTCCCTGACCTGTCTGGTGAAGGGCTTCTACCCTTCCGATATCGCCGTGGAG

TGGGAGTCTAACGGCCAGCCCGAGAACAACTACAAGACCACCCCTCCTGTGCTGGACTCC

GACGGCTCCTTCTTCCTGTACTCCAAGCTGACCGTGGACAAGTCCCGGTGGCAGCAGGGC

AACGTGTTCTCCTGCTCCGTGATGCACGAGGCCCTGCACAACCACTACACCCAGAAGAGC

CTGTCTCTGTCTCCTGGCAAGTGA
```

Humanized 131R005/131R007/131R008 Light chain variable region
(SEQ ID NO: 72)

```
DIVLTQSPASLAVSLGQRATITCKASQSVDYDGDSYMNWYQQKPGQPPKLLIYAASNLES

GIPARFSGSGSGTDFTLTINPVEAEDVATYYCQQSNEDPLTFGAGTKLELKR
```

Humanized 131R005/131R007/131R008 Light chain with predicted signal sequence underlined
(SEQ ID NO: 73)

```
MKHLWFFLLLVAAPRWVLSDIVLTQSPASLAVSLGQRATITCKASQSVDYDGDSYMNWYQ

QKPGQPPKLLIYAASNLESGIPARFSGSGSGTDFTLTINPVEAEDVATYYCQQSNEDPLT

FGAGTKLELKRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC
```

Humanized 131R005/131R007/131R008 Light chain without predicted signal sequence underlined
(SEQ ID NO: 74)

```
DIVLTQSPASLAVSLGQRATITCKASQSVDYDGDSYMNWYQQKPGQPPKLLIYAASNLES

GIPARFSGSGSGTDFTLTINPVEAEDVATYYCQQSNEDPLTFGAGTKLELKRTVAAPSVF

IFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC
```

Humanized 131R005/131R007/131R008 Light chain variable region nucleic acid
(SEQ ID NO: 75)

GATATCGTCCTGACCCAAAGCCCTGCTTCACTTGCTGTGAGCCTGGGGCAACGCGCCACC

ATCACTTGCAAGGCATCTCAGAGCGTGGACTATGATGGAGACTCTTACATGAATTGGTAT

CAACAGAAGCCAGGTCAACCTCCCAAACTGCTGATCTACGCCGCATCTAATCTTGAAAGC

GGCATCCCGGCTCGGTTCTCTGGTTCTGGATCAGGAACCGACTTCACCCTCACCATTAAC

CCAGTGGAGGCCGAGGACGTGGCTACTTACTACTGCCAGCAGTCAAACGAGGACCCCCTG

ACTTTCGGAGCCGGGACCAAGCTGGAGCTTAAGCGT

Humanized 131R005/131R007/131R008 Light chain with signal sequence nucleic acid
(SEQ ID NO: 76)

ATGAAACATCTTTGGTTCTTCCTTCTGCTGGTCGCTGCTCCTCGGTGGGTGCTTAGCGAT

ATCGTCCTGACCCAAAGCCCTGCTTCACTTGCTGTGAGCCTGGGGCAACGCGCCACCATC

ACTTGCAAGGCATCTCAGAGCGTGGACTATGATGGAGACTCTTACATGAATTGGTATCAA

CAGAAGCCAGGTCAACCTCCCAAACTGCTGATCTACGCCGCATCTAATCTTGAAAGCGGC

ATCCCGGCTCGGTTCTCTGGTTCTGGATCAGGAACCGACTTCACCCTCACCATTAACCCA

GTGGAGGCCGAGGACGTGGCTACTTACTACTGCCAGCAGTCAAACGAGGACCCCCTGACT

TTCGGAGCCGGGACCAAGCTGGAGCTTAAGCGTACGGTGGCCGCACCGTCAGTCTTTATC

TTTCCACCCTCCGACGAACAGCTTAAGTCAGGCACTGCCTCAGTCGTGTGTCTCCTCAAT

AACTTCTACCCCAGGGAGGCCAAGGTGCAGTGGAAAGTGGACAACGCCCTCCAGTCCGGG

AACTCTCAAGAAAGCGTCACCGAGCAGGACAGCAAGGACTCCACCTACTCACTGTCAAGC

ACTCTCACCCTCTCAAAGGCCGATTATGAGAAGCACAAGGTGTACGCATGCGAAGTGACC

CATCAGGGTCTGTCCTCTCCTGTCACCAAGTCCTTCAATAGAGGAGAATGTTGA

Humanized 131R005/131R007/131R008 Light chain without predicted signal sequence nucleic acid
(SEQ ID NO: 77)

GATATCGTCCTGACCCAAAGCCCTGCTTCACTTGCTGTGAGCCTGGGGCAACGCGCCACC

ATCACTTGCAAGGCATCTCAGAGCGTGGACTATGATGGAGACTCTTACATGAATTGGTAT

CAACAGAAGCCAGGTCAACCTCCCAAACTGCTGATCTACGCCGCATCTAATCTTGAAAGC

GGCATCCCGGCTCGGTTCTCTGGTTCTGGATCAGGAACCGACTTCACCCTCACCATTAAC

CCAGTGGAGGCCGAGGACGTGGCTACTTACTACTGCCAGCAGTCAAACGAGGACCCCCTG

ACTTTCGGAGCCGGGACCAAGCTGGAGCTTAAGCGTACGGTGGCCGCACCGTCAGTCTTT

ATCTTTCCACCCTCCGACGAACAGCTTAAGTCAGGCACTGCCTCAGTCGTGTGTCTCCTC

AATAACTTCTACCCCAGGGAGGCCAAGGTGCAGTGGAAAGTGGACAACGCCCTCCAGTCC

GGGAACTCTCAAGAAAGCGTCACCGAGCAGGACAGCAAGGACTCCACCTACTCACTGTCA

AGCACTCTCACCCTCTCAAAGGCCGATTATGAGAAGCACAAGGTGTACGCATGCGAAGTG

ACCCATCAGGGTCTGTCCTCTCCTGTCACCAAGTCCTTCAATAGAGGAGAATGTTGA

Variant Heavy chain CDR1
(SEQ ID NO: 78)
DYSIH

Variant Heavy chain CDR2
(SEQ ID NO: 79)
YIYPSNGDSGYNQKFK

Variant Heavy chain CDR3
(SEQ ID NO: 80)
TYFANNFD

Variant Light chain CDR1
(SEQ ID NO: 81)
KASQSVDYDGDSYMN

-continued

Variant Light chain CDR2

(SEQ ID NO: 82)

AASNLES

Variant Light chain CDR3

(SEQ ID NO: 83)

QQSNEDPLTF

Humanized 131R010 Heavy chain (IgG1) with signal sequence nucleic acid (SEQ ID NO: 84)

ATGAAACACTTGTGGTTCTTTCTGCTCCTTGTCGCAGCACCACGGTGGGTGCTGTCGCAA

GTGCAATTGGTGCAGTCCGGAGCGGAAGTGAAGAAGCCTGGTGCCTCGGTCAAAGTCTCA

TGCAAGGCCAGCGGATACACTTTCACCGACTACTCCATCCATTGGGTGAGGCAGGCTCCG

GGCCAGGGCCTGGAGTGGATTGGGTACATCTACCCGTCGAACGGAGATTCGGGGTACAAT

CAGAAGTTCAAGAACCGCGTGACCATGACTCGGGACACCTCAACTTCCACGGCTTATATG

GAACTGAGCCGCCTGAGATCCGAGGACACTGCGGTGTACTACTGTGCCACCTACTTTGCG

AACAATTTCGATTACTGGGGACAAGGAACCACGCTCACTGTCAGCTCAGCCAGCACCAAG

GGCCCCTCCGTGTTCCCTCTGGCCCCTTCCTCCAAGTCCACCTCCGGCGGCACCGCCGCT

CTGGGCTGCCTGGTGAAGGACTACTTCCCTGAGCCTGTGACCGTGTCCTGGAACTCTGGC

GCCCTGACCTCTGGCGTGCACACCTTCCCAGCCGTGCTGCAGTCCTCCGGCCTGTACTCC

CTGTCCTCCGTGGTGACCGTGCCTTCCTCCTCCCTGGGCACCCAGACCTACATCTGCAAC

GTGAACCACAAGCCTTCCAACACCAAGGTGGAAAGCGGGTGGAGCCTAAGTCCTGCGAC

AAGACCCACACCTGCCCTCCCTGCCCTGCCCCTGAGCTGCTGGGCGGACCTTCCGTGTTC

CTGTTCCCTCCTAAGCCTAAGGACACCCTGATGATCTCCCGGACCCCTGAGGTGACCTGC

GTGGTGGTGGACGTGTCCCACGAGGATCCTGAGGTGAAGTTCAATTGGTACGTGGACGGC

GTGGAGGTOCACAACGCTAAGACCAAGCCAAGGGAGGAGCAGTACAACTCCACCTACCGG

GTGGTGTCTGTGCTGACCGTGCTGCACCAGGACTGGCTGAACGGCAAAGAATACAAGTGC

AAGGTCTCCAACAAGGCCCTGCCCGCTCCCATCGAGAAAACCATCTCCAAGGCCAAGGGC

CAGCCTCGCGAGCCTCAGGTGTACACCCTGCCACCCAGCCGGGAGGAGATGACCAAGAAC

CAGGTGTCCCTGACCTGTCTGGTGAAGGGCTTCTACCCTTCCGATATCGCCGTGGAGTGG

GAGTCTAACGGCCAGCCCGAGAACAACTACAAGACCACCCCTCCTGTGCTGGACTCCGAC

GGCTCCTTCTTCCTGTACTCCAAGCTGACCGTGGACAAGTCCCGGTGGCAGCAGGGCAAC

GTGTTCTCCTGCTCCGTGATGCACGAGGCCCTGCACAACCACTACACCCAGAAGAGCCTG

TCTCTGTCTCCTGGCAAGTGATAA

Humanized 131R010 Heavy chain (IgG1) without signal sequence nucleic acid (SEQ ID NO: 85)

CAAGTGCAATTGGTGCAGTCCGGAGCGGAAGTGAAGAAGCCTGGTGCCTCGGTCAAAGTC

TCATGCAAGGCCAGCGGATACACTTTCACCGACTACTCCATCCATTGGGTGAGGCAGGCT

CCGGGCCAGGGCCTGGAGTGGATTGGGTACATCTACCCGTCGAACGGAGATTCGGGGTAC

AATCAGAAGTTCAAGAACCGCGTGACCATGACTCGGGACACCTCAACTTCCACGGCTTAT

ATGGAACTGAGCCGCCTGAGATCCGAGGACACTGCGGTGTACTACTGTGCCACCTACTTT

GCGAACAATTTCGATTACTGGGGACAAGGAACCACGCTCACTGTCAGCTCAGCCAGCACC

AAGGGCCCCTCCGTGTTCCCTCTGGCCCCTTCCTCCAAGTCCACCTCCGGCGGCACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCAGCCGTGCTGCAGTCCTCCGGCCTGTAC

TCCCTGTCCTCCGTGGTGACCGTGCCTTCCTCCTCCCTGGGCACCCAGACCTACATCTGC

AACGTGAACCACAAGCCTTCCAACACCAAGGTGGACAAGCGGGTGGAGCCTAAGTCCTGC

```
GACAAGACCCACACCTGCCCTCCCTGCCCTGCCCCTGAGCTGCTGGGCGGACCTTCCGTG

TTCCTGTTCCCTCCTAAGCCTAAGGACACCCTGATGATCTCCCGGACCCCTGAGGTGACC

TGCGTGGTGGTGGACGTGTCCCACGAGGATCCTGAGGTGAAGTTCAATTGGTACGTGGAC

GGCGTGGAGGTGCACAACGCTAAGACCAAGCCAAGGGAGGAGCAGTACAACTCCACCTAC

CGGGTGGTGTCTGTGCTGACCGTGCTGCACCAGGACTGGCTGAACGGCAAAGAATACAAG

TGCAAGGTCTCCAACAAGGCCCTGCCCGCTCCCATCGAGAAAACCATCTCCAAGGCCAAG

GGCCAGCCTCGCGAGCCTCAGGTGTACACCCTGCCACCCAGCCGGGAGGAGATGACCAAG

AACCAGGTGTCCCTGACCTGTCTGGTGAAGGGCTTCTACCCTTCCGATATCGCCGTGGAG

TGGGAGTCTAACGGCCAGCCCGAGAACAACTACAAGACCACCCCTCCTGTGCTGGACTCC

GACGGCTCCTTCTTCCTGTACTCCAAGCTGACCGTGGACAAGTCCCGGTGGCAGCAGGGC

AACGTGTTCTCCTGCTCCGTGATGCACGAGGCCCTGCACAACCACTACACCCAGAAGAGC

CTGTCTCTGTCTCCTGGCAAGTGATAA
```

Humanized 131R010/131R011 Light chain variable region (SEQ ID NO: 86)

```
DIQMTQSPSSLSASVGDRVTITCKASQSVDYDGDSYMNWYQQKPGKAPKLLIYAASNLES

GVPSRFSGSGSGTDFTLTISPVQAEDFATYYCQQSNEDPLTFGAGTKLELKR
```

Humanized 131R010/131R011 Light chain with predicted signal sequence underlined (SEQ ID NO: 87)

```
MKHLWFFLLLLVAAPRWVLSDIQMTQSPSSLSASVGDRVTITCKASQSVDYDGDSYMNWYQ

QKPGKAPKLLIYAASNLESGVPSRFSGSGSGTDFTLTISPVQAEDFATYYCQQSNEDPLT

FGAGTKLELKRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC
```

Humanized 131R010/131R011 Light chain without predicted signal sequence (SEQ ID NO: 88)

```
DIQMTQSPSSLSASVGDRVTITCKASQSVDYDGDSYMNWYQQKPGKAPKLLIYAASNLES

GVPSRFSGSGSGTDFTLTISPVQAEDFATYYCQQSNEDPLTFGAGTKLELKRTVAAPSVF

IFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC
```

Humanized 131R010/131R011 Light chain variable region nucleic acid (SEQ ID NO: 89)

```
GATATCCAGATGACTCAGTCGCCCTCATCGTTGAGCGCCTCGGTCGGGGATCGCGTGACT

ATTACTTGTAAAGCGTCCCAGAGCGTGGACTACGACGGAGATTCCTACATGAACTGGTAT

CAGCAAAAACCGGGAAAGGCTCCTAAACTTCTCATCTACGCAGCCTCGAATCTGGAATCA

GGAGTCCCGAGCCGGTTCAGCGGATCAGGCTCCGGTACTGATTTTACCCTCACGATCTCG

CCAGTGCAAGCCGAGGACTTCGCGACCTACTACTGCCAACAGTCCAACGAGGACCCGCTG

ACCTTCGGCGCAGGGACCAAGCTGGAACTGAAGCGT
```

Humanized 131R010/131R011 Light chain with signal sequence nucleic acid (SEQ ID NO: 90)

```
ATGAAACACCTGTGGTTCTTCCTCCTGCTGGTGGCAGCTCCCAGATGGGTCCTGTCCGAT

ATCCAGATGACTCAGTCGCCCTCATCGTTGAGCGCCTCGGTCGGGGATCGCGTGACTATT

ACTTGTAAAGCGTCCCAGAGCGTGGACTACGACGGAGATTCCTACATGAACTGGTATCAG

CAAAAACCGGGAAAGGCTCCTAAACTTCTCATCTACGCAGCCTCGAATCTGGAATCAGGA

GTCCCGAGCCGGTTCAGCGGATCAGGCTCCGGTACTGATTTTACCCTCACGATCTCGCCA

GTGCAAGCCGAGGACTTCGCGACCTACTACTGCCAACAGTCCAACGAGGACCCGCTGACC

TTCGGCGCAGGGACCAAGCTGGAACTGAAGCGTACGGTGGCCGCTCCATCCGTGTTTATC
```

-continued

TTTCCGCCGTCCGATGAGCAGCTCAAGTCGGGCACTGCCAGCGTGGTCTGCCTGCTTAAC

AATTTCTACCCTAGGGAAGCCAAGGTGCAGTGGAAGGTGGATAACGCGCTCCAATCCGGT

AACTCGCAAGAGAGCGTGACCGAACAGGACTCAAAGGACTCGACGTACAGCCTGTCATCG

ACCTTGACTCTCTCAAAGGCCGACTACGAAAAGCACAAGGTCTACGCGTGCGAAGTCACC

CATCAGGGACTGTCCTCGCCTGTGACCAAGAGCTTCAATCGCGGAGAGTGCTGA

Humanized 131R010/131R011 Light chain without signal sequence nucleic acid (SEQ ID NO: 91)

GATATCCAGATGACTCAGTCGCCCTCATCGTTGAGCGCCTCGGTCGGGGATCGCGTGACT

ATTACTTGTAAAGCGTCCCAGAGCGTGGACTACGACGGAGATTCCTACATGAACTGGTAT

CAGCAAAAACCGGGAAAGGCTCCTAAACTTCTCATCTACGCAGCCTCGAATCTGGAATCA

GGAGTCCCGAGCCGGTTCAGCGGATCAGGCTCCGGTACTGATTTTACCCTCACGATCTCG

CCAGTGCAAGCCGAGGACTTCGCGACCTACTACTGCCAACAGTCCAACGAGGACCCGCTG

ACCTTCGGCGCAGGGACCAAGCTGGAACTGAAGCGTACGGTGGCCGCTCCATCCGTGTTT

ATCTTTCCGCCGTCCGATGAGCAGCTCAAGTCGGGCACTGCCAGCGTGGTCTGCCTGCTT

AACAATTTCTACCCTAGGGAAGCCAAGGTGCAGTGGAAGGTGGATAACGCGCTCCAATCC

GGTAACTCGCAAGAGAGCGTGACCGAACAGGACTCAAAGGACTCGACGTACAGCCTGTCA

TCGACCTTGACTCTCTCAAAGGCCGACTACGAAAAGCACAAGGTCTACGCGTGCGAAGTC

ACCCATCAGGGACTGTCCTCGCCTGTGACCAAGAGCTTCAATCGCGGAGAGTGCTGA

Humanized 131R011 Heavy chain variable region nucleic acid (SEQ ID NO: 92)

CAAGTGCAATTGGTGCAGTCCGGAGCGGAAGTGAAGAAGCCTGGTGCCTCGGTCAAAGTC

TCATGCAAGGCCAGCGGATACACTTTCACCGACTACTCCATCCATTGGGTGAGGCAGGCT

CCGGGCCAGGGCCTGGAGTGGATTGGGTACATCTACCCGTCGAACGGAGATTCGGGGTAC

AATCAGAAGTTCAAGAACCGCGTGACCATGACTCGGGACACCTCAACTTCCACGGCTTAT

ATGGAACTGAGCCGCCTGAGATCCGAGGACACTGCGGTGTACTACTGTGCCACCTACTTT

GCGAACAATTTCGATTACTGGGGACAAGGAACCACGCTCACTGTCAGCTCA

Humanized 131R011 Heavy chain (IgG2) with signal sequence nucleic acid (SEQ ID NO: 93)

ATGAAACACTTGTGGTTCTTTCTGCTCCTTGTCGCAGCACCACGGTGGGTGCTGTCGCAA

GTGCAATTGGTGCAGTCCGGAGCGGAAGTGAAGAAGCCTGGTGCCTCGGTCAAAGTCTCA

TGCAAGGCCAGCGGATACACTTTCACCGACTACTCCATCCATTGGGTGAGGCAGGCTCCG

GGCCAGGGCCTGGAGTGGATTGGGTACATCTACCCGTCGAACGGAGATTCGGGGTACAAT

CAGAAGTTCAAGAACCGCGTGACCATGACTCGGGACACCTCAACTTCCACGGCTTATATG

GAACTGAGCCGCCTGAGATCCGAGGACACTGCGGTGTACTACTGTGCCACCTACTTTGCG

AACAATTTCGATTACTGGGGACAAGGAACCACGCTCACTGTCAGCTCAGCCAGCACCAAG

GGCCCCTCCGTGTTCCCTCTGGCCCCTTGCTCCCGGTCCACCTCTGAGTCTACCGCCGCT

CTGGGCTGCCTGGTGAAGGACTACTTCCCTGAGCCTGTGACCGTGTCCTGGAACTCTGGC

GCCCTGACCTCTGGCGTGCACACCTTCCCTGCCGTGCTGCAGTCCTCCGGCCTGTACTCC

CTGTCCTCCGTGGTGACCGTGCCTTCCTCCAACTTCGGCACCCAGACCTACACCTGCAAC

GTGGACCACAAGCCTTCCAACACCAAGGTGGACAAGACCGTGGAGCGGAAGTGCTGCGTG

GAGTGCCCTCCTTGTCCTGCTCCTCCTGTGGCTGGCCCTTCTGTGTTCCTGTTCCCTCCT

AAGCCTAAGGACACCCTGATGATCTCCCGGACCCCTGAAGTGACCTGCGTGGTGGTGGAC

GTGTCCCACGAGGACCCTGAGGTGCAGTTCAATTGGTACGTGGACGGCGTGGAGGTGCAC

AACGCCAAGACCAAGCCTCGGGAGGAACAGTTCAACTCCACCTTCCGGGTGGTGTCTGTG

-continued

CTGACCGTGGTGCACCAGGACTGGCTGAACGGCAAAGAATACAAGTGCAAGGTGTCCAAC

AAGGGCCTGCCTGCCCCTATCGAAAAGACCATCTCTAAGACCAAGGGCCAGCCTCGCGAG

CCTCAGGTCTACACCCTGCCTCCTAGCCGGGAGGAAATGACCAAGAACCAGGTGTCCCTG

ACCTGTCTGGTGAAGGGCTTCTACCCTTCCGATATCGCCGTGGAGTGGGAGTCTAACGGC

CAGCCTGAGAACAACTACAAGACCACCCCTCCTATGCTGGACTCCGACGGCTCCTTCTTC

CTGTACTCCAAGCTGACAGTGGACAAGTCCCGGTGGCAGCAGGGCAACGTGTTCTCCTGC

TCCGTGATGCACGAGGCCCTGCACAACCACTACACCCAGAAGTCCCTGTCCCTGTCTCCT

GGCAAGTGATAA

Humanized 131R011 Heavy chain (IgG2) without signal sequence nucleic acid
(SEQ ID NO: 94)

CAAGTGCAATTGGTGCAGTCCGGAGCGGAAGTGAAGAAGCCTGGTGCCTCGGTCAAAGTC

TCATGCAAGGCCAGCGGATACACTTTCACCGACTACTCCATCCATTGGGTGAGGCAGGCT

CCGGGCCAGGGCCTGGAGTGGATTGGGTACATCTACCCGTCGAACGGAGATTCGGGGTAC

AATCAGAAGTTCAAGAACCGCGTGACCATGACTCGGGACACCTCAACTTCCACGGCTTAT

ATGGAACTGAGCCGCCTGAGATCCGAGGACACTGCGGTGTACTACTGTGCCACCTACTTT

GCGAACAATTTCGATTAGTGGGGACAAGGAACCACGCTCACTGTCAGCTCAGCCAGCACC

AAGGGCCCCTCCGTGTTCCCTCTGGCCCCTTGCTCCCGGTCCACCTCTGAGTCTACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCTGCCGTGCTGCAGTCCTCCGGCCTGTAC

TCCCTGTCCTCCGTGGTGACCGTGCCTTCCTCCAACTTCGGCACCCAGACCTACACCTGC

AACGTGGACCACAAGCCTTCCAACACCAAGGTGGACAAGACCGTGGAGCGGAAGTGCTGC

GTGGAGTGCCCTCCTTGTCCTGCTCCTCCTGTGGCTGGCCCTTCTGTGTTCCTGTTCCCT

CCTAAGCCTAAGGACACCCTGATGATCTCCCGGACCCCTGAAGTGACCTGCGTGGTGGTG

GACGTGTCCCACGAGGACCCTGAGGTGCAGTTCAATTGGTACGTGGACGGCGTGGAGGTG

CACAACGCCAAGACCAAGCCTCGGGAGGAACAGTTCAACTCCACCTTCCGGGTGGTGTCT

GTGCTGACCGTGGTGCACCAGGACTGGCTGAACGGCAAAGAATACAAGTGCAAGGTGTCC

AACAAGGGCCTGCCTGCCCCTATCGAAAAGACCATCTCTAAGACCAAGGGCCAGCCTCGC

GAGCCTCAGGTCTACACCCTGCCTCCTAGCCGGGAGGAAATGACCAAGAACCAGGTGTCC

CTGACCTGTCTGGTGAAGGGCTTCTACCCTTCCGATATCGCCGTGGAGTGGGAGTCTAAC

GGCCAGCCTGAGAACAACTACAAGACCACCCCTCCTATGCTGGACTCCGACGGCTCCTTC

TTCCTGTACTCCAAGCTGACAGTGGACAAGTCCCGGTGGCAGCAGGGCAACGTGTTCTCC

TGCTCCGTGATGCACGAGGCCCTGCACAACCACTACACCCAGAAGTCCCTGTCCCTGTCT

CCTGGCAAGTGATAA

Humanized 131R010 Heavy chain variable region
(SEQ ID NO: 95)

CAAGTGCAATTGGTGCAGTCCGGAGCGGAAGTGAAGAAGCCTGGTGCCTCGGTCAAAGTC

TCATGCAAGGCCAGCGGATACACTTTCACCGACTACTCCATCCATTGGGTGAGGCAGGCT

CCGGGCCAGGGCCTGGAGTGGATTGGGTACATCTACCCGTCGAACGGAGATTCGGGGTAC

AATCAGAAGTTCAAGAACCGCGTGACCATGACTCGGGACACCTCAACTTCCACGGCTTAT

ATGGAACTGAGCCGCCTGAGATCCGAGGACACTGCGGTGTACTACTGTGCCACCTACTTT

GCGAACAATTTCGATTACTGGGGACAAGGAACCACGCTCACTGTCAGCTC

What is claimed is:

1. An isolated monoclonal antibody that specifically binds human R-spondin 3 (RSPO3), which comprises:
   (a) a heavy chain CDR1 comprising KASGYTFTDYS (SEQ ID NO:9), KASGYTFTSYTF (SEQ ID NO:34), or DYSIH (SEQ ID NO:78), a heavy chain CDR2 comprising IYPSNGDS (SEQ ID NO:10) or YIYPSNGDSYNQKFK (SEQ ID NO:79), and a heavy chain CDR3 comprising ATYFANYFDY (SEQ ID NO:11), ATYFANNFDY (SEQ ID NO:35), or TYFANNFD (SEQ ID NO:80); and
   (b) a light chain CDR1 comprising QSVDYDGDSYM (SEQ ID NO:12) or KASQSVDYDGDSYMN (SEQ ID NO:81), a light chain CDR2 comprising AAS (SEQ ID NO:13) or AASNLES (SEQ ID NO:82), and a light chain CDR3 comprising QQSNEDPLT (SEQ ID NO:14) or QQSNEDPLTF (SEQ ID NO:83).

2. The antibody of claim 1, which comprises:
   (a) a heavy chain CDR1 comprising KASGYTFTDYS (SEQ ID NO:9), a heavy chain CDR2 comprising IYPSNGDS (SEQ ID NO:10), and a heavy chain CDR3 comprising TYFANNFD (SEQ ID NO:80); and
   (b) a light chain CDR1 comprising QSVDYDGDSYM (SEQ ID NO:12), a light chain CDR2 comprising AAS (SEQ ID NO:13), and a light chain CDR3 comprising QQSNEDPLT (SEQ ID NO:14).

3. The antibody of claim 1, which comprises:
   (a) a heavy chain variable region having at least 90% sequence identity to SEQ ID NO:15, SEQ ID NO:16, SEQ ID NO:36, SEQ ID NO:37, SEQ ID NO:44, SEQ ID NO:45, or SEQ ID NO:62; and
   (b) a light chain variable region having at least 90% sequence identity to SEQ ID NO:17, SEQ ID NO:72, or SEQ ID NO:86.

4. An isolated monoclonal antibody that specifically binds human RSPO3, which comprises:
(a) a heavy chain variable region comprising SEQ ID NO:15 and a light chain variable region comprising SEQ ID NO:17 or SEQ ID NO:72;
(b) a heavy chain variable region comprising SEQ ID NO:16 and a light chain variable region comprising SEQ ID NO:17 or SEQ ID NO:72;
(c) a heavy chain variable region comprising SEQ ID NO:36 and a light chain variable region comprising SEQ ID NO:17 or SEQ ID NO:72;
(d) a heavy chain variable region comprising SEQ ID NO:37 and a light chain variable region comprising SEQ ID NO:17 or SEQ ID NO:72;
(e) a heavy chain variable region comprising SEQ ID NO:44 and a light chain variable region comprising SEQ ID NO:17, SEQ ID NO:72, or SEQ ID NO:86;
(f) a heavy chain variable region comprising SEQ ID NO:45 and a light chain variable region comprising SEQ ID NO:17, SEQ ID NO:72, or SEQ ID NO:86; or
(g) a heavy chain variable region comprising SEQ ID NO:62 and a light chain variable region comprising SEQ ID NO:17, SEQ ID NO:72, or SEQ ID NO:86.

5. The antibody of claim 1, which is a recombinant antibody, a chimeric antibody, a bispecific antibody, a humanized antibody, an IgG1 antibody, an IgG2 antibody, or an antibody fragment comprising an antigen binding site.

6. An isolated monoclonal antibody comprising:
(a) a heavy chain sequence of SEQ ID NO:27, SEQ ID NO:28, SEQ ID NO:39, SEQ ID NO:42, SEQ ID NO:48, SEQ ID NO:49, SEQ ID NO:64, or SEQ ID NO:69; and
(b) a light chain sequence of SEQ ID NO:29, SEQ ID NO:74, or SEQ ID NO:88.

7. The antibody of claim 6, which comprises:
(a) a heavy chain sequence of SEQ ID NO:48 and a light chain sequence of SEQ ID NO:74 or SEQ ID NO:88;
(b) a heavy chain sequence of SEQ ID NO:64 and a light chain sequence of SEQ ID NO:74 or SEQ ID NO:88; or
(c) a heavy chain sequence of SEQ ID NO:69 and a light chain sequence of SEQ ID NO:74 or SEQ ID NO:88.

8. An isolated monoclonal antibody comprising the heavy chain variable region encoded by the plasmid deposited with ATCC as PTA-120420 and the light chain variable region encoded by the plasmid deposited with ATCC as PTA-120421.

9. An isolated polypeptide comprising a sequence selected from the group consisting of: SEQ ID NO:15, SEQ ID NO:16, SEQ ID NO:21, SEQ ID NO:22, SEQ ID NO:23, SEQ ID NO:27, SEQ ID NO:28, SEQ ID NO:36, SEQ ID NO:37, SEQ ID NO:38, SEQ ID NO:39, SEQ ID NO:41, SEQ ID NO:42, SEQ ID NO:44, SEQ ID NO:45, SEQ ID NO:46, SEQ ID NO:47, SEQ ID NO:48, SEQ ID NO:49, SEQ ID NO:62, SEQ ID NO:63, SEQ ID NO:64 SEQ ID NO:68, SEQ ID NO:69, SEQ ID NO:72, SEQ ID NO:73, SEQ ID NO:74, SEQ ID NO:86, SEQ ID NO:87, and SEQ ID NO:88.

10. A cell comprising or producing the antibody of claim 1.

11. A pharmaceutical composition comprising the antibody of claim 1 and a pharmaceutically acceptable carrier.

12. The antibody of claim 1, which comprises:
(a) a heavy chain CDR1 comprising DYSIH (SEQ ID NO:78), a heavy chain CDR2 comprising YIYPSNGDSGYNQKFK (SEQ ID NO:79), and a heavy chain CDR3 comprising TYFANNFD (SEQ ID NO:80); and
(b) a light chain CDR1 comprising KASQSVDYDGDSYMN (SEQ ID NO:81), a light chain CDR2 comprising AASNLES (SEQ ID NO:82), and a light chain CDR3 comprising QQSNEDPLT (SEQ ID NO:14).

13. The antibody of claim 12, which is a recombinant antibody, a chimeric antibody, a bispecific antibody, a humanized antibody, an IgG1 antibody, an IgG2 antibody, or an antibody fragment comprising an antigen binding site.

14. A pharmaceutical composition comprising the antibody of claim 12 and a pharmaceutically acceptable carrier.

15. An isolated monoclonal antibody that specifically binds human RSPO3, which comprises a heavy chain variable region comprising SEQ ID NO:44 and a light chain variable region comprising SEQ ID NO:86.

* * * * *

SEQUENCE LISTING

<160> NUMBER OF SEQ ID NOS: 95

<210> SEQ ID NO 1
<211> LENGTH: 263
<212> TYPE: PRT
<213> ORGANISM: Homo sapiens

<400> SEQUENCE: 1

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260

<210> SEQ ID NO 2
<211> LENGTH: 243
<212> TYPE: PRT
<213> ORGANISM: Homo sapiens

<400> SEQUENCE: 2

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg

```
            50                  55                  60
Arg Glu Gly Met Arg Gln Tyr Gly Glu Cys Leu His Ser Cys Pro Ser
 65                  70                  75                  80

Gly Tyr Tyr Gly His Arg Ala Pro Asp Met Asn Arg Cys Ala Arg Cys
                 85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
                115                 120                 125

Pro Asp Gly Phe Ala Pro Leu Glu Glu Thr Met Glu Cys Val Glu Gly
        130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
            195                 200                 205

Thr Pro Lys Ala Lys Glu Lys Arg Asn Lys Lys Lys Arg Lys Leu
        210                 215                 220

Ile Glu Arg Ala Gln Glu Gln His Ser Val Phe Leu Ala Thr Asp Arg
225                 230                 235                 240

Ala Asn Gln

<210> SEQ ID NO 3
<211> LENGTH: 272
<212> TYPE: PRT
<213> ORGANISM: Homo sapiens

<400> SEQUENCE: 3

Met His Leu Arg Leu Ile Ser Trp Leu Phe Ile Ile Leu Asn Phe Met
  1               5                  10                  15

Glu Tyr Ile Gly Ser Gln Asn Ala Ser Arg Gly Arg Gln Arg Arg
             20                  25                  30

Met His Pro Asn Val Ser Gln Gly Cys Gln Gly Gly Cys Ala Thr Cys
         35                  40                  45

Ser Asp Tyr Asn Gly Cys Leu Ser Cys Lys Pro Arg Leu Phe Phe Ala
 50                  55                  60

Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
        130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
```

```
                         180                 185                 190
Thr Asn Glu Thr Arg Lys Cys Thr Val Gln Arg Lys Lys Cys Gln Lys
            195                 200                 205
Gly Glu Arg Gly Lys Lys Gly Arg Glu Arg Lys Arg Lys Lys Pro Asn
            210                 215                 220
Lys Gly Glu Ser Lys Glu Ala Ile Pro Asp Ser Lys Ser Leu Glu Ser
225                 230                 235                 240
Ser Lys Glu Ile Pro Glu Gln Arg Glu Asn Lys Gln Gln Gln Lys Lys
            245                 250                 255
Arg Lys Val Gln Asp Lys Gln Lys Ser Val Ser Val Ser Thr Val His
            260                 265                 270
```

<210> SEQ ID NO 4
<211> LENGTH: 272
<212> TYPE: PRT
<213> ORGANISM: Homo sapiens

<400> SEQUENCE: 4

```
Met His Leu Arg Leu Ile Ser Trp Leu Phe Ile Ile Leu Asn Phe Met
1               5                   10                  15
Glu Tyr Ile Gly Ser Gln Asn Ala Ser Arg Gly Arg Arg Gln Arg Arg
            20                  25                  30
Met His Pro Asn Val Ser Gln Gly Cys Gln Gly Gly Cys Ala Thr Cys
            35                  40                  45
Ser Asp Tyr Asn Gly Cys Leu Ser Cys Lys Pro Arg Leu Phe Phe Ala
    50                  55                  60
Leu Glu Arg Ile Gly Met Lys Gln Ile Gly Val Cys Leu Ser Ser Cys
65                  70                  75                  80
Pro Ser Gly Tyr Tyr Gly Thr Arg Tyr Pro Asp Ile Asn Lys Cys Thr
                85                  90                  95
Lys Cys Lys Ala Asp Cys Asp Thr Cys Phe Asn Lys Asn Phe Cys Thr
            100                 105                 110
Lys Cys Lys Ser Gly Phe Tyr Leu His Leu Gly Lys Cys Leu Asp Asn
            115                 120                 125
Cys Pro Glu Gly Leu Glu Ala Asn Asn His Thr Met Glu Cys Val Ser
        130                 135                 140
Ile Val His Cys Glu Val Ser Glu Trp Asn Pro Trp Ser Pro Cys Thr
145                 150                 155                 160
Lys Lys Gly Lys Thr Cys Gly Phe Lys Arg Gly Thr Glu Thr Arg Val
                165                 170                 175
Arg Glu Ile Ile Gln His Pro Ser Ala Lys Gly Asn Leu Cys Pro Pro
            180                 185                 190
Thr Asn Glu Thr Arg Lys Cys Thr Val Gln Arg Lys Lys Cys Gln Lys
            195                 200                 205
Gly Glu Arg Gly Lys Lys Gly Arg Glu Arg Lys Arg Lys Lys Pro Asn
            210                 215                 220
Lys Gly Glu Ser Lys Glu Ala Ile Pro Asp Ser Lys Ser Leu Glu Ser
225                 230                 235                 240
Ser Lys Glu Ile Pro Glu Gln Arg Glu Asn Lys Gln Gln Gln Lys Lys
            245                 250                 255
Arg Lys Val Gln Asp Lys Gln Lys Ser Val Ser Val Ser Thr Val His
            260                 265                 270
```

<210> SEQ ID NO 5
<211> LENGTH: 251

```
<212> TYPE: PRT
<213> ORGANISM: Homo sapiens

<400> SEQUENCE: 5

Gln Asn Ala Ser Arg Gly Arg Gln Arg Met His Pro Asn Val
1               5                   10                  15

Ser Gln Gly Cys Gln Gly Gly Cys Ala Thr Cys Ser Asp Tyr Asn Gly
            20                  25                  30

Cys Leu Ser Cys Lys Pro Arg Leu Phe Phe Ala Leu Glu Arg Ile Gly
        35                  40                  45

Met Lys Gln Ile Gly Val Cys Leu Ser Ser Cys Pro Ser Gly Tyr Tyr
    50                  55                  60

Gly Thr Arg Tyr Pro Asp Ile Asn Lys Cys Thr Lys Cys Lys Ala Asp
65                  70                  75                  80

Cys Asp Thr Cys Phe Asn Lys Asn Phe Cys Thr Lys Cys Lys Ser Gly
                85                  90                  95

Phe Tyr Leu His Leu Gly Lys Cys Leu Asp Asn Cys Pro Glu Gly Leu
            100                 105                 110

Glu Ala Asn Asn His Thr Met Glu Cys Val Ser Ile Val His Cys Glu
        115                 120                 125

Val Ser Glu Trp Asn Pro Trp Ser Pro Cys Thr Lys Lys Gly Lys Thr
    130                 135                 140

Cys Gly Phe Lys Arg Gly Thr Glu Thr Arg Val Arg Glu Ile Ile Gln
145                 150                 155                 160

His Pro Ser Ala Lys Gly Asn Leu Cys Pro Pro Thr Asn Glu Thr Arg
                165                 170                 175

Lys Cys Thr Val Gln Arg Lys Lys Cys Gln Lys Gly Glu Arg Gly Lys
            180                 185                 190

Lys Gly Arg Glu Arg Lys Arg Lys Pro Asn Lys Gly Glu Ser Lys
        195                 200                 205

Glu Ala Ile Pro Asp Ser Lys Ser Leu Glu Ser Ser Lys Glu Ile Pro
    210                 215                 220

Glu Gln Arg Glu Asn Lys Gln Gln Lys Lys Arg Lys Val Gln Asp
225                 230                 235                 240

Lys Gln Lys Ser Val Ser Val Ser Thr Val His
            245                 250

<210> SEQ ID NO 6
<211> LENGTH: 52
<212> TYPE: PRT
<213> ORGANISM: Homo sapiens

<400> SEQUENCE: 6

Pro Asn Val Ser Gln Gly Cys Gln Gly Gly Cys Ala Thr Cys Ser Asp
1               5                   10                  15

Tyr Asn Gly Cys Leu Ser Cys Lys Pro Arg Leu Phe Phe Ala Leu Glu
            20                  25                  30

Arg Ile Gly Met Lys Gln Ile Gly Val Cys Leu Ser Ser Cys Pro Ser
        35                  40                  45

Gly Tyr Tyr Gly
    50

<210> SEQ ID NO 7
<211> LENGTH: 44
<212> TYPE: PRT
<213> ORGANISM: Homo sapiens
```

-continued

<400> SEQUENCE: 7

Ile Asn Lys Cys Thr Lys Cys Lys Ala Asp Cys Asp Thr Cys Phe Asn
1               5                   10                  15

Lys Asn Phe Cys Thr Lys Cys Lys Ser Gly Phe Tyr Leu His Leu Gly
            20                  25                  30

Lys Cys Leu Asp Asn Cys Pro Glu Gly Leu Glu Ala
        35                  40

<210> SEQ ID NO 8
<211> LENGTH: 61
<212> TYPE: PRT
<213> ORGANISM: Homo sapiens

<400> SEQUENCE: 8

His Cys Glu Val Ser Glu Trp Asn Pro Trp Ser Pro Cys Thr Lys Lys
1               5                   10                  15

Gly Lys Thr Cys Gly Phe Lys Arg Gly Thr Glu Thr Arg Val Arg Glu
            20                  25                  30

Ile Ile Gln His Pro Ser Ala Lys Gly Asn Leu Cys Pro Pro Thr Asn
        35                  40                  45

Glu Thr Arg Lys Cys Thr Val Gln Arg Lys Lys Cys Gln
    50                  55                  60

<210> SEQ ID NO 9
<211> LENGTH: 11
<212> TYPE: PRT
<213> ORGANISM: Artificial sequence
<220> FEATURE:
<223> OTHER INFORMATION: 131R002/131R003 Heavy chain CDR1

<400> SEQUENCE: 9

Lys Ala Ser Gly Tyr Thr Phe Thr Asp Tyr Ser
1               5                   10

<210> SEQ ID NO 10
<211> LENGTH: 8
<212> TYPE: PRT
<213> ORGANISM: Artificial sequence
<220> FEATURE:
<223> OTHER INFORMATION: 131R002/131R003 Heavy chain CDR2

<400> SEQUENCE: 10

Ile Tyr Pro Ser Asn Gly Asp Ser
1               5

<210> SEQ ID NO 11
<211> LENGTH: 10
<212> TYPE: PRT
<213> ORGANISM: Artificial sequence
<220> FEATURE:
<223> OTHER INFORMATION: 131R002/131R003 Heavy chain CDR3

<400> SEQUENCE: 11

Ala Thr Tyr Phe Ala Asn Tyr Phe Asp Tyr
1               5                   10

<210> SEQ ID NO 12
<211> LENGTH: 11
<212> TYPE: PRT
<213> ORGANISM: Artificial sequence
<220> FEATURE:
<223> OTHER INFORMATION: 131R002/131R003 Light chain CDR1

<400> SEQUENCE: 12

```
Gln Ser Val Asp Tyr Asp Gly Asp Ser Tyr Met
1               5                   10

<210> SEQ ID NO 13
<211> LENGTH: 3
<212> TYPE: PRT
<213> ORGANISM: Artificial sequence
<220> FEATURE:
<223> OTHER INFORMATION: 131R002/131R003 Light chain CDR2

<400> SEQUENCE: 13

Ala Ala Ser
1

<210> SEQ ID NO 14
<211> LENGTH: 9
<212> TYPE: PRT
<213> ORGANISM: Artificial sequence
<220> FEATURE:
<223> OTHER INFORMATION: 131R002/131R003 Light chain CDR3

<400> SEQUENCE: 14

Gln Gln Ser Asn Glu Asp Pro Leu Thr
1               5

<210> SEQ ID NO 15
<211> LENGTH: 120
<212> TYPE: PRT
<213> ORGANISM: Artificial sequence
<220> FEATURE:
<223> OTHER INFORMATION: 131R002 Heavy chain variable region

<400> SEQUENCE: 15

Gln Val Gln Leu Gln Glu Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Ser Ile His Trp Val Lys Gln Asn His Gly Lys Ser Leu Asp Trp Ile
        35                  40                  45

Gly Tyr Ile Tyr Pro Ser Asn Gly Asp Ser Gly Tyr Asn Gln Lys Phe
    50                  55                  60

Lys Asn Arg Ala Thr Leu Thr Val Asp Thr Ser Ser Ser Thr Ala Tyr
65                  70                  75                  80

Leu Glu Val Arg Arg Leu Thr Phe Glu Asp Ser Ala Val Tyr Tyr Cys
                85                  90                  95

Ala Thr Tyr Phe Ala Asn Tyr Phe Asp Tyr Trp Gly Gln Gly Thr Thr
            100                 105                 110

Leu Thr Val Ser Ser Ala Ser Thr
        115                 120

<210> SEQ ID NO 16
<211> LENGTH: 120
<212> TYPE: PRT
<213> ORGANISM: Artificial sequence
<220> FEATURE:
<223> OTHER INFORMATION: 131R003 Heavy chain variable region

<400> SEQUENCE: 16

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30
```

```
Ser Ile His Trp Val Lys Gln Asn His Gly Lys Ser Leu Asp Trp Ile
            35                  40                  45

Gly Tyr Ile Tyr Pro Ser Asn Gly Asp Ser Gly Tyr Asn Gln Lys Phe
        50                  55                  60

Lys Asn Arg Ala Thr Leu Thr Val Asp Thr Ser Tyr Ser Thr Ala Tyr
 65                  70                  75                  80

Leu Glu Val Arg Arg Leu Thr Phe Glu Asp Ser Ala Val Tyr Tyr Cys
                85                  90                  95

Ala Thr Tyr Phe Ala Asn Tyr Phe Asp Tyr Trp Gly Gln Gly Thr Thr
            100                 105                 110

Leu Thr Val Ser Ser Ala Ser Thr
            115                 120

<210> SEQ ID NO 17
<211> LENGTH: 112
<212> TYPE: PRT
<213> ORGANISM: Artificial sequence
<220> FEATURE:
<223> OTHER INFORMATION: 131R002/131R003 Light chain variable region

<400> SEQUENCE: 17

Asp Ile Val Leu Thr Gln Ser Pro Ala Ser Leu Ala Val Ser Leu Gly
 1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

<210> SEQ ID NO 18
<211> LENGTH: 360
<212> TYPE: DNA
<213> ORGANISM: Artificial sequence
<220> FEATURE:
<223> OTHER INFORMATION: 131R002 Heavy chain variable region nucleotide
      sequence

<400> SEQUENCE: 18
caggtacaat tgcaagaatc cggacccgaa cttgtgaagc cggagcgtc  agtcaagatc      60 tcgtgtaagg ccagcgggta cacctttacg gattattcga tccattgggt aaaacagaat    120
cacgggaagt cgctcgactg gattggttat atctacccgt ccaacggtga ttcgggatac    180
aaccagaagt tcaaaaatcg ggccacactt acagtggaca tcgtcgtc  aactgcatat    240 ctcgaggtcc gcagactgac gtttgaggac tcagctgtct actattgcgc gacttatttc    300
gccaactact tcgattactg gggccagggg acgacactga cggtcagctc cgcgagcacc    360

<210> SEQ ID NO 19
<211> LENGTH: 360
<212> TYPE: DNA
<213> ORGANISM: Artificial sequence
<220> FEATURE:
```

<223> OTHER INFORMATION: 131R003 Heavy chain variable region nucleotide
      sequence

<400> SEQUENCE: 19

```
caggtgcaac ttaaacagtc ggggcctgag ttggtcaaac caggagcctc agtaaagatt    60
agctgcaaag catcaggtta tacctttacg gattactcga tccactgggt gaagcagaac   120
cacggaaagt cactggattg gatcgggtac atctacccct cgaatggaga ttcggggtat   180
aaccaaaagt tcaaaaaccg ggccacgctg actgtggaca cgtcgtattc caccgcatat   240
ttggaagtcc gcagactcac gttcgaggac tccgcggtat actattgtgc cacatacttt   300
gcgaattact ttgactactg gggtcagggc acaacgctta ctgtctccag cgcgtcaaca   360
```

<210> SEQ ID NO 20
<211> LENGTH: 336
<212> TYPE: DNA
<213> ORGANISM: Artificial sequence
<220> FEATURE:
<223> OTHER INFORMATION: 131R002/131R003 Light chain variable region
      nucleotide sequence

<400> SEQUENCE: 20

```
gacatcgtgc tcacacagag ccctgcatcg ctcgcagtat cgcttggtca gcgagcgacc    60
atttcatgca aagcgtcaca atcggtagat tacgacggag actcctacat gaactggtat   120
cagcagaaac cagggcagcc cccgaagttg ctcatctacg ccgcgtccaa tctggagtca   180
ggcattcccg ccagattcag cgggagcggg tcaggaacgg atttttaccct caatatccat   240
ccggtagagg aggaagatgc ggcgacttac tattgtcagc agtcgaatga ggacccactc   300
acgttcgggg ctggaacaaa actggaactt aaacgg                              336
```

<210> SEQ ID NO 21
<211> LENGTH: 462
<212> TYPE: PRT
<213> ORGANISM: Artificial sequence
<220> FEATURE:
<223> OTHER INFORMATION: 131R002 Heavy chain amino acid sequence

<400> SEQUENCE: 21

```
Met Lys His Leu Trp Phe Phe Leu Leu Val Ala Ala Pro Arg Trp
1               5                   10                  15

Val Leu Ser Gln Val Gln Leu Gln Glu Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Ser Ile His Trp Val Lys Gln Asn His Gly Lys Ser Leu
    50                  55                  60

Asp Trp Ile Gly Tyr Ile Tyr Pro Ser Asn Gly Asp Ser Gly Tyr Asn
65                  70                  75                  80

Gln Lys Phe Lys Asn Arg Ala Thr Leu Thr Val Asp Thr Ser Ser Ser
                85                  90                  95

Thr Ala Tyr Leu Glu Val Arg Arg Leu Thr Phe Glu Asp Ser Ala Val
            100                 105                 110

Tyr Tyr Cys Ala Thr Tyr Phe Ala Asn Tyr Phe Asp Tyr Trp Gly Gln
        115                 120                 125

Gly Thr Thr Leu Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160
```

-continued

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
        180                 185                 190

Leu Gln Ser Ser Gly Leu Tyr Ser Leu Ser Ser Val Val Thr Val Pro
    195                 200                 205

Ser Ser Asn Phe Gly Thr Gln Thr Tyr Thr Cys Asn Val Asp His Lys
210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 22
<211> LENGTH: 462
<212> TYPE: PRT
<213> ORGANISM: Artificial sequence
<220> FEATURE:
<223> OTHER INFORMATION: 131R003 Heavy chain amino acid sequence

<400> SEQUENCE: 22

Met Lys His Leu Trp Phe Phe Leu Leu Leu Val Ala Ala Pro Arg Trp
1               5                   10                  15

Val Leu Ser Gln Val Gln Leu Lys Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Ser Ile His Trp Val Lys Gln Asn His Gly Lys Ser Leu
    50                  55                  60

```
Asp Trp Ile Gly Tyr Ile Tyr Pro Ser Asn Gly Asp Ser Gly Tyr Asn
 65                  70                  75                  80

Gln Lys Phe Lys Asn Arg Ala Thr Leu Thr Val Asp Thr Ser Tyr Ser
                 85                  90                  95

Thr Ala Tyr Leu Glu Val Arg Arg Leu Thr Phe Glu Asp Ser Ala Val
            100                 105                 110

Tyr Tyr Cys Ala Thr Tyr Phe Ala Asn Tyr Phe Asp Tyr Trp Gly Gln
            115                 120                 125

Gly Thr Thr Leu Thr Val Ser Ser Ala Ser Thr Lys Gly Pro Ser Val
130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Asn Phe Gly Thr Gln Thr Tyr Thr Cys Asn Val Asp His Lys
210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Gln Phe Asn Trp Tyr Val Asp Gly Val Glu Val His Asn Ala Lys Thr
290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
                340                 345                 350

Lys Thr Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
450                 455                 460

<210> SEQ ID NO 23
<211> LENGTH: 237
```

<212> TYPE: PRT
<213> ORGANISM: Artificial sequence
<220> FEATURE:
<223> OTHER INFORMATION: 131R002/131R003 Light chain amino acid
      sequence

<400> SEQUENCE: 23

Met Lys His Leu Trp Phe Phe Leu Leu Leu Val Ala Ala Pro Arg Trp
1               5                   10                  15

Val Leu Ser Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Tyr Asp Gly Asp Ser Tyr Met Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Asn Glu Asp Pro Leu Thr Phe Gly Ala Gly Thr Lys Leu Glu
        115                 120                 125

Leu Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 24
<211> LENGTH: 1389
<212> TYPE: DNA
<213> ORGANISM: Artificial sequence
<220> FEATURE:
<223> OTHER INFORMATION: 131R002 Heavy chain nucleotide sequence

<400> SEQUENCE: 24
atgaaacact tgtggttctt tcttttgctg gtggcagcgc ctaggtgggt gctcagccag      60
gtacaattgc aagaatccgg acccgaactt gtgaagcccg gagcgtcagt caagatctcg     120
tgtaaggcca gcgggtacac ctttacggat tattcgatcc attgggtaaa acagaatcac     180
gggaagtcgc tcgactggat tggttatatc tacccgtcca acggtgattc gggatacaac     240
cagaagttca aaatcgggc cacacttaca gtggacacat cgtcgtcaac tgcatatctc      300
gaggtccgca gactgacgtt tgaggactca gctgtctact attgcgcgac ttatttcgcc     360
aactacttcg attactgggg ccaggggacg acactgacgg tcagctccgc gagcaccaag     420
ggcccctccg tgttccctct ggccccttgc tccggtccca cctctgagtc taccgccgct     480

```
ctgggctgcc tggtgaagga ctacttccct gagcctgtga ccgtgtcctg gaactctggc      540
gccctgacct ctggcgtgca caccttccct gccgtgctgc agtcctccgg cctgtactcc      600
ctgtcctccg tggtgaccgt gccttcctcc aacttcggca cccagaccta cacctgcaac      660
gtggaccaca gccttccaa caccaaggtg acaagaccg tggagcggaa gtgctgcgtg        720
gagtgccctc cttgtcctgc tcctcctgtg gctggccctt ctgtgttcct gttccctcct      780
aagcctaagg acaccctgat gatctcccgg accctgaag tgacctgcgt ggtggtggac       840
gtgtcccacg aggaccctga ggtgcagttc aattggtacg tggacggcgt ggaggtgcac     900
aacgccaaga ccaagcctcg ggaggaacag ttcaactcca ccttccgggt ggtgtctgtg      960
ctgaccgtgg tgcaccagga ctggctgaac ggcaaagaat acaagtgcaa ggtgtccaac     1020
aagggcctgc ctgcccctat cgaaaagacc atctctaaga ccaagggcca gcctcgcgag     1080
cctcaggtct acaccctgcc tcctagccgg gaggaaatga ccaagaacca ggtgtccctg     1140
acctgtctgg tgaagggctt ctaccccttcc gatatcgccg tggagtggga gtctaacggc    1200
cagcctgaga caactacaa gaccacccct cctatgctgg actccgacgg ctccttcttc      1260
ctgtactcca agctgacagt ggacaagtcc cggtggcagc agggcaacgt gttctcctgc     1320
tccgtgatgc acgaggccct gcacaaccac tacacccaga gtccctgtc cctgtctcct      1380 ggcaagtga                                                              1389
```

<210> SEQ ID NO 25
<211> LENGTH: 1389
<212> TYPE: DNA
<213> ORGANISM: Artificial sequence
<220> FEATURE:
<223> OTHER INFORMATION: 131R003 Heavy chain nucleotide sequence

<400> SEQUENCE: 25

```
atgaagcatc tttggttctt cctgctcttg gtggctgcgc cgaggtgggt gctcagccag      60
gtgcaactta acagtcggg gcctgagttg gtcaaaccag gagcctcagt aaagattagc      120
tgcaaagcat caggttatac ctttacggat tactcgatcc actgggtgaa gcagaaccac      180
ggaaagtcac tggattggat cgggtacatc taccccctcga atggagattc ggggtataac    240
caaaagttca aaaccgggc acgctgact gtggacacgt cgtattccac cgcatatttg       300
gaagtccgca gactcacgtt cgaggactcc gcggtatact attgtgccac atactttgcg     360
aattactttg actactgggg tcagggcaca acgcttactg tctccagcgc gtcaacaaag     420 ggccctccg tgttccctct ggccccttgc tccggtcca cctctgagtc taccgccgct       480
ctgggctgcc tggtgaagga ctacttccct gagcctgtga ccgtgtcctg gaactctggc    540
gccctgacct ctggcgtgca caccttccct gccgtgctgc agtcctccgg cctgtactcc    600
ctgtcctccg tggtgaccgt gccttcctcc aacttcggca cccagaccta cacctgcaac    660
gtggaccaca gccttccaa caccaaggtg acaagaccg tggagcggaa gtgctgcgtg      720
gagtgccctc cttgtcctgc tcctcctgtg gctggccctt ctgtgttcct gttccctcct    780
aagcctaagg acaccctgat gatctcccgg accctgaag tgacctgcgt ggtggtggac     840
gtgtcccacg aggaccctga ggtgcagttc aattggtacg tggacggcgt ggaggtgcac   900
aacgccaaga ccaagcctcg ggaggaacag ttcaactcca ccttccgggt ggtgtctgtg    960
ctgaccgtgg tgcaccagga ctggctgaac ggcaaagaat acaagtgcaa ggtgtccaac   1020
aagggcctgc ctgcccctat cgaaaagacc atctctaaga ccaagggcca gcctcgcgag   1080
cctcaggtct acaccctgcc tcctagccgg gaggaaatga ccaagaacca ggtgtccctg   1140
```

-continued

```
acctgtctgg tgaagggctt ctacccttcc gatatcgccg tggagtggga gtctaacggc   1200
cagcctgaga caactacaa gaccaccct cctatgctgg actccgacgg ctccttcttc   1260
ctgtactcca agctgacagt ggacaagtcc cggtggcagc agggcaacgt gttctcctgc   1320
tccgtgatgc acgaggccct gcacaaccac tacacccaga gtccctgtc cctgtctcct   1380 ggcaagtga                                                          1389
```

<210> SEQ ID NO 26
<211> LENGTH: 714
<212> TYPE: DNA
<213> ORGANISM: Artificial sequence
<220> FEATURE:
<223> OTHER INFORMATION: 131R002/131R003 Light chain nucleotide sequence

<400> SEQUENCE: 26

```
atgaagcacc tctggttctt tcttcttctg gtcgcagcgc cgagatgggt acttagcgac    60
atcgtgctca cacagagccc tgcatcgctc gcagtatcgc ttggtcagcg agcgaccatt   120
tcatgcaaag cgtcacaatc ggtagattac gacggagact cctacatgaa ctggtatcag   180
cagaaaccag gcagccccc gaagttgctc atctacgccg cgtccaatct ggagtcaggc   240
attcccgcca gattcagcgg gagcgggtca ggaacggatt ttaccctcaa tatccatccg   300
gtagaggagg aagatgcggc gacttactat tgtcagcagt cgaatgagga cccactcacg   360
ttcggggctg gaacaaaact ggaacttaaa cggactgtgg cggctccctc agtgttcatc   420
ttccctccct ccgacgaaca attgaagtcg gtactgcctc ccgtcgtctg tttgttgaac   480 aactttatc cgagggaagc caaggtgcag tggaaggtgg ataatgcgct gcagagcggt   540
aactcgcaag agtcagtcac agagcaagac tcgaaggatt cgacgtattc gctcagcagc   600
acattgacgc tgtcgaaggc agattacgag aaacacaagg tgtacgcgtg cgaggtcacc   660
catcagggat gtgtcgtcacc cgtgacgaaa tcctttaacc gcggagaatg ctga        714
```

<210> SEQ ID NO 27
<211> LENGTH: 443
<212> TYPE: PRT
<213> ORGANISM: Artificial sequence
<220> FEATURE:
<223> OTHER INFORMATION: 131R002 Heavy chain amino acid sequence

<400> SEQUENCE: 27

```
Gln Val Gln Leu Gln Glu Ser Gly Pro Glu Leu Val Lys Pro Gly Ala
  1               5                  10                  15

Ser Val Lys Ile Ser Cys Lys Ala Ser Gly Tyr Thr Phe Thr Asp Tyr
             20                  25                  30

Ser Ile His Trp Val Lys Gln Asn His Gly Lys Ser Leu Asp Trp Ile
         35                  40                  45

Gly Tyr Ile Tyr Pro Ser Asn Gly Asp Ser Tyr Asn Gln Lys Phe
     50                  55                  60

Lys Asn Arg Ala Thr Leu Thr Val Asp Thr Ser Ser Ser Thr Ala Tyr
 65                  70                  75                  80

Leu Glu Val Arg Arg Leu Thr Phe Glu Asp Ser Ala Val Tyr Tyr Cys
             85                  90                  95

Ala Thr Tyr Phe Ala Asn Tyr Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125
```

```
Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 28
<211> LENGTH: 443
<212> TYPE: PRT
<213> ORGANISM: Artificial sequence
<220> FEATURE:
<223> OTHER INFORMATION: 131R003 Heavy chain amino acid sequence

<400> SEQUENCE: 28

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Ser Ile His Trp Val Lys Gln Asn His Gly Lys Ser Leu Asp Trp Ile
        35                  40                  45
```

-continued

Gly Tyr Ile Tyr Pro Ser Asn Gly Asp Ser Gly Tyr Asn Gln Lys Phe
              50                  55                  60

Lys Asn Arg Ala Thr Leu Thr Val Asp Thr Ser Tyr Ser Thr Ala Tyr
 65                  70                  75                  80

Leu Glu Val Arg Arg Leu Thr Phe Glu Asp Ser Ala Val Tyr Tyr Cys
                     85                  90                  95

Ala Thr Tyr Phe Ala Asn Tyr Phe Asp Tyr Trp Gly Gln Gly Thr Thr
                100                 105                 110

Leu Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 29
<211> LENGTH: 218

<212> TYPE: PRT
<213> ORGANISM: Artificial sequence
<220> FEATURE:
<223> OTHER INFORMATION: 131R002/131R003 Light chain amino acid
      sequence

<400> SEQUENCE: 29

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 30
<211> LENGTH: 1332
<212> TYPE: DNA
<213> ORGANISM: Artificial sequence
<220> FEATURE:
<223> OTHER INFORMATION: 131R002 Heavy chain amino acid sequence

<400> SEQUENCE: 30
caggtacaat tgcaagaatc cggacccgaa cttgtgaagc ccggagcgtc agtcaagatc      60
tcgtgtaagg ccagcgggta cacctttacg gattattcga tccattgggt aaaacagaat     120
cacgggaagt cgctcgactg gattggttat atctacccgt ccaacggtga ttcgggatac     180
aaccagaagt tcaaaaatcg ggccacactt acagtggaca tcgtcgtc aactgcatat       240 ctcgaggtcc gcagactgac gtttgaggac tcagctgtct actattgcgc gacttatttc     300
gccaactact cgattactg gggccagggg acgacactga cggtcagctc cgcgagcacc      360
aagggcccct ccgtgttccc tctggcccct gctcccggt ccacctctga gtctaccgcc      420
gctctgggct gcctggtgaa ggactacttc cctgagcctg tgaccgtgtc ctggaactct     480
ggcgccctga cctctggcgt gcacaccttc ctgccgtgc tgcagtcctc cggcctgtac      540
tccctgtcct ccgtggtgac cgtgccttcc tccaacttcg gcacccagac ctacacctgc    600

```
aacgtggacc acaagccttc aacaccaag gtggacaaga ccgtggagcg aagtgctgc      660 gtggagtgcc ctccttgtcc tgctcctcct gtggctggcc cttctgtgtt cctgttccct    720
cctaagccta aggacaccct gatgatctcc cggacccctg aagtgacctg cgtggtggtg    780
gacgtgtccc acgaggaccc tgaggtgcag ttcaattggt acgtggacgg cgtggaggtg    840
cacaacgcca agaccaagcc tcgggaggaa cagttcaact ccaccttccg ggtggtgtct    900
gtgctgaccg tggtgcacca ggactggctg aacggcaaag aatacaagtg caaggtgtcc    960
aacaagggcc tgcctgcccc tatcgaaaag accatctcta agaccaaggg ccagcctcgc   1020
gagcctcagg tctacaccct gcctcctagc cgggaggaaa tgaccaagaa ccaggtgtcc   1080
ctgacctgtc tggtgaaggg cttctaccct tccgatatcg ccgtggagtg ggagtctaac   1140
ggccagcctg agaacaacta caagaccacc cctcctatgc tggactccga cggctccttc   1200
ttcctgtact ccaagctgac agtggacaag tcccggtggc agcagggcaa cgtgttctcc   1260
tgctccgtga tgcacgaggc cctgcacaac cactacaccc agaagtccct gtccctgtct   1320
cctggcaagt ga                                                       1332
```

<210> SEQ ID NO 31
<211> LENGTH: 1332
<212> TYPE: DNA
<213> ORGANISM: Artificial sequence
<220> FEATURE:
<223> OTHER INFORMATION: 131R003 Heavy chain amino acid sequence

<400> SEQUENCE: 31

```
caggtgcaac ttaaacagtc ggggcctgag ttggtcaaac caggagcctc agtaaagatt     60
agctgcaaag catcaggtta tacctttacg gattactcga tccactgggt gaagcagaac    120
cacggaaagt cactggattg gatcgggtac atctacccct cgaatggaga ttcggggtat    180
aaccaaaagt tcaaaaaccg ggccacgctg actgtggaca cgtcgtattc caccgcatat    240
ttggaagtcc gcagactcac gttcgaggac tccgcgtat  actattgtgc cacatacttt    300
gcgaattact ttgactactg gggtcagggc acaacgctta ctgtctccag cgcgtcaaca    360
aagggcccct ccgtgttccc tctggcccct gctcccggt  ccacctctga gtctaccgcc    420
gctctgggct gcctggtgaa ggactacttc cctgagcctg tgaccgtgtc ctggaactct    480
ggcgccctga cctctggcgt gcacaccttc cctgccgtgc tgcagtcctc cggcctgtac    540
tccctgtcct ccgtggtgac cgtgccttcc tccaacttcg gcacccagac ctacacctgc    600
aacgtggacc acaagccttc caacaccaag gtggacaaga ccgtggagcg aagtgctgc     660 gtggagtgcc ctccttgtcc tgctcctcct gtggctggcc cttctgtgtt cctgttccct    720
cctaagccta aggacaccct gatgatctcc cggacccctg aagtgacctg cgtggtggtg    780
gacgtgtccc acgaggaccc tgaggtgcag ttcaattggt acgtggacgg cgtggaggtg    840
cacaacgcca agaccaagcc tcgggaggaa cagttcaact ccaccttccg ggtggtgtct    900
gtgctgaccg tggtgcacca ggactggctg aacggcaaag aatacaagtg caaggtgtcc    960
aacaagggcc tgcctgcccc tatcgaaaag accatctcta agaccaaggg ccagcctcgc   1020
gagcctcagg tctacaccct gcctcctagc cgggaggaaa tgaccaagaa ccaggtgtcc   1080
ctgacctgtc tggtgaaggg cttctaccct tccgatatcg ccgtggagtg ggagtctaac   1140
ggccagcctg agaacaacta caagaccacc cctcctatgc tggactccga cggctccttc   1200
ttcctgtact ccaagctgac agtggacaag tcccggtggc agcagggcaa cgtgttctcc   1260
```

```
tgctccgtga tgcacgaggc cctgcacaac cactacaccc agaagtccct gtccctgtct   1320
cctggcaagt ga                                                       1332
```

<210> SEQ ID NO 32
<211> LENGTH: 657
<212> TYPE: DNA
<213> ORGANISM: Artificial sequence
<220> FEATURE:
<223> OTHER INFORMATION: 131R002/131R003 Light chain amino acid
      sequence

<400> SEQUENCE: 32

```
gacatcgtgc tcacacagag ccctgcatcg ctcgcagtat cgcttggtca gcgagcgacc     60
atttcatgca aagcgtcaca atcggtagat tacgacggag actcctacat gaactggtat   120
cagcagaaac cagggcagcc cccgaagttg ctcatctacg ccgcgtccaa tctggagtca   180
ggcattcccg ccagattcag cgggagcggg tcaggaacgg attttaccct caatatccat   240
ccggtagagg aggaagatgc ggcgacttac tattgtcagc agtcgaatga ggacccactc   300
acgttcgggg ctggaacaaa actggaactt aaacggactg tggcggctcc ctcagtgttc   360
atcttccctc cctccgacga acaattgaag tcgggtactg cctccgtcgt ctgtttgttg   420
aacaactttt atccgaggga agccaaggtg cagtggaagg tggataatgc gctgcagagc   480
ggtaactcgc aagagtcagt cacagagcaa gactcgaagg attcgacgta ttcgctcagc   540
agcacattga cgctgtcgaa ggcagattac gagaaacaca aggtgtacgc gtgcgaggtc   600
acccatcagg gattgtcgtc acccgtgacg aaatccttta accgcggaga atgctga     657
```

<210> SEQ ID NO 33
<211> LENGTH: 8
<212> TYPE: PRT
<213> ORGANISM: Artificial sequence
<220> FEATURE:
<223> OTHER INFORMATION: FLAG Tag

<400> SEQUENCE: 33

Asp Tyr Lys Asp Asp Asp Asp Lys
1               5

<210> SEQ ID NO 34
<211> LENGTH: 12
<212> TYPE: PRT
<213> ORGANISM: Artificial sequence
<220> FEATURE:
<223> OTHER INFORMATION: 131R003 Heavy chain CDR1 variant

<400> SEQUENCE: 34

Lys Ala Ser Gly Tyr Thr Phe Thr Ser Tyr Thr Phe
1               5                   10

<210> SEQ ID NO 35
<211> LENGTH: 10
<212> TYPE: PRT
<213> ORGANISM: Artificial sequence
<220> FEATURE:
<223> OTHER INFORMATION: 131R003 Heavy chain CDR3 variant

<400> SEQUENCE: 35

Ala Thr Tyr Phe Ala Asn Asn Phe Asp Tyr
1               5                   10

<210> SEQ ID NO 36
<211> LENGTH: 117

```
<212> TYPE: PRT
<213> ORGANISM: Artificial sequence
<220> FEATURE:
<223> OTHER INFORMATION: 131R003 Heavy chain variable region - Variant 1

<400> SEQUENCE: 36

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Ser Ile His Trp Val Lys Gln Asn His Gly Lys Ser Leu Asp Trp Ile
        35                  40                  45

Gly Tyr Ile Tyr Pro Ser Asn Gly Asp Ser Gly Tyr Asn Gln Lys Phe
    50                  55                  60

Lys Asn Arg Ala Thr Leu Thr Val Asp Thr Ser Tyr Ser Thr Ala Tyr
65                  70                  75                  80

Leu Glu Val Arg Arg Leu Thr Phe Glu Asp Ser Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser
        115

<210> SEQ ID NO 37
<211> LENGTH: 117
<212> TYPE: PRT
<213> ORGANISM: Artificial sequence
<220> FEATURE:
<223> OTHER INFORMATION: 131R003 Heavy chain variable region - Variant 2

<400> SEQUENCE: 37

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
            20                  25                  30

Thr Phe His Trp Val Lys Gln Asn His Gly Lys Ser Leu Asp Trp Ile
        35                  40                  45

Gly Tyr Ile Tyr Pro Ser Asn Gly Asp Ser Gly Tyr Asn Gln Lys Phe
    50                  55                  60

Lys Asn Arg Ala Thr Leu Thr Val Asp Thr Ser Tyr Ser Thr Ala Tyr
65                  70                  75                  80

Leu Glu Val Arg Arg Leu Thr Phe Glu Asp Ser Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser
        115

<210> SEQ ID NO 38
<211> LENGTH: 462
<212> TYPE: PRT
<213> ORGANISM: Artificial sequence
<220> FEATURE:
<223> OTHER INFORMATION: 131R003 Heavy chain - Variant 1

<400> SEQUENCE: 38

Met Lys His Leu Trp Phe Phe Leu Leu Leu Val Ala Ala Pro Arg Trp
1               5                   10                  15

Val Leu Ser Gln Val Gln Leu Lys Gln Ser Gly Pro Glu Leu Val Lys
```

-continued

```
                 20                  25                  30
Pro Gly Ala Ser Val Lys Ile Ser Cys Lys Ala Ser Gly Tyr Thr Phe
             35                  40                  45
Thr Asp Tyr Ser Ile His Trp Val Lys Gln Asn His Gly Lys Ser Leu
         50                  55                  60
Asp Trp Ile Gly Tyr Ile Tyr Pro Ser Asn Gly Asp Ser Gly Tyr Asn
 65                  70                  75                  80
Gln Lys Phe Lys Asn Arg Ala Thr Leu Thr Val Asp Thr Ser Tyr Ser
                 85                  90                  95
Thr Ala Tyr Leu Glu Val Arg Arg Leu Thr Phe Glu Asp Ser Ala Val
            100                 105                 110
Tyr Tyr Cys Ala Thr Tyr Phe Ala Asn Asn Phe Asp Tyr Trp Gly Gln
        115                 120                 125
Gly Thr Thr Leu Thr Val Ser Ser Ala Ser Thr Lys Gly Pro Ser Val
    130                 135                 140
Phe Pro Leu Ala Pro Cys Ser Arg Ser Thr Ser Glu Ser Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Asn Phe Gly Thr Gln Thr Tyr Thr Cys Asn Val Asp His Lys
    210                 215                 220
Pro Ser Asn Thr Lys Val Asp Lys Thr Val Glu Arg Lys Cys Cys Val
225                 230                 235                 240
Glu Cys Pro Pro Cys Pro Ala Pro Pro Val Ala Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Gln Phe Asn Trp Tyr Val Asp Gly Val Glu Val His Asn Ala Lys Thr
    290                 295                 300
Lys Pro Arg Glu Glu Gln Phe Asn Ser Thr Phe Arg Val Val Ser Val
305                 310                 315                 320
Leu Thr Val Val His Gln Asp Trp Leu Asn Gly Lys Glu Tyr Lys Cys
                325                 330                 335
Lys Val Ser Asn Lys Gly Leu Pro Ala Pro Ile Glu Lys Thr Ile Ser
            340                 345                 350
Lys Thr Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Met Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
```

Asn His Tyr Thr Gln Lys Ser Leu Ser Leu Ser Pro Gly Lys
             450                 455                 460

<210> SEQ ID NO 39
<211> LENGTH: 443
<212> TYPE: PRT
<213> ORGANISM: Artificial sequence
<220> FEATURE:
<223> OTHER INFORMATION: 131R003 Heavy chain - Variant 1 without
      predicted signal sequence

<400> SEQUENCE: 39

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Ser Ile His Trp Val Lys Gln Asn His Gly Lys Ser Leu Asp Trp Ile
        35                  40                  45

Gly Tyr Ile Tyr Pro Ser Asn Gly Asp Ser Gly Tyr Asn Gln Lys Phe
    50                  55                  60

Lys Asn Arg Ala Thr Leu Thr Val Asp Thr Ser Tyr Ser Thr Ala Tyr
65                  70                  75                  80

Leu Glu Val Arg Arg Leu Thr Phe Glu Asp Ser Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu

```
                340             345              350
Glu Met Thr Lys Asn Gln Val Ser Leu Thr Cys Leu Val Lys Gly Phe
            355                  360                 365
Tyr Pro Ser Asp Ile Ala Val Glu Trp Glu Ser Asn Gly Gln Pro Glu
        370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
            435                 440
```

<210> SEQ ID NO 40
<211> LENGTH: 1389
<212> TYPE: DNA
<213> ORGANISM: Artificial sequence
<220> FEATURE:
<223> OTHER INFORMATION: 131R003 Heavy chain - Variant 1 nucleic acid

<400> SEQUENCE: 40

```
atgaagcatc tttggttctt cctgctcttg gtggctgcgc cgaggtgggt gctcagccag    60
gtgcaactta aacagtcggg gcctgagttg gtcaaaccag agcctcagt aaagattagc    120
tgcaaagcat caggttatac ctttacggat tactcgatcc actgggtgaa gcagaaccac    180
ggaaagtcac tggattggat cgggtacatc taccccctcga atggagattc ggggtataac    240
caaaagttca aaaccgggc acgctgact gtggacacgt cgtattccac cgcatatttg    300
gaagtccgca gactcacgtt cgaggactcc gcggtatact attgtgccac atactttgcg    360
aataactttg actactgggg tcagggcaca acgcttactg tctccagcgc gtcaacaaag    420
ggcccctccg tgttccctct ggcccccttgc tccggtccca cctctgagtc taccgccgct    480
ctgggctgcc tggtgaagga ctacttccct gagcctgtga ccgtgtcctg gaactctggc    540
gccctgacct ctggcgtgca caccttccct gccgtgctgc agtcctccgg cctgtactcc    600
ctgtcctccg tggtgaccgt gccttcctcc aacttcggca cccagaccta cacctgcaac    660
gtggaccaca gccttccaa caccaaggtg gacaagaccg tggagcggaa gtgctgcgtg    720
gagtgccctc cttgtcctgc tcctcctgtg gctggccctt ctgtgttcct gttccctcct    780
aagcctaagg acaccctgat gatctcccgg accctgaag tgacctgcgt ggtggtggac    840
gtgtcccacg aggaccctga ggtgcagttc aattggtacg tggacggcgt ggaggtgcac    900
aacgccaaga ccaagcctcg ggaggaacag ttcaactcca ccttccgggt ggtgtctgtg    960
ctgaccgtgg tgcaccagga ctggctgaac ggcaaagaat acaagtgcaa ggtgtccaac   1020
aagggcctgc ctgccccta tcgaaaagacc atctctaaga ccaagggcca gcctcgcgag   1080
cctcaggtct acaccctgcc tcctagccgg gaggaaatga ccaagaacca ggtgtccctg   1140
acctgtctgg tgaagggctt ctaccccttcc gatatcgccg tggagtggga gtctaacggc   1200
cagcctgaga caactacaa gaccacccct cctatgctgg actccgacgg ctccttcttc   1260
ctgtactcca agctgacagt ggacaagtcc cggtggcagc agggcaacgt gttctcctgc   1320
tccgtgatgc acgaggccct gcacaaccac tacacccaga gtccctgtc cctgtctcct   1380
ggcaagtga                                                           1389
```

```
<210> SEQ ID NO 41
<211> LENGTH: 462
<212> TYPE: PRT
<213> ORGANISM: Artificial sequence
<220> FEATURE:
<223> OTHER INFORMATION: 131R003 Heavy chain - Variant 2

<400> SEQUENCE: 41
```

| | | | | | | | | | | | | | | |
|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 |

| Val | Leu | Ser | Gln | Val | Gln | Leu | Lys | Gln | Ser | Gly | Pro | Glu | Leu | Val | Lys |
|---|---|---|---|---|---|---|---|---|---|---|---|---|---|---|---|
| | | | 20 | | | | | 25 | | | | | 30 | | |

| Pro | Gly | Ala | Ser | Val | Lys | Ile | Ser | Cys | Lys | Ala | Ser | Gly | Tyr | Thr | Phe |
|---|---|---|---|---|---|---|---|---|---|---|---|---|---|---|---|
| | | 35 | | | | | 40 | | | | | 45 | | | |

| Thr | Ser | Tyr | Thr | Phe | His | Trp | Val | Lys | Gln | Asn | His | Gly | Lys | Ser | Leu |
|---|---|---|---|---|---|---|---|---|---|---|---|---|---|---|---|
| 50 | | | | | 55 | | | | | 60 | | | | | |

| Asp | Trp | Ile | Gly | Tyr | Ile | Tyr | Pro | Ser | Asn | Gly | Asp | Ser | Gly | Tyr | Asn |
|---|---|---|---|---|---|---|---|---|---|---|---|---|---|---|---|
| 65 | | | | | 70 | | | | | 75 | | | | | 80 |

| Gln | Lys | Phe | Lys | Asn | Arg | Ala | Thr | Leu | Thr | Val | Asp | Thr | Ser | Tyr | Ser |
|---|---|---|---|---|---|---|---|---|---|---|---|---|---|---|---|
| | | | | 85 | | | | | 90 | | | | | 95 | |

| Thr | Ala | Tyr | Leu | Glu | Val | Arg | Arg | Leu | Thr | Phe | Glu | Asp | Ser | Ala | Val |
|---|---|---|---|---|---|---|---|---|---|---|---|---|---|---|---|
| | | | 100 | | | | | 105 | | | | | 110 | | |

| Tyr | Tyr | Cys | Ala | Thr | Tyr | Phe | Ala | Asn | Asn | Phe | Asp | Tyr | Trp | Gly | Gln |
|---|---|---|---|---|---|---|---|---|---|---|---|---|---|---|---|
| | | 115 | | | | | 120 | | | | | 125 | | | |

| Gly | Thr | Thr | Leu | Thr | Val | Ser | Ser | Ala | Ser | Thr | Lys | Gly | Pro | Ser | Val |
|---|---|---|---|---|---|---|---|---|---|---|---|---|---|---|---|
| | 130 | | | | | 135 | | | | | 140 | | | | |

| Phe | Pro | Leu | Ala | Pro | Cys | Ser | Arg | Ser | Thr | Ser | Glu | Ser | Thr | Ala | Ala |
|---|---|---|---|---|---|---|---|---|---|---|---|---|---|---|---|
| 145 | | | | | 150 | | | | | 155 | | | | | 160 |

| Leu | Gly | Cys | Leu | Val | Lys | Asp | Tyr | Phe | Pro | Glu | Pro | Val | Thr | Val | Ser |
|---|---|---|---|---|---|---|---|---|---|---|---|---|---|---|---|
| | | | | 165 | | | | | 170 | | | | | 175 | |

| Trp | Asn | Ser | Gly | Ala | Leu | Thr | Ser | Gly | Val | His | Thr | Phe | Pro | Ala | Val |
|---|---|---|---|---|---|---|---|---|---|---|---|---|---|---|---|
| | | | 180 | | | | | 185 | | | | | 190 | | |

| Leu | Gln | Ser | Ser | Gly | Leu | Tyr | Ser | Leu | Ser | Ser | Val | Val | Thr | Val | Pro |
|---|---|---|---|---|---|---|---|---|---|---|---|---|---|---|---|
| | | 195 | | | | | 200 | | | | | 205 | | | |

| Ser | Ser | Asn | Phe | Gly | Thr | Gln | Thr | Tyr | Thr | Cys | Asn | Val | Asp | His | Lys |
|---|---|---|---|---|---|---|---|---|---|---|---|---|---|---|---|
| | 210 | | | | | 215 | | | | | 220 | | | | |

| Pro | Ser | Asn | Thr | Lys | Val | Asp | Lys | Thr | Val | Glu | Arg | Lys | Cys | Cys | Val |
|---|---|---|---|---|---|---|---|---|---|---|---|---|---|---|---|
| 225 | | | | | 230 | | | | | 235 | | | | | 240 |

| Glu | Cys | Pro | Pro | Cys | Pro | Ala | Pro | Pro | Val | Ala | Gly | Pro | Ser | Val | Phe |
|---|---|---|---|---|---|---|---|---|---|---|---|---|---|---|---|
| | | | | 245 | | | | | 250 | | | | | 255 | |

| Leu | Phe | Pro | Pro | Lys | Pro | Lys | Asp | Thr | Leu | Met | Ile | Ser | Arg | Thr | Pro |
|---|---|---|---|---|---|---|---|---|---|---|---|---|---|---|---|
| | | | 260 | | | | | 265 | | | | | 270 | | |

| Glu | Val | Thr | Cys | Val | Val | Val | Asp | Val | Ser | His | Glu | Asp | Pro | Glu | Val |
|---|---|---|---|---|---|---|---|---|---|---|---|---|---|---|---|
| | | 275 | | | | | 280 | | | | | 285 | | | |

| Gln | Phe | Asn | Trp | Tyr | Val | Asp | Gly | Val | Glu | Val | His | Asn | Ala | Lys | Thr |
|---|---|---|---|---|---|---|---|---|---|---|---|---|---|---|---|
| | 290 | | | | | 295 | | | | | 300 | | | | |

| Lys | Pro | Arg | Glu | Glu | Gln | Phe | Asn | Ser | Thr | Phe | Arg | Val | Val | Ser | Val |
|---|---|---|---|---|---|---|---|---|---|---|---|---|---|---|---|
| 305 | | | | | 310 | | | | | 315 | | | | | 320 |

| Leu | Thr | Val | Val | His | Gln | Asp | Trp | Leu | Asn | Gly | Lys | Glu | Tyr | Lys | Cys |
|---|---|---|---|---|---|---|---|---|---|---|---|---|---|---|---|
| | | | | 325 | | | | | 330 | | | | | 335 | |

| Lys | Val | Ser | Asn | Lys | Gly | Leu | Pro | Ala | Pro | Ile | Glu | Lys | Thr | Ile | Ser |
|---|---|---|---|---|---|---|---|---|---|---|---|---|---|---|---|
| | | | 340 | | | | | 345 | | | | | 350 | | |

| Lys | Thr | Lys | Gly | Gln | Pro | Arg | Glu | Pro | Gln | Val | Tyr | Thr | Leu | Pro | Pro |
|---|---|---|---|---|---|---|---|---|---|---|---|---|---|---|---|
| | | 355 | | | | | 360 | | | | | 365 | | | |

| Ser | Arg | Glu | Glu | Met | Thr | Lys | Asn | Gln | Val | Ser | Leu | Thr | Cys | Leu | Val |

```
                370                 375                 380
Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
                450                 455                 460

<210> SEQ ID NO 42
<211> LENGTH: 443
<212> TYPE: PRT
<213> ORGANISM: Artificial sequence
<220> FEATURE:
<223> OTHER INFORMATION: 131R003 Heavy chain - Variant 2

<400> SEQUENCE: 42

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
                20                  25                  30

Thr Phe His Trp Val Lys Gln Asn His Gly Lys Ser Leu Asp Trp Ile
            35                  40                  45

Gly Tyr Ile Tyr Pro Ser Asn Gly Asp Ser Gly Tyr Asn Gln Lys Phe
        50                  55                  60

Lys Asn Arg Ala Thr Leu Thr Val Asp Thr Ser Tyr Ser Thr Ala Tyr
65                  70                  75                  80

Leu Glu Val Arg Arg Leu Thr Phe Glu Asp Ser Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
```

```
                275                 280                 285
Glu Glu Gln Phe Asn Ser Thr Phe Arg Val Val Ser Val Leu Thr Val
            290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
            435                 440

<210> SEQ ID NO 43
<211> LENGTH: 1389
<212> TYPE: DNA
<213> ORGANISM: Artificial sequence
<220> FEATURE:
<223> OTHER INFORMATION: 131R003 Heavy chain - Variant 2 nucleic acid

<400> SEQUENCE: 43
atgaagcatc tttggttctt cctgctcttg gtggctgcgc cgaggtgggt gctcagccag      60
gtgcaactta acagtcggg gcctgagttg gtcaaaccag agcctcagt aaagattagc      120
tgcaaagcat caggatacac cttcactagc tatacattcc actgggtgaa gcagaaccac      180
ggaaagtcac tggattggat cgggtacatc taccccctcga atggagattc ggggtataac      240
caaaagttca aaaccgggc acgctgact gtggacacgt cgtattccac cgcatatttg      300
gaagtccgca gactcacgtt cgaggactcc gcggtatact attgtgccac atactttgcg      360
aataactttg actactgggg tcagggcaca acgcttactg tctccagcgc gtcaacaaag      420
ggccctcg tgttccctct ggccccttgc tcccggtcca cctctgagtc taccgccgct      480
ctgggctgcc tggtgaagga ctacttccct gagcctgtga ccgtgtcctg gaactctggc      540
gccctgacct ctggcgtgca caccttccct gccgtgctgc agtcctccgg cctgtactcc      600
ctgtcctccg tggtgaccgt gccttcctcc aacttcggca cccagaccta cacctgcaac      660
gtggaccaca gccttccaa caccaaggtg gacaagaccg tggagcggaa gtgctgcgtg      720
gagtgccctc cttgtcctgc tcctcctgtg gctggccctt ctgtgttcct gttccctcct      780
aagcctaagg acaccctgat gatctcccgg acccctgaag tgacctgcgt ggtggtggac      840
gtgtcccacg aggaccctga ggtgcagttc aattggtacg tggacggcgt ggaggtgcac      900
aacgccaaga ccaagcctcg ggaggaacag ttcaactcca ccttccgggt ggtgtctgtg      960
ctgaccgtgg tgcaccagga ctggctgaac ggcaagaat acaagtgcaa ggtgtccaac     1020
aagggcctgc ctgcccctat cgaaagacc atctctaaga ccaagggcca gcctcgcgag     1080
cctcaggtct acaccctgcc tcctagccgg gaggaaatga ccaagaacca ggtgtccctg     1140
```

```
acctgtctgg tgaagggctt ctacccttcc gatatcgccg tggagtggga gtctaacggc    1200
cagcctgaga caactacaa gaccacccct cctatgctgg actccgacgg ctccttcttc    1260
ctgtactcca agctgacagt ggacaagtcc cggtggcagc agggcaacgt gttctcctgc    1320
tccgtgatgc acgaggccct gcacaaccac tacacccaga gtccctgtc cctgtctcct    1380 ggcaagtga                                                            1389
```

```
<210> SEQ ID NO 44
<211> LENGTH: 117
<212> TYPE: PRT
<213> ORGANISM: Artificial sequence
<220> FEATURE:
<223> OTHER INFORMATION: Humanized 131R005/131R007/131R008/131R010/
      131R011 Heavy chain variable region

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile His Trp Val Arg Gln Ala Pro Gly Gln Gly Leu Glu Trp Ile
        35                  40                  45

Gly Tyr Ile Tyr Pro Ser Asn Gly Asp Ser Tyr Asn Gln Lys Phe
    50                  55                  60

Lys Asn Arg Val Thr Met Thr Arg Asp Thr Ser Thr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser
        115
```

```
<210> SEQ ID NO 45
<211> LENGTH: 117
<212> TYPE: PRT
<213> ORGANISM: Artificial sequence
<220> FEATURE:
<223> OTHER INFORMATION: Humanized 131R006A Heavy chain variable region

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Phe His Trp Val Arg Gln Ala Pro Gly Gln Gly Leu Glu Trp Ile
        35                  40                  45

Gly Tyr Ile Tyr Pro Ser Asn Gly Asp Ser Tyr Asn Gln Lys Phe
    50                  55                  60

Lys Asn Arg Val Thr Met Thr Arg Asp Thr Ser Thr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser
        115
```

<210> SEQ ID NO 46
<211> LENGTH: 462
<212> TYPE: PRT
<213> ORGANISM: Artificial sequence
<220> FEATURE:
<223> OTHER INFORMATION: Humanized 131R005/131R007/131R011 Heavy chain (IgG2)

<400> SEQUENCE: 46

```
Met Lys His Leu Trp Phe Phe Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ser Ile His Trp Val Arg Gln Ala Pro Gly Gln Gly Leu
    50                  55                  60

Glu Trp Ile Gly Tyr Ile Tyr Pro Ser Asn Gly Asp Ser Gly Tyr Asn
65                  70                  75                  80

Gln Lys Phe Lys Asn Arg Val Thr Met Thr Arg Asp Thr Ser Thr Ser
                85                  90                  95

Thr Ala Tyr Met Glu Leu Ser Arg Leu Arg Ser Glu Asp Thr Ala Val
            100                 105                 110

Tyr Tyr Cys Ala Thr Tyr Phe Ala Asn Asn Phe Asp Tyr Trp Gly Gln
        115                 120                 125

Gly Thr Thr Leu Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
```

```
                355                 360                 365
Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
                450                 455                 460

<210> SEQ ID NO 47
<211> LENGTH: 462
<212> TYPE: PRT
<213> ORGANISM: Artificial sequence
<220> FEATURE:
<223> OTHER INFORMATION: Humanized 131R006A Heavy chain

<400> SEQUENCE: 47

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Ser Tyr Thr Phe His Trp Val Arg Gln Ala Pro Gly Gln Gly Leu
                50                  55                  60

Glu Trp Ile Gly Tyr Ile Tyr Pro Ser Asn Gly Asp Ser Gly Tyr Asn
65              70                  75                  80

Gln Lys Phe Lys Asn Arg Val Thr Met Thr Arg Asp Thr Ser Thr Ser
                85                  90                  95

Thr Ala Tyr Met Glu Leu Ser Arg Leu Arg Ser Glu Asp Thr Ala Val
                100                 105                 110

Tyr Tyr Cys Ala Thr Tyr Phe Ala Asn Asn Phe Asp Tyr Trp Gly Gln
                115                 120                 125

Gly Thr Thr Leu Thr Val Ser Ser Ala Ser Thr Lys Gly Pro Ser Val
                130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Asn Phe Gly Thr Gln Thr Tyr Thr Cys Asn Val Asp His Lys
                210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
```

```
                260                 265                 270
Glu Val Thr Cys Val Val Val Asp Val Ser His Glu Asp Pro Glu Val
            275                 280                 285

Gln Phe Asn Trp Tyr Val Asp Gly Val Glu Val His Asn Ala Lys Thr
        290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
            325                 330                 335

Lys Val Ser Asn Lys Gly Leu Pro Ala Pro Ile Glu Lys Thr Ile Ser
        340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
        450                 455                 460

<210> SEQ ID NO 48
<211> LENGTH: 443
<212> TYPE: PRT
<213> ORGANISM: Artificial sequence
<220> FEATURE:
<223> OTHER INFORMATION: Humanized 131R005/131R007/131R011 Heavy chain
      (IgG2)

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile His Trp Val Arg Gln Ala Pro Gly Gln Gly Leu Glu Trp Ile
        35                  40                  45

Gly Tyr Ile Tyr Pro Ser Asn Gly Asp Ser Gly Tyr Asn Gln Lys Phe
    50                  55                  60

Lys Asn Arg Val Thr Met Thr Arg Asp Thr Ser Thr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Asn
        180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
        290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 49
<211> LENGTH: 443
<212> TYPE: PRT
<213> ORGANISM: Artificial sequence
<220> FEATURE:
<223> OTHER INFORMATION: Humanized 131R006A Heavy chain

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Phe His Trp Val Arg Gln Ala Pro Gly Gln Gly Leu Glu Trp Ile
        35                  40                  45

Gly Tyr Ile Tyr Pro Ser Asn Gly Asp Ser Gly Tyr Asn Gln Lys Phe
    50                  55                  60

Lys Asn Arg Val Thr Met Thr Arg Asp Thr Ser Thr Ser Thr Ala Tyr
65                  70                  75                  80
```

```
Met Glu Leu Ser Arg Leu Arg Ser Glu Asp Thr Ala Val Tyr Tyr Cys
                    85                  90                  95

Ala Thr Tyr Phe Ala Asn Asn Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 50
<211> LENGTH: 351
<212> TYPE: DNA
<213> ORGANISM: Artificial sequence
<220> FEATURE:
<223> OTHER INFORMATION: Humanized 131R005/131R007 Heavy chain variable
      region nucleic acid

<400> SEQUENCE: 50
```

```
caagtccaat tggtccagag cggtgccgaa gtgaagaaac cgggagcttc cgtgaaagtg      60
agctgcaagg cttctggata caccttcact gactattcaa tccactgggt gagacaggca     120
cctggtcagg gactggagtg gattggatac atctacccct caaatgggga ctctggctac     180
aaccaaaagt tcaagaaccg ggtgactatg accagagata cctcaacatc tactgcctac     240
atggaactca gcaggctgcg ctcagaggac accgcagtgt attactgtgc cacctacttc     300
gctaataact cgactattg ggggcagggc accaccctga ctgtcagctc a               351
```

<210> SEQ ID NO 51
<211> LENGTH: 351
<212> TYPE: DNA
<213> ORGANISM: Artificial sequence
<220> FEATURE:
<223> OTHER INFORMATION: Humanized 131R006A Heavy chain variable region
      nucleic acid

<400> SEQUENCE: 51

```
caagtccaat tggtccagag cggtgccgaa gtgaagaaac cgggagcttc cgtgaaagtg      60
agctgcaagg cttctggata caccttcact agctatacat tccactgggt gagacaggca     120
cctggtcagg gactggagtg gattggatac atctacccct caaatgggga ctctggctac     180
aaccaaaagt tcaagaaccg ggtgactatg accagagata cctcaacatc tactgcctac     240
atggaactca gcaggctgcg ctcagaggac accgcagtgt attactgtgc cacctacttc     300
gctaataact cgactattg ggggcagggc accaccctga ctgtcagctc a               351
```

<210> SEQ ID NO 52
<211> LENGTH: 1389
<212> TYPE: DNA
<213> ORGANISM: Artificial sequence
<220> FEATURE:
<223> OTHER INFORMATION: Humanized 131R005/131R007 Heavy chain nucleic
      acid

<400> SEQUENCE: 52

```
atgaagcatc tgtggttttt cctcctcctt gtcgccgctc cacgctgggt gctttcccaa      60
gtccaattgg tccagagcgg tgccgaagtg aagaaaccgg agcttccgt gaaagtgagc     120 tgcaaggctt ctggatacac cttcactgac tattcaatcc actgggtgag acaggcacct     180 ggtcaggac tggagtggat tggatacatc taccccctcaa atggggactc tggctacaac     240
caaaagttca gaaccgggt gactatgacc agagatacct caacatctac tgcctacatg     300
gaactcagca ggctgcgctc agaggacacc gcagtgtatt actgtgccac ctacttcgct     360
aataacttcg actattgggg gcagggcacc accctgactg tcagctcagc ctcaaccaag     420
ggccccctcg tgttccctct ggccccttgc tccggtccca cctctgagtc tacccgcgct     480
ctgggctgcc tggtgaagga ctacttccct gagcctgtga ccgtgtcctg aactctggc     540 gccctgacct ctggcgtgca caccttccct gccgtgctgc agtccccgg cctgtactcc     600 ctgtcctccg tggtgaccgt gccttcctcc aacttcggca cccagaccta cctgcaac     660 gtggaccaca gccttccaa caccaaggtg gacaagaccg tggagcggaa gtgctgcgtg     720
gagtgccctc cttgtcctgc tcctcctgtg ctggcccctt ctgtgttcct gttccctcct     780
aagcctaagg acaccctgat gatctcccgg acccctgaag tgacctgcgt ggtggtggac     840
gtgtcccacg aggaccctga ggtgcagttc aattggtacg tggacggcgt ggaggtgcac     900
aacgccaaga ccaagcctcg ggaggaacag ttcaactcca ccttccgggt ggtgtctgtg     960
```

```
ctgaccgtgg tgcaccagga ctggctgaac ggcaaagaat acaagtgcaa ggtgtccaac    1020
aagggcctgc ctgcccctat cgaaaagacc atctctaaga ccaagggcca gcctcgcgag    1080
cctcaggtct acaccctgcc tcctagccgg gaggaaatga ccaagaacca ggtgtccctg    1140
acctgtctgg tgaagggctt ctacccttcc gatatcgccg tggagtggga gtctaacggc    1200
cagcctgaga caactacaa gaccacccct cctatgctgg actccgacgg ctccttcttc     1260
ctgtactcca agctgacagt ggacaagtcc cggtggcagc agggcaacgt gttctcctgc    1320
tccgtgatgc acgaggccct gcacaaccac tacacccaga gtccctgtc cctgtctcct     1380 ggcaagtga                                                             1389

<210> SEQ ID NO 53
<211> LENGTH: 1389
<212> TYPE: DNA
<213> ORGANISM: Artificial sequence
<220> FEATURE:
<223> OTHER INFORMATION: Humanized 131R006A Heavy chain nucleic acid

<400> SEQUENCE: 53
atgaagcatc tgtggttttt cctcctcctt gtcgccgctc cacgctgggt gctttcccaa    60
gtccaattgg tccagagcgg tgccgaagtg aagaaaccgg gagcttccgt gaaagtgagc    120
tgcaaggctt ctggatacac cttcactagc tatacattcc actgggtgag acaggcacct    180
ggtcagggac tggagtggat ggatacatc taccccctcaa atgggggactc tggctacaac    240 caaaagttca gaaccgggt gactatgacc agagatacct caacatctac tgcctacatg    300
gaactcagca ggctgcgctc agaggacacc gcagtgtatt actgtgccac ctacttcgct    360
aataacttcg actattgggg gcagggcacc accctgactg tcagctcagc ctcaaccaag    420 ggcccctcg tgttccctct ggcccccttgc tccggtccaa cctctgagtc taccgccgct    480
ctgggctgcc tggtgaagga ctacttccct gagcctgtga ccgtgtcctg aactctggc    540 gccctgacct ctggcgtgca ccttcctgcc gtgctgc agtcctccgg cctgtactcc       600
ctgtcctccg tggtgaccgt gccttcctcc aacttcggca cccagaccta cctgcaac    660 gtggaccaca gccttccaa caccaaggtg gacaagaccg tggagcggaa gtgctgcgtg     720
gagtgccctc cttgtcctgc tcctcctgtg gctggcct ctgtgttcct gttccctcct     780
aagcctaagg acaccctgat gatctcccgg acccctgaag tgacctgcgt ggtggtggac    840
gtgtcccacg aggaccctga ggtgcagttc aattggtacg tggacggcgt ggaggtgcac    900
aacgccaaga ccaagcctcg ggaggaacag ttcaactcca ccttccgggt ggtgtctgtg    960
ctgaccgtgg tgcaccagga ctggctgaac ggcaaagaat acaagtgcaa ggtgtccaac    1020
aagggcctgc ctgcccctat cgaaaagacc atctctaaga ccaagggcca gcctcgcgag    1080
cctcaggtct acaccctgcc tcctagccgg gaggaaatga ccaagaacca ggtgtccctg    1140
acctgtctgg tgaagggctt ctacccttcc gatatcgccg tggagtggga gtctaacggc    1200
cagcctgaga caactacaa gaccacccct cctatgctgg actccgacgg ctccttcttc     1260
ctgtactcca agctgacagt ggacaagtcc cggtggcagc agggcaacgt gttctcctgc    1320
tccgtgatgc acgaggccct gcacaaccac tacacccaga gtccctgtc cctgtctcct     1380 ggcaagtga                                                             1389

<210> SEQ ID NO 54
<211> LENGTH: 1332
<212> TYPE: DNA
<213> ORGANISM: Artificial sequence
```

<220> FEATURE:
<223> OTHER INFORMATION: Humanized 131R005/131R007 Heavy chain nucleic acid

<400> SEQUENCE: 54

| | | | | | | |
|---|---|---|---|---|---|---|
| caagtccaat | tggtccagag | cggtgccgaa | gtgaagaaac | cgggagcttc | cgtgaaagtg | 60 |
| agctgcaagg | cttctggata | caccttcact | gactattcaa | tccactgggt | gagacaggca | 120 |
| cctggtcagg | gactggagtg | gattggatac | atctacccct | caaatgggga | ctctggctac | 180 |
| aaccaaaagt | tcaagaaccg | ggtgactatg | accagagata | cctcaacatc | tactgcctac | 240 |
| atggaactca | gcaggctgcg | ctcagaggac | accgcagtgt | attactgtgc | cacctacttc | 300 |
| gctaataact | tcgactattg | ggggcagggc | accaccctga | ctgtcagctc | agcctcaacc | 360 |
| aagggcccct | ccgtgttccc | tctggcccct | tgctcccggt | ccactctga | gtctaccgcc | 420 |
| gctctgggct | gcctggtgaa | ggactacttc | cctgagcctg | tgaccgtgtc | ctggaactct | 480 |
| ggcgccctga | cctctggcgt | gcacaccttc | cctgccgtgc | tgcagtcctc | cggcctgtac | 540 |
| tccctgtcct | ccgtggtgac | cgtgccttcc | tccaacttcg | gcacccagac | ctacacctgc | 600 |
| aacgtggacc | acaagccttc | caacaccaag | gtggacaaga | ccgtggagcg | gaagtgctgc | 660 |
| gtggagtgcc | ctccttgtcc | tgctcctcct | gtggctggcc | cttctgtgtt | cctgttccct | 720 |
| cctaagccta | aggacaccct | gatgatctcc | cggacccctg | aagtgacctg | cgtggtggtg | 780 |
| gacgtgtccc | acgaggaccc | tgaggtgcag | ttcaattggt | acgtggacgg | cgtggaggtg | 840 |
| cacaacgcca | agaccaagcc | tcgggaggaa | cagttcaact | ccaccttccg | ggtggtgtct | 900 |
| gtgctgaccg | tggtgcacca | ggactggctg | aacggcaaag | aatacaagtg | caaggtgtcc | 960 |
| aacaagggcc | tgcctgcccc | tatcgaaaag | accatctcta | agaccaaggg | ccagcctcgc | 1020 |
| gagcctcagg | tctacaccct | gcctccctagc | cgggaggaaa | tgaccaagaa | ccaggtgtcc | 1080 |
| ctgacctgtc | tggtgaaggg | cttctaccct | tccgatatcg | ccgtggagtg | ggagtctaac | 1140 |
| ggccagcctg | agaacaacta | caagaccacc | cctcctatgc | tggactccga | cggctccttc | 1200 |
| ttcctgtact | ccaagctgac | agtggacaag | tcccggtggc | agcagggcaa | cgtgttctcc | 1260 |
| tgctccgtga | tgcacgaggc | cctgcacaac | cactacaccc | agaagtccct | gtccctgtct | 1320 |
| cctggcaagt | ga | | | | | 1332 |

<210> SEQ ID NO 55
<211> LENGTH: 1332
<212> TYPE: DNA
<213> ORGANISM: Artificial sequence
<220> FEATURE:
<223> OTHER INFORMATION: Humanized 131R006A Heavy chain - nucleic acid

<400> SEQUENCE: 55

| | | | | | | |
|---|---|---|---|---|---|---|
| caagtccaat | tggtccagag | cggtgccgaa | gtgaagaaac | cgggagcttc | cgtgaaagtg | 60 |
| agctgcaagg | cttctggata | caccttcact | agctatacat | tccactgggt | gagacaggca | 120 |
| cctggtcagg | gactggagtg | gattggatac | atctacccct | caaatgggga | ctctggctac | 180 |
| aaccaaaagt | tcaagaaccg | ggtgactatg | accagagata | cctcaacatc | tactgcctac | 240 |
| atggaactca | gcaggctgcg | ctcagaggac | accgcagtgt | attactgtgc | cacctacttc | 300 |
| gctaataact | tcgactattg | ggggcagggc | accaccctga | ctgtcagctc | agcctcaacc | 360 |
| aagggcccct | ccgtgttccc | tctggcccct | tgctcccggt | ccactctga | gtctaccgcc | 420 |
| gctctgggct | gcctggtgaa | ggactacttc | cctgagcctg | tgaccgtgtc | ctggaactct | 480 |
| ggcgccctga | cctctggcgt | gcacaccttc | cctgccgtgc | tgcagtcctc | cggcctgtac | 540 |

```
tccctgtcct ccgtggtgac cgtgccttcc tccaacttcg gcacccagac ctacacctgc    600
aacgtggacc acaagccttc caacaccaag gtggacaaga ccgtggagcg aaagtgctgc    660
gtggagtgcc ctccttgtcc tgctcctcct gtggctggcc cttctgtgtt cctgttccct    720
cctaagccta aggacaccct gatgatctcc cggacccctg aagtgacctg cgtggtggtg    780
gacgtgtccc acgaggaccc tgaggtgcag ttcaattggt acgtggacgg cgtggaggtg    840
cacaacgcca agaccaagcc tcgggaggaa cagttcaact ccaccttccg ggtggtgtct    900
gtgctgaccg tggtgcacca ggactggctg aacggcaaag aatacaagtg caaggtgtcc    960
aacaagggcc tgcctgcccc tatcgaaaag accatctcta agaccaaggg ccagcctcgc   1020
gagcctcagg tctacaccct gcctcctagc cgggaggaaa tgaccaagaa ccaggtgtcc   1080
ctgacctgtc tggtgaaggg cttctaccct tccgatatcg ccgtggagtg ggagtctaac   1140
ggccagcctg agaacaacta caagaccacc cctcctatgc tggactccga cggctccttc   1200
ttcctgtact ccaagctgac agtggacaag tcccggtggc agcagggcaa cgtgttctcc   1260
tgctccgtga tgcacgaggc cctgcacaac cactacaccc agaagtccct gtccctgtct   1320
cctggcaagt ga                                                       1332
```

<210> SEQ ID NO 56
<211> LENGTH: 330
<212> TYPE: PRT
<213> ORGANISM: Artificial sequence
<220> FEATURE:
<223> OTHER INFORMATION: Human IgG1 Heavy chain constant region

<400> SEQUENCE: 56

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
            210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 326
<212> TYPE: PRT
<213> ORGANISM: Artificial sequence
<220> FEATURE:
<223> OTHER INFORMATION: Human IgG2 Heavy chain constant region

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
```

```
                        245                 250                 255
Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 58
<211> LENGTH: 377
<212> TYPE: PRT
<213> ORGANISM: Artificial sequence
<220> FEATURE:
<223> OTHER INFORMATION: Human IgG3 Heavy chain constant region

<400> SEQUENCE: 58

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
```

```
                    275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
        355                 360                 365
Lys Ser Leu Ser Leu Ser Pro Gly Lys
    370                 375

<210> SEQ ID NO 59
<211> LENGTH: 327
<212> TYPE: PRT
<213> ORGANISM: Artificial sequence
<220> FEATURE:
<223> OTHER INFORMATION: Human IgG4 Heavy chain constant region

<400> SEQUENCE: 59

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
```

```
                 260                 265                 270
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 60
<211> LENGTH: 326
<212> TYPE: PRT
<213> ORGANISM: Artificial sequence
<220> FEATURE:
<223> OTHER INFORMATION: Human IgG2 Heavy chain constant region (13A
      Chain variant)

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Lys Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Lys Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 61
<211> LENGTH: 326
<212> TYPE: PRT
<213> ORGANISM: Artificial sequence
<220> FEATURE:
<223> OTHER INFORMATION: Human IgG2 Heavy chain constant region (13B
      Chain variant)

<400> SEQUENCE: 61

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Glu Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Glu
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
```

```
Ser Leu Ser Pro Gly Lys
            325

<210> SEQ ID NO 62
<211> LENGTH: 117
<212> TYPE: PRT
<213> ORGANISM: Artificial sequence
<220> FEATURE:
<223> OTHER INFORMATION: Humanized 131R006B Heavy chain variable region

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Ile His Trp Val Arg Gln Ala Pro Gly Gln Gly Leu Glu Trp Ile
            35                  40                  45

Gly Tyr Ile Tyr Pro Ser Asn Gly Asp Ser Gly Tyr Asn Gln Lys Phe
        50                  55                  60

Lys Asn Arg Val Thr Met Thr Val Asp Thr Ser Tyr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
                100                 105                 110

Leu Thr Val Ser Ser
            115

<210> SEQ ID NO 63
<211> LENGTH: 462
<212> TYPE: PRT
<213> ORGANISM: Artificial sequence
<220> FEATURE:
<223> OTHER INFORMATION: Humanized 131R006B Heavy chain

<400> SEQUENCE: 63

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Ser Ile His Trp Val Arg Gln Ala Pro Gly Gln Gly Leu
        50                  55                  60

Glu Trp Ile Gly Tyr Ile Tyr Pro Ser Asn Gly Asp Ser Gly Tyr Asn
65                  70                  75                  80

Gln Lys Phe Lys Asn Arg Val Thr Met Thr Val Asp Thr Ser Tyr Ser
                85                  90                  95

Thr Ala Tyr Met Glu Leu Ser Arg Leu Arg Ser Glu Asp Thr Ala Val
                100                 105                 110

Tyr Tyr Cys Ala Thr Tyr Phe Ala Asn Asn Phe Asp Tyr Trp Gly Gln
            115                 120                 125

Gly Thr Thr Leu Thr Val Ser Ser Ala Ser Thr Lys Gly Pro Ser Val
        130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
```

165                 170                 175
Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Asn Phe Gly Thr Gln Thr Tyr Thr Cys Asn Val Asp His Lys
            210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
            245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Gln Phe Asn Trp Tyr Val Asp Gly Val Glu Val His Asn Ala Lys Thr
            290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
            325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 64
<211> LENGTH: 443
<212> TYPE: PRT
<213> ORGANISM: Artificial sequence
<220> FEATURE:
<223> OTHER INFORMATION: Humanized 131R006B Heavy chain

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile His Trp Val Arg Gln Ala Pro Gly Gln Gly Leu Glu Trp Ile
            35                  40                  45

Gly Tyr Ile Tyr Pro Ser Asn Gly Asp Ser Gly Tyr Asn Gln Lys Phe
    50                  55                  60

Lys Asn Arg Val Thr Met Thr Val Asp Thr Ser Tyr Ser Thr Ala Tyr

```
                65                  70                  75                  80
            Met Glu Leu Ser Arg Leu Arg Ser Glu Asp Thr Ala Val Tyr Tyr Cys
                            85                  90                  95

Ala Thr Tyr Phe Ala Asn Asn Phe Asp Tyr Trp Gly Gln Gly Thr Thr
                            100                 105                 110

Leu Thr Val Ser Ser Ala Ser Thr Lys Gly Pro Ser Val Phe Pro Leu
                            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
            145                 150                 155                 160

Gly Ala Leu Thr Ser Gly Val His Thr Phe Pro Ala Val Leu Gln Ser
                            165                 170                 175

Ser Gly Leu Tyr Ser Leu Ser Ser Val Val Thr Val Pro Ser Ser Asn
                            180                 185                 190

Phe Gly Thr Gln Thr Tyr Thr Cys Asn Val Asp His Lys Pro Ser Asn
                            195                 200                 205

Thr Lys Val Asp Lys Thr Val Glu Arg Lys Cys Cys Val Glu Cys Pro
                            210                 215                 220

Pro Cys Pro Ala Pro Pro Val Ala Gly Pro Ser Val Phe Leu Phe Pro
            225                 230                 235                 240

Pro Lys Pro Lys Asp Thr Leu Met Ile Ser Arg Thr Pro Glu Val Thr
                            245                 250                 255

Cys Val Val Val Asp Val Ser His Glu Asp Pro Glu Val Gln Phe Asn
                            260                 265                 270

Trp Tyr Val Asp Gly Val Glu Val His Asn Ala Lys Thr Lys Pro Arg
                            275                 280                 285

Glu Glu Gln Phe Asn Ser Thr Phe Arg Val Val Ser Val Leu Thr Val
                            290                 295                 300

Val His Gln Asp Trp Leu Asn Gly Lys Glu Tyr Lys Cys Lys Val Ser
            305                 310                 315                 320

Asn Lys Gly Leu Pro Ala Pro Ile Glu Lys Thr Ile Ser Lys Thr Lys
                            325                 330                 335

Gly Gln Pro Arg Glu Pro Gln Val Tyr Thr Leu Pro Pro Ser Arg Glu
                            340                 345                 350

Glu Met Thr Lys Asn Gln Val Ser Leu Thr Cys Leu Val Lys Gly Phe
                            355                 360                 365

Tyr Pro Ser Asp Ile Ala Val Glu Trp Glu Ser Asn Gly Gln Pro Glu
                            370                 375                 380

Asn Asn Tyr Lys Thr Thr Pro Pro Met Leu Asp Ser Asp Gly Ser Phe
            385                 390                 395                 400

Phe Leu Tyr Ser Lys Leu Thr Val Asp Lys Ser Arg Trp Gln Gln Gly
                            405                 410                 415

Asn Val Phe Ser Cys Ser Val Met His Glu Ala Leu His Asn His Tyr
                            420                 425                 430

Thr Gln Lys Ser Leu Ser Leu Ser Pro Gly Lys
                            435                 440

<210> SEQ ID NO 65
<211> LENGTH: 351
<212> TYPE: DNA
<213> ORGANISM: Artificial sequence
<220> FEATURE:
<223> OTHER INFORMATION: Humanized 131R006B Heavy chain variable region
      nucleic acid
```

<400> SEQUENCE: 65

```
caagtccaat tggtccagag cggtgccgaa gtgaagaaac cgggagcttc cgtgaaagtg      60
agctgcaagg cttctggata caccttcact gactattcaa tccactgggt gagacaggca     120
cctggtcagg gactggagtg gattggatac atctacccct caaatgggga ctctggctac     180
aaccaaaagt tcaagaaccg ggtgactatg accgtggata cctcatactc tactgcctac     240
atggaactca gcaggctgcg ctcagaggac accgcagtgt attactgtgc cacctacttc     300
gctaataact tcgactattg ggggcagggc accaccctga ctgtcagctc a              351
```

<210> SEQ ID NO 66
<211> LENGTH: 1389
<212> TYPE: DNA
<213> ORGANISM: Artificial sequence
<220> FEATURE:
<223> OTHER INFORMATION: Humanized 131R006B Heavy chain nucleic acid

<400> SEQUENCE: 66

```
atgaagcatc tgtggttttt cctcctcctt gtcgccgctc acgctgggt gctttcccaa       60
gtccaattgg tccagagcgg tgccgaagtg aagaaaccgg agcttccgt gaaagtgagc     120
tgcaaggctt ctggatacac cttcactgac tattcaatcc actgggtgag acaggcacct    180
ggtcagggac tggagtggat tggatacatc taccccctcaa atggggactc tggctacaac    240
caaaagttca gaaccgggt gactatgacc gtggatacct catactctac tgcctacatg     300
gaactcagca ggctgcgctc agaggacacc gcagtgtatt actgtgccac ctacttcgct    360
aataacttcg actattgggg gcagggcacc accctgactg tcagctcagc ctcaaccaag    420
ggcccctccg tgttccctct ggccccttgc tccggtccca cctctgagtc taccgccgct    480
ctgggctgcc tggtgaagga ctacttccct gagcctgtga ccgtgtcctg gaactctggc    540
gccctgacct ctggcgtgca caccttccct gccgtgctgc agtcctccgg cctgtactcc    600
ctgtcctccg tggtgaccgt gccttcctcc aacttcggca cccagaccta cacctgcaac    660
gtggaccaca gccttccaa caccaaggtg acaagaccg tggagcggaa gtgctgcgtg      720
gagtgccctc cttgtcctgc tcctcctgtg gctggcccctt ctgtgttcct gttccctcct    780
aagcctaagg acaccctgat gatctcccgg accccctgaag tgacctgcgt ggtggtggac    840
gtgtcccacg aggaccctga ggtgcagttc aattggtacg tggacggcgt ggaggtgcac    900
aacgccaaga ccaagcctcg ggaggaacag ttcaactcca ccttcgggt ggtgtctgtg      960
ctgaccgtgt gcaccagga ctggctgaac ggcaaagaat acaagtgcaa ggtgtccaac    1020
aagggcctgc ctgccccctat cgaaaagacc atctctaaga ccaagggcca gcctcgcgag   1080
cctcaggtct acaccctgcc tcctagccgg aggaaatga ccaagaacca ggtgtccctg    1140
acctgtctgg tgaagggctt ctaccctcc gatatcgccg tggagtggga gtctaacggc    1200
cagcctgaga caactacaa gaccacccct cctatgctgg actccgacgg ctccttcttc     1260
ctgtactcca gctgacagt ggacaagtcc cggtggcagc agggcaacgt gttctcctgc    1320
tccgtgatgc acgaggccct gcacaaccac tacacccaga gtccctgtc cctgtctcct    1380
ggcaagtga                                                          1389
```

<210> SEQ ID NO 67
<211> LENGTH: 1332
<212> TYPE: DNA
<213> ORGANISM: Artificial sequence
<220> FEATURE:

<223> OTHER INFORMATION: Humanized 131R006B Heavy chain nucleic acid

<400> SEQUENCE: 67

```
caagtccaat tggtccagag cggtgccgaa gtgaagaaac cgggagcttc cgtgaaagtg      60
agctgcaagg cttctggata caccttcact gactattcaa tccactgggt gagacaggca     120
cctggtcagg gactggagtg gattggatac atctacccct caaatgggga ctctggctac     180
aaccaaaagt tcaagaaccg ggtgactatg accgtggata cctcatactc tactgcctac     240
atggaactca gcaggctgcg ctcagaggac accgcagtgt attactgtgc cacctacttc     300
gctaataact tcgactattg ggggcagggc accaccctga ctgtcagctc agcctcaacc     360
aagggcccct ccgtgttccc tctggcccct gctcccggt ccacctctga gtctaccgcc     420
gctctgggct gcctggtgaa ggactacttc cctgagcctg tgaccgtgtc ctggaactct     480
ggcgccctga cctctggcgt gcacaccttc cctgccgtgc tgcagtcctc cggcctgtac     540
tccctgtcct ccgtggtgac cgtgccttcc tccaacttcg cacccagac ctacacctgc      600
aacgtggacc acaagccttc caacaccaag gtggacaaga ccgtggagcg gaagtgctgc     660
gtggagtgcc ctccttgtcc tgctcctcct gtggctggcc cttctgtgtt cctgttccct     720
cctaagccta aggacaccct gatgatctcc cggacccctg aagtgacctg cgtggtggtg     780
gacgtgtccc acgaggaccc tgaggtgcag ttcaattggt acgtggacgg cgtggaggtg     840
cacaacgcca agaccaagcc tcgggaggaa cagttcaact ccaccttccg ggtggtgtct     900
gtgctgaccg tggtgcacca ggactggctg aacggcaaag aatacaagtg caaggtgtcc     960
aacaaggggc tgcctgcccc tatcgaaaag accatctcta agaccaaggg ccagcctcgc    1020
gagcctcagg tctacaccct gcctcctagc cgggaggaaa tgaccaagaa ccaggtgtcc    1080
ctgacctgtc tggtgaaggg cttctaccct tccgatatcg ccgtggagtg ggagtctaac    1140
ggccagcctg agaacaacta caagaccacc ctcctatgc tggactccga cggctccttc    1200
ttcctgtact ccaagctgac agtggacaag tcccggtggc agcagggcaa cgtgttctcc    1260
tgctccgtga tgcacgaggc cctgcacaac cactacaccc agaagtccct gtccctgtct    1320
cctggcaagt ga                                                        1332
```

<210> SEQ ID NO 68
<211> LENGTH: 466
<212> TYPE: PRT
<213> ORGANISM: Artificial sequence
<220> FEATURE:
<223> OTHER INFORMATION: Humanized 131R008/131R010 Heavy chain (IgG1)

<400> SEQUENCE: 68

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Ser Ile His Trp Val Arg Gln Ala Pro Gly Gln Gly Leu
        50                  55                  60

Glu Trp Ile Gly Tyr Ile Tyr Pro Ser Asn Gly Asp Ser Gly Tyr Asn
65                  70                  75                  80

Gln Lys Phe Lys Asn Arg Val Thr Met Thr Arg Asp Thr Ser Thr Ser
                85                  90                  95

Thr Ala Tyr Met Glu Leu Ser Arg Leu Arg Ser Glu Asp Thr Ala Val
```

```
                100             105             110
Tyr Tyr Cys Ala Thr Tyr Phe Ala Asn Asn Phe Asp Tyr Trp Gly Gln
            115             120             125

Gly Thr Thr Leu Thr Val Ser Ser Ala Ser Thr Lys Gly Pro Ser Val
        130             135             140

Phe Pro Leu Ala Pro Ser Ser Lys Ser Thr Ser Gly Gly Thr Ala Ala
145             150             155             160

Leu Gly Cys Leu Val Lys Asp Tyr Phe Pro Glu Pro Val Thr Val Ser
            165             170             175

Trp Asn Ser Gly Ala Leu Thr Ser Gly Val His Thr Phe Pro Ala Val
        180             185             190

Leu Gln Ser Ser Gly Leu Tyr Ser Leu Ser Ser Val Val Thr Val Pro
    195             200             205

Ser Ser Ser Leu Gly Thr Gln Thr Tyr Ile Cys Asn Val Asn His Lys
210             215             220

Pro Ser Asn Thr Lys Val Asp Lys Arg Val Glu Pro Lys Ser Cys Asp
225             230             235             240

Lys Thr His Thr Cys Pro Pro Cys Pro Ala Pro Glu Leu Leu Gly Gly
            245             250             255

Pro Ser Val Phe Leu Phe Pro Pro Lys Pro Lys Asp Thr Leu Met Ile
            260             265             270

Ser Arg Thr Pro Glu Val Thr Cys Val Val Val Asp Val Ser His Glu
        275             280             285

Asp Pro Glu Val Lys Phe Asn Trp Tyr Val Asp Gly Val Glu Val His
290             295             300

Asn Ala Lys Thr Lys Pro Arg Glu Glu Gln Tyr Asn Ser Thr Tyr Arg
305             310             315             320

Val Val Ser Val Leu Thr Val Leu His Gln Asp Trp Leu Asn Gly Lys
            325             330             335

Glu Tyr Lys Cys Lys Val Ser Asn Lys Ala Leu Pro Ala Pro Ile Glu
            340             345             350

Lys Thr Ile Ser Lys Ala Lys Gly Gln Pro Arg Glu Pro Gln Val Tyr
        355             360             365

Thr Leu Pro Pro Ser Arg Glu Glu Met Thr Lys Asn Gln Val Ser Leu
    370             375             380

Thr Cys Leu Val Lys Gly Phe Tyr Pro Ser Asp Ile Ala Val Glu Trp
385             390             395             400

Glu Ser Asn Gly Gln Pro Glu Asn Asn Tyr Lys Thr Thr Pro Pro Val
            405             410             415

Leu Asp Ser Asp Gly Ser Phe Phe Leu Tyr Ser Lys Leu Thr Val Asp
            420             425             430

Lys Ser Arg Trp Gln Gln Gly Asn Val Phe Ser Cys Ser Val Met His
        435             440             445

Glu Ala Leu His Asn His Tyr Thr Gln Lys Ser Leu Ser Leu Ser Pro
450             455             460

Gly Lys
465

<210> SEQ ID NO 69
<211> LENGTH: 447
<212> TYPE: PRT
<213> ORGANISM: Artificial sequence
<220> FEATURE:
<223> OTHER INFORMATION: Humanized 131R008/131R010 Heavy chain (IgG1)
```

```
<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile His Trp Val Arg Gln Ala Pro Gly Gln Gly Leu Glu Trp Ile
        35                  40                  45

Gly Tyr Ile Tyr Pro Ser Asn Gly Asp Ser Gly Tyr Asn Gln Lys Phe
    50                  55                  60

Lys Asn Arg Val Thr Met Thr Arg Asp Thr Ser Thr Ser Thr Ala Tyr
65                  70                  75                  80

Met Glu Leu Ser Arg Leu Arg Ser Glu Asp Thr Ala Val Tyr Tyr Cys
                85                  90                  95

Ala Thr Tyr Phe Ala Asn Asn Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 70
<211> LENGTH: 1401
<212> TYPE: DNA
<213> ORGANISM: Artificial sequence
<220> FEATURE:
<223> OTHER INFORMATION: Humanized 131R008 Heavy chain (IgG1)

<400> SEQUENCE: 70

```
atgaagcatc tgtggttttt cctcctcctt gtcgccgctc cacgctgggt gctttcccaa       60
gtccaattgg tccagagcgg tgccgaagtg aagaaaccgg gagcttccgt gaaagtgagc      120
tgcaaggctt ctggatacac cttcactgac tattcaatcc actgggtgag acaggcacct      180
ggtcagggac tggagtggat tggatacatc taccccctcaa atggggactc tggctacaac    240
caaaagttca gaaccgggt gactatgacc agagatacct caacatctac tgcctacatg       300
gaactcagca ggctgcgctc agaggacacc gcagtgtatt actgtgccac ctacttcgct      360
aataacttcg actattgggg gcagggcacc accctgactg tcagctcagc ctcaaccaag      420
ggcccctccg tgttccctct ggccccttcc tccaagtcca cctccggcgg caccgccgct      480
ctgggctgcc tggtgaagga ctacttccct gagcctgtga ccgtgtcctg gaactctggc      540
gccctgacct ctggcgtgca caccttccca gccgtgctgc agtcctccgg cctgtactcc      600
ctgtcctccg tggtgaccgt gccttcctcc tccctgggca cccagaccta catctgcaac      660
gtgaaccaca gccttccaa caccaaggtg gacaagcggg tggagcctaa gtcctgcgac        720
aagacccaca cctgccctcc ctgccctgcc ctgagctgtg ggcggacct tccgtgttc         780
ctgttccctc ctaagcctaa ggacaccctg atgatctccc ggaccctga ggtgacctgc        840
gtggtggtgg acgtgtccca cgaggatcct gaggtgaagt tcaattggta cgtggacggc      900
gtggaggtgc acaacgctaa gaccaagcca agggaggagc agtacaactc cacctaccgg      960
gtggtgtctg tgctgaccgt gctgcaccag gactggctga acggcaaaga atacaagtgc    1020
aaggtctcca acaaggccct gcccgctccc atcgagaaaa ccatctccaa ggccaagggc    1080
cagcctcgcg agcctcaggt gtacaccctg ccacccagcc gggaggagat gaccaagaac    1140
caggtgtccc tgacctgtct ggtgaagggc ttctacccct tcgatatcgc cgtggagtgg    1200
gagtctaacg gccagcccga gaacaactac aagaccaccc ctcctgtgct ggactccgac    1260
ggctccttct tcctgtactc caagctgacc gtggacaagt cccggtggca gcagggcaac    1320
gtgttctcct gctccgtgat gcacgaggcc ctgcacaacc actacaccca gaagagcctg    1380
tctctgtctc ctggcaagtg a                                                1401
```

<210> SEQ ID NO 71
<211> LENGTH: 1344
<212> TYPE: DNA
<213> ORGANISM: Artificial sequence
<220> FEATURE:
<223> OTHER INFORMATION: Humanized 131R008 Heavy chain (IgG1)

<400> SEQUENCE: 71

```
caagtccaat tggtccagag cggtgccgaa gtgaagaaac cgggagcttc cgtgaaagtg       60
agctgcaagg cttctggata caccttcact gactattcaa tccactgggt gagacaggca     120
```

```
cctggtcagg gactggagtg gattggatac atctacccct caaatgggga ctctggctac      180
aaccaaaagt tcaagaaccg ggtgactatg accagagata cctcaacatc tactgcctac      240
atggaactca gcaggctgcg ctcagaggac accgcagtgt attactgtgc cacctacttc      300
gctaataact tcgactattg ggggcagggc accaccctga ctgtcagctc agcctcaacc      360
aagggcccct ccgtgttccc tctggcccct tcctccaagt ccacctccgg cggcaccgcc      420
gctctgggct gcctggtgaa ggactacttc cctgagcctg tgaccgtgtc ctggaactct      480
ggcgccctga cctctggcgt gcacaccttc ccagccgtgc tgcagtcctc cggcctgtac      540
tccctgtcct ccgtggtgac cgtgccttcc tcctccctgg cacccagac ctacatctgc       600 aacgtgaacc acaagccttc caacaccaag gtggacaagc gggtggagcc taagtcctgc      660
gacaagaccc acacctgccc ctcctgcccc gcccctgagc tgctgggcgg accttccgtg      720
ttcctgttcc ctcctaagcc taaggacacc ctgatgatct cccggacccc tgaggtgacc      780
tgcgtggtgg tggacgtgtc ccacgaggat cctgaggtga agttcaattg gtacgtggac      840
ggcgtggagg tgcacaacgc taagaccaag ccaagggagg agcagtacaa ctccacctac      900
cgggtggtgt ctgtgctgac cgtgctgcac caggactggc tgaacggcaa agaatacaag      960
tgcaaggtct ccaacaaggc cctgcccgct cccatcgaga aaaccatctc caaggccaag     1020
ggccagcctc gcgagcctca ggtgtacacc ctgccaccca gcgggagga tgaccaag       1080 aaccaggtgt ccctgacctg tctggtgaag ggcttctacc cttccgatat cgccgtggag     1140
tgggagtcta acggccagcc cgagaacaac tacaagacca cccctcctgt gctggactcc     1200
gacggctcct tcttcctgta ctccaagctg accgtggaca gtcccggtg cagcagggc       1260 aacgtgttct cctgctccgt gatgcacgag gccctgcaca accactacac ccagaagagc     1320
ctgtctctgt ctcctggcaa gtga                                            1344
```

```
<210> SEQ ID NO 72
<211> LENGTH: 112
<212> TYPE: PRT
<213> ORGANISM: Artificial sequence
<220> FEATURE:
<223> OTHER INFORMATION: Humanized 131R005/131R007/131R008 Light chain
      variable region

<400> SEQUENCE: 72
```

```
Asp Ile Val Leu Thr Gln Ser Pro Ala Ser Leu Ala Val Ser Leu Gly
1               5                   10                  15

Gln Arg Ala Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Val Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110
```

```
<210> SEQ ID NO 73
<211> LENGTH: 237
<212> TYPE: PRT
<213> ORGANISM: Artificial sequence
```

<220> FEATURE:
<223> OTHER INFORMATION: Humanized 131R005/131R007/131R008 Light chain

<400> SEQUENCE: 73

```
Met Lys His Leu Trp Phe Phe Leu Leu Leu Val Ala Ala Pro Arg Trp
1               5                   10                  15

Val Leu Ser Asp Ile Val Leu Thr Gln Ser Pro Ala Ser Leu Ala Val
            20                  25                  30

Ser Leu Gly Gln Arg Ala Thr Ile Thr Cys Lys Ala Ser Gln Ser Val
        35                  40                  45

Asp Tyr Asp Gly Asp Ser Tyr Met Asn Trp Tyr Gln Gln Lys Pro Gly
    50                  55                  60

Gln Pro Pro Lys Leu Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Thr Ile Asn Pro Val Glu Ala Glu Asp Val Ala Thr Tyr Tyr Cys Gln
            100                 105                 110

Gln Ser Asn Glu Asp Pro Leu Thr Phe Gly Ala Gly Thr Lys Leu Glu
        115                 120                 125

Leu Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 74
<211> LENGTH: 218
<212> TYPE: PRT
<213> ORGANISM: Artificial sequence
<220> FEATURE:
<223> OTHER INFORMATION: Humanized 131R005/131R007/131R008 Light chain

<400> SEQUENCE: 74

```
Asp Ile Val Leu Thr Gln Ser Pro Ala Ser Leu Ala Val Ser Leu Gly
1               5                   10                  15

Gln Arg Ala Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Val Ala Thr Tyr Tyr Cys Gln Gln Ser Asn
                85                  90                  95

Glu Asp Pro Leu Thr Phe Gly Ala Gly Thr Lys Leu Glu Leu Lys Arg
```

```
                100               105                110
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 75
<211> LENGTH: 336
<212> TYPE: DNA
<213> ORGANISM: Artificial sequence
<220> FEATURE:
<223> OTHER INFORMATION: Humanized 131R005/131R007/131R008 Light chain

<400> SEQUENCE: 75
gatatcgtcc tgacccaaag ccctgcttca cttgctgtga gcctggggca acgcgccacc    60
atcacttgca aggcatctca gagcgtggac tatgatggag actcttacat gaattggtat   120
caacagaagc caggtcaacc tcccaaactg ctgatctacg ccgcatctaa tcttgaaagc   180
ggcatcccgg ctcggttctc tggttctgga tcaggaaccg acttcaccct caccattaac   240
ccagtggagg ccgaggacgt ggctacttac tactgccagc agtcaaacga ggaccccctg   300
actttcggag ccgggaccaa gctggagctt aagcgt                             336

<210> SEQ ID NO 76
<211> LENGTH: 714
<212> TYPE: DNA
<213> ORGANISM: Artificial sequence
<220> FEATURE:
<223> OTHER INFORMATION: Humanized 131R005/131R007/131R008 Light chain

<400> SEQUENCE: 76
atgaaacatc tttggttctt ccttctgctg gtcgctgctc ctcggtgggt gcttagcgat    60
atcgtcctga cccaaagccc tgcttcactt gctgtgagcc tggggcaacg cgccaccatc   120
acttgcaagg catctcagag cgtggactat gatggagact cttacatgaa ttggtatcaa   180
cagaagccag gtcaacctcc caaactgctg atctacgccg catctaatct tgaaagcggc   240
atcccggctc ggttctctgg ttctggatca ggaaccgact tcaccctcac cattaaccca   300
gtggaggccg aggacgtggc tacttactac tgccagcagt caaacgagga ccccctgact   360
ttcggagccg gaccaagct ggagcttaag cgtacggtgg ccgcaccgtc agtctttatc   420
tttccaccct ccgacgaaca gcttaagtca ggcactgcct cagtcgtgtg tctcctcaat   480
aacttctacc caggagggc caaggtgcag tggaaagtgg acaacgccct ccagtccggg   540
aactctcaag aaagcgtcac cgagcaggac agcaaggact ccacctactc actgtcaagc   600
actctcaccc tctcaaaggc cgattatgag aagcacaagg tgtacgcatg cgaagtgacc   660
catcagggtc tgtcctctcc tgtcaccaag tccttcaata gaggagaatg ttga          714
```

<210> SEQ ID NO 77
<211> LENGTH: 657
<212> TYPE: DNA
<213> ORGANISM: Artificial sequence
<220> FEATURE:
<223> OTHER INFORMATION: Humanized 131R005/131R007/131R008 Light chain

<400> SEQUENCE: 77

```
gatatcgtcc tgacccaaag ccctgcttca cttgctgtga gcctggggca acgcgccacc    60
atcacttgca aggcatctca gagcgtggac tatgatggag actcttacat gaattggtat   120
caacagaagc caggtcaacc tcccaaactg ctgatctacg ccgcatctaa tcttgaaagc   180
ggcatcccgg ctcggttctc tggttctgga tcaggaaccg acttcaccct caccattaac   240
ccagtggagg ccgaggacgt ggctacttac tactgccagc agtcaaacga ggaccccctg   300
actttcggag ccgggaccaa gctggagctt aagcgtacgg tggccgcacc gtcagtcttt   360
atctttccac cctccgacga acagcttaag tcaggcactg cctcagtcgt gtgtctcctc   420
aataacttct accccaggga ggccaagtg cagtggaaag tggacaacgc cctccagtcc   480
gggaactctc aagaaagcgt caccgagcag acagcaagg actccaccta ctcactgtca   540
agcactctca ccctctcaaa ggccgattat gagaagcaca aggtgtacgc atgcgaagtg   600
acccatcagg gtctgtcctc tcctgtcacc aagtccttca atagaggaga atgttga      657
```

<210> SEQ ID NO 78
<211> LENGTH: 5
<212> TYPE: PRT
<213> ORGANISM: Artificial sequence
<220> FEATURE:
<223> OTHER INFORMATION: Variant Heavy chain CDR1

<400> SEQUENCE: 78

Asp Tyr Ser Ile His
1               5

<210> SEQ ID NO 79
<211> LENGTH: 16
<212> TYPE: PRT
<213> ORGANISM: Artificial sequence
<220> FEATURE:
<223> OTHER INFORMATION: Variant Heavy chain CDR2

<400> SEQUENCE: 79

Tyr Ile Tyr Pro Ser Asn Gly Asp Ser Gly Tyr Asn Gln Lys Phe Lys
1               5                   10                  15

<210> SEQ ID NO 80
<211> LENGTH: 8
<212> TYPE: PRT
<213> ORGANISM: Artificial sequence
<220> FEATURE:
<223> OTHER INFORMATION: Variant Heavy chain CDR3

<400> SEQUENCE: 80

Thr Tyr Phe Ala Asn Asn Phe Asp
1               5

<210> SEQ ID NO 81
<211> LENGTH: 15
<212> TYPE: PRT
<213> ORGANISM: Artificial sequence
<220> FEATURE:
<223> OTHER INFORMATION: Variant Light chain CDR1

<400> SEQUENCE: 81

Lys Ala Ser Gln Ser Val Asp Tyr Asp Gly Asp Ser Tyr Met Asn
1               5                   10                  15

<210> SEQ ID NO 82
<211> LENGTH: 7
<212> TYPE: PRT
<213> ORGANISM: Artificial sequence
<220> FEATURE:
<223> OTHER INFORMATION: Variant Light chain CDR2

<400> SEQUENCE: 82

Ala Ala Ser Asn Leu Glu Ser
1               5

<210> SEQ ID NO 83
<211> LENGTH: 10
<212> TYPE: PRT
<213> ORGANISM: Artificial sequence
<220> FEATURE:
<223> OTHER INFORMATION: Variant Light chain CDR3

<400> SEQUENCE: 83

Gln Gln Ser Asn Glu Asp Pro Leu Thr Phe
1               5                   10

<210> SEQ ID NO 84
<211> LENGTH: 1404
<212> TYPE: DNA
<213> ORGANISM: Artificial sequence
<220> FEATURE:
<223> OTHER INFORMATION: Humanized 131R010 Heavy chain (IgG1)

<400> SEQUENCE: 84

| | | | | | |
|---|---|---|---|---|---|
| atgaaacact | tgtggttctt | tctgctccct | gtcgcagcac | cacggtgggt | gctgtcgcaa | 60 |
| gtgcaattgg | tgcagtccgg | agcggaagtg | aagaagcctg | gtgcctcggt | caaagtctca | 120 |
| tgcaaggcca | gcggatacac | tttcaccgac | tactccatcc | attgggtgag | gcaggctccg | 180 |
| ggccagggcc | tggagtggat | tgggtacatc | tacccgtcga | acggagattc | ggggtacaat | 240 |
| cagaagttca | agaaccgcgt | gaccatgact | cgggacacct | caacttccac | ggcttatatg | 300 |
| gaactgagcc | gcctgagatc | cgaggacact | gcggtgtact | actgtgccac | ctactttgcg | 360 |
| aacaatttcg | attactgggg | acaaggaacc | acgctcactg | tcagctcagc | cagcaccaag | 420 |
| ggccccctccg | tgttccctct | ggccccttcc | tccaagtcca | cctccggcgg | caccgccgct | 480 |
| ctgggctgcc | tggtgaagga | ctacttccct | gagcctgtga | ccgtgtcctg | gaactctggc | 540 |
| gccctgacct | ctggcgtgca | caccttccca | gccgtgctgc | agtcctccgg | cctgtactcc | 600 |
| ctgtcctccg | tggtgaccgt | gccttcctcc | tccctgggca | cccagaccta | catctgcaac | 660 |
| gtgaaccaca | agccttccaa | caccaaggtg | gacaagcggg | tggagcctaa | gtcctgcgac | 720 |
| aagacccaca | cctgccctcc | ctgccctgcc | cctgagctgc | tgggcggacc | ttccgtgttc | 780 |
| ctgttccctc | ctaagcctaa | ggacaccctg | atgatctccc | ggacccctga | ggtgacctgc | 840 |
| gtggtggtgg | acgtgtccca | cgaggatcct | gaggtgaagt | tcaattggta | cgtggacggc | 900 |
| gtggaggtgc | acaacgctaa | gaccaagcca | agggaggagc | agtacaactc | cacctaccgg | 960 |
| gtggtgtctg | tgctgaccgt | gctgcaccag | gactggctga | acggcaaaga | atacaagtgc | 1020 |
| aaggtctccca | acaaggccct | gccgctcccc | atcgagaaaa | ccatctccaa | ggccaagggc | 1080 |
| cagcctcgcg | agcctcaggt | gtacaccctg | ccacccagcc | gggaggagat | gaccaagaac | 1140 |

| caggtgtccc tgacctgtct ggtgaagggc ttctacccct ccgatatcgc cgtggagtgg | 1200 |
| gagtctaacg gccagcccga gaacaactac aagaccaccc ctcctgtgct ggactccgac | 1260 |
| ggctccttct tcctgtactc caagctgacc gtggacaagt cccggtggca gcagggcaac | 1320 |
| gtgttctcct gctccgtgat gcacgaggcc ctgcacaacc actacaccca gaagagcctg | 1380 |
| tctctgtctc ctggcaagtg ataa | 1404 |

<210> SEQ ID NO 85
<211> LENGTH: 1347
<212> TYPE: DNA
<213> ORGANISM: Artificial sequence
<220> FEATURE:
<223> OTHER INFORMATION: Humanized 131R010 Heavy chain (IgG1)

<400> SEQUENCE: 85

| caagtgcaat tggtgcagtc cggagcggaa gtgaagaagc ctggtgcctc ggtcaaagtc | 60 |
| tcatgcaagg ccagcggata cactttcacc gactactcca tccattgggt gaggcaggct | 120 |
| ccgggccagg gctggagtg gattgggtac atctacccgt cgaacggaga ttcgggtac | 180 |
| aatcagaagt tcaagaaccg cgtgaccatg actcgggaca cctcaacttc acggcttat | 240 |
| atggaactga gccgctgag atccgaggac actgcggtgt actactgtgc cacctacttt | 300 |
| gcgaacaatt tcgattactg gggacaagga accacgctca ctgtcagctc agccagcacc | 360 |
| aagggcccct ccgtgttccc tctggcccct tcctccaagt ccacctccgg cggcaccgcc | 420 |
| gctctgggct gcctggtgaa ggactacttc cctgagcctg tgaccgtgtc ctggaactct | 480 |
| ggcgccctga cctctggcgt gcacaccttc ccagccgtgc tgcagtcctc cggcctgtac | 540 |
| tccctgtcct ccgtggtgac cgtgccttcc tctccctgg caccagac ctacatctgc | 600 |
| aacgtgaacc acaagccttc caacaccaag gtggacaagc gggtggagcc taagtcctgc | 660 |
| gacaagaccc acacctgccc tccctgccct gcccctgagc tgctgggcgg accttccgtg | 720 |
| ttcctgttcc ctcctaagcc taaggacacc ctgatgatct cccggacccc tgaggtgacc | 780 |
| tgcgtggtgg tggacgtgtc ccacgaggat cctgaggtga agttcaattg gtacgtggac | 840 |
| ggcgtggagg tgcacaacgc taagaccaag ccaaggagg agcagtacaa ctccacctac | 900 |
| cgggtggtgt ctgtgctgac cgtgctgcac caggactggc tgaacggcaa agaatacaag | 960 |
| tgcaaggtct ccaacaaggc cctgccggct cccatcgaga aaaccatctc caaggccaag | 1020 |
| ggccagcctc gcgagcctca ggtgtacacc ctgccacca gcgggagga gatgaccaag | 1080 |
| aaccaggtgt ccctgacctg tctggtgaag ggcttctacc cttccgatat cgccgtggag | 1140 |
| tgggagtcta acgccagcc cgagaacaac tacaagacca cccctcctgt gctggactcc | 1200 |
| gacggctcct tcttcctgta ctccaagctg accgtggaca gtcccggtg cagcagggc | 1260 |
| aacgtgttct cctgctccgt gatgcacgag gccctgcaca accactacac ccagaagagc | 1320 |
| ctgtctctgt ctcctggcaa gtgataa | 1347 |

<210> SEQ ID NO 86
<211> LENGTH: 112
<212> TYPE: PRT
<213> ORGANISM: Artificial sequence
<220> FEATURE:
<223> OTHER INFORMATION: Humanized 131R010/131R011 Light chain variable region

<400> SEQUENCE: 86

Asp Ile Gln Met Thr Gln Ser Pro Ser Ser Leu Ser Ala Ser Val Gly
1               5                   10                  15

```
Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Pro Val Gln Ala Glu Asp Phe Ala Thr Tyr Tyr Cys Gln Gln Ser Asn
                 85                  90                  95

Glu Asp Pro Leu Thr Phe Gly Ala Gly Thr Lys Leu Glu Leu Lys Arg
            100                 105                 110
```

<210> SEQ ID NO 87
<211> LENGTH: 237
<212> TYPE: PRT
<213> ORGANISM: Artificial sequence
<220> FEATURE:
<223> OTHER INFORMATION: Humanized 131R010/131R011 Light chain

<400> SEQUENCE: 87

```
Met Lys His Leu Trp Phe Phe Leu Leu Leu Val Ala Ala Pro Arg Trp
 1               5                  10                  15

Val Leu Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Ser Val
            35                  40                  45

Asp Tyr Asp Gly Asp Ser Tyr Met Asn Trp Tyr Gln Gln Lys Pro Gly
 50                  55                  60

Lys Ala Pro Lys Leu Leu Ile Tyr Ala Ala Ser Asn Leu Glu Ser Gly
 65                  70                  75                  80

Val Pro Ser Arg Phe Ser Gly Ser Gly Ser Gly Thr Asp Phe Thr Leu
                 85                  90                  95

Thr Ile Ser Pro Val Gln Ala Glu Asp Phe Ala Thr Tyr Tyr Cys Gln
            100                 105                 110

Gln Ser Asn Glu Asp Pro Leu Thr Phe Gly Ala Gly Thr Lys Leu Glu
            115                 120                 125

Leu Lys Arg Thr Val Ala Ala Pro Ser Val Phe Ile Phe Pro Pro Ser
 130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
 210                 215                 220

Ser Ser Pro Val Thr Lys Ser Phe Asn Arg Gly Glu Cys
225                 230                 235
```

<210> SEQ ID NO 88
<211> LENGTH: 218
<212> TYPE: PRT
<213> ORGANISM: Artificial sequence
<220> FEATURE:
<223> OTHER INFORMATION: Humanized 131R010/131R011 Light chain

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Pro Val Gln Ala Glu Asp Phe Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 89
<211> LENGTH: 336
<212> TYPE: DNA
<213> ORGANISM: Artificial sequence
<220> FEATURE:
<223> OTHER INFORMATION: Humanized 131R010/131R011 Light chain variable
      region nucleic acid

<400> SEQUENCE: 89
gatatccaga tgactcagtc gccctcatcg ttgagcgcct cggtcgggga tcgcgtgact    60
attacttgta aagcgtccca gagcgtggac tacgacggag attcctacat gaactggtat   120
cagcaaaaac cgggaaaggc tcctaaactt ctcatctacg cagcctcgaa tctggaatca   180
ggagtcccga gccggttcag cggatcaggc tccggtactg attttaccct cacgatctcg   240
ccagtgcaag ccgaggactt cgcgacctac tactgccaac agtccaacga ggaccccgctg   300 accttcggcg cagggaccaa gctggaactg aagcgt                              336

<210> SEQ ID NO 90
<211> LENGTH: 714
<212> TYPE: DNA
<213> ORGANISM: Artificial sequence
<220> FEATURE:
<223> OTHER INFORMATION: Humanized 131R010/131R011 Light chain

<400> SEQUENCE: 90

```
atgaaacacc tgtggttctt cctcctgctg gtggcagctc ccagatgggt cctgtccgat    60
atccagatga ctcagtcgcc ctcatcgttg agcgcctcgg tcggggatcg cgtgactatt   120
acttgtaaag cgtcccagag cgtggactac gacggagatt cctacatgaa ctggtatcag   180
caaaaaccgg aaaggctcc taaacttctc atctacgcag cctcgaatct ggaatcagga   240
gtcccgagcc ggttcagcgg atcaggctcc ggtactgatt ttaccctcac gatctcgcca   300
gtgcaagccg aggacttcgc gacctactac tgccaacagt ccaacgagga cccgctgacc   360 tcggcgcag ggaccaagct ggaactgaag cgtacggtgg ccgctccatc cgtgtttatc    420
tttccgccgt ccgatgagca gctcaagtcg gcactgcca gcgtggtctg cctgcttaac    480
aatttctacc ctagggaagc caaggtgcag tggaaggtgg ataacgcgct ccaatccggt   540
aactcgcaag agagcgtgac cgaacaggac tcaaaggact cgacgtacag cctgtcatcg   600
accttgactc tctcaaaggc cgactacgaa aagcacaagg tctacgcgtg cgaagtcacc   660
catcagggac tgtcctcgcc tgtgaccaag agcttcaatc gcggagagtg ctga         714

<210> SEQ ID NO 91
<211> LENGTH: 657
<212> TYPE: DNA
<213> ORGANISM: Artificial sequence
<220> FEATURE:
<223> OTHER INFORMATION: Humanized 131R010/131R011 Light chain

<400> SEQUENCE: 91
gatatccaga tgactcagtc gccctcatcg ttgagcgcct cggtcgggga tcgcgtgact    60
attacttgta aagcgtccca gagcgtggac tacgacggag attcctacat gaactggtat   120
cagcaaaaac cggaaaggc tcctaaactt ctcatctacg cagcctcgaa tctggaatca   180
ggagtcccga gccggttcag cggatcaggc tccggtactg attttaccct cacgatctcg   240
ccagtgcaag ccgaggactt cgcgacctac tactgccaac agtccaacga ggacccgctg   300
accttcggcg cagggaccaa gctggaactg aagcgtacgg tggccgctcc atccgtgttt   360
atctttccgc cgtccgatga gcagctcaag tcgggcactg ccagcgtggt ctgcctgctt   420
aacaatttct accctaggga agccaaggtg cagtggaagg tggataacgc gctccaatcc   480
ggtaactcgc aagagagcgt gaccgaacag gactcaaagg actcgacgta cagcctgtca   540
tcgaccttga ctctctcaaa ggccgactac gaaaagcaca aggtctacgc gtgcgaagtc   600
acccatcagg gactgtcctc gcctgtgacc aagagcttca atcgcggaga gtgctga      657

<210> SEQ ID NO 92
<211> LENGTH: 351
<212> TYPE: DNA
<213> ORGANISM: Artificial sequence
<220> FEATURE:
<223> OTHER INFORMATION: Humanized 131R011 Heavy chain variable region
      nucleic acid

<400> SEQUENCE: 92
caagtgcaat tggtgcagtc cggagcggaa gtgaagaagc tggtgcctc ggtcaaagtc     60 tcatgcaagg ccagcggata cactttcacc gactactcca tccattgggt gaggcaggct   120
ccgggccagg gcctggagtg gattgggtac atctacccgt cgaacggaga ttcggggtac   180
aatcagaagt tcaagaaccg cgtgaccatg actcggaca cctcaacttc acggcttat    240 atggaactga gccgctgag atccgaggac actgcggtgt actactgtgc cacctacttt   300
gcgaacaatt tcgattactg gggacaagga accacgctca ctgtcagctc a            351
```

```
<210> SEQ ID NO 93
<211> LENGTH: 1392
<212> TYPE: DNA
<213> ORGANISM: Artificial sequence
<220> FEATURE:
<223> OTHER INFORMATION: Humanized 131R011 Heavy chain (IgG2)

<400> SEQUENCE: 93
atgaaacact tgtggttctt tctgctcctt gtcgcagcac cacggtgggt gctgtcgcaa      60
gtgcaattgg tgcagtccgg agcggaagtg aagaagcctg gtgcctcggt caaagtctca     120
tgcaaggcca gcggatacac tttcaccgac tactccatcc attgggtgag gcaggctccg     180
ggccagggcc tggagtggat tgggtacatc taccegtcga acggagattc ggggtacaat     240
cagaagttca agaaccgcgt gaccatgact cgggacacct caacttccac ggcttatatg     300
gaactgagcc gcctgagatc cgaggacact gcggtgtact actgtgccac ctactttgcg     360
aacaatttcg attactgggg acaaggaacc acgctcactg tcagctcagc cagcaccaag     420
ggcccctccg tgttccctct ggccccttgc tcccggtcca cctctgagtc taccgccgct     480
ctgggctgcc tggtgaagga ctacttccct gagcctgtga ccgtgtcctg gaactctggc     540
gccctgacct ctggcgtgca caccttccct gccgtgctgc agtcctccgg cctgtactcc     600
ctgtcctccg tggtgaccgt gccttcctcc aacttcggca cccagaccta cacctgcaac     660
gtggaccaca gccttccaa caccaaggtg gacaagaccg tggagcggaa gtgctgcgtg      720
gagtgccctc cttgtcctgc tcctcctgtg gctggcccct tctgtgttcct gttccctcct    780 aagcctaagg acaccctgat gatctcccgg acccctgaag tgacctgcgt ggtggtggac     840
gtgtcccacg aggaccctga ggtgcagttc aattggtacg tggacggcgt ggaggtgcac     900
aacgccaaga ccaagcctcg ggaggaacag ttcaactcca ccttccgggt ggtgtctgtg     960
ctgaccgtgg tgcaccagga ctggctgaac ggcaaagaat acaagtgcaa ggtgtccaac    1020
aagggcctgc ctgcccctat cgaaaagacc atctctaaga ccaagggcca gcctcgcgag    1080
cctcaggtct acaccctgcc tcctagccgg gaggaaatga ccaagaacca ggtgtccctg    1140
acctgtctgg tgaagggctt ctaccttcc gatatcgccg tggagtggga gtctaacggc     1200
cagcctgaga caactacaa gaccacccct cctatgctgg actccgacgg ctccttcttc      1260
ctgtactcca agctgacagt ggacaagtcc cggtggcagc agggcaacgt gttctcctgc    1320
tccgtgatgc acgaggccct gcacaaccac tacacccaga gtccctgtc cctgtctcct    1380 ggcaagtgat aa                                                        1392

<210> SEQ ID NO 94
<211> LENGTH: 1335
<212> TYPE: DNA
<213> ORGANISM: Artificial sequence
<220> FEATURE:
<223> OTHER INFORMATION: Humanized 131R011 Heavy chain (IgG2)

<400> SEQUENCE: 94
caagtgcaat tggtgcagtc cggagcggaa gtgaagaagc ctggtgcctc ggtcaaagtc      60
tcatgcaagg ccagcggata cactttcacc gactactcca tccattgggt gaggcaggct     120
ccgggccagg gcctggagtg gattgggtac atctacccgt cgaacggaga ttcggggtac     180
aatcagaagt tcaagaaccg cgtgaccatg actcgggaca cctcaacttc cacggcttat     240
atggaactga gccgcctgag atccgaggac actgcggtgt actactgtgc cacctacttt    300
```

```
gcgaacaatt tcgattactg gggacaagga accacgctca ctgtcagctc agccagcacc      360
aagggcccct ccgtgttccc tctggcccct tgctcccggt ccacctctga gtctaccgcc      420
gctctgggct gcctggtgaa ggactacttc cctgagcctg tgaccgtgtc ctggaactct      480
ggcgccctga cctctggcgt gcacaccttc cctgccgtgc tgcagtcctc cggcctgtac      540
tccctgtcct ccgtggtgac cgtgccttcc tccaacttcg gcacccagac ctacacctgc      600
aacgtggacc acaagccttc caacaccaag gtggacaaga ccgtggagcg gaagtgctgc      660
gtggagtgcc ctccttgtcc tgctcctcct gtggctggcc cttctgtgtt cctgttccct      720
cctaagccta aggacaccct gatgatctcc cggacccctg aagtgacctg cgtggtggtg      780
gacgtgtccc acgaggaccc tgaggtgcag ttcaattggt acgtggacgg cgtggaggtg      840
cacaacgcca agaccaagcc tcgggaggaa cagttcaact ccaccttccg ggtggtgtct      900
gtgctgaccg tggtgcacca ggactggctg aacggcaaag aatacaagtg caaggtgtcc      960
aacaagggcc tgcctgcccc tatcgaaaag accatctcta agaccaaggg ccagcctcgc     1020
gagcctcagg tctacaccct gcctcctagc cgggaggaaa tgaccaagaa ccaggtgtcc     1080
ctgacctgtc tggtgaaggg cttctaccct tccgatatcg ccgtggagtg ggagtctaac     1140
ggccagcctg agaacaacta caagaccacc cctcctatgc tggactccga cggctccttc     1200
ttcctgtact ccaagctgac agtggacaag tcccggtggc agcagggcaa cgtgttctcc     1260
tgctccgtga tgcacgaggc cctgcacaac cactacaccc agaagtccct gtccctgtct     1320
cctggcaagt gataa                                                      1335

<210> SEQ ID NO 95
<211> LENGTH: 350
<212> TYPE: DNA
<213> ORGANISM: Artificial sequence
<220> FEATURE:
<223> OTHER INFORMATION: Humanized 131R010 Heavy chain variable region

<400> SEQUENCE: 95
caagtgcaat tggtgcagtc cggagcggaa gtgaagaagc ctggtgcctc ggtcaaagtc       60
tcatgcaagg ccagcggata cactttcacc gactactcca tccattgggt gaggcaggct      120
ccgggccagg gcctggagtg gattgggtac atctacccgt cgaacggaga ttcggggtac      180
aatcagaagt tcaagaaccg cgtgaccatg actcgggaca cctcaacttc cacggcttat      240
atggaactga gccgcctgag atccgaggac actgcggtgt actactgtgc cacctacttt      300
gcgaacaatt tcgattactg gggacaagga accacgctca ctgtcagctc                 350
```